United States Patent
Kahne et al.

(10) Patent No.: US 11,713,335 B2
(45) Date of Patent: Aug. 1, 2023

(54) AMINOCOUMARIN COMPOUNDS AND METHODS OF THEIR USE

(71) Applicant: President and Fellows of Harvard College, Cambridge, MA (US)

(72) Inventors: Daniel Kahne, Brookline, MA (US); Michael D. Mandler, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 16/979,972

(22) PCT Filed: Mar. 12, 2019

(86) PCT No.: PCT/US2019/021883
§ 371 (c)(1),
(2) Date: Sep. 11, 2020

(87) PCT Pub. No.: WO2019/178119
PCT Pub. Date: Sep. 19, 2019

(65) Prior Publication Data
US 2021/0009621 A1    Jan. 14, 2021

Related U.S. Application Data

(60) Provisional application No. 62/641,823, filed on Mar. 12, 2018.

(51) Int. Cl.
C07H 17/075    (2006.01)
A61K 9/00      (2006.01)
A61K 38/12     (2006.01)

(52) U.S. Cl.
CPC .......... *C07H 17/075* (2013.01); *A61K 9/0014* (2013.01); *A61K 9/0019* (2013.01); *A61K 9/0043* (2013.01); *A61K 9/0053* (2013.01); *A61K 38/12* (2013.01)

(58) Field of Classification Search
CPC ............................... C07H 17/075; C07H 17/06
See application file for complete search history.

(56) References Cited

U.S. PATENT DOCUMENTS

| | | | | |
|---|---|---|---|---|
| 3,890,297 | A * | 6/1975 | Dolak | C07H 17/075 536/17.9 |
| 4,510,132 | A | 4/1985 | Vaara | |
| 8,198,419 | B2 | 6/2012 | Thorson | |
| 9,763,996 | B2 | 9/2017 | Vaara et al. | |
| 11,191,773 | B2 | 12/2021 | Kahne et al. | |
| 2002/0095026 | A1 * | 7/2002 | Farrar | C07H 13/10 536/55 |
| 2011/0082098 | A1 | 4/2011 | Calvet et al. | |
| 2012/0252745 | A1 | 10/2012 | Blagg et al. | |
| 2012/0264924 | A1 | 10/2012 | Thorson | |
| 2013/0244230 | A1 | 9/2013 | Luider et al. | |
| 2016/0206684 | A1 | 7/2016 | Vaara et al. | |
| 2016/0222061 | A1 | 8/2016 | Brown et al. | |
| 2016/0289217 | A1 | 10/2016 | Blagg et al. | |
| 2017/0000831 | A1 | 1/2017 | Pouillot et al. | |
| 2020/0163985 | A1 | 5/2020 | Kahne et al. | |
| 2021/0009621 | A1 | 1/2021 | Kahne et al. | |
| 2022/0202843 | A1 | 6/2022 | Kahne et al. | |

FOREIGN PATENT DOCUMENTS

WO    WO-2019/178119 A1    9/2019

OTHER PUBLICATIONS

Ofek et al., Antimicrobial Agents and Chemotherapy, 1994, 38(2), p. 374-377. (Year: 1994).*
Heide, L., International Journal of Medical Microbiology, 2014, 304(1), p. 31-36. (Year: 2014).*
Mandler et al., "Novobiocin Enhances Polymyxin Activity by Stimulating Lipopolysaccharide Transport," Journal of the American Chemical Society, 140: 6749-6753 (2018).
Garneau-Tsodikova et al., "Installation of the pyrrolyl-2-carboxyl pharmacophore by CouN1 and CouN7 in the late biosynthetic steps of the aminocoumarin antibiotics clorobiocin and coumermycin A1," Biochemistry, 45(28):8568-8578 (2006).
International Search Report and Written Opinion for International Application No. PCT/US2018/042283 dated Oct. 17, 2018.
International Search Report and Written Opinion for International Application No. PCT/US2019/021883 dated Jul. 3, 2019.
Invitation to Pay Additional Fees for International Application No. PCT/US2019/021883 dated Apr. 24, 2019.
May et al., "The antibiotic novobiocin binds and activates the ATPase that powers lipopolysaccharide transport," Journal of the American Chemical Society, 139(48):17221-17224 (2017).
Sherman et al., "Decoupling catalytic activity from biological function of the ATPase that powers lipopolysaccharide transport," PNAS, 111(13):4982-4987 (2014).
Xu et al., "New aminocoumarin antibiotics formed by a combined mutational and chemoenzymatic approach utilizing the carbamoyltransferase NovN," Chemistry and Biology, 11(5):655-662 (2004).
Zhao et al., "Engineering an antibiotic to fight cancer: optimization of the novobiocin scaffold to produce anti-proliferative agents," Journal of Medicinal Chemistry, 54(11):3839-3853 (2011).
Kapur et al., "Treatment of clinical cases of mastitis with special Formula 17900-Forte," Indian Journal of Veterinary Medicine, 5(2): 107 (1985).
Loutet et al., "Identification of synergists that potentiate the action of polymyxin B against Burkholderia cenocepacia," International Journal of Antimicrobial Agents, 46: 376-380 (2015).

\* cited by examiner

Primary Examiner — Jonathan S Lau
(74) Attorney, Agent, or Firm — Foley Hoag LLP; Susan M. Abelleira; Laura A. Wzorek

(57) ABSTRACT

Disclosed are aminocoumarin compounds, pharmaceutical compositions containing aminocoumarin compounds, and methods of their use, e.g., in the treatment of a Gram-negative bacterial infection.

14 Claims, 1 Drawing Sheet

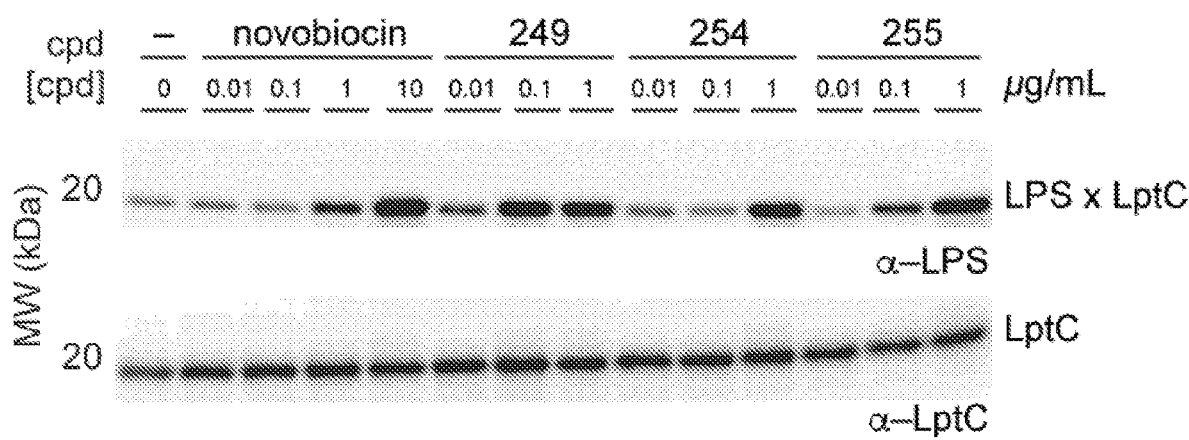

AMINOCOUMARIN COMPOUNDS AND METHODS OF THEIR USE

CROSS-REFERENCE TO RELATED APPLICATIONS

This application claims the benefit of U.S. Provisional Application No. 62/641,823, filed Mar. 12, 2018, which is hereby incorporated by reference in its entirety.

STATEMENT AS TO FEDERALLY FUNDED RESEARCH

This invention was made with government support under grant numbers GM066174, AI109764, and AI081059, awarded by the National Institutes of Health, and DGE-1144152 awarded by the National Science Foundation. The government has certain rights in the invention.

FIELD OF THE INVENTION

The invention relates to compounds, pharmaceutical compositions containing them, and methods of their medical use.

BACKGROUND

Gram-negative bacterial pathogens, including *Escherichia coli, Acinetobacter baumannii, Pseudomonas aeruginosa*, and *Klebsiella pneumoniae*, are responsible for more than 35% of the most common hospital-acquired infections. These nosocomial infections can cause severe pneumonia and infections of the urinary tract, site of surgery, and bloodstream. Today, more than 70% of these infections are resistant to at least one of the most commonly used antibiotics. Antibiotic resistance has emerged to all classes of clinically used antibiotics and poses a growing threat to public health. The majority of resistant infections are caused by six problematic pathogens (the so-called ESKAPE pathogens), of which four are Gram-negative (*Pseudomonas aeruginosa, Acinetobacter baumannii, Klebsiella pneumoniae*, and *Enterobacter* species). There is a need for new therapies that are effective against Gram-negative bacteria.

SUMMARY OF THE INVENTION

In general, the invention provides aminocoumarin compounds, pharmaceutical compositions containing them, and methods of their medical use.

Disclosed herein are compound of formula (X):

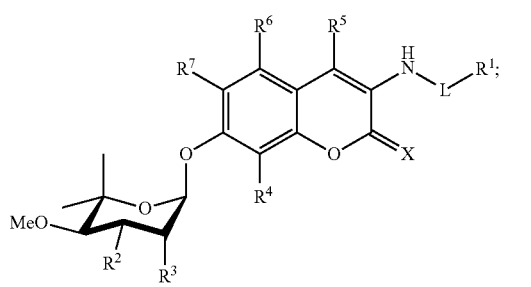

(X)

or a pharmaceutically acceptable salt thereof, wherein
X is O or S;
L is —CO— or —SO$_2$—;
R$^1$ is phenyl or heteroaryl substituted by 1 or more substituents, wherein at least one substituent is —OR$^{50}$;
R$^{50}$ is optionally substituted aryl or optionally substituted heteroaryl;
each of R$^2$ and R$^3$ is independently hydroxyl, —O—CO—NH—R$^{10}$, or —O—CO—R$^{11}$;
each of R$^4$, R$^6$, and R$^7$ is independently hydrogen, halogen, optionally substituted C$_{1-6}$ alkyl, optionally substituted C$_{1-6}$ alkoxy, or optionally substituted C$_{6-10}$ aryl;
R$^5$ is halogen, hydroxyl, or optionally substituted C$_{1-6}$ alkoxy;
R$^{10}$, when present, is hydrogen, optionally substituted C$_{1-6}$ alkyl, optionally substituted C$_{3-10}$ cycloalkyl, optionally substituted heteroaryl, or optionally substituted C$_{6-10}$ aryl; and
R$^{11}$, when present, is optionally substituted heteroaryl or optionally substituted C$_{6-10}$ aryl; and
wherein when R$^1$ is

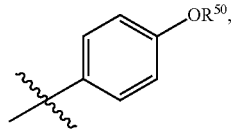

then R$^{50}$ is not phenyl substituted by alkyl.

Disclosed herein are methods of treating a subject having a Gram-negative bacterial infection, the method comprising administering to the subject an effective amount of a compound of the invention. In some embodiments, the methods further comprise administering an effective amount of a polymyxin or a pharmaceutically acceptable salt thereof. In certain embodiments, the Gram-negative bacterial infection is a urinary tract infection, meningeal infection, eye infection, lung infection, or bacteremia.

Disclosed herein are compounds of the invention, optionally with a polymyxin, for use in treating a Gram-negative bacterial infection in a subject in need thereof. Also disclosed are uses of a compound of the invention, optionally with a polymyxin, in the manufacture of a medicament for treating a Gram-negative bacterial infection in a subject in need thereof.

BRIEF DESCRIPTION OF THE DRAWINGS

FIG. 1 shows a Western blot showing lipopolysaccharide release upon treatment with the compounds of the invention.

DEFINITIONS

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about. In some embodiments, the term "about," as used herein, represents a value that is in the range of ±10% of the value that follows the term "about."

The term "acyl," as used herein, represents a monovalent substituent —C(O)—R, where R is alkyl, aryl, arylalkyl, cycloalkyl, haloalkyl, heteroaryl, or heterocyclyl.

The term "acyloxy," as used herein, represents a monovalent substituent —OR, where R is acyl.

The term "alkenyl," as used herein, represents an acyclic, straight or branched chain, monovalent hydrocarbon group containing one or more carbon-carbon double bonds. Unless otherwise specified, an unsubstituted alkenyl has a carbon count from two to six. Non-limiting examples of the alkenyl groups include ethenyl, prop-1-enyl, prop-2-enyl, 1-methylethenyl, but-1-enyl, but-2-enyl, but-3-enyl, 1-methylprop-1-enyl, 2-methylprop-1-enyl, 1-methylprop-2-enyl, and the like. An optionally substituted alkenyl is an alkenyl group that is optionally substituted as described herein for alkyl.

The term "allylic," as used herein, describes an alkenyl group wherein a carbon-carbon double bond is connected to a methylene group, and the methylene group represents the point of attachment to the rest of the molecule. An exemplary allylic alkenyl group attached to a phenyl group is depicted below:

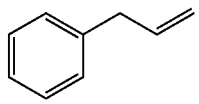

The term "alkoxy," as used herein, represents a chemical substituent of formula —OR, where R is a $C_{1-6}$ alkyl group, unless otherwise specified. An optionally substituted alkoxy is an alkoxy group that is optionally substituted as described herein for alkyl.

The term "alkyl," as used herein, represents an acyclic, straight or branched chain, saturated hydrocarbon group, which, when unsubstituted, has from one to six carbon atoms, unless otherwise specified. Non-limiting examples of alkyl groups include methyl, ethyl, n-propyl, iso-propyl, n-butyl, sec-butyl, iso-butyl, tert-butyl, neopentyl, and the like. Alkyl may be optionally substituted, valency permitting, with one, two, three, four, or five unsubstituted substituents independently selected from the group consisting of: alkoxy; acyloxy; aryloxy; arylalkoxy; cycloalkyl; cycloalkoxy; halogen; heterocyclyl; heteroaryl; heterocyclyloxy; heteroaryloxy; hydroxyl; nitro; thiol; azido, =O; =S; and —NR$_2$, where each R is independently hydrogen, alkyl, acyl, aryl, arylalkyl, cycloalkyl, heterocyclyl, or heteroaryl.

The term "alkynyl," as used herein, represents an acyclic, straight or branched chain, monovalent hydrocarbon group of from two to six carbon atoms containing one or more carbon-carbon triple bonds. Non-limiting examples of alkynyl groups include ethynyl, 1-propynyl, 2-propynyl, 2-butynyl, and the like. An optionally substituted alkynyl is an alkynyl that is optionally substituted as described herein for alkyl.

The term "amide", as used herein, refers to a group

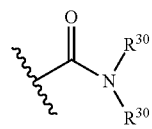

wherein each $R^{30}$ independently represents a hydrogen or hydrocarbyl group, or two $R^{30}$ are taken together with the N atom to which they are attached complete a heterocycle having from 4 to 8 atoms in the ring structure.

The term "amino," as used herein, represents both unsubstituted and substituted amines and salts thereof, e.g., a moiety that can be represented by

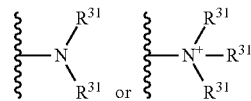

wherein each $R^{31}$ independently represents a hydrogen or a hydrocarbyl group, or two $R^{31}$ are taken together with the N atom to which they are attached complete a heterocycle having from 4 to 8 atoms in the ring structure. The term "aminoalkyl", as used herein, refers to an alkyl group substituted with an amino group. In some embodiments, an amino group is a monovalent substituent —NH$_2$ or a divalent substituent —NH—.

The term "aryl," as used herein, represents a monocyclic, bicyclic, or tricyclic carbocyclic ring system having one or two aromatic rings. Unless otherwise specified, unsubstituted aryl groups have a carbon count of six to fourteen. All ring atoms within an unsubstituted carbocyclic aryl group are carbon atoms. Non-limiting examples of carbocyclic aryl groups include phenyl, naphthyl, 1,2-dihydronaphthyl, 1,2,3,4-tetrahydronaphthyl, fluorenyl, indanyl, indenyl, etc. Unless otherwise specified, aryl may be optionally substituted with one, two, three, four, or five substituents independently selected from the group consisting of: alkyl; acyl; acyloxy; alkenyl; alkynyl; alkoxy; aryl; aryloxy; arylalkoxy; cycloalkyl; cycloalkoxy; halogen; heterocyclyl; heteroaryl; heterocyclyloxy; heteroaryloxy; hydroxyl; nitro; thiol; cyano; —NR$_2$, where each R is independently hydrogen, alkyl, acyl, aryl, arylalkyl, cycloalkyl, heterocyclyl, or heteroaryl; —COOR$^A$, where R$^A$ is hydrogen, alkyl, aryl, arylalkyl, cycloalkyl, heterocyclyl, or heteroaryl; and —CON(R$^B$)$_2$, where each R$^B$ is independently hydrogen, alkyl, aryl, arylalkyl, cycloalkyl, heterocyclyl, or heteroaryl.

The term "aryl alkenyl," as used herein, represents an alkenyl group substituted with one or two aryl group(s). In optionally substituted aryl alkenyl, each of the aryl and alkenyl portions may be independently, optionally substituted as described herein for aryl and alkyl, respectively.

The term "aryl alkyl," as used herein, represents an alkyl group substituted with one or two aryl group(s). In optionally substituted aryl alkyl, each of the aryl and alkyl portions may be independently, optionally substituted as described herein for aryl and alkyl, respectively.

The term "arylalkoxy," as used herein, represents a substituent of formula —OR, where R is arylalkyl. In optionally substituted aryl alkoxy, the arylalkyl is optionally substituted as described herein for aryl alkyl.

The term "aryloxy," as used herein, represents a chemical substituent of formula —OR, where R is aryl. In optionally substituted aryloxy, the aryl group is optionally substituted as described herein for aryl.

The term "bacterial infection," as used herein, refers to the invasion of an individual's cells, tissues, and/or organs by bacteria (e.g., *Escherichia coli, Acinetobacter baumannii, Pseudomonas aeruginosa,* or *Klebsiella pneumoniae*), thus, causing an infection. In some embodiments, the bacteria may grow, multiply, and/or produce toxins in the individual's cells, tissues, and/or organs. In some embodiments, a bacterial infection can be any situation in which the presence of a bacteria population(s) is latent within or damaging to a host body. Thus, an individual is "suffering"

from a bacterial infection when a latent bacterial population is detectable in or on the individual's body, an excessive amount of a bacterial population is present in or on the individual's body, or when the presence of a bacterial population(s) is damaging to the cells, tissues, and/or organs of the individual.

The term "carbonyl," as used herein, represents a —C(O)— group.

The expression "$C_{x-y}$," as used herein, indicates that the group, the name of which immediately follows the expression, when unsubstituted, contains a total of from x to y carbon atoms. If the group is a composite group (e.g., aryl alkyl), $C_{x-y}$ indicates that the portion, the name of which immediately follows the expression, when unsubstituted, contains a total of from x to y carbon atoms. For example, ($C_{6-10}$-aryl)-$C_{1-6}$-alkyl is a group, in which the aryl portion, when unsubstituted, contains a total of from 6 to 10 carbon atoms, and the alkyl portion, when unsubstituted, contains a total of from 1 to 6 carbon atoms.

The term "cycloalkyl," as used herein, represents a monovalent, cyclic, non-aromatic, hydrocarbon group having from three to ten carbons, unless otherwise specified. Cycloalkyl groups may be monocyclic, bicyclic, spirocyclic, or caged (e.g., adamantyl). Fused bicyclic cycloalkyl groups may be of bicyclo[p.q.0]alkyl type, in which each of p and q is, independently, 1, 2, 3, 4, 5, 6, or 7, provided that the sum of p and q is 2, 3, 4, 5, 6, 7, or 8. Alternatively, fused bicyclic cycloalkyl groups may include bridged cycloalkyl structures, e.g., bicyclo[p.q.r]alkyl, in which r is 1, 2, or 3, each of p and q is, independently, 1, 2, 3, 4, 5, or 6, provided that the sum of p, q, and r is 3, 4, 5, 6, 7, or 8. The spirocyclic cycloalkyl group may be spiro[p.q]alkyl, in which each of p and q is, independently, 2, 3, 4, 5, 6, or 7, provided that the sum of p and q is 4, 5, 6, 7, 8, or 9. Cycloalkyl may be saturated or unsaturated. An unsaturated cycloalkyl contains one or two carbon-carbon double bonds. Non-limiting examples of cycloalkyl include cyclopropyl, cyclobutyl, cyclopentyl, cyclohexyl, cyclohex-1-enyl, cyclohex-2-enyl, cyclohex-3-enyl, cycloheptyl, 1-bicyclo[2.2.1]heptyl, 2-bicyclo[2.2.1]heptyl, 5-bicyclo[2.2.1]heptyl, 7-bicyclo[2.2.1]heptyl, and decalinyl. The cycloalkyl group may be optionally substituted with one, two, three, four, or five substituents independently selected from the group consisting of: alkyl; alkoxy; acyloxy; aryloxy; arylalkoxy; cycloalkyl; cycloalkoxy; halogen; heterocyclyl; heteroaryl; heterocyclyloxy; heteroaryloxy; hydroxyl; nitro; thiol; =O; =S; —$NR_2$, where each R is independently hydrogen, alkyl, acyl, aryl, arylalkyl, cycloalkyl, heterocyclyl, or heteroaryl; —$COOR^A$, where $R^A$ is hydrogen, alkyl, aryl, arylalkyl, cycloalkyl, heterocyclyl, or heteroaryl; and —$CON(R^B)_2$, where each $R^B$ is independently hydrogen, alkyl, aryl, arylalkyl, cycloalkyl, heterocyclyl, or heteroaryl.

The term "cycloalkoxy," as used herein, represents a group —OR, where R is cycloalkyl.

The term "effective amount," as used herein, is meant the amount of drug (e.g., an aminocoumarin compound or a pharmaceutically acceptable salt thereof and/or a polymyxin or a pharmaceutically acceptable salt thereof) required to treat or prevent a bacterial infection or a disease associated with a bacterial infection. The effective amount of drug used to practice the methods described herein for therapeutic or prophylactic treatment of conditions caused by or contributed to by a bacterial infection varies depending upon the manner of administration, the age, body weight, and general health of the individual. Ultimately, the attending physician will decide the appropriate amount and dosage regimen. Such amount is referred to as an "effective amount."

The term "haloalkyl," as used herein, represents an alkyl substituted with one or more halogens (e.g., fluorine) as described herein. Non-limiting examples of haloalkyl include trifluoromethyl, 2,2,2-trifluoroethyl, and pentafluoroethyl.

The term "haloalkoxy," as used herein, represents a substituted —OR, where R is haloalkyl.

The term "halogen," as used herein, represents a halogen selected from bromine, chlorine, iodine, and fluorine.

The term "heteroaryl," as used herein, represents a monocyclic, bicyclic, tricyclic, or tetracyclic ring system having fused or bridging 5-, 6-, 7-, or 8-membered rings, the ring system containing one, two, three, or four heteroatoms independently selected from the group consisting of nitrogen, oxygen, and sulfur; where at least one of the rings is an aromatic ring. Non-limiting examples of heteroaryl groups include benzimidazolyl, benzofuryl, benzothiazolyl, benzothienyl, benzoxazolyl, furyl, imidazolyl, indolyl, isoindazolyl, isoquinolinyl, isothiazolyl, isothiazolyl, isoxazolyl, oxadiazolyl, oxazolyl, purinyl, pyrrolyl, pyridinyl, pyrazinyl, pyrimidinyl, qunazolinyl, quinolinyl, thiadiazolyl (e.g., 1,3,4-thiadiazole), thiazolyl, thienyl, triazolyl, tetrazolyl, dihydroindolyl, tetrahydroquinolyl, tetrahydroisoquinolyl, etc. The term bicyclic, tricyclic, and tetracyclic heteroaryls include at least one ring having at least one heteroatom as described above and at least one aromatic ring. For example, a ring having at least one heteroatom may be fused to one, two, or three carbocyclic rings, e.g., an aryl ring, a cyclohexane ring, a cyclohexene ring, a cyclopentane ring, a cyclopentene ring, or another monocyclic heterocyclic ring. Examples of fused heteroaryls include 1,2,3,5,8,8a-hexahydroindolizine; 2,3-dihydrobenzofuran; 2,3-dihydroindole; and 2,3-dihydrobenzothiophene. Heteroaryl may be optionally substituted with one, two, three, four, or five substituents independently selected from the group consisting of: alkyl; alkoxy; acyloxy; aryloxy; arylalkoxy; cycloalkyl; cycloalkoxy; halogen; haloalkyl; haloalkoxy; heterocyclyl; heteroaryl; heterocyclyloxy; heteroaryloxy; hydroxyl; nitro; thiol; =O; —$NR_2$, where each R is independently hydrogen, alkyl, acyl, aryl, arylalkyl, cycloalkyl, heterocyclyl, or heteroaryl; —$COOR^A$, where $R^A$ is hydrogen, alkyl, aryl, arylalkyl, cycloalkyl, heterocyclyl, or heteroaryl; and —$CON(R^B)_2$, where each $R^B$ is independently hydrogen, alkyl, aryl, arylalkyl, cycloalkyl, heterocyclyl, or heteroaryl.

The term "heteroaryloxy," as used herein, represents a group —OR, where R is heteroaryl.

The term "heterocyclyl," as used herein, represents a monocyclic, bicyclic, tricyclic, or tetracyclic non-aromatic ring system having fused or bridging 4-, 5-, 6-, 7-, or 8-membered rings, unless otherwise specified, the ring system containing one, two, three, or four heteroatoms independently selected from the group consisting of nitrogen, oxygen, and sulfur. Non-aromatic 5-membered heterocyclyl has zero or one double bonds, non-aromatic 6- and 7-membered heterocyclyl groups have zero to two double bonds, and non-aromatic 8-membered heterocyclyl groups have zero to two double bonds and/or zero or one carbon-carbon triple bond. Heterocyclyl groups have a carbon count of 1 to 16 carbon atoms unless otherwise specified. Certain heterocyclyl groups may have a carbon count up to 9 carbon atoms. Non-aromatic heterocyclyl groups include pyrrolinyl, pyrrolidinyl, pyrazolinyl, pyrazolidinyl, imidazolinyl, imidazolidinyl, piperidinyl, homopiperidinyl, piperazinyl, pyridazinyl, oxazolidinyl, isoxazolidinyl, morpholinyl, thiomorpholinyl, thiazolidinyl, isothiazolidinyl, thiazolidinyl, tetrahydrofuranyl, dihydrofuranyl, tetrahydrothienyl, dihydrothienyl, pyranyl, dihydropyranyl, dithiazolyl, etc.

The term "heterocyclyl" also represents a heterocyclic compound having a bridged multicyclic structure in which one or more carbons and/or heteroatoms bridges two non-adjacent members of a monocyclic ring, e.g., quinuclidine, tropanes, or diaza-bicyclo[2.2.2]octane. The term "heterocyclyl" includes bicyclic, tricyclic, and tetracyclic groups in which any of the above heterocyclic rings is fused to one, two, or three carbocyclic rings, e.g., a cyclohexane ring, a cyclohexene ring, a cyclopentane ring, a cyclopentene ring, or another heterocyclic ring. Examples of fused heterocyclyls include 1,2,3,5,8,8a-hexahydroindolizine; 2,3-dihydrobenzofuran; 2,3-dihydroindole; and 2,3-dihydrobenzothiophene. The heterocyclyl group may be unsubstituted or substituted with one, two, three, four or five substituents independently selected from the group consisting of: alkyl; alkoxy; acyloxy; aryloxy; arylalkoxy; cycloalkyl; cycloalkoxy; halogen; haloalkyl; haloalkoxy; heterocyclyl; heteroaryl; heterocyclyloxy; heteroaryloxy; hydroxyl; nitro; thiol; $=$O; $=$S; —$NR_2$, where each R is independently hydrogen, alkyl, acyl, aryl, arylalkyl, cycloalkyl, heterocyclyl, or heteroaryl; —$COOR^A$, where $R^A$ is hydrogen, alkyl, aryl, arylalkyl, cycloalkyl, heterocyclyl, or heteroaryl; and —$CON(R^B)_2$, where each $R^B$ is independently hydrogen, alkyl, aryl, arylalkyl, cycloalkyl, heterocyclyl, or heteroaryl.

The term "heterocyclyloxy," as used herein, represents a group —OR, where R is heterocyclyl.

The terms "hydroxyl" and "hydroxy," as used interchangeably herein, represent —OH.

The term "hydrocarbyl", as used herein, refers to a group that is bonded through a carbon atom that does not have a $=$O or $=$S substituent, and typically has at least one carbon-hydrogen bond and a primarily carbon backbone, but may optionally include heteroatoms.

Thus, groups like methyl, ethoxyethyl, 2-pyridyl, and trifluoromethyl are considered to be hydrocarbyl for the purposes of this application, but substituents such as acetyl (which has a $=$O substituent on the linking carbon) and ethoxy (which is linked through oxygen, not carbon) are not. Hydrocarbyl groups include, but are not limited to aryl, heteroaryl, carbocycle, heterocyclyl, alkyl, alkenyl, alkynyl, and combinations thereof.

The term "oxo," as used herein, represents a divalent oxygen atom (e.g., the structure of oxo may be shown as $=$O).

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "pharmaceutically acceptable," as used herein, refers to those compounds, materials, compositions, and/or dosage forms, which are suitable for contact with the tissues of an individual (e.g., a human), without excessive toxicity, irritation, allergic response and other problem complications commensurate with a reasonable benefit/risk ratio.

The term "polymyxin compound," as used herein, refers to antibiotic compounds and pharmaceutically acceptable salts thereof including polymyxin A, polymyxin B, polymyxin C, polymyxin D, and polymyxin E (also known as colistin), and any compounds, prodrugs, or analogs with structural similarity to these compounds. Polymyxin compounds include those described in U.S. Pat. Nos. 9,096,649, 9,090,669, 9,067,974, 8,680,234, 8,642,535, 8,329,645, 8,193,148, 7,807,637, 7,507,718, 6,579,696, 6,380,356, and 5,177,059, and US Publication Nos. 20170137469, 20170073373, 20160287661, 20160206684, 20140162937, 20140142030, 20140134669, 20120316105, 20120283176, 20100292136, 20100279347, 20090215677, 20090203881, and 20080281684. Polymyxin compounds also include molecules having similar structures and antibacterial properties and that function with a similar mechanism as any of the compounds listed above. Polymyxin compounds do not include polymyxin B nonapeptide.

In certain embodiments, compounds of the invention may be racemic. In certain embodiments, compounds of the invention may be enriched in one enantiomer. For example, a compound of the invention may have greater than about 30% ee, about 40% ee, about 50% ee, about 60% ee, about 70% ee, about 80% ee, about 90% ee, or even about 95% or greater ee. In certain embodiments, compounds of the invention may have more than one stereocenter. In certain such embodiments, compounds of the invention may be enriched in one or more diastereomer. For example, a compound of the invention may have greater than about 30% de, about 40% de, about 50% de, about 60% de, about 70% de, about 80% de, about 90% de, or even about 95% or greater de.

In certain embodiments, the therapeutic preparation may be enriched to provide predominantly one enantiomer of a compound (e.g., of Formula (I)). An enantiomerically enriched mixture may comprise, for example, at least about 60 mol percent of one enantiomer, or more preferably at least about 75, about 90, about 95, or even about 99 mol percent. In certain embodiments, the compound enriched in one enantiomer is substantially free of the other enantiomer, wherein substantially free means that the substance in question makes up less than about 10%, or less than about 5%, or less than about 4%, or less than about 3%, or less than about 2%, or less than about 1% as compared to the amount of the other enantiomer, e.g., in the composition or compound mixture. For example, if a composition or compound mixture contains about 98 grams of a first enantiomer and about 2 grams of a second enantiomer, it would be said to contain about 98 mol percent of the first enantiomer and only about 2% of the second enantiomer.

In certain embodiments, the therapeutic preparation may be enriched to provide predominantly one diastereomer of a compound (e.g., of Formula (I)). A diastereomerically enriched mixture may comprise, for example, at least about 60 mol percent of one diastereomer, or more preferably at least about 75, about 90, about 95, or even about 99 mol percent.

The compounds of the present invention furthermore optionally contain one or more asymmetric centers, depending upon the location and nature of the various substituents desired. It is possible that one or more asymmetric carbon atoms are present in the (R) or (S) configuration, which can result in racemic mixtures in the case of a single asymmetric center, and in diastereomeric mixtures in the case of multiple asymmetric centers.

Preferred compounds are those which produce the more desirable biological activity. Separated, pure or partially purified isomers and stereoisomers or racemic or diastereomeric mixtures of the compounds of the present invention are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., HPLC columns using a chiral phase), with or without conventional derivatisation, optimally chosen to maximise the separation of the enantiomers. Suitable HPLC columns using a chiral phase are commercially available, such as those manufactured by Daicel, e.g., Chiracel OD and Chiracel OJ, for example, among many others, which are all routinely selectable. Enzymatic separations, with or without derivatisation, are also useful. The optically active compounds of the present invention can likewise be obtained by chiral syntheses utilizing optically active starting materials, enantioselective catalytic reactions, and other suitable methods. In order to distinguish different types of isomers from each other reference is made to IUPAC Rules Section E (Pure Appl Chem 45, 11-30, 1976).

The present invention includes all possible stereoisomers of the compounds of the present invention as single stereoisomers, or as any mixture of said stereoisomers, in any ratio. Isolation of a single stereoisomer, e.g., a single enantiomer or a single diastereomer, of a compound of the present invention may be achieved by any suitable method, such as chromatography, especially chiral chromatography, for example.

The term "protecting against a bacterial infection" or "preventing a bacterial infection" as used herein, refers to preventing an individual from developing a bacterial infection or decreasing the risk that an individual may develop a bacterial infection (e.g., a bacterial infection caused by *Escherichia coli*, *Acinetobacter baumannii*, *Pseudomonas aeruginosa*, or *Klebsiella pneumoniae*). Prophylactic drugs used in methods of protecting against a bacterial infection in an individual are often administered to the individual prior to any detection of the bacterial infection. In some embodiments of methods of protecting against a bacterial infection, an individual (e.g., an individual at risk of developing a bacterial infection) may be administered a compound of the invention to prevent the bacterial infection development or decrease the risk of the bacterial infection development.

The term "protecting group," as used herein, represents a group intended to protect a hydroxy, an amino, or a carbonyl from participating in one or more undesirable reactions during chemical synthesis. The term "O-protecting group," as used herein, represents a group intended to protect a hydroxy or carbonyl group from participating in one or more undesirable reactions during chemical synthesis. The term "N-protecting group," as used herein, represents a group intended to protect a nitrogen containing (e.g., an amino or hydrazine) group from participating in one or more undesirable reactions during chemical synthesis. Commonly used O- and N-protecting groups are disclosed in Greene, "Protective Groups in Organic Synthesis," $3^{rd}$ Edition (John Wiley & Sons, New York, 1999), which is incorporated herein by reference. Exemplary O- and N-protecting groups include alkanoyl, aryloyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, t-butyldimethylsilyl, tri-iso-propylsilyloxymethyl, 4,4'-dimethoxytrityl, isobutyryl, phenoxyacetyl, 4-isopropylpehenoxyacetyl, dimethylformamidino, and 4-nitrobenzoyl.

Exemplary O-protecting groups for protecting carbonyl containing groups include, but are not limited to: acetals, acylals, 1,3-dithianes, 1,3-dioxanes, 1,3-dioxolanes, and 1,3-dithiolanes.

Other O-protecting groups include, but are not limited to: substituted alkyl, aryl, and aryl-alkyl ethers (e.g., trityl; methylthiomethyl; methoxymethyl; benzyloxymethyl; siloxymethyl; 2,2,2,-trichloroethoxymethyl; tetrahydropyranyl; tetrahydrofuranyl; ethoxyethyl; 1-[2-(trimethylsilyl)ethoxy]ethyl; 2-trimethylsilylethyl; t-butyl ether; p-chlorophenyl, p-methoxyphenyl, p-nitrophenyl, benzyl, p-methoxybenzyl, and nitrobenzyl); silyl ethers (e.g., trimethylsilyl; triethylsilyl; triisopropylsilyl; dimethylisopropylsilyl; t-butyldimethylsilyl; t-butyldiphenylsilyl; tribenzylsilyl; triphenylsilyl; and diphenymethylsilyl); carbonates (e.g., methyl, methoxymethyl, 9-fluorenylmethyl; ethyl; 2,2, 2-trichloroethyl; 2-(trimethylsilyl)ethyl; vinyl, allyl, nitrophenyl; benzyl; methoxybenzyl; 3,4-dimethoxybenzyl; and nitrobenzyl).

Other N-protecting groups include, but are not limited to, chiral auxiliaries such as protected or unprotected D, L or D, L-amino acids such as alanine, leucine, phenylalanine, and the like; sulfonyl-containing groups such as benzenesulfonyl, p-toluenesulfonyl, and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyl oxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, phenylthiocarbonyl, and the like, arylalkyl groups such as benzyl, triphenylmethyl, benzyloxymethyl, and the like and silyl groups such as trimethylsilyl, and the like. Useful N-protecting groups are formyl, acetyl, benzoyl, pivaloyl, t-butylacetyl, alanyl, phenylsulfonyl, benzyl, t-butyloxycarbonyl (Boc), and benzyloxycarbonyl (Cbz).

The term "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys. Preferred subjects are humans.

In some embodiments, the term "subject," as used herein, represents a human or non-human animal (e.g., a mammal) that is suffering from a bacterial infection (e.g., a gram-negative bacterial infection) or is at risk of contracting a bacterial infection (e.g., a gram-negative bacterial infection), as determined by a qualified professional (e.g., a doctor or a nurse practitioner) with or without known in the art laboratory test(s) of sample(s) from the patient.

The term "treating" or "to treat," as used herein, refers to a therapeutic treatment of a bacterial infection in an individual. In some embodiments, a therapeutic treatment may slow the progression of the bacterial infection, improve the individual's outcome, and/or eliminate the infection. In some embodiments, a therapeutic treatment of a bacterial infection in an individual may alleviate or ameliorate of one or more symptoms or conditions associated with the bacterial infection, diminish the extent of the bacterial infection, stabilize (i.e., not worsening) the state of the bacterial infection, prevent the spread of the bacterial infection, and/or delay or slow the progress of the bacterial infection, as compared to the state and/or the condition of the bacterial infection in the absence of therapeutic treatment.

DETAILED DESCRIPTION

In general, the invention provides aminocoumarin compounds and methods of their use in the treatment of bacterial infections (e.g., a Gram-negative bacterial infection).

Gram-negative bacteria are challenging to kill with antibiotics because of their outer membrane containing lipopolysaccharide (LPS). Polymyxins are the drugs of last resort for treating Gram-negative bacterial infections. These drugs bind LPS and disrupt the outer membrane; however, toxicity of polymyxins limits their usefulness. Compounds of the invention may be used alone or in combination with polymyxins for treating bacterial infections (e.g., Gram-negative bacterial infections). Without wishing to be bound by theory, a compound of the invention may have a dual activity: a compound of the invention may exhibit an antibiotic activity by (i) binding a bacterial gyrase to inhibit DNA supercoiling and (ii) by stimulating LPS transport through binding LptB in the LPS export system. Compounds of the invention having the dual activity may be used for treating bacterial infections (e.g., Gram-negative bacterial infections) either alone or in combination with a polymyxin compound. Alternatively, compounds of the invention may have LPS transport agonist activity and reduced or no gyrase inhibition activity; these compounds may lack lethality but may be useful for enhancing the efficacy of polymyxins. A combination therapy including a compound of the invention and a polymyxin compound may be advantageous to a polymyxin compound monotherapy, because the use of a compound of the invention may allow for reducing dosages of a polymyxin compound, thereby reducing polymyxin toxicity-related effects.

Aminocoumarin Compounds Disclosed herein are compounds of formula (X):

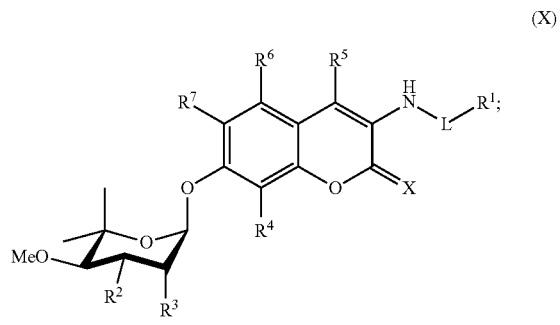

(X)

or a pharmaceutically acceptable salt thereof,
wherein
X is O or S;
L is —CO— or —SO$_2$—;
$R^1$ is phenyl or heteroaryl substituted by 1 or more substituents, wherein at least one substituent is —OR$^{50}$;
$R^{50}$ is optionally substituted aryl or optionally substituted heteroaryl;
each of $R^2$ and $R^3$ is independently hydroxyl, —O—CO—NH—R$^{10}$, or —O—CO—R$^{11}$;
each of $R^4$, $R^6$, and $R^7$ is independently hydrogen, halogen, optionally substituted C$_{1-6}$ alkyl, optionally substituted C$_{1-6}$ alkoxy, or optionally substituted C$_{6-10}$ aryl;
$R^5$ is halogen, hydroxyl, or optionally substituted C$_{1-6}$ alkoxy;
$R^{10}$, when present, is hydrogen, optionally substituted C$_{1-6}$ alkyl, optionally substituted C$_{3-10}$ cycloalkyl, optionally substituted heteroaryl, or optionally substituted C$_{6-10}$ aryl; and
$R^{11}$, when present, is optionally substituted heteroaryl or optionally substituted C$_{6-10}$ aryl; and
wherein when $R^1$ is

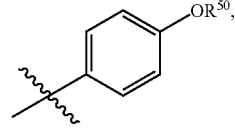

then $R^{50}$ is not phenyl substituted by alkyl.

In some embodiments, $R^1$ is heteroaryl substituted by 1 or more substituents, wherein at least one substituent is —OR$^{50}$. In certain embodiments, $R^1$ is pyridyl substituted by 1 or more substituents, wherein at least one substituent is —OR$^{50}$. In other embodiments, $R^1$ is phenyl substituted by 1 or more substituents, wherein at least one substituent is —OR$^0$.

In some embodiments, $R^1$ is

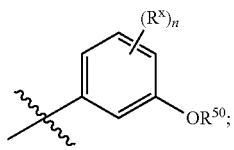

wherein each $R^x$ is independently a substituent selected from the group consisting of halo, nitro, cyano, hydroxyl, optionally substituted alkyl, hydroxyalkyl, haloalkyl, aminoalkyl, optionally substituted alkoxy, haloalkoxy, optionally substituted alkenyl, optionally substituted alkynyl, optionally substituted aryl, optionally substituted heteroaryl, optionally substituted cycloalkyl, and optionally substituted heterocycloalkyl; and n is an integer from 0-4. In certain embodiments, $R^1$ is

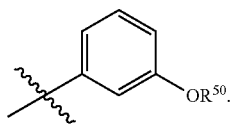

In some embodiments, $R^{50}$ is aryl substituted by one or more substituents each independently selected from the group consisting of halo, nitro, cyano, hydroxyl, optionally substituted alkyl, hydroxyalkyl, haloalkyl, aminoalkyl, optionally substituted alkoxy, haloalkoxy, optionally substituted alkenyl, optionally substituted alkynyl, optionally substituted aryl, optionally substituted heteroaryl, optionally substituted cycloalkyl, and optionally substituted heterocycloalkyl. In certain embodiments, $R^{50}$ is optionally substituted heteroaryl.

In some embodiments, L is —CO—. In other embodiments, X is O.

In some embodiments, the compound of the invention is of formula (XA):

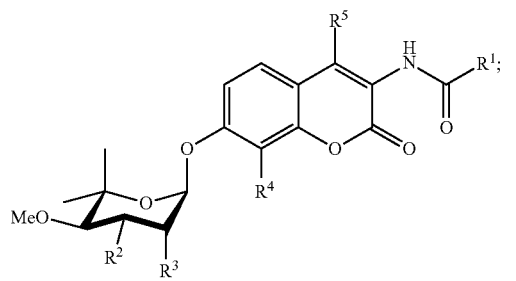

or a pharmaceutically acceptable salt thereof.

In some embodiments, $R^3$ is hydroxyl. In certain embodiments, $R^2$ is —O—CO—NH—$R^{10}$. In some embodiments, $R^{10}$ is H. In certain embodiments, $R^4$ is optionally substituted $C_{1-6}$ alkyl. In preferred embodiments, $R^4$ is methyl. In other embodiments, $R^5$ is hydroxyl.

In some embodiments, $R^1$ is selected from the following table:

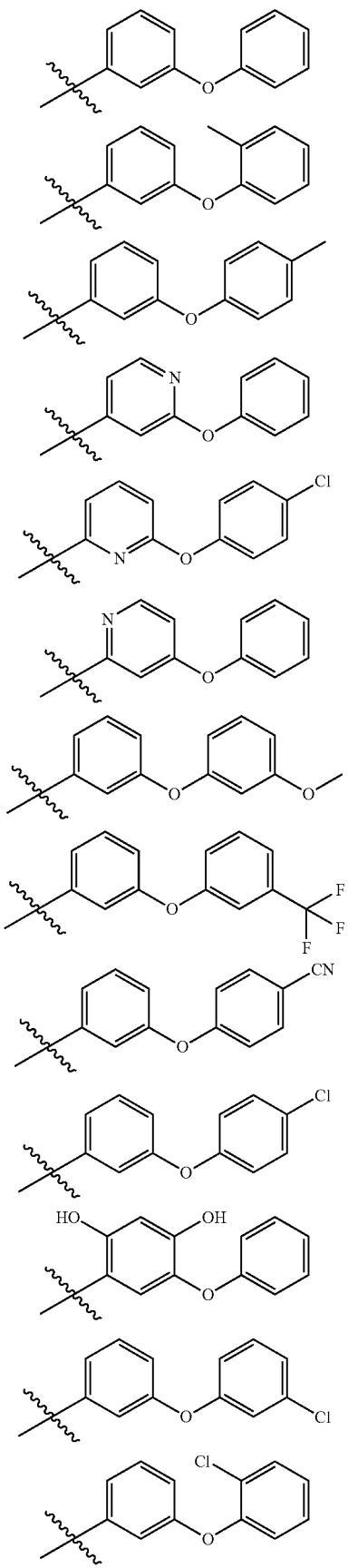

-continued
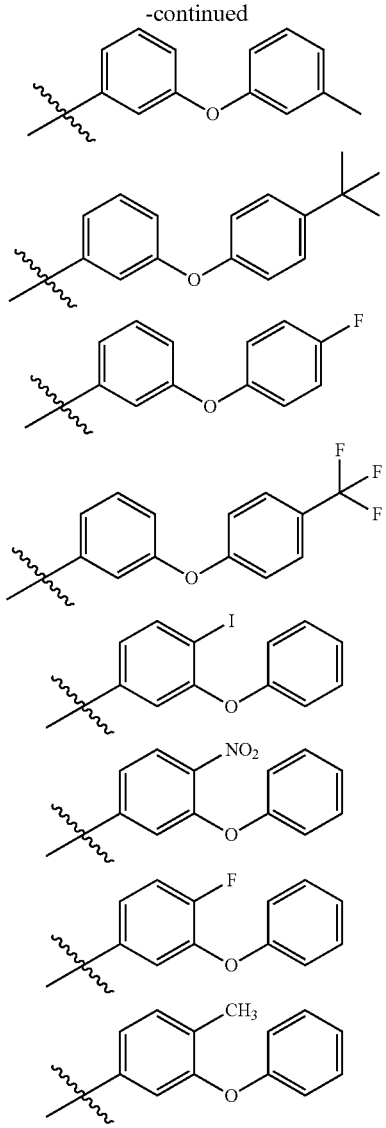
-continued
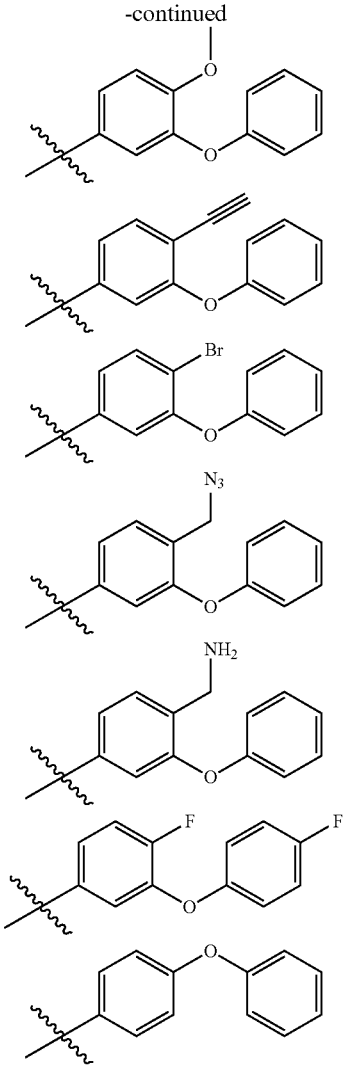
Disclosed herein are compounds having the following structures:
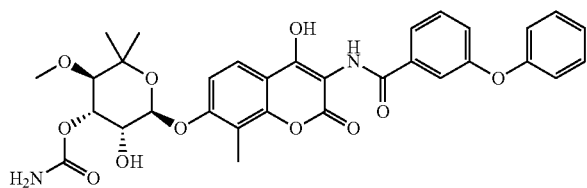
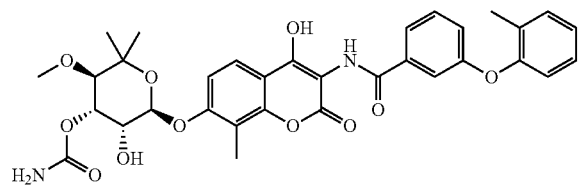
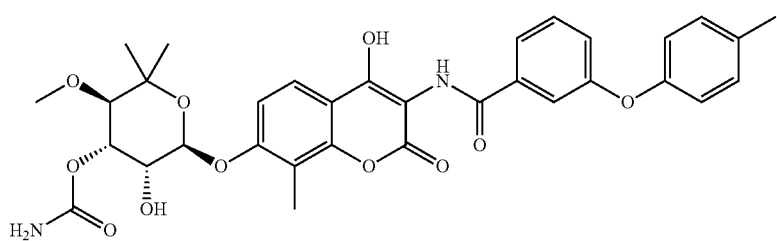

-continued
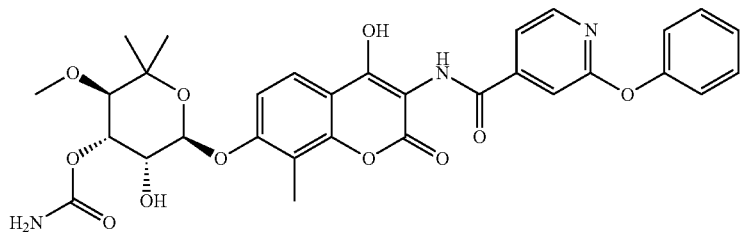
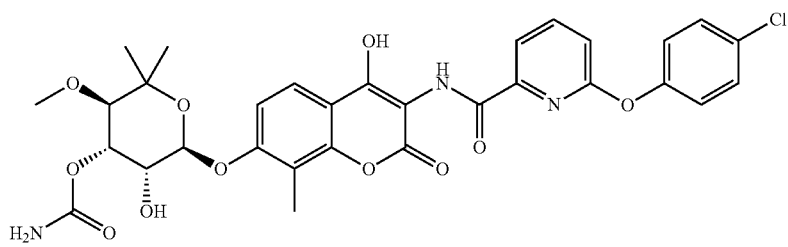
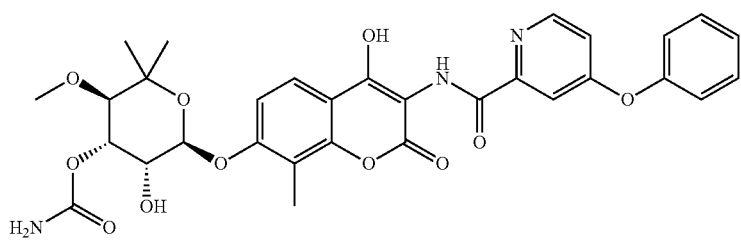
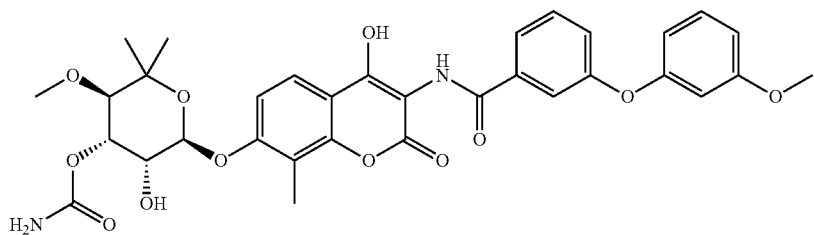
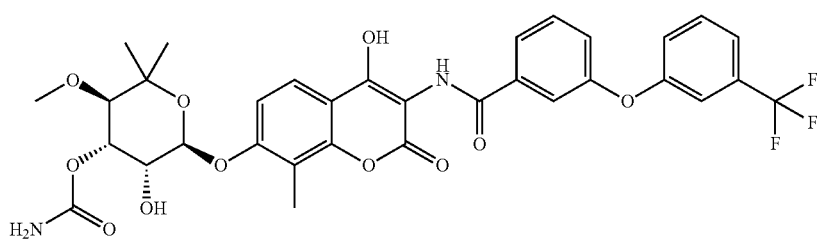
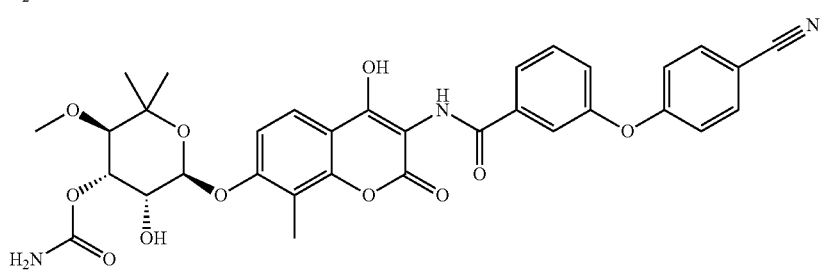
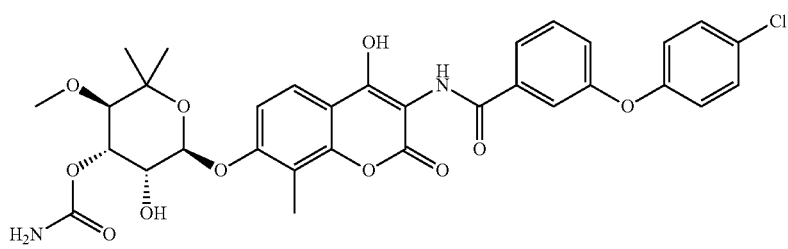

-continued
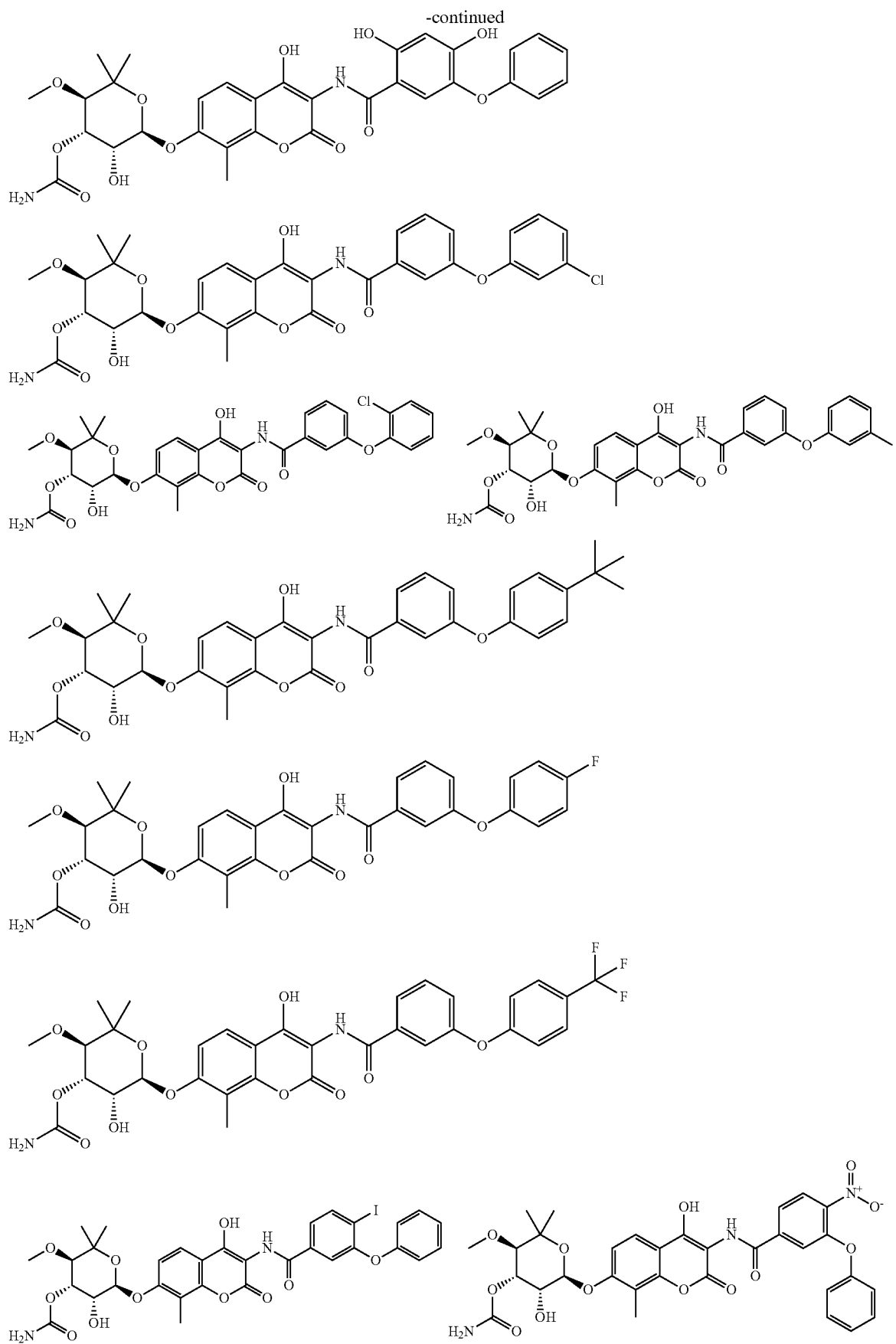

-continued
| 21 | 22 |
|---|---|
| 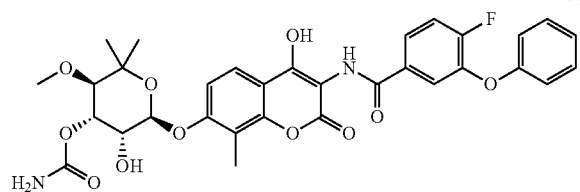 | 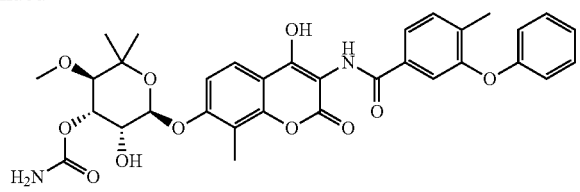 |
| 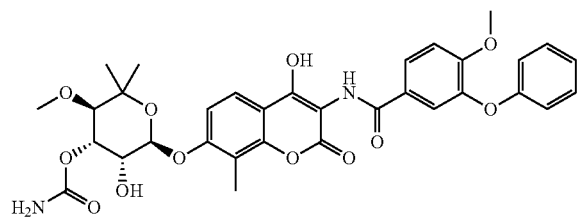 | 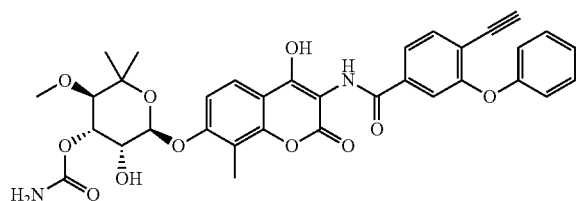 |
| 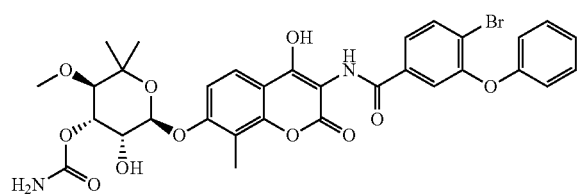 | 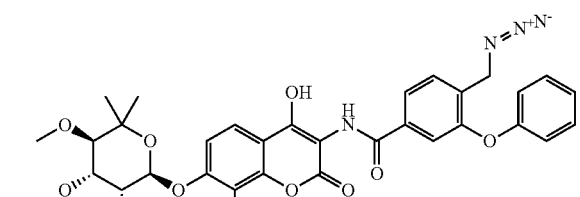 |
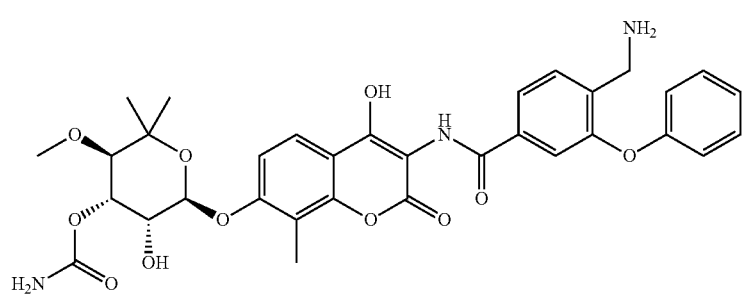
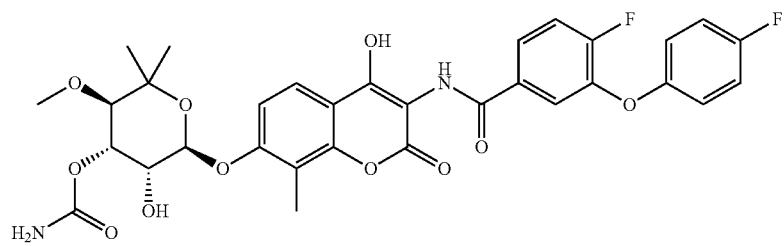
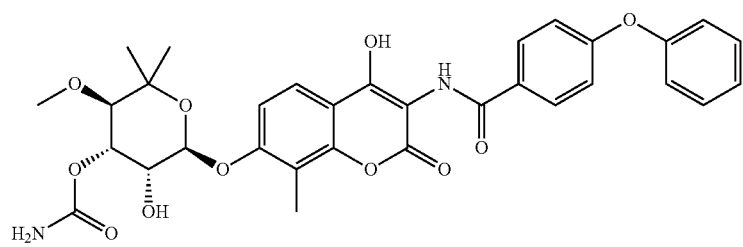

Disclosed herein are compounds of formula (XX):

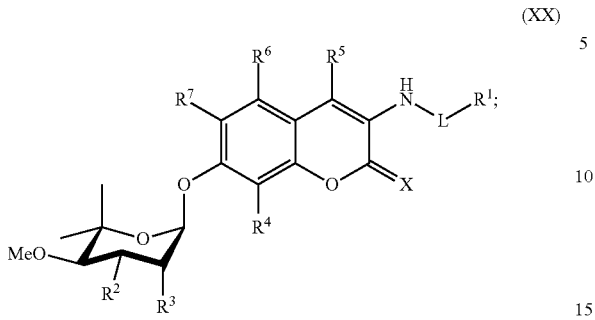

or a pharmaceutically acceptable salt thereof,
wherein
X is O or S;
L is —CO— or —SO$_2$—;
R$^1$ is unsubstituted phenyl, substituted phenyl, optionally substituted C$_{6-10}$ aryl C$_{1-4}$ alkyl, optionally substituted C$_{6-10}$ aryl C$_{2-4}$ alkenyl, o-phenylphenyl, optionally substituted C$_{3-10}$ cycloalkyl, optionally substituted C$_{1-9}$ heteroaryl comprising at least one nitrogen heteroatom within the heteroaryl ring system, benzofuryl, optionally substituted furyl, or —NHR$^8$,
wherein the substituted phenyl is substituted:
(i) at one and only one of its meta position relative to L, with optionally substituted C$_{6-10}$ aryl, optionally substituted C$_{1-6}$ alkyl, optionally substituted C$_{3-6}$ alkenyl comprising an allylic carbon-carbon double bond, optionally substituted C$_{6-10}$ aryl C$_{1-4}$ alkyl, optionally substituted C$_{1-6}$ alkoxy, optionally substituted C$_{6-10}$ aryloxy, optionally substituted (C$_{6-10}$ aryl)-C$_{1-6}$ alkoxy, optionally substituted C$_{3-10}$ cycloalkyl, optionally substituted C$_{1-9}$ heteroaryl comprising at least one nitrogen heteroatom within the heteroaryl ring system, optionally substituted C$_{3-9}$ heterocyclyl, or —SF$_5$; or
(ii) at its para position relative to L with hydroxyl, optionally substituted C$_{6-10}$ aryl C$_{1-4}$ alkyl, optionally substituted C$_{6-10}$ aryl C$_{2-4}$ alkynyl, optionally substituted C$_{6-10}$ aryl, optionally substituted C$_{3-10}$ cycloalkyl, optionally substituted C$_{1-6}$ alkoxy, optionally substituted C$_{6-10}$ aryloxy, or optionally substituted (C$_{6-10}$ aryl)-C$_{1-6}$ alkoxy;
and, valency permitting, the substituted phenyl is further optionally substituted with 1, 2, 3, or 4 substituents independently selected from the group consisting of halogen, hydroxyl, —N(R$^9$)$_2$, optionally substituted C$_{1-6}$ alkoxy, optionally substituted C$_{6-10}$ aryloxy, or optionally substituted C$_{6-10}$ aryl;
each of R$^2$ and R$^3$ is independently hydroxyl, —O—CO—NH—R$^{10}$, or —O—CO—R$^{11}$;
each of R$^4$, R$^6$, and R$^7$ is independently hydrogen, halogen, optionally substituted C$_{1-6}$ alkyl, optionally substituted C$_{1-6}$ alkoxy, or optionally substituted C$_{6-10}$ aryl;
R$^5$ is halogen, hydroxyl, or optionally substituted C$_{1-6}$ alkoxy;
R$^8$ is optionally substituted C$_{6-10}$ aryl;
each R$^9$ is independently H or optionally substituted C$_{1-6}$ alkyl;
R$^{10}$, when present, is hydrogen, optionally substituted C$_{1-6}$ alkyl, optionally substituted C$_{3-10}$ cycloalkyl, or optionally substituted C$_{6-10}$ aryl; and R$^{11}$, when present, is optionally substituted C$_{1-9}$ heteroaryl or optionally substituted C$_{6-10}$ aryl; and
wherein, when R$^5$ is hydroxyl, then R$^1$ is substituted phenyl or benzofuryl,
wherein the substituted phenyl is substituted:
(i) at one and only one of its meta position relative to L, with:
C$_{1-6}$ alkyl substituted with aryloxy, arylalkoxy, cycloalkyl, cycloalkoxy, heterocyclyl, heteroaryl, heterocyclyloxy, heteroaryloxy, nitro, thiol, =S, or —NR$^y$$_2$, where each R$^y$ is independently aryl, arylalkyl, cycloalkyl, heterocyclyl, or heteroaryl;
C$_{3-6}$ alkenyl comprising an allylic carbon-carbon double bond and substituted with aryloxy, arylalkoxy, cycloalkyl, cycloalkoxy, heterocyclyl, heteroaryl, heterocyclyloxy, heteroaryloxy, nitro, thiol, =S, or —NR$^y$2, where each R$^y$ is independently aryl, arylalkyl, cycloalkyl, heterocyclyl, or heteroaryl;
optionally substituted C$_{6-10}$ aryloxy;
optionally substituted (C$_{6-10}$ aryl)-C$_{1-6}$ alkoxy;
optionally substituted C$_{3-10}$ cycloalkyl;
optionally substituted C$_{1-9}$ heteroaryl comprising at least one nitrogen heteroatom within the heteroaryl ring system;
optionally substituted C$_{3-9}$ heterocyclyl; or —SF$_5$; or
(ii) at its para position relative to L, with optionally substituted C$_{6-10}$ aryl C$_{1-4}$ alkyl, optionally substituted C$_{6-10}$ aryl C$_{2-4}$ alkynyl, optionally substituted C$_{3-10}$ cycloalkyl, or optionally substituted (C$_{6-10}$ aryl)-C$_{1-6}$ alkoxy;
and, valency permitting, the substituted phenyl is further optionally substituted with 1, 2, 3, or 4 substituents independently selected from the group consisting of halogen, hydroxyl, —N(R$^9$)$_2$, optionally substituted C$_{1-6}$ alkoxy, optionally substituted C$_{6-10}$ aryloxy, optionally substituted (C$_{6-10}$ aryl)-C$_{1-6}$ alkoxy, or optionally substituted C$_{6-10}$ aryl.
In some embodiments, L is —CO—. In other embodiments, X is O.

Disclosed herein are compounds of formula (XXA)

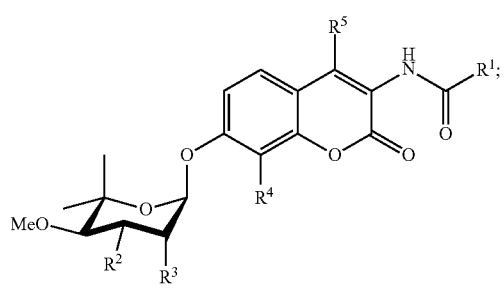

or a pharmaceutically acceptable salt thereof.
In some embodiments, R$^3$ is hydroxyl. In some embodiments, R$^2$ is —O—CO—NH—R$^0$. In certain embodiments, R$^{10}$ is H. In other embodiments, R$^2$ is —O—CO—R$^{11}$. In some embodiments, R$^{11}$ is optionally substituted C$_{1-9}$ heteroaryl.

Disclosed herein are compounds of formula (XX-II):

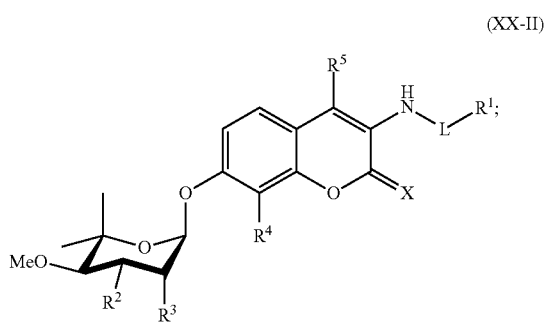

(XX-II)

or a pharmaceutically acceptable salt thereof,
wherein
X is O or S;
L is —CO— or —SO$_2$—;
R$^1$ is substituted phenyl or benzofuryl,
  wherein the substituted phenyl is substituted:
  (i) at one and only one of its meta position relative to L, with:
    C$_{1-6}$ alkyl substituted with aryloxy, arylalkoxy, cycloalkyl, cycloalkoxy, heterocyclyl, heteroaryl, heterocyclyloxy, heteroaryloxy, nitro, thiol, =S, or —NR$^y$$_2$, where each R$^y$ is independently aryl, arylalkyl, cycloalkyl, heterocyclyl, or heteroaryl;
    C$_{3-6}$ alkenyl comprising an allylic carbon-carbon double bond and substituted with aryloxy, arylalkoxy, cycloalkyl, cycloalkoxy, heterocyclyl, heteroaryl, heterocyclyloxy, heteroaryloxy, nitro, thiol, =S, or —NR$^y$$_2$, where each R$^y$ is independently aryl, arylalkyl, cycloalkyl, heterocyclyl, or heteroaryl;
    optionally substituted C$_{6-10}$ aryloxy;
    optionally substituted (C$_{6-10}$ aryl)-C$_{1-6}$ alkoxy;
    optionally substituted C$_{3-10}$ cycloalkyl;
    optionally substituted C$_{1-9}$ heteroaryl comprising at least one nitrogen heteroatom within the heteroaryl ring system;
    optionally substituted C$_{3-9}$ heterocyclyl; or —SF$_5$; or
  (ii) at its para position relative to L, with optionally substituted C$_{6-10}$ aryl C$_{1-4}$ alkyl, optionally substituted C$_{6-10}$ aryl C$_{2-4}$ alkynyl, optionally substituted C$_{3-10}$ cycloalkyl, or optionally substituted (C$_{6-10}$ aryl)-C$_{1-6}$ alkoxy;
and, valency permitting, the substituted phenyl is further optionally substituted with 1, 2, 3, or 4 substituents independently selected from the group consisting of halogen, hydroxyl, —N(R$^9$)$_2$, optionally substituted C$_{1-6}$ alkoxy, optionally substituted C$_{6-10}$ aryloxy, optionally substituted (C$_{6-10}$ aryl)-C$_{1-6}$ alkoxy, or optionally substituted C$_{6-10}$ aryl;
each of R$^2$ and R$^3$ is independently hydroxyl, —O—CO—NH—R$^{10}$, or —O—CO—R$^{11}$, provided that at least one of R$^2$ and R$^3$ is —O—CO—NH—R$^{10}$ or —O—CO—R$^{11}$;
R$^4$ is hydrogen, halogen, optionally substituted C$_{1-6}$ alkyl, optionally substituted C$_{1-6}$ alkoxy, or optionally substituted C$_{6-10}$ aryl;
R$^5$ is halogen, hydroxyl, or optionally substituted C$_{1-6}$ alkoxy;
R$^8$ is optionally substituted C$_{6-10}$ aryl;

each R$^9$ is independently H or optionally substituted C$_{1-6}$ alkyl;
R$^{10}$, when present, is hydrogen, optionally substituted C$_{2-6}$ alkyl, optionally substituted C$_{3-10}$ cycloalkyl; or optionally substituted C$_{6-10}$ aryl; and
R$^{11}$, when present, is optionally substituted C$_{1-9}$ heteroaryl.

In some embodiments, L is —CO—. In other embodiments, X is O. In certain embodiments, R$^4$ is optionally substituted C$_{1-6}$ alkyl, such as methyl. In some embodiments, R$^5$ is hydroxyl. In other embodiments, R$^3$ is hydroxyl. In some embodiments, R$^2$ is —O—CO—NH—R$^0$. In certain embodiments, R$^{10}$ is H. In other embodiments, R$^2$ is —O—CO—R$^{11}$. In some embodiments, one and only one of R$^2$ and R$^3$ is —O—CO—NH—R$^{10}$ or —CO—R$^{11}$. In certain embodiments, R$^2$ is —O—CO—NH—R$^{10}$ or —O—CO—R$^{11}$. In some embodiments, R$^2$ is —O—CO—NH—R$^{10}$ or —O—CO—R$^{11}$. In certain embodiments, R$^{10}$, when present, is hydrogen, optionally substituted C$_{3-10}$ cycloalkyl; or optionally substituted C$_{6-10}$ aryl.

In some embodiments, one and only one of R$^2$ and R$^3$ is:

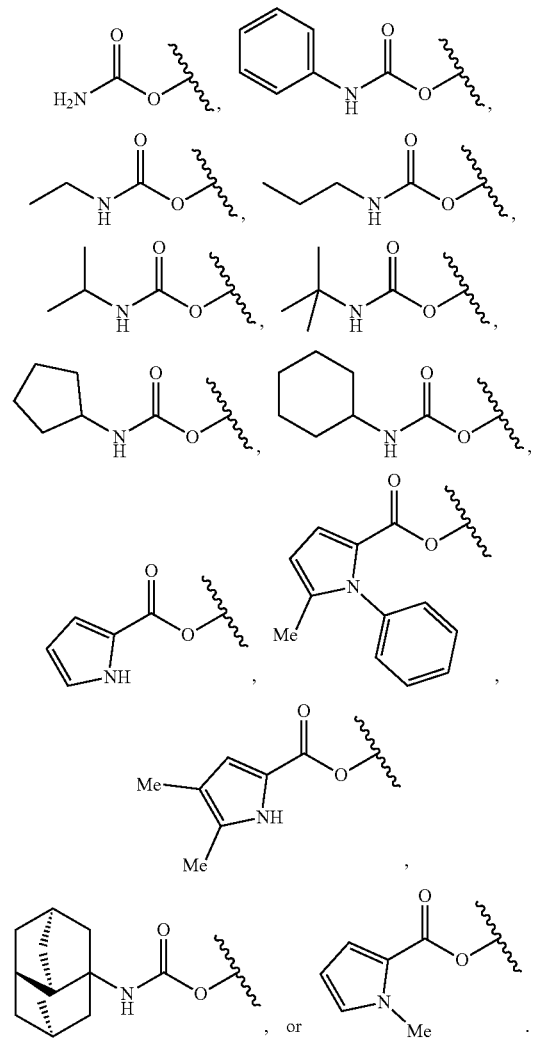

In certain embodiments, R² is:

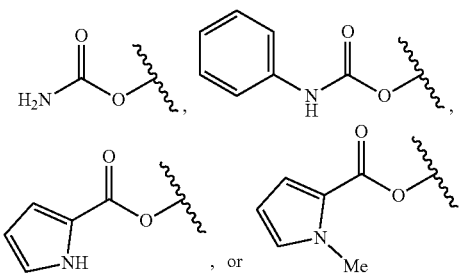

In some embodiments, R¹ is a substituted phenyl. In certain embodiments, the substituted
  phenyl is substituted at one and only one of its meta position relative to L, with:
    $C_{1-6}$ alkyl substituted with aryloxy, arylalkoxy, cycloalkyl, cycloalkoxy, heterocyclyl, heteroaryl, heterocyclyloxy, heteroaryloxy, nitro, thiol, =S, or —NR₂, where each $R^y$ is independently aryl, arylalkyl, cycloalkyl, heterocyclyl, or heteroaryl;
    $C_{3-6}$ alkenyl comprising an allylic carbon-carbon double bond and substituted with aryloxy, arylalkoxy, cycloalkyl, cycloalkoxy, heterocyclyl, heteroaryl, heterocyclyloxy, heteroaryloxy, nitro, thiol, =S, or —NR$^y$₂, where each R$^y$ is independently aryl, arylalkyl, cycloalkyl, heterocyclyl, or heteroaryl;
    optionally substituted $C_{6-10}$ aryloxy;
    optionally substituted ($C_{6-10}$ aryl)-$C_{1-6}$ alkoxy;
    optionally substituted $C_{3-10}$ cycloalkyl;
    optionally substituted $C_{1-9}$ heteroaryl comprising at least one nitrogen heteroatom within the heteroaryl ring system;
    optionally substituted $C_{3-9}$ heterocyclyl; or
    —SF₅; and
  valency permitting, the substituted phenyl is further optionally substituted with 1, 2, 3, or 4 substituents independently selected from the group consisting of halogen, hydroxyl, —N(R⁹)₂, optionally substituted $C_{1-6}$ alkoxy, optionally substituted $C_{6-10}$ aryloxy, optionally substituted ($C_{6-10}$ aryl)-$C_{1-6}$ alkoxy, or optionally substituted $C_{6-10}$ aryl.

In some embodiments, R¹ is:

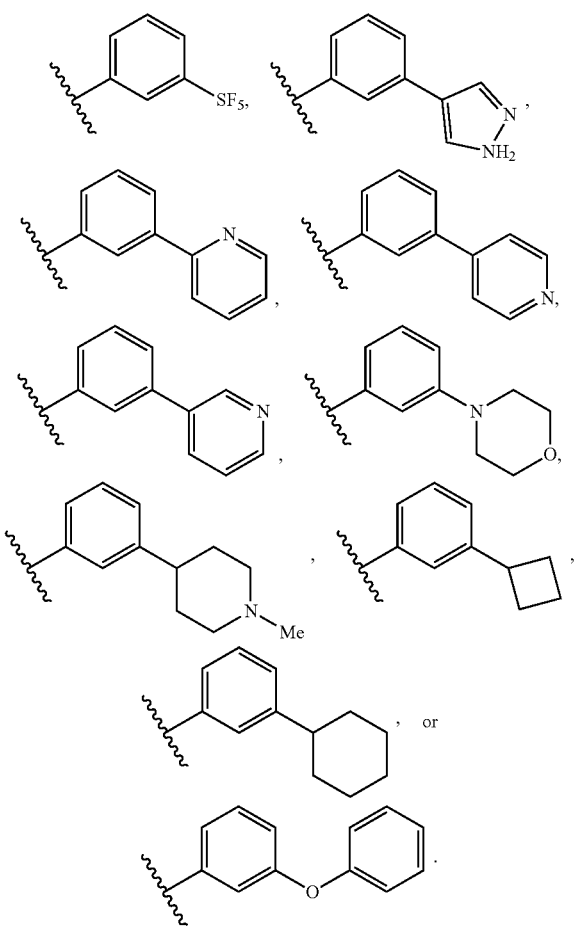

Disclosed herein are compounds, or a pharmaceutically acceptable salt thereof, selected from the following table:

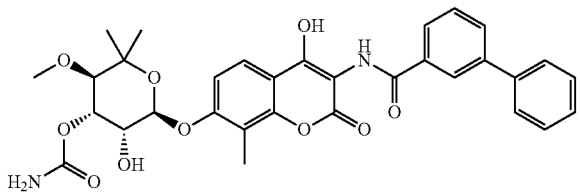
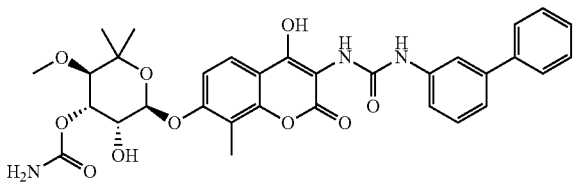
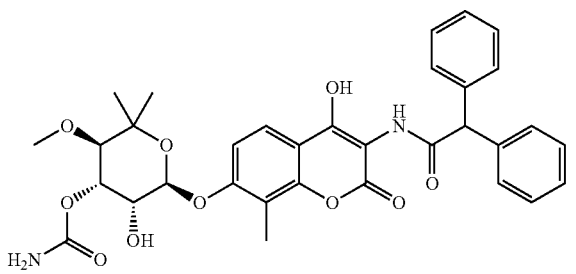
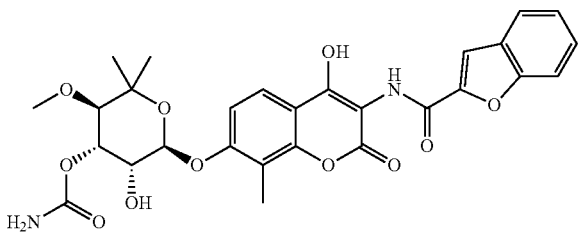

-continued
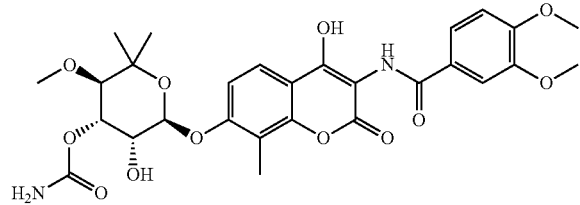
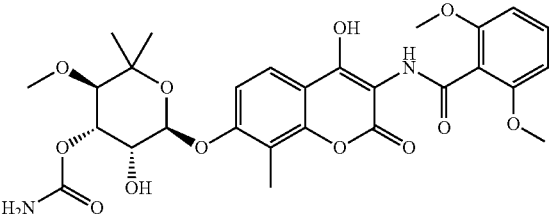
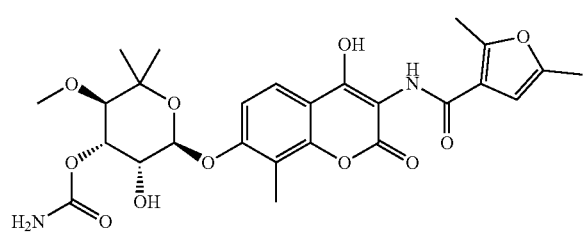
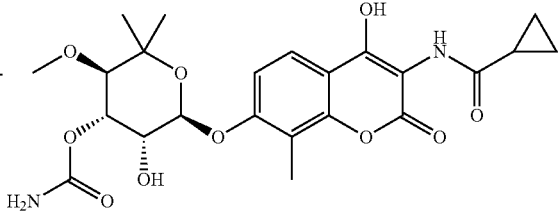
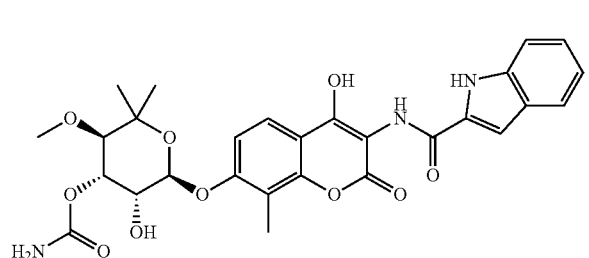
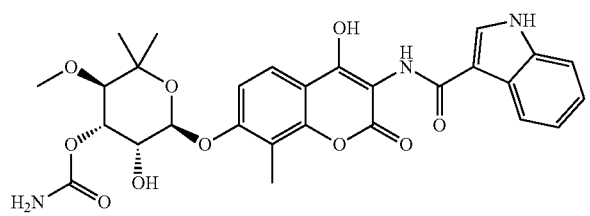
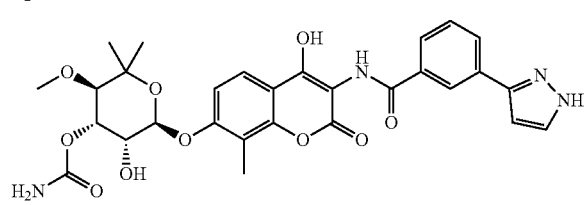
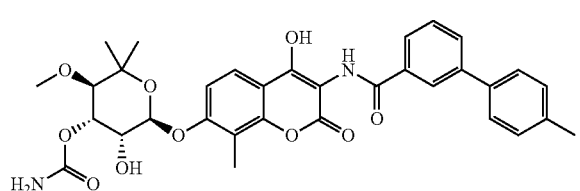
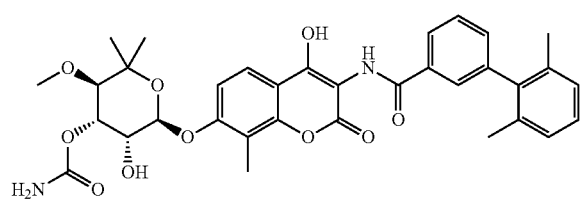
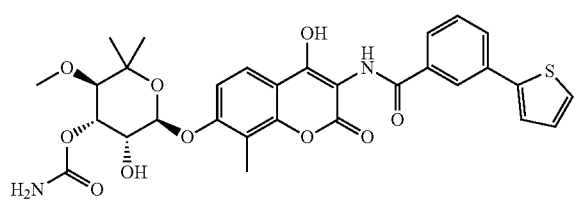
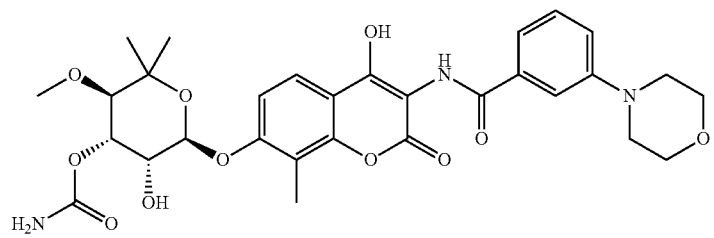
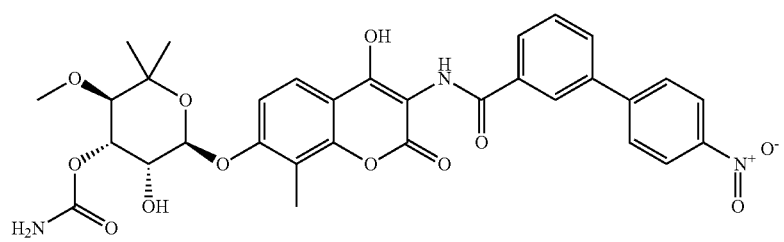

-continued
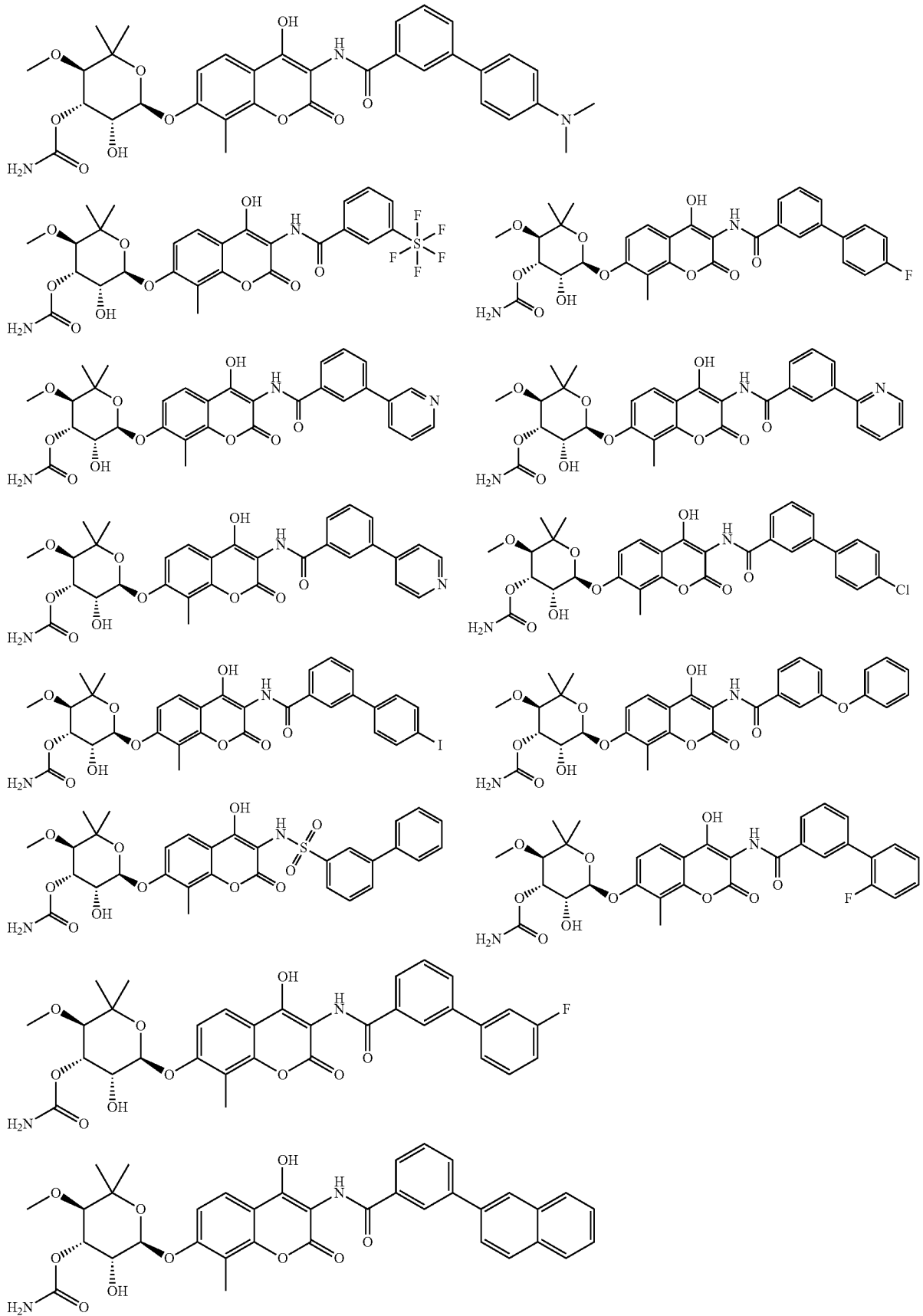

33 34
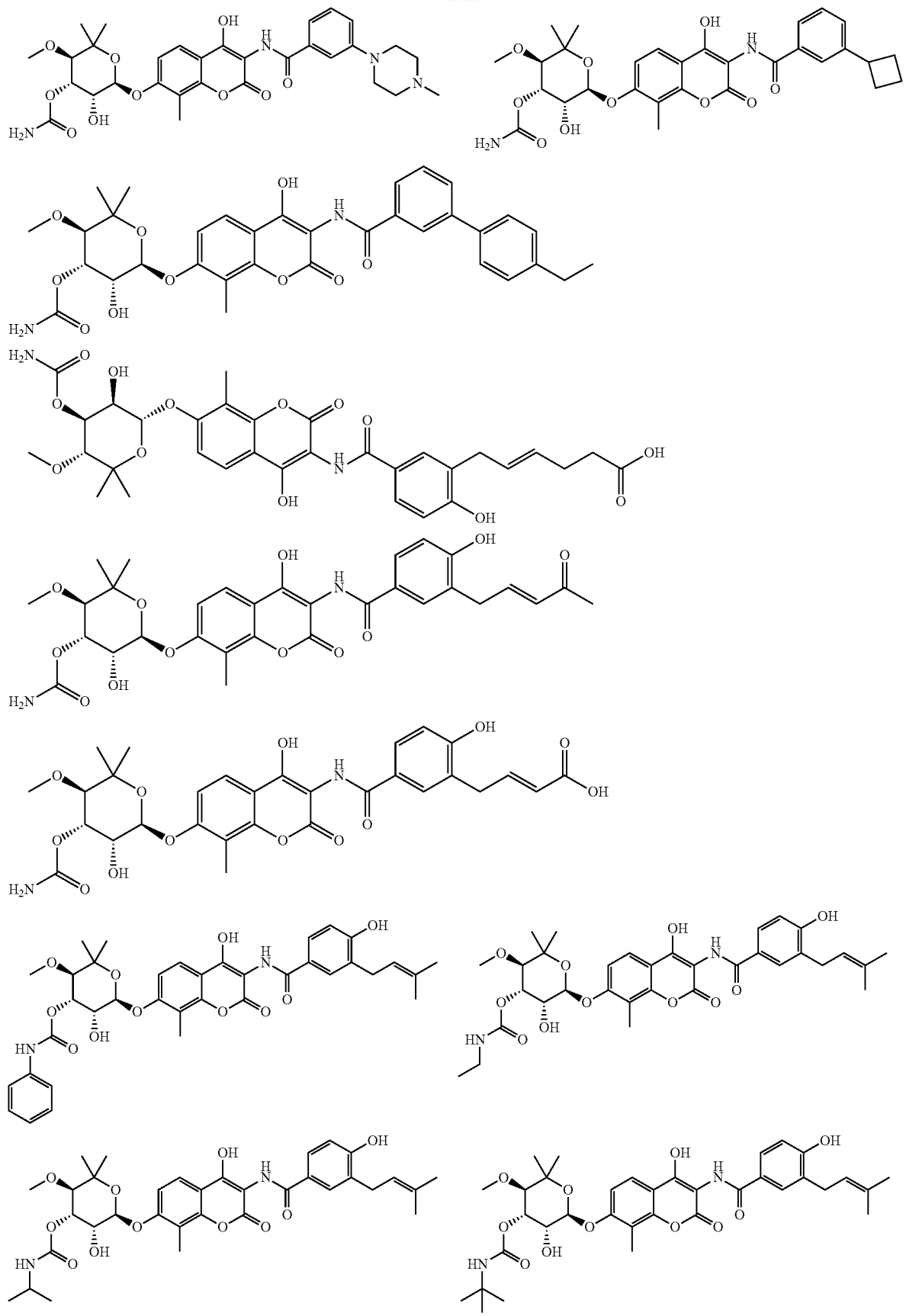
-continued

35
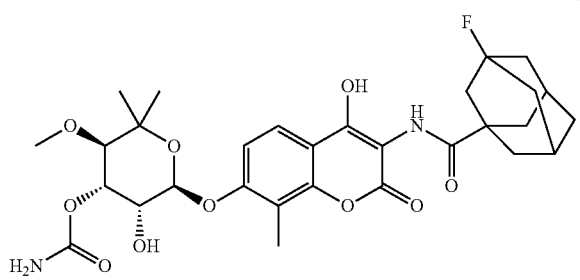
36
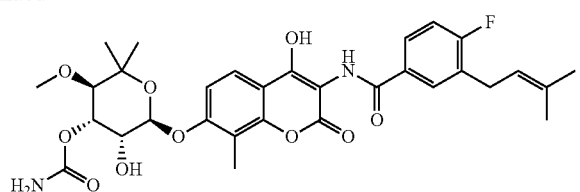
-continued
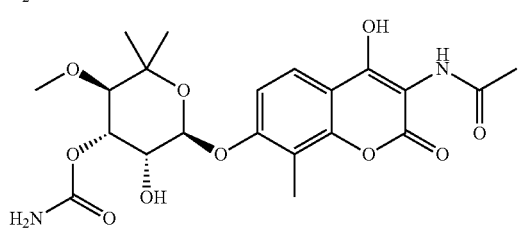
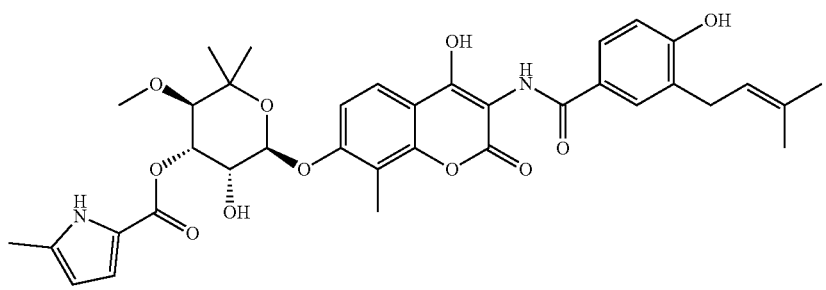
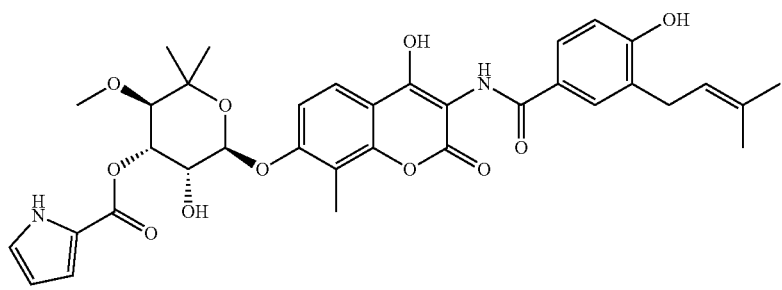
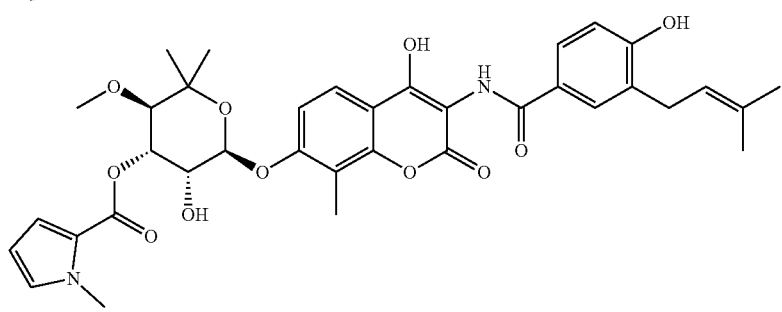
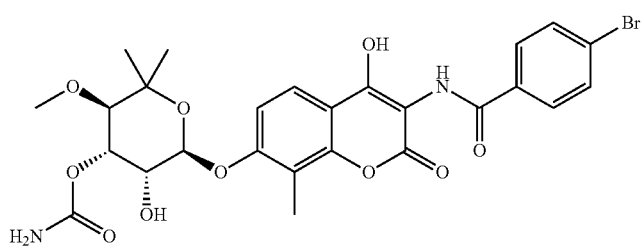

-continued
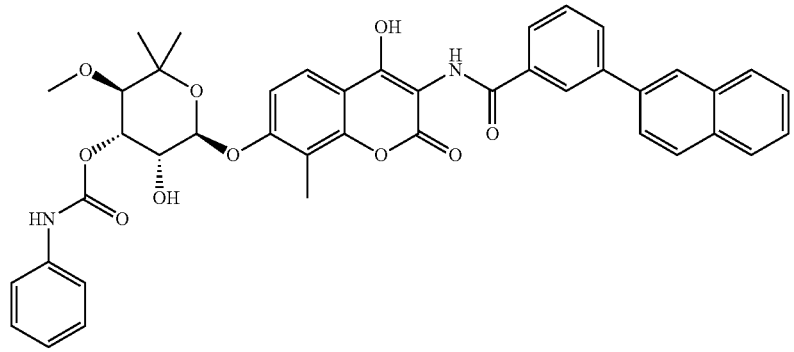
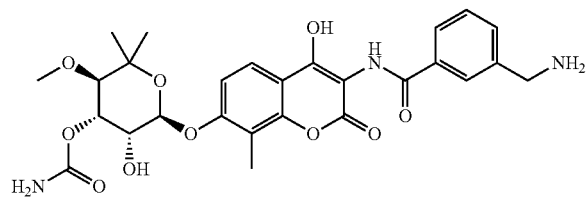
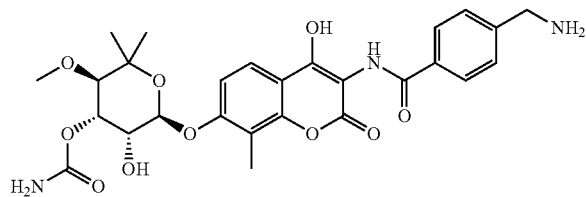
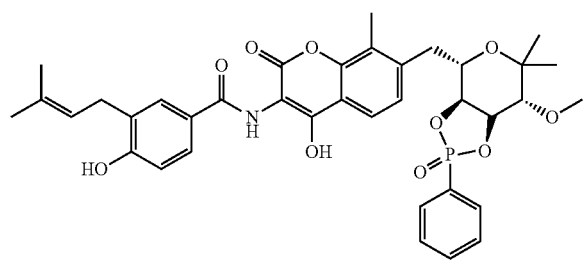
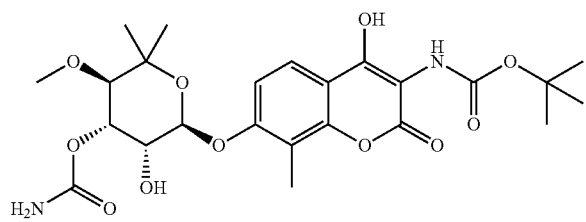
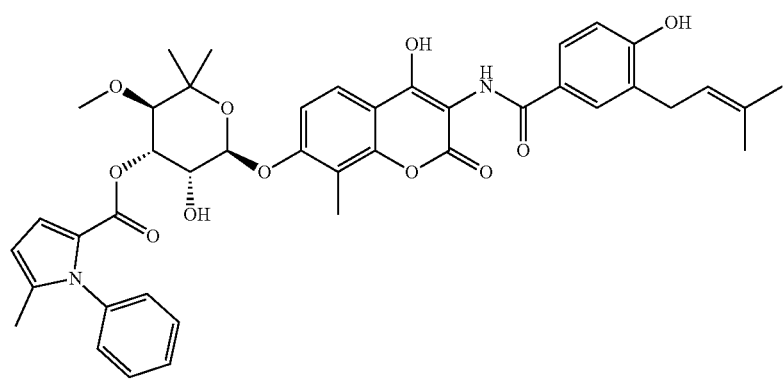
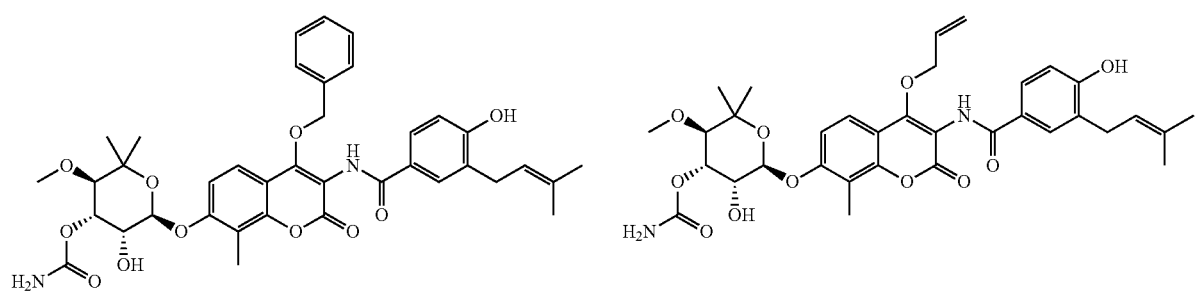

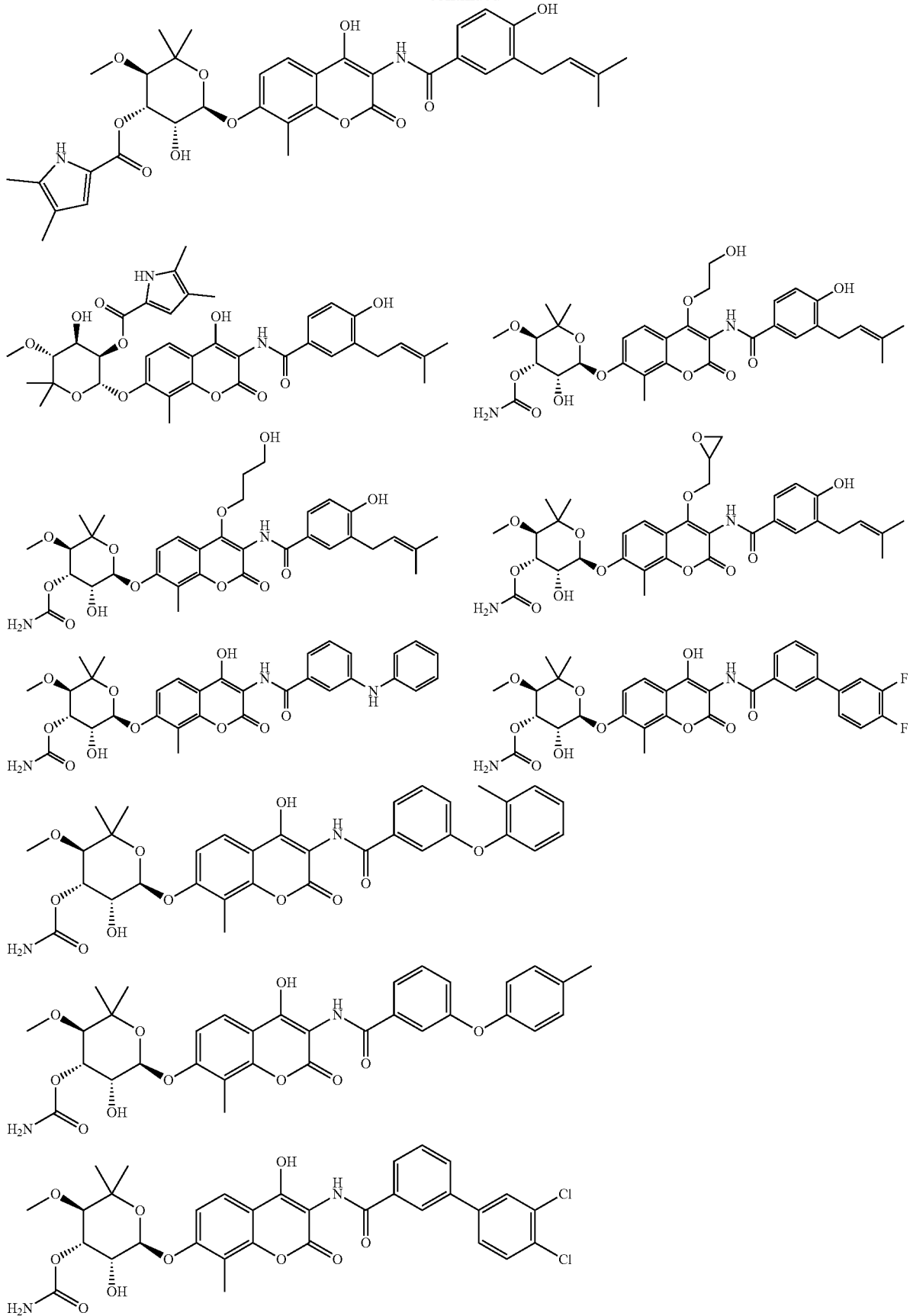

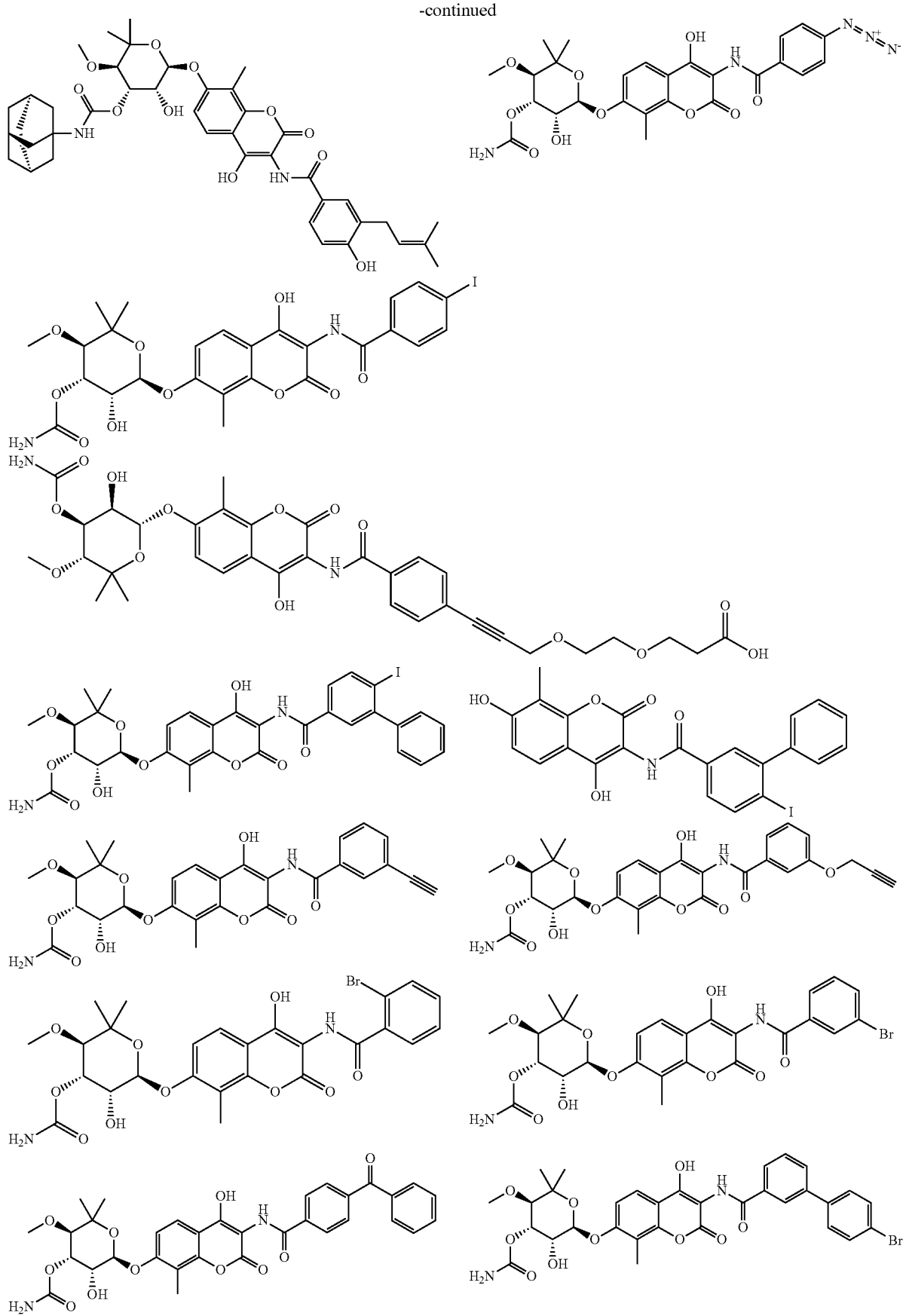

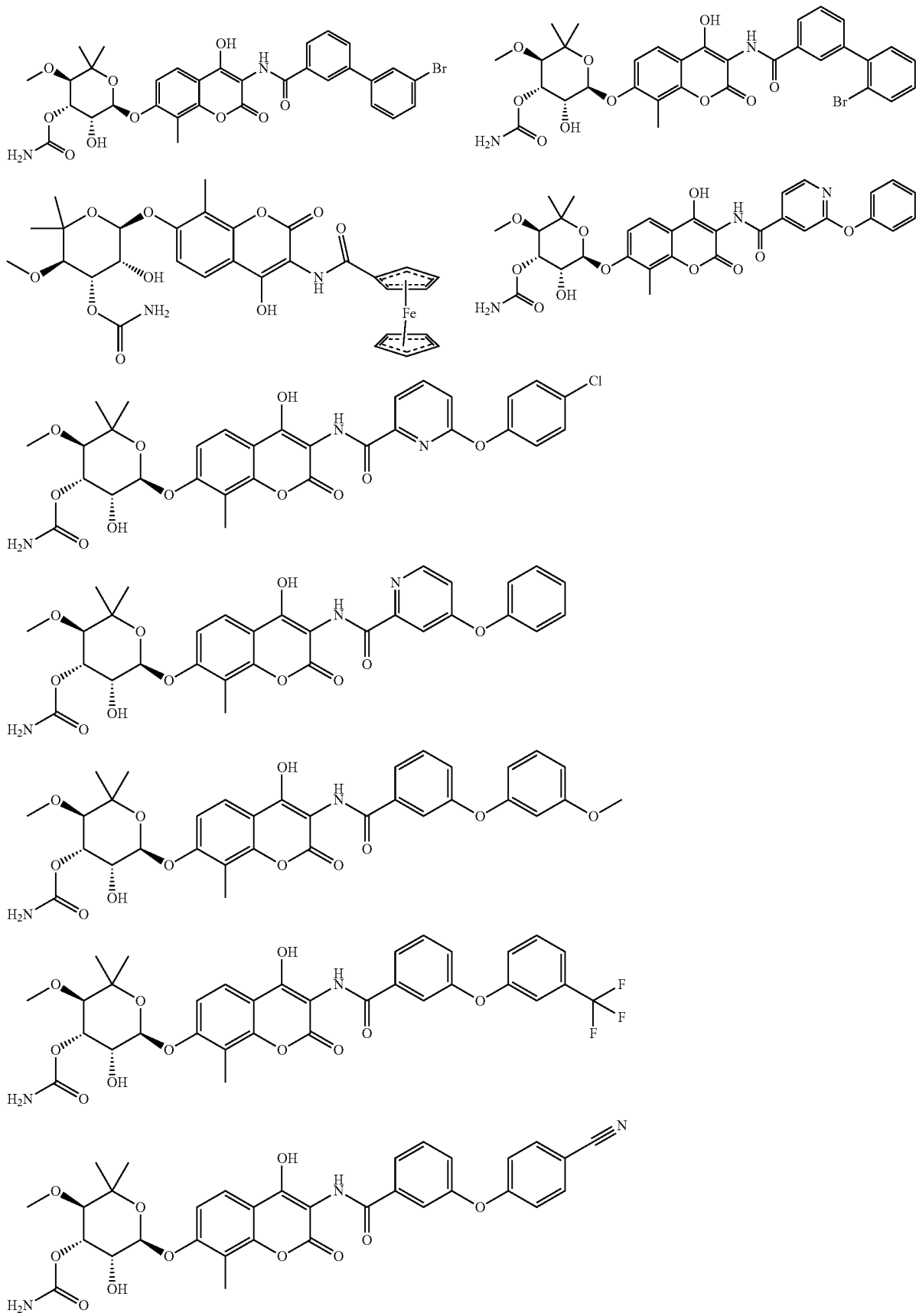

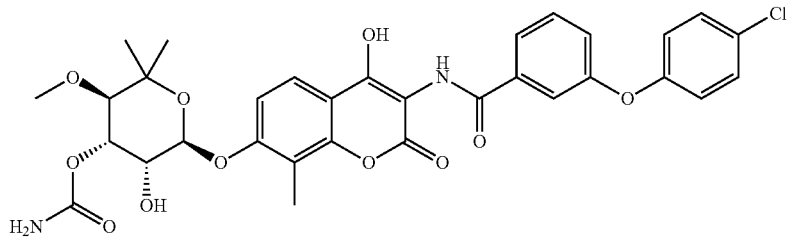
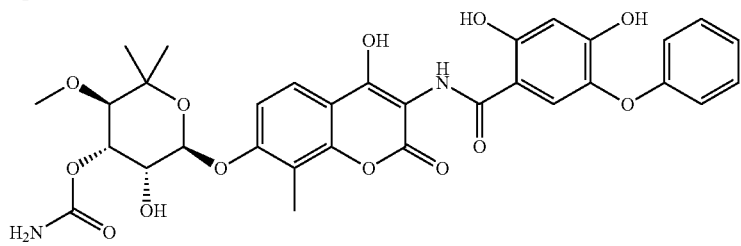
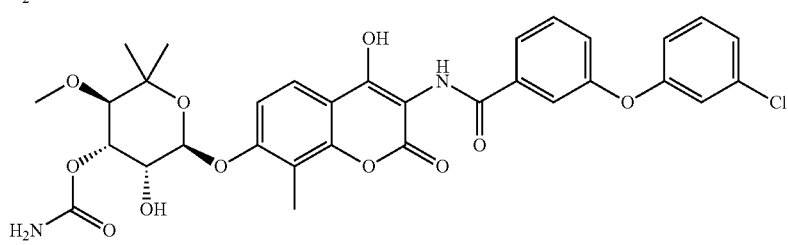
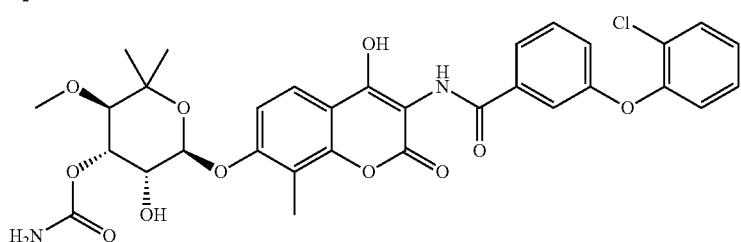
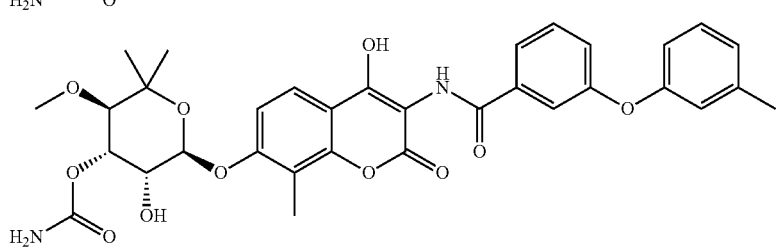
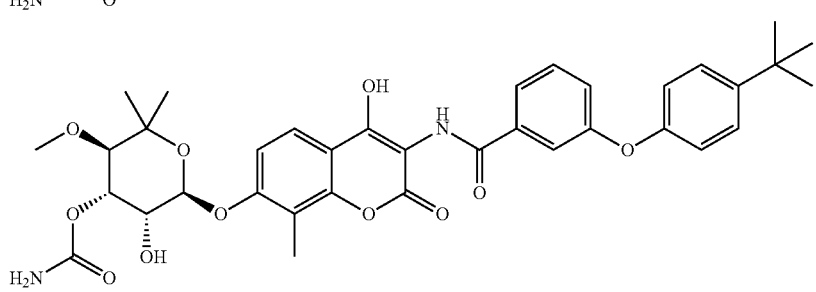
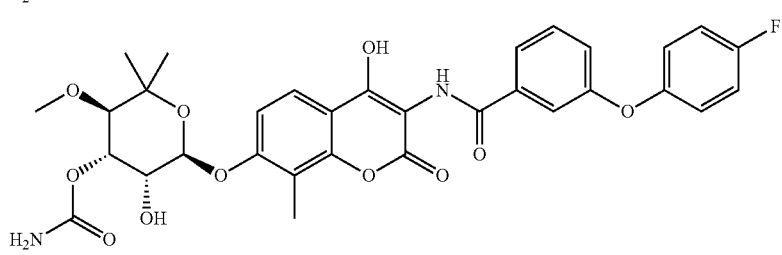

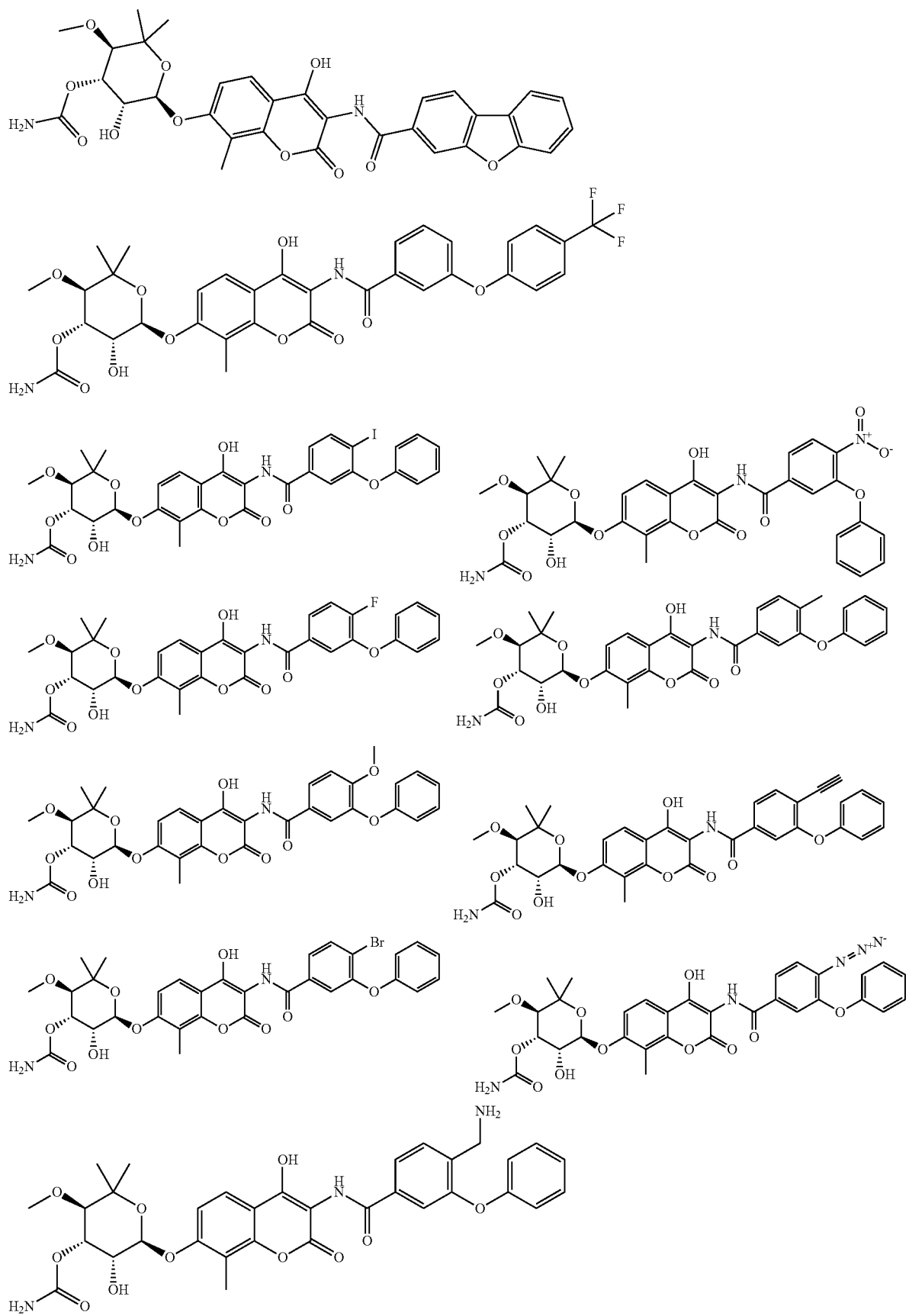

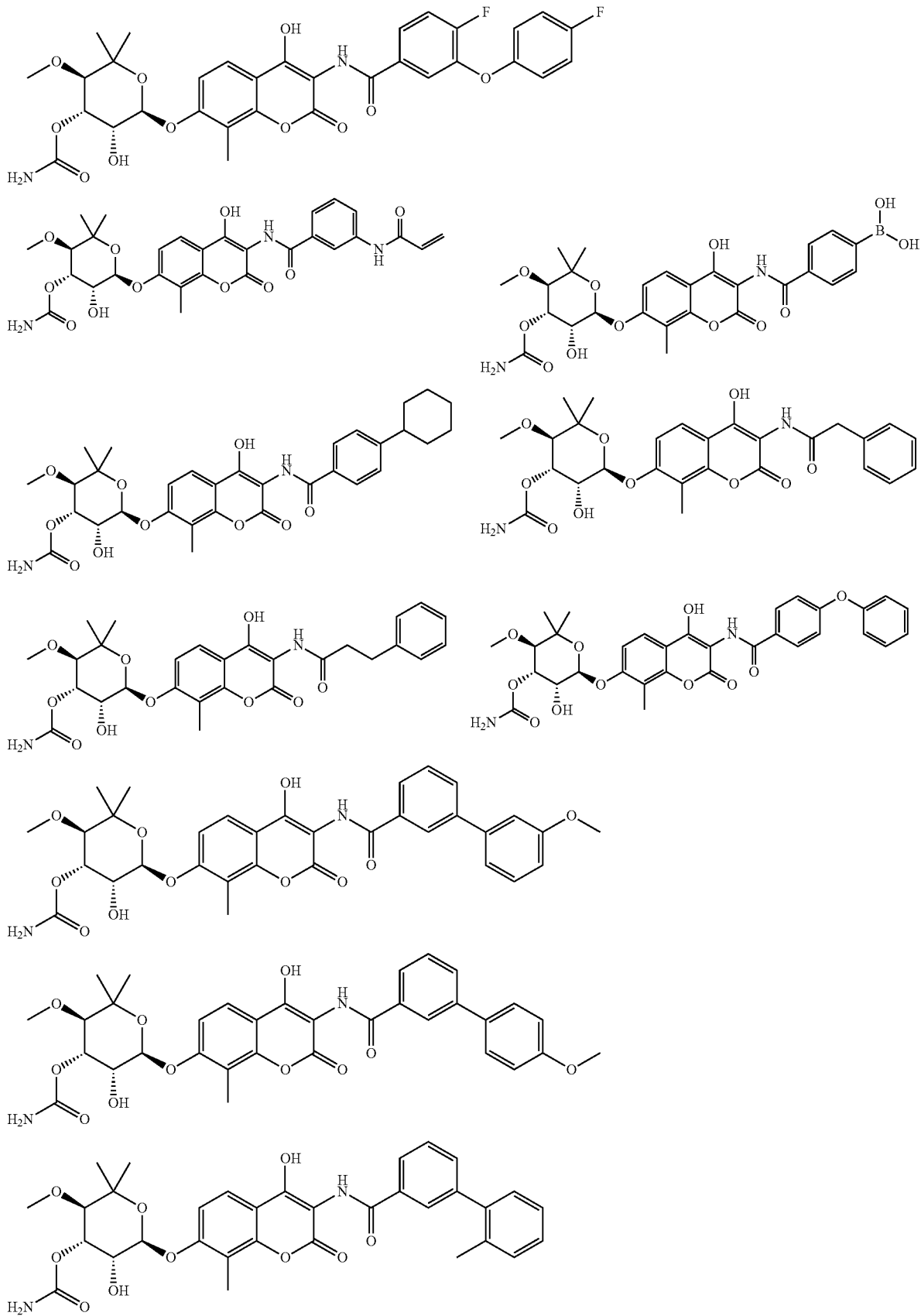

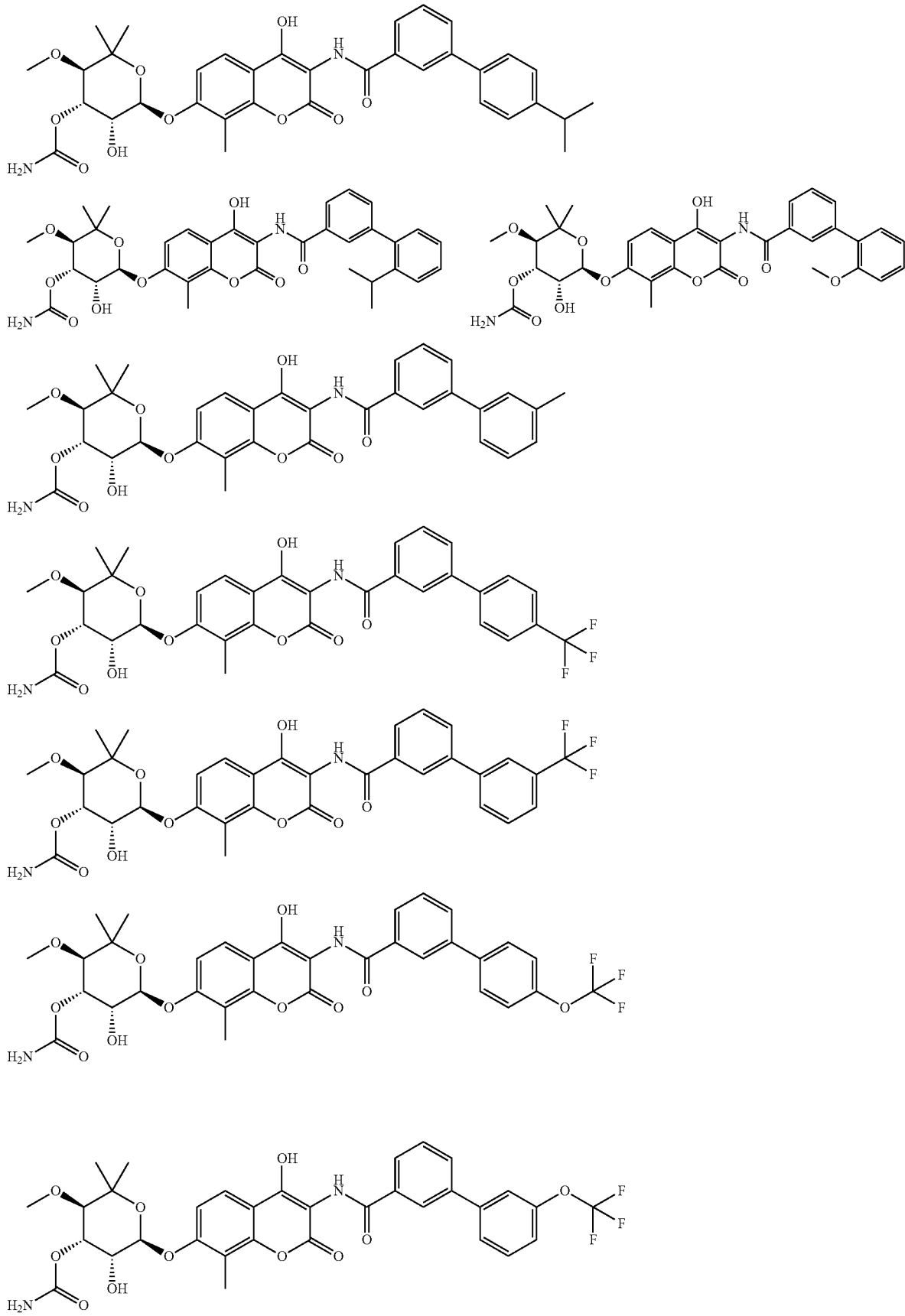

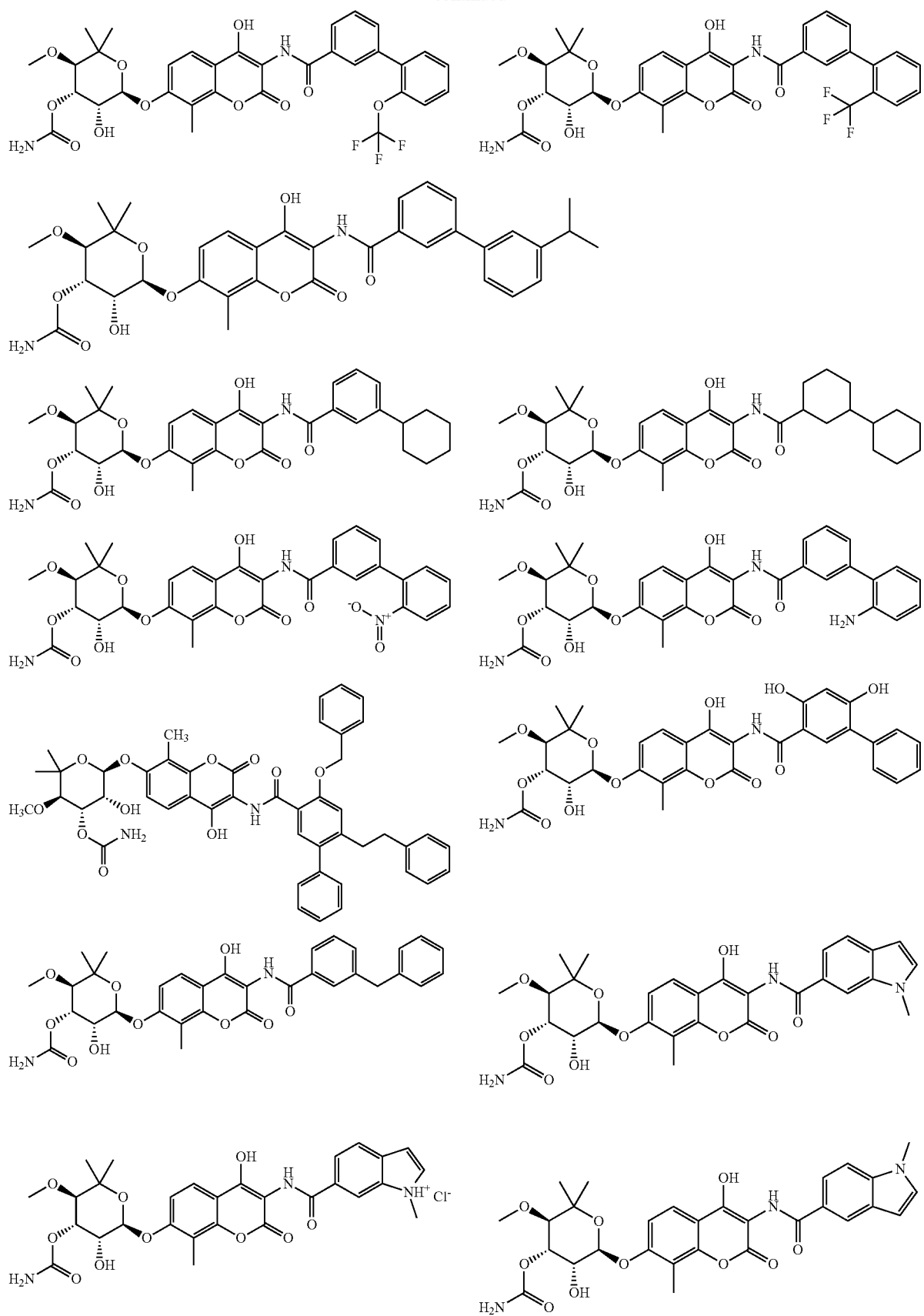

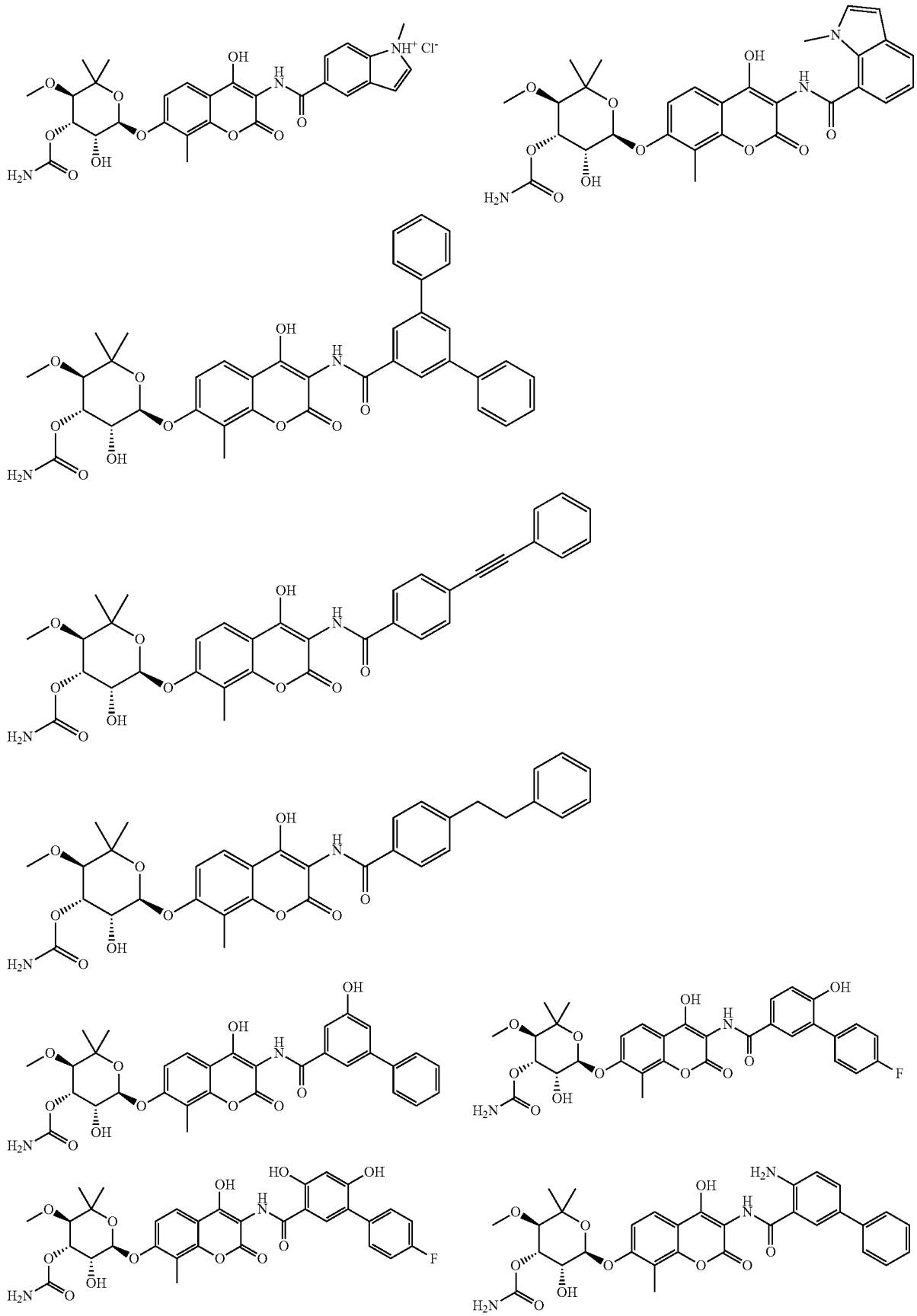

-continued
| 57 | 58 |
|---|---|
| 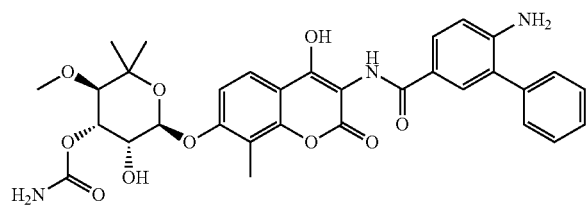 | 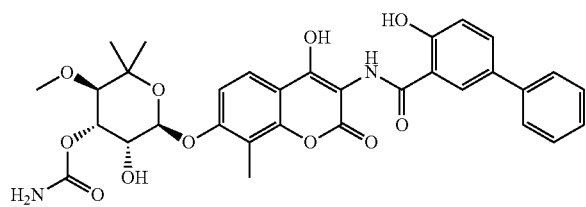 |
| 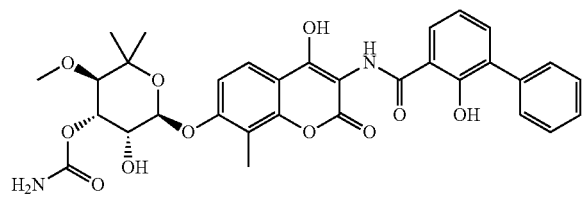 | 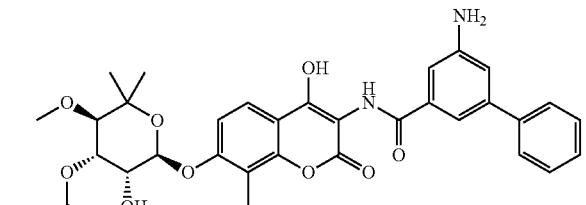 |
| 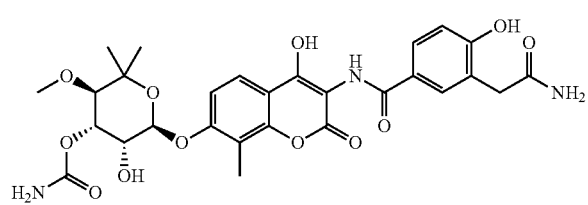 | 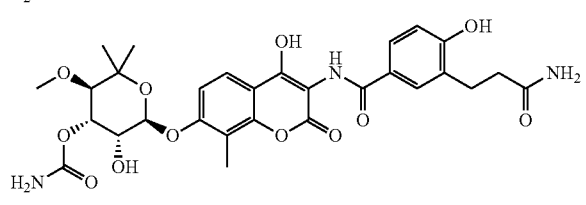 |
| 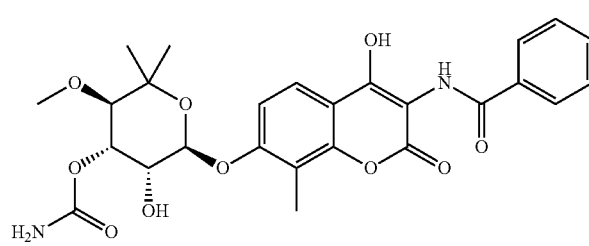 |  |
| 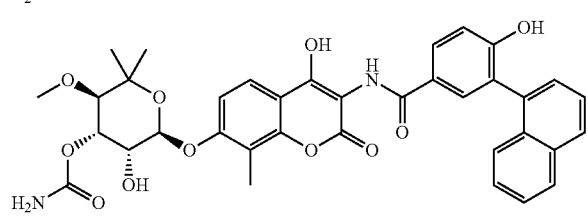 | 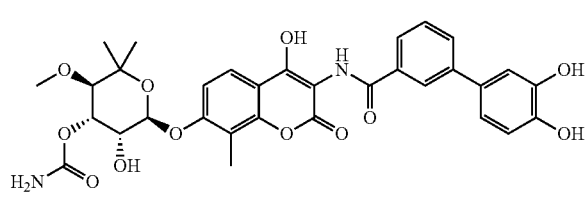 |
| 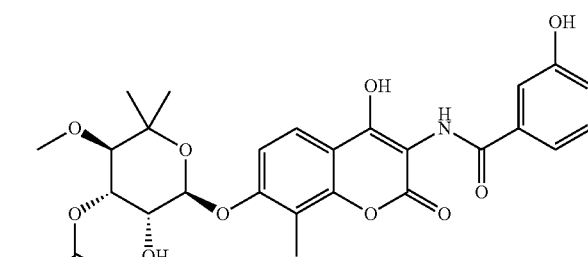 |  |
| 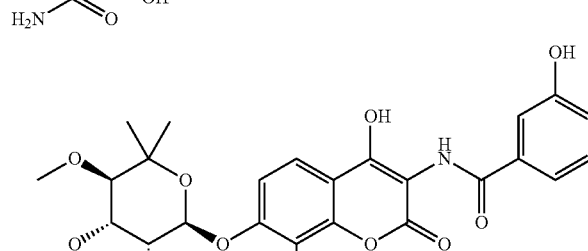 |  |

-continued
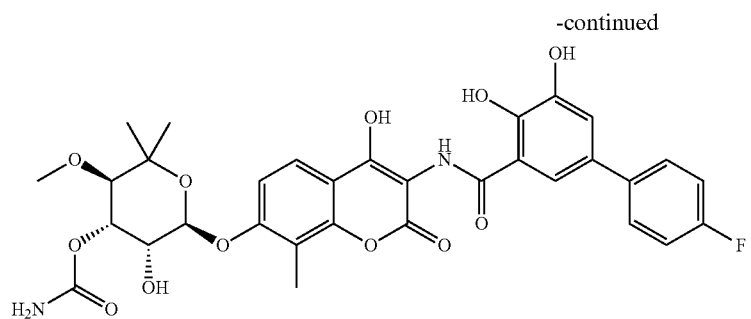
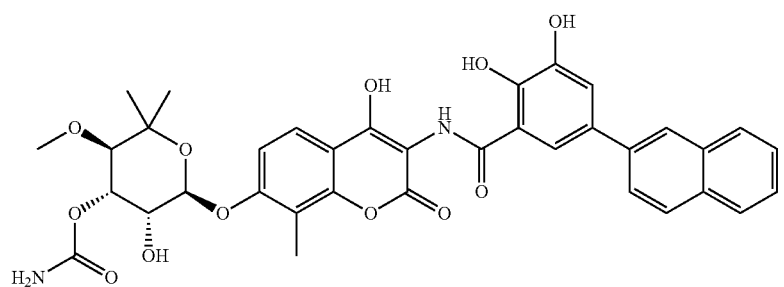
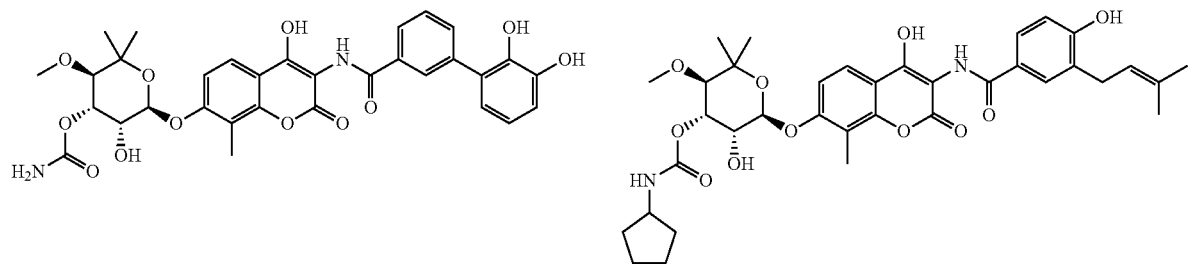
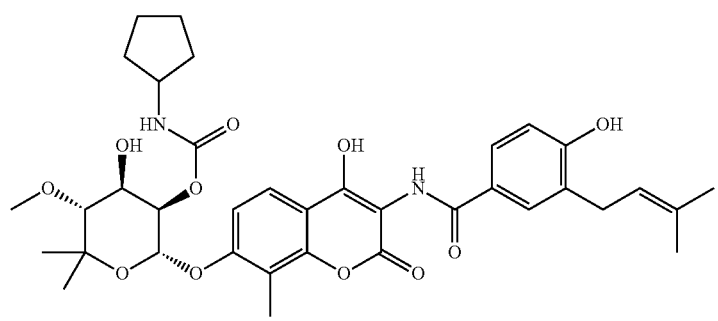
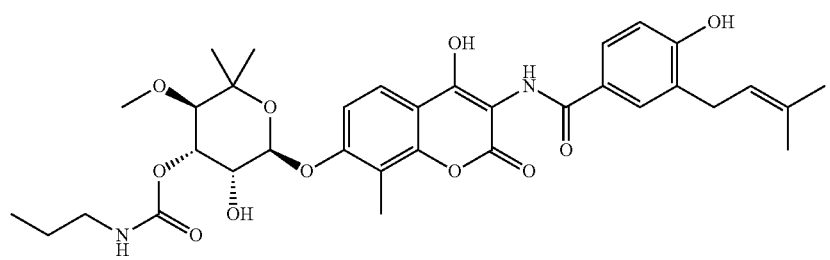

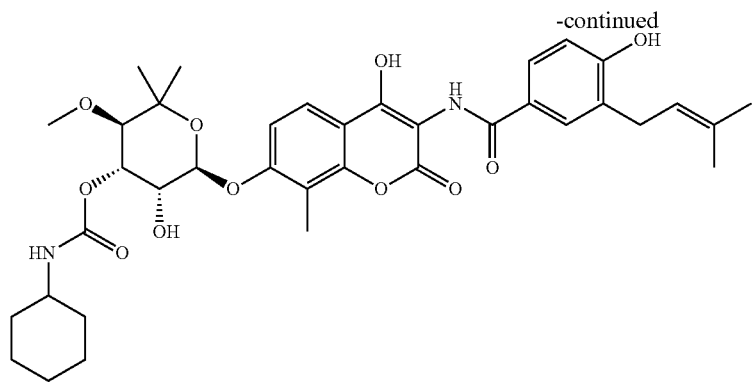

Disclosed herein are compounds of formula (XY):

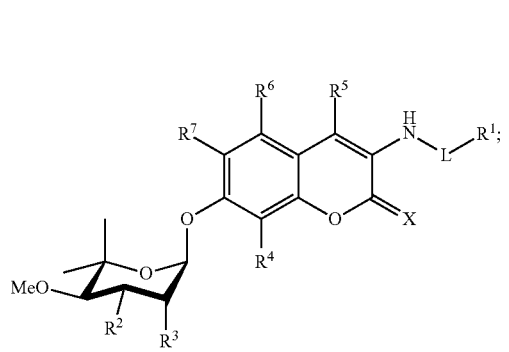

or a pharmaceutically acceptable salt thereof,
wherein
  X is O or S;
  L is —CO— or —SO$_2$—;
  each of R$^2$ and R$^3$ is independently hydroxyl, —O—CO—NH—R$^{10}$, or —O—CO—R$^{11}$;
  each of R$^4$, R$^6$, and R$^7$ is independently hydrogen, halogen, optionally substituted C$_{1-6}$ alkyl, optionally substituted C$_{1-6}$ alkoxy, or optionally substituted C$_{6-10}$ aryl;
  R$^5$ is halogen, hydroxyl, or optionally substituted C$_{1-6}$ alkoxy;
  R$^8$ is optionally substituted C$_{6-10}$ aryl;
  each R$^9$ is independently H or optionally substituted C$_{1-6}$ alkyl;
  R$^{10}$, when present, is hydrogen, optionally substituted C$_{1-6}$ alkyl, optionally substituted C$_{3-10}$ cycloalkyl, or optionally substituted C$_{6-10}$ aryl; and
  R$^{11}$, when present, is optionally substituted C$_{1-9}$ heteroaryl or optionally substituted C$_{6-10}$ aryl; and
  R$^1$ is selected from the group consisting of

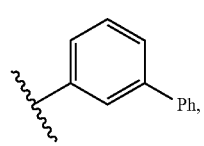 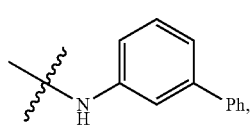

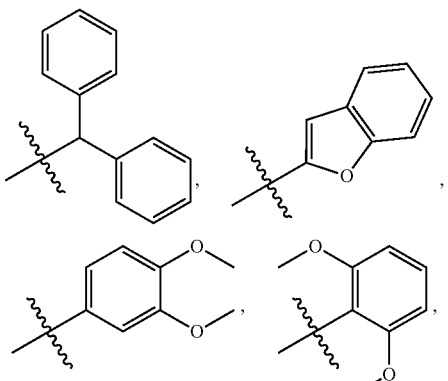

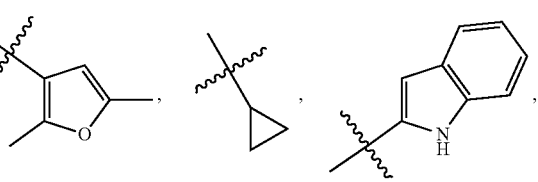

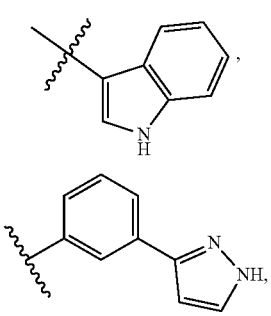

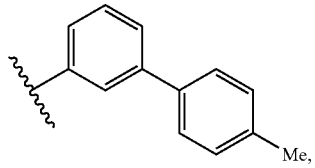

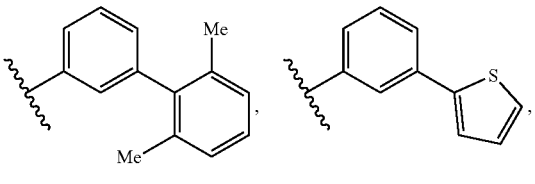

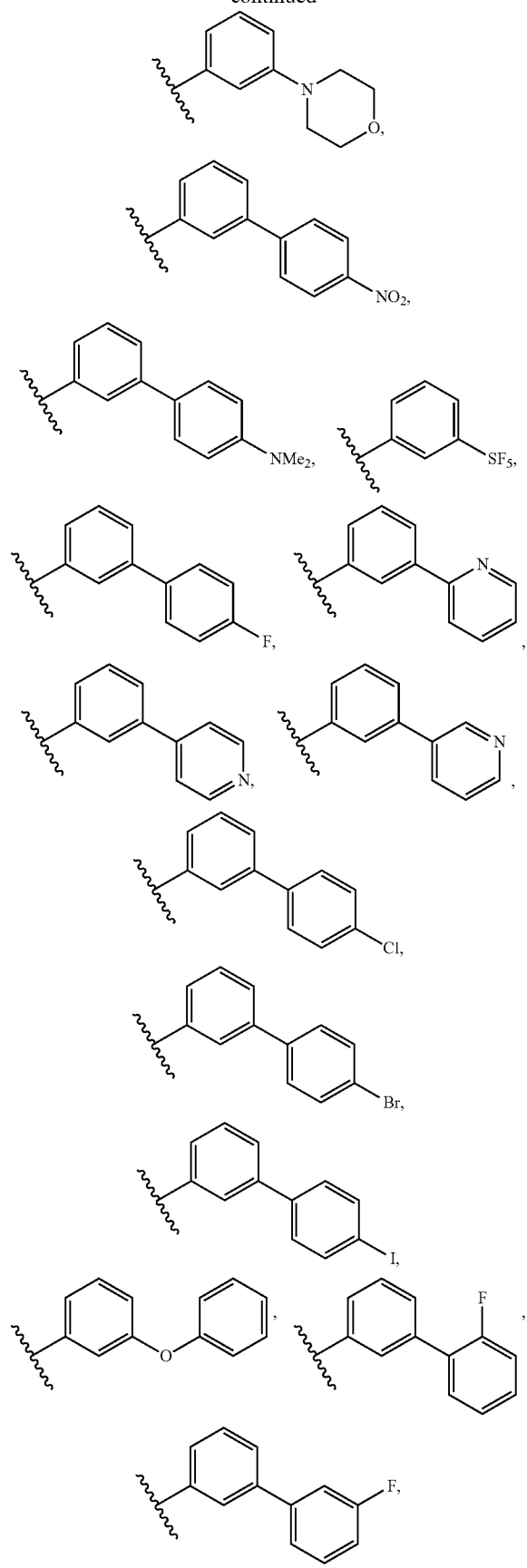
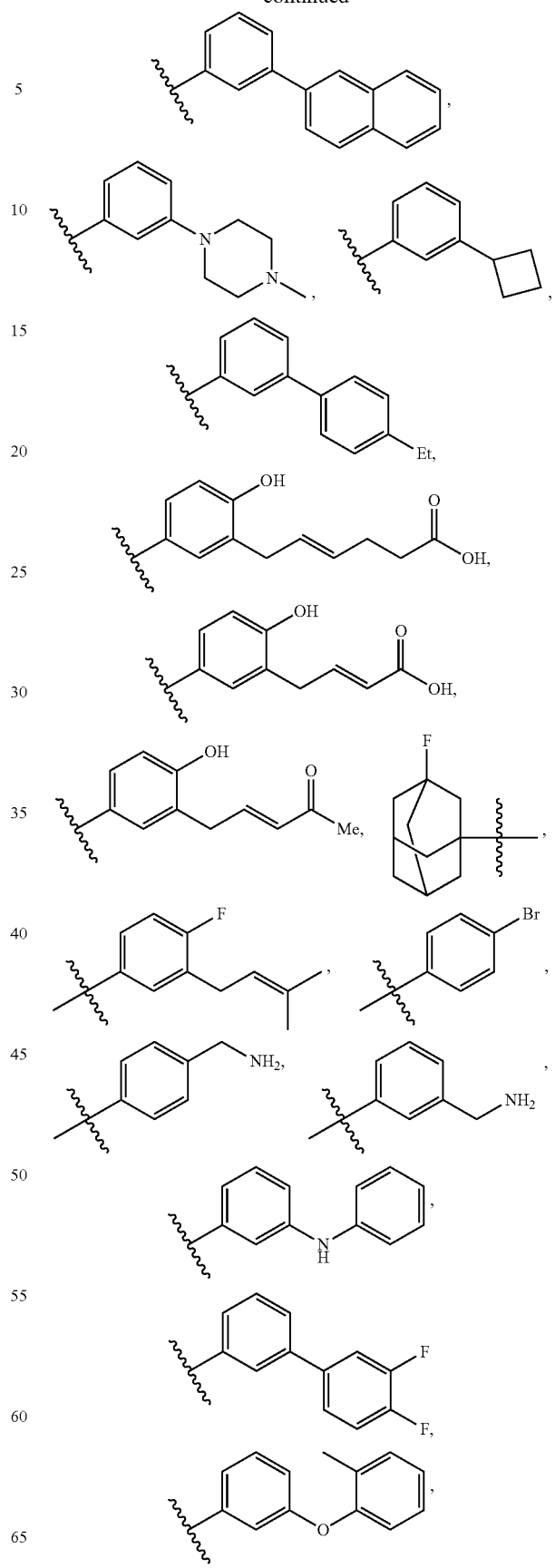

-continued
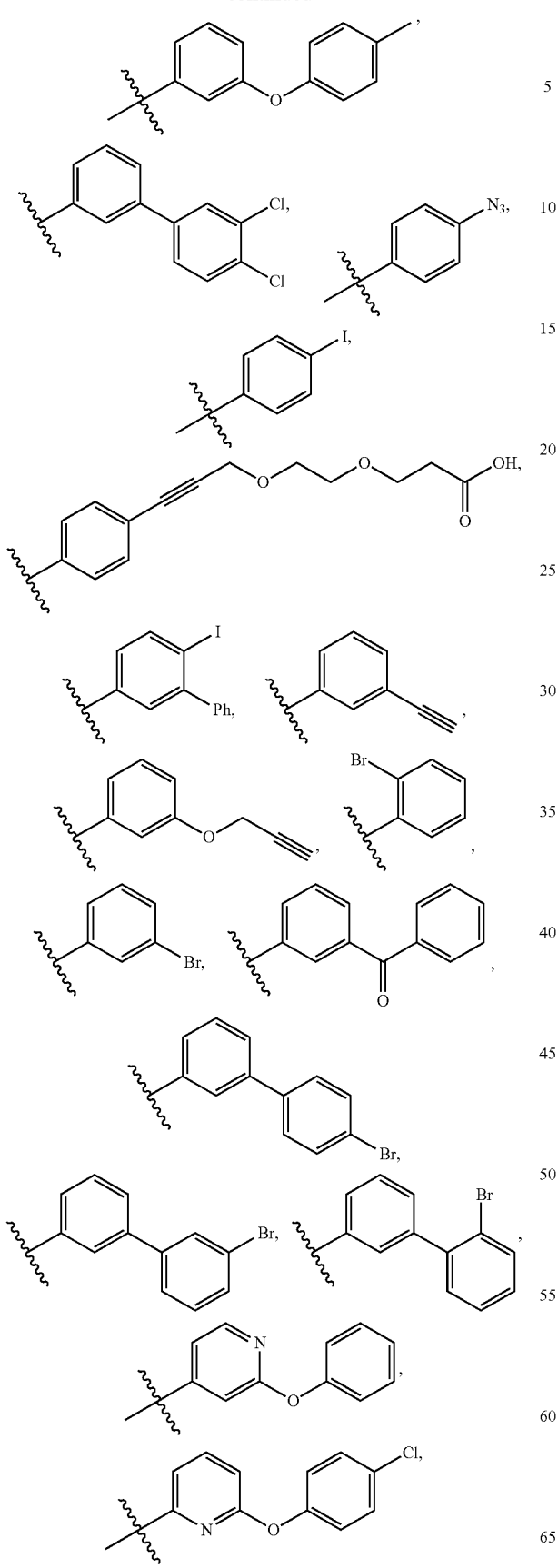
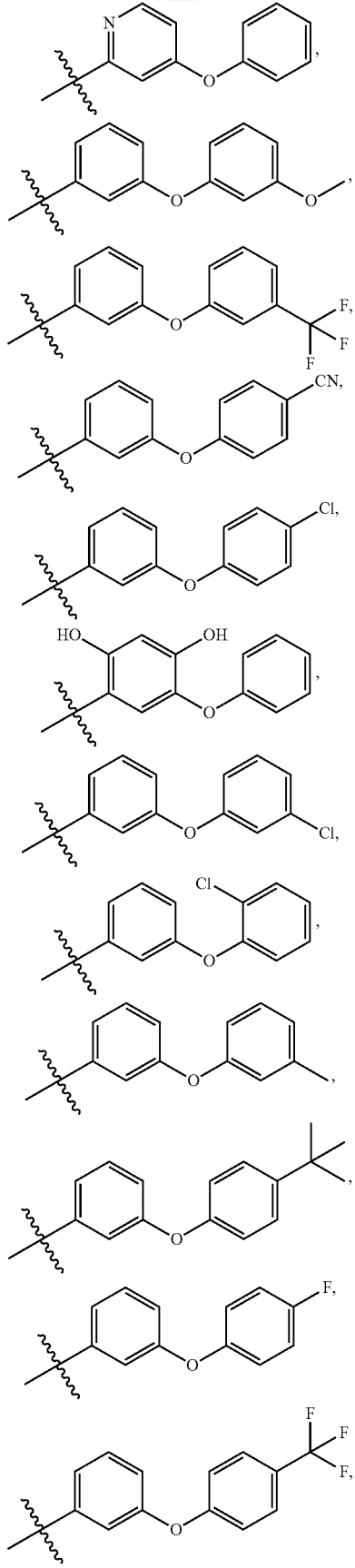

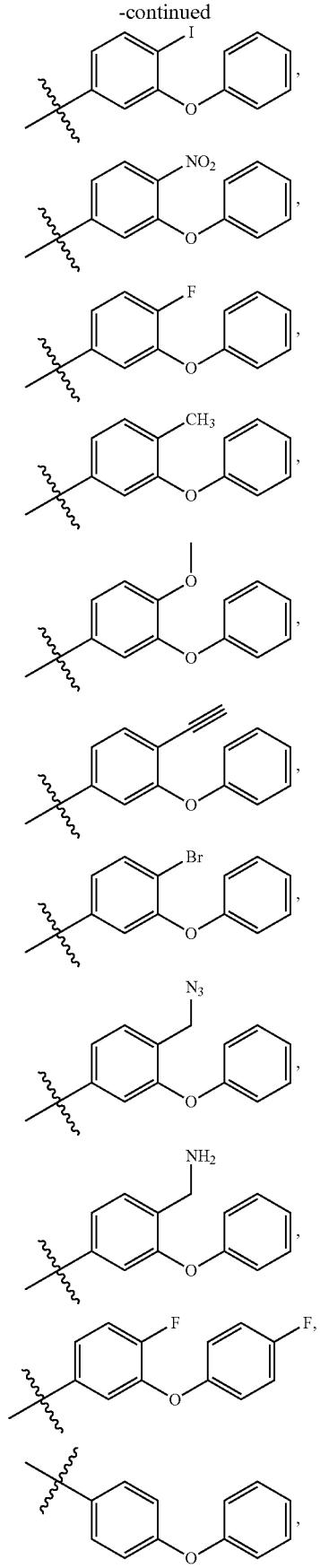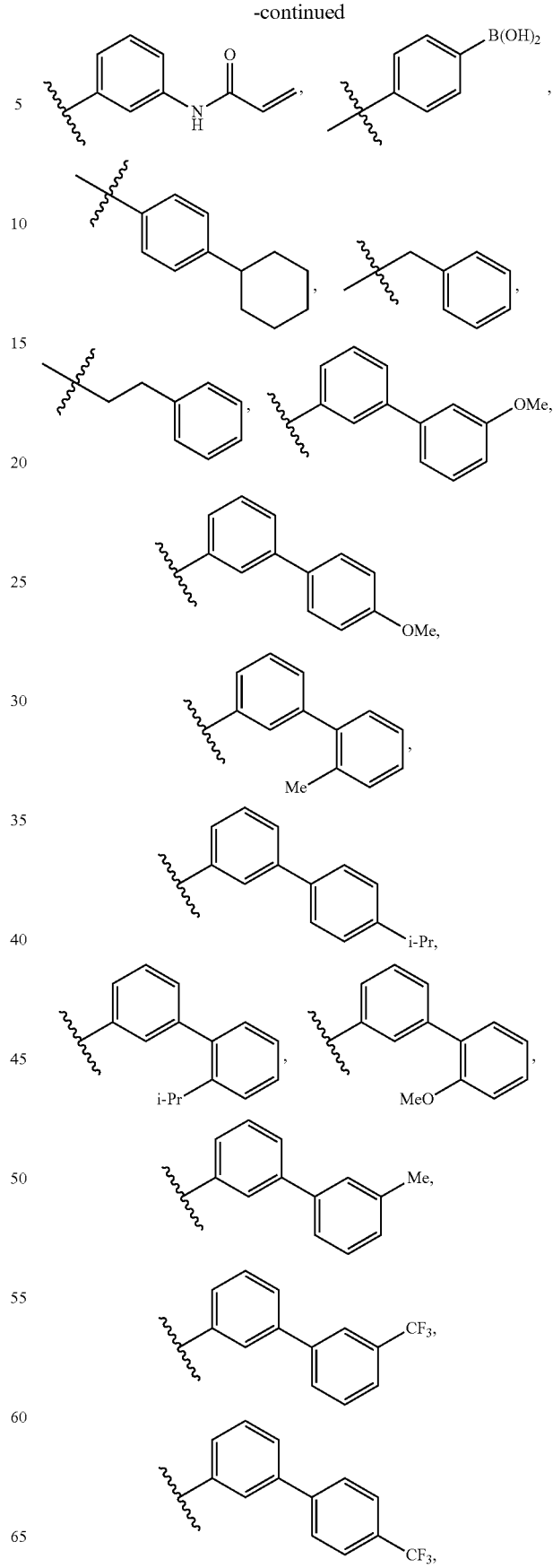

-continued
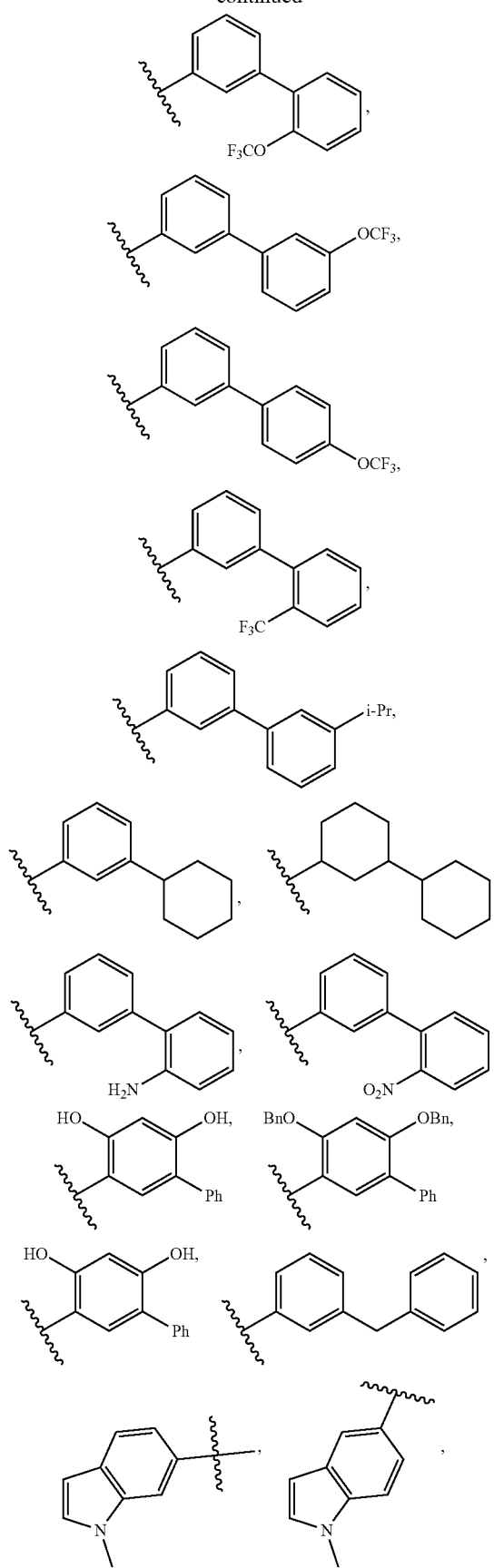
-continued
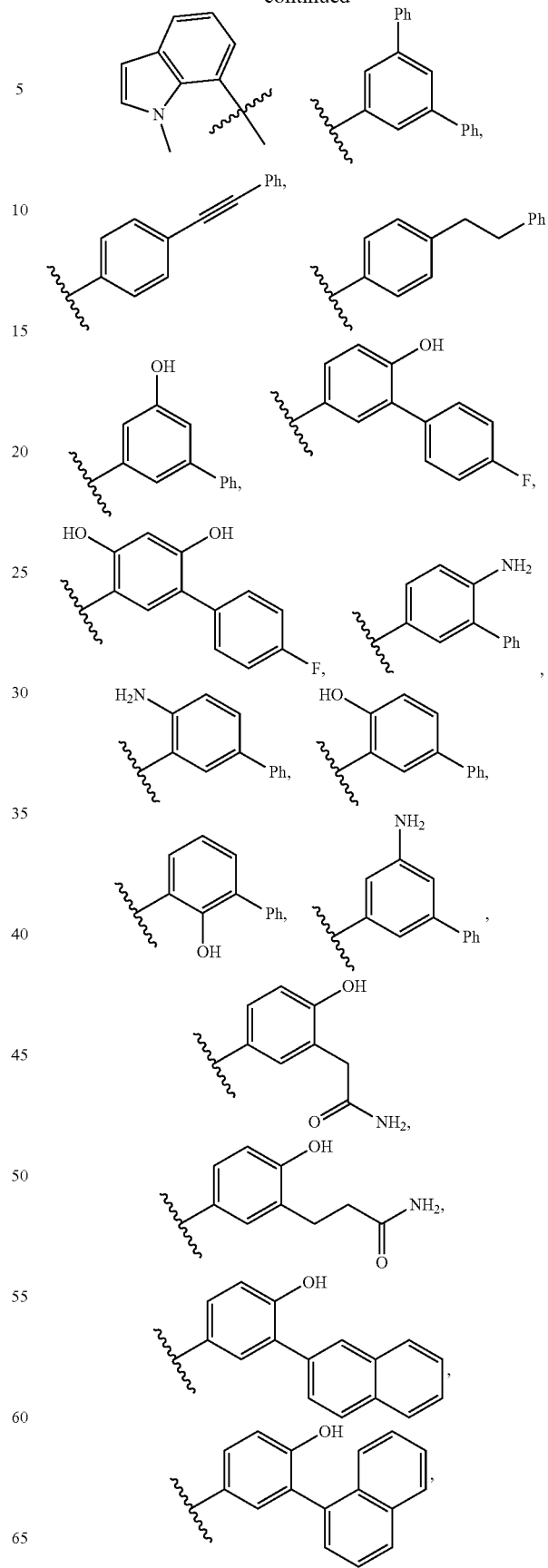

-continued

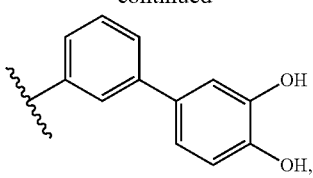

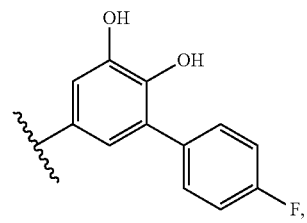

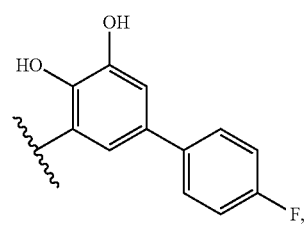

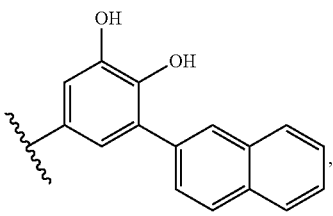

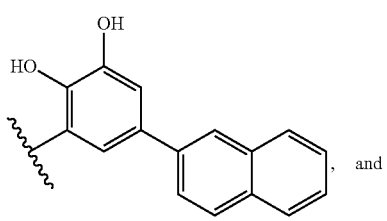

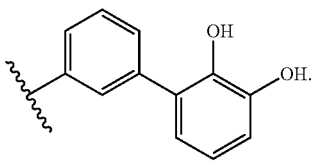

In some embodiments, L is —CO—. In certain embodiments, X is O. In some embodiments, R⁴ is optionally substituted $C_{1-6}$ alkyl, such as methyl. In some embodiments, R⁵ is hydroxyl. In other embodiments, R³ is hydroxyl. In certain embodiments, R² is —O—CO—NH—R¹⁰. In some embodiments, R¹⁰ is H.

Disclosed herein are compounds of formula (I):

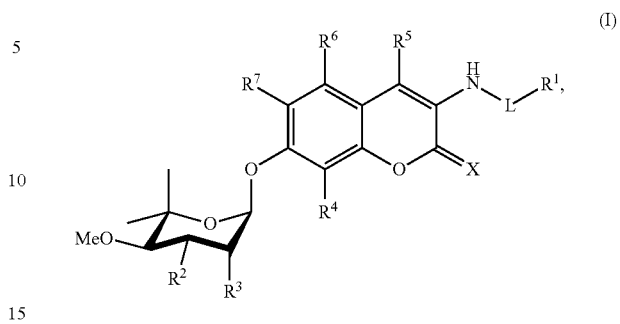

(I)

or a pharmaceutically acceptable salt thereof,
wherein
X is O or S;
L is —CO— or —SO₂—;
R¹ is unsubstituted phenyl, substituted phenyl, optionally substituted $C_{6-10}$ aryl $C_{1-4}$ alkyl, optionally substituted $C_{6-10}$ aryl $C_{2-4}$ alkenyl, o-phenylphenyl, optionally substituted $C_{3-10}$ cycloalkyl, optionally substituted $C_{1-9}$ heteroaryl comprising at least one nitrogen heteroatom within the heteroaryl ring system, benzofuryl, optionally substituted furyl, or —NHR⁸,
wherein the substituted phenyl is substituted:
(i) at one and only one of its meta position relative to L, with optionally substituted $C_{6-10}$ aryl, optionally substituted $C_{1-6}$ alkyl, optionally substituted $C_{3-6}$ alkenyl comprising an allylic carbon-carbon double bond, optionally substituted $C_{6-10}$ aryl $C_{1-4}$ alkyl, optionally substituted $C_{1-6}$ alkoxy, optionally substituted $C_{6-10}$ aryloxy, optionally substituted ($C_{6-10}$ aryl)-$C_{1-6}$ alkoxy, optionally substituted $C_{3-10}$ cycloalkyl, optionally substituted $C_{1-9}$ heteroaryl comprising at least one nitrogen heteroatom within the heteroaryl ring system, optionally substituted $C_{3-9}$ heterocyclyl, or —SF₅; or
(ii) at its para position relative to L with hydroxyl, optionally substituted $C_{6-10}$ aryl $C_{1-4}$ alkyl, optionally substituted $C_{6-10}$ aryl $C_{2-4}$ alkynyl, optionally substituted $C_{6-10}$ aryl, optionally substituted $C_{3-10}$ cycloalkyl, optionally substituted $C_{1-6}$ alkoxy, optionally substituted $C_{6-10}$ aryloxy, or optionally substituted ($C_{6-10}$ aryl)-$C_{1-6}$ alkoxy;
and, valency permitting, the substituted phenyl is further optionally substituted with 1, 2, 3, or 4 substituents independently selected from the group consisting of halogen, hydroxyl, —N(R⁹)₂, optionally substituted $C_{1-6}$ alkoxy, optionally substituted $C_{6-10}$ aryloxy, or optionally substituted $C_{6-10}$ aryl;
each of R² and R³ is independently hydroxyl, —O—CO—NH—R¹⁰, or —O—CO—R¹;
each of R⁴, R⁶, and R⁷ is independently hydrogen, halogen, optionally substituted $C_{1-6}$ alkyl, optionally substituted $C_{1-6}$ alkoxy, or optionally substituted $C_{6-10}$ aryl;
R⁵ is halogen, hydroxyl, or optionally substituted $C_{1-6}$ alkoxy;
R⁸ is optionally substituted $C_{6-10}$ aryl;
each R⁹ is independently H or optionally substituted $C_{1-6}$ alkyl;
R¹⁰, when present, is hydrogen, optionally substituted $C_{1-6}$ alkyl, optionally substituted $C_{3-10}$ cycloalkyl, or optionally substituted $C_{6-10}$ aryl; and
R¹¹, when present, is optionally substituted $C_{1-9}$ heteroaryl or optionally substituted $C_{6-10}$ aryl;
and wherein, when $R^5$ is hydroxyl, $R^1$ is substituted phenyl, optionally substituted $C_{6-10}$ aryl $C_{1-4}$ alkyl, optionally substituted $C_{6-10}$ aryl $C_{2-4}$ alkenyl, o-phenylphenyl, optionally substituted $C_{3-10}$ cycloalkyl, optionally substituted $C_{1-9}$ heteroaryl comprising at least one nitrogen heteroatom within the heteroaryl ring system, benzofuryl, or optionally substituted furyl, wherein the substituted phenyl is substituted, (i) at one and only one of its meta position relative to L, with optionally substituted $C_{6-10}$ aryl, substituted $C_{1-6}$ alkyl, substituted $C_{3-6}$ alkenyl comprising an allylic carbon-carbon double bond, optionally substituted $C_{6-10}$ aryl $C_{1-4}$ alkyl, optionally substituted $C_{1-6}$ alkoxy, optionally substituted $C_{6-10}$ aryloxy, optionally substituted ($C_{6-10}$ aryl)-$C_{1-6}$ alkoxy, optionally substituted $C_{3-10}$ cycloalkyl, optionally substituted $C_{1-9}$ heteroaryl comprising at least one nitrogen heteroatom within the heteroaryl ring system, optionally substituted $C_{3-9}$ heterocyclyl, or —$SF_5$; or (ii) at its para position relative to L, with hydroxyl, optionally substituted $C_{6-10}$ aryl $C_{1-4}$ alkyl, optionally substituted $C_{6-10}$ aryl $C_{2-4}$ alkynyl, optionally substituted $C_{6-10}$ aryl, optionally substituted $C_{3-10}$ cycloalkyl, optionally substituted $C_{1-6}$ alkoxy, optionally substituted $C_{6-10}$ aryloxy, or optionally substituted ($C_{6-10}$ aryl)-$C_{1-6}$ alkoxy;

and, valency permitting, the substituted phenyl is further optionally substituted with 1, 2, 3, or 4 substituents independently selected from the group consisting of halogen, hydroxyl, —$N(R^9)_2$, optionally substituted $C_{1-6}$ alkoxy, optionally substituted $C_{6-10}$ aryloxy, optionally substituted ($C_{6-10}$ aryl)-$C_{1-6}$ alkoxy, or optionally substituted $C_{6-10}$ aryl.

In some embodiments, L is —CO—. In other embodiments, X is O.

Disclosed herein are compounds of formula (IA):

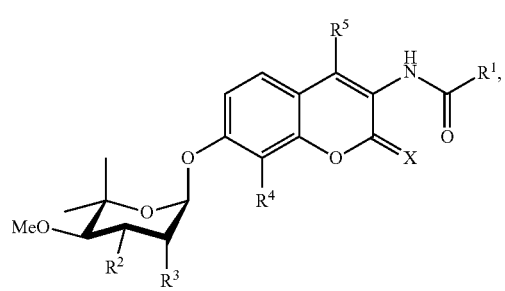

(IA)

or a pharmaceutically acceptable salt thereof. In some embodiments, $R^{11}$, when present, is optionally substituted $C_{1-9}$ heteroaryl.

Disclosed herein are compounds of formula (II):

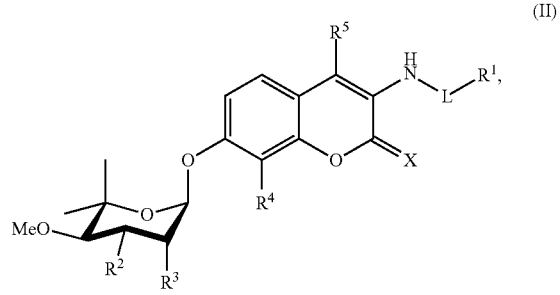

(II)

or a pharmaceutically acceptable salt thereof,
wherein
X is O or S;
L is —CO— or —$SO_2$—;
$R^1$ is unsubstituted phenyl, substituted phenyl, optionally substituted $C_{6-10}$ aryl $C_{1-4}$ alkyl, optionally substituted $C_{6-10}$ aryl $C_{2-4}$ alkenyl, o-phenylphenyl, optionally substituted $C_{3-10}$ cycloalkyl, optionally substituted $C_{1-9}$ heteroaryl comprising at least one nitrogen heteroatom within the heteroaryl ring system, benzofuryl, optionally substituted furyl, or —$NHR^8$,
wherein the substituted phenyl is substituted:
(i) at one and only one of its meta position relative to L, with optionally substituted $C_{6-10}$ aryl, optionally substituted $C_{1-6}$ alkyl, optionally substituted $C_{3-6}$ alkenyl comprising an allylic carbon-carbon double bond, optionally substituted $C_{6-10}$ aryl $C_{1-4}$ alkyl, optionally substituted $C_{1-6}$ alkoxy, optionally substituted $C_{6-10}$ aryloxy, optionally substituted ($C_{6-10}$ aryl)-$C_{1-6}$ alkoxy, optionally substituted $C_{3-10}$ cycloalkyl, optionally substituted $C_{1-9}$ heteroaryl comprising at least one nitrogen heteroatom within the heteroaryl ring system, optionally substituted $C_{3-9}$ heterocyclyl, or —$SF_5$; or
(ii) at its para position relative to L with hydroxyl, optionally substituted $C_{6-10}$ aryl $C_{1-4}$ alkyl, optionally substituted $C_{6-10}$ aryl $C_{2-4}$ alkynyl, optionally substituted $C_{6-10}$ aryl, optionally substituted $C_{3-10}$ cycloalkyl, optionally substituted $C_{1-6}$ alkoxy, or optionally substituted $C_{6-10}$ aryloxy;
and, valency permitting, the substituted phenyl is further optionally substituted with 1, 2, 3, or 4 substituents independently selected from the group consisting of halogen, hydroxyl, —$N(R^9)_2$, optionally substituted $C_{1-6}$ alkoxy, optionally substituted $C_{6-10}$ aryloxy, or optionally substituted $C_{6-10}$ aryl;
each of $R^2$ and $R^3$ is independently hydroxyl, —O—CO—NH—$R^{10}$, or —O—CO—$R^{11}$, provided that at least one of $R^2$ and $R^3$ is —O—CO—NH—$R^{10}$ or —O—CO—$R^{11}$;
$R^4$ is hydrogen, halogen, optionally substituted $C_{1-6}$ alkyl, optionally substituted $C_{1-6}$ alkoxy, or optionally substituted $C_{6-10}$ aryl;
$R^5$ is halogen, hydroxyl, or optionally substituted $C_{1-6}$ alkoxy;
$R^8$ is optionally substituted $C_{6-10}$ aryl;
each $R^9$ is independently H or optionally substituted $C_{1-6}$ alkyl;
$R^{10}$, when present, is hydrogen, optionally substituted $C_{2-6}$ alkyl, optionally substituted $C_{3-10}$ cycloalkyl; or optionally substituted $C_{6-10}$ aryl; and
$R^{11}$, when present, is optionally substituted $C_{1-9}$ heteroaryl that is not 5-methyl-pyrrol-2-yl, 2-indolyl, or 3-indolyl.

In some embodiments, L is —CO—. In certain embodiments, X is O. In some embodiments, one and only one of $R^2$ and $R^3$ is —O—CO—NH—$R^{10}$ or —O—CO—$R^{11}$. In other embodiments, $R^3$ is —O—CO—NH—$R^{10}$ or —CO—$R^{11}$. In some embodiments, $R^{10}$, when present, is hydrogen, optionally substituted $C_{3-10}$ cycloalkyl; or optionally substituted $C_{6-10}$ aryl.

In some embodiments, one and only one of $R^2$ and $R^3$ is:

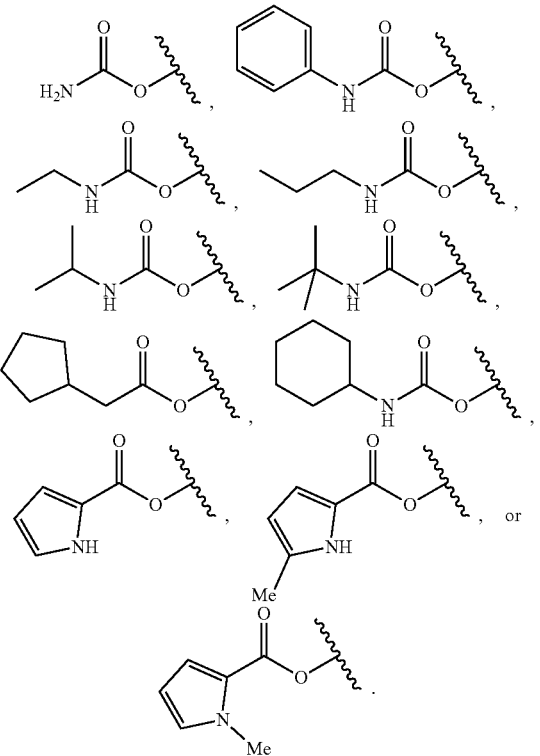

In other embodiments, one and only one of $R^2$ and $R^3$ is:

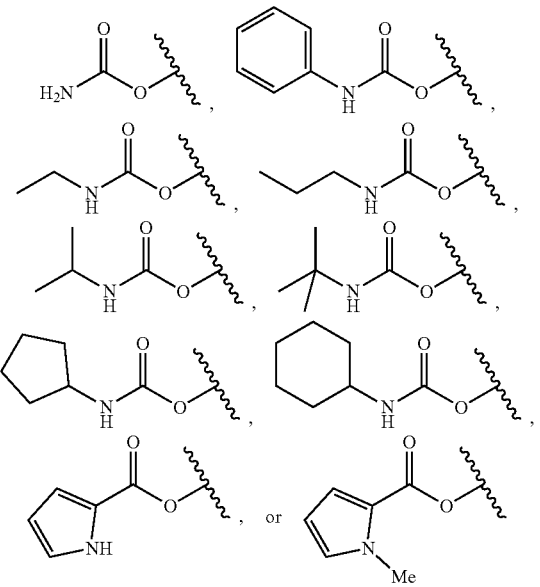

In certain embodiments, $R^3$ is:

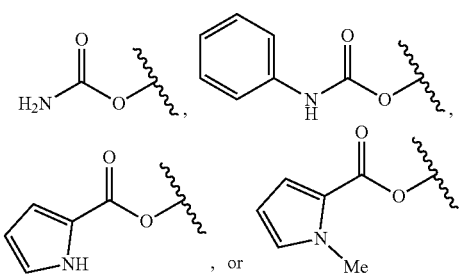

In certain embodiments, $R^2$ is:

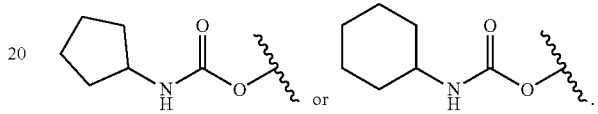

In some embodiments, $R^2$ is hydroxyl.

In some embodiments, $R^1$ is a substituted phenyl. In certain embodiments, the substituted phenyl is substituted at one and only one of its meta position relative to L, with optionally substituted $C_{6-10}$ aryl, optionally substituted $C_{1-6}$ alkyl, optionally substituted $C_{3-6}$ alkenyl comprising an allylic carbon-carbon double bond, optionally substituted $C_{6-10}$ aryl $C_{1-4}$ alkyl, optionally substituted $C_{1-6}$ alkoxy, optionally substituted $C_{6-10}$ aryloxy, optionally substituted ($C_{6-10}$ aryl)-$C_{1-6}$ alkoxy, optionally substituted $C_{3-10}$ cycloalkyl, optionally substituted $C_{1-9}$ heteroaryl comprising at least one nitrogen heteroatom within the heteroaryl ring system, optionally substituted $C_{3-9}$ heterocyclyl, or —$SF_5$; and, valency permitting, the substituted phenyl is further optionally substituted with 1, 2, 3, or 4 substituents independently selected from the group consisting of halogen, hydroxyl, —N(R')$_2$, optionally substituted $C_{1-6}$ alkoxy, optionally substituted $C_{6-10}$ aryloxy, optionally substituted ($C_{6-10}$ aryl)-$C_{1-6}$ alkoxy, or optionally substituted $C_{6-10}$ aryl.

In certain embodiments, $R^1$ is:

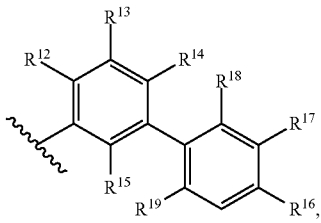

wherein
each of $R^{12}$, $R^{14}$, and $R^{15}$ is independently hydrogen, —N(R$^9$)$_2$, hydroxyl, halogen, or $C_{1-6}$ alkoxy;
$R^{13}$ is hydrogen, —N(R$^9$)$_2$, hydroxyl, halogen, $C_{1-6}$ alkoxy, or ($C_{6-10}$ aryl)-$C_{1-6}$ alkoxy;
$R^{19}$ is hydrogen, hydrogen, —N(R$^9$)$_2$, hydroxyl, halogen, nitro, optionally substituted $C_{1-6}$ alkyl, or optionally substituted $C_{1-6}$ alkoxy; and
(i) $R^{16}$ is hydrogen, —N(R$^9$)$_2$, hydroxyl, halogen, nitro, optionally substituted $C_{1-6}$ alkyl, or optionally substituted $C_{1-6}$ alkoxy; and each of $R^{17}$ and $R^{18}$ is independently hydrogen, $-N(R^9)_2$, hydroxyl, halogen, optionally substituted $C_{1-6}$ alkyl, or optionally substituted $C_{1-6}$ alkoxy; or $R^7$ and $R^{18}$, together with the ring to which they are attached, combine to form:

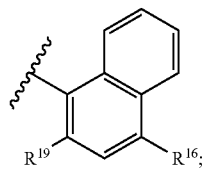

or (ii) $R^8$ is hydrogen, $-N(R^9)_2$, hydroxyl, halogen, nitro, optionally substituted $C_{1-6}$ alkyl, or optionally substituted $C_{1-6}$ alkoxy; and $R^{16}$ and $R^{17}$, together with the ring to which they are attached, combine to form:

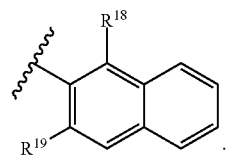

In some embodiments, $R^{12}$ is hydrogen or hydroxyl. In other embodiments, $R^{13}$ is hydrogen or hydroxyl. In certain embodiments, $R^{14}$ is hydrogen, hydroxyl, or $-N(R^9)_2$. In other embodiments, $R^{15}$ is hydrogen or hydroxyl. In some embodiments, $R^{16}$ is hydrogen, $-N(R^9)_2$, hydroxyl, halogen, optionally substituted $C_{1-6}$ alkyl, or optionally substituted $C_{1-6}$ alkoxy. In some embodiments, $R^{17}$ is hydrogen, halogen, optionally substituted $C_{1-6}$ alkyl, or optionally substituted $C_{1-6}$ alkoxy. In some embodiments, $R^{18}$ is hydrogen, halogen, optionally substituted $C_{1-6}$ alkyl, or optionally substituted $C_{1-6}$ alkoxy.

In some embodiments, $R^{16}$ and $R^{17}$, together with the ring to which they are attached, combine to form:

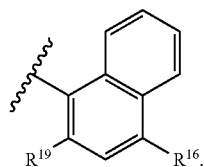

In other embodiments, $R^{17}$ and $R^{18}$, together with the ring to which they are attached, combine to form:

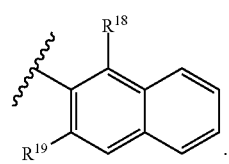

In some embodiments, $R^{19}$ is hydrogen, halogen, nitro, or optionally substituted $C_{1-6}$ alkyl.

In some embodiments, $R^1$ is:

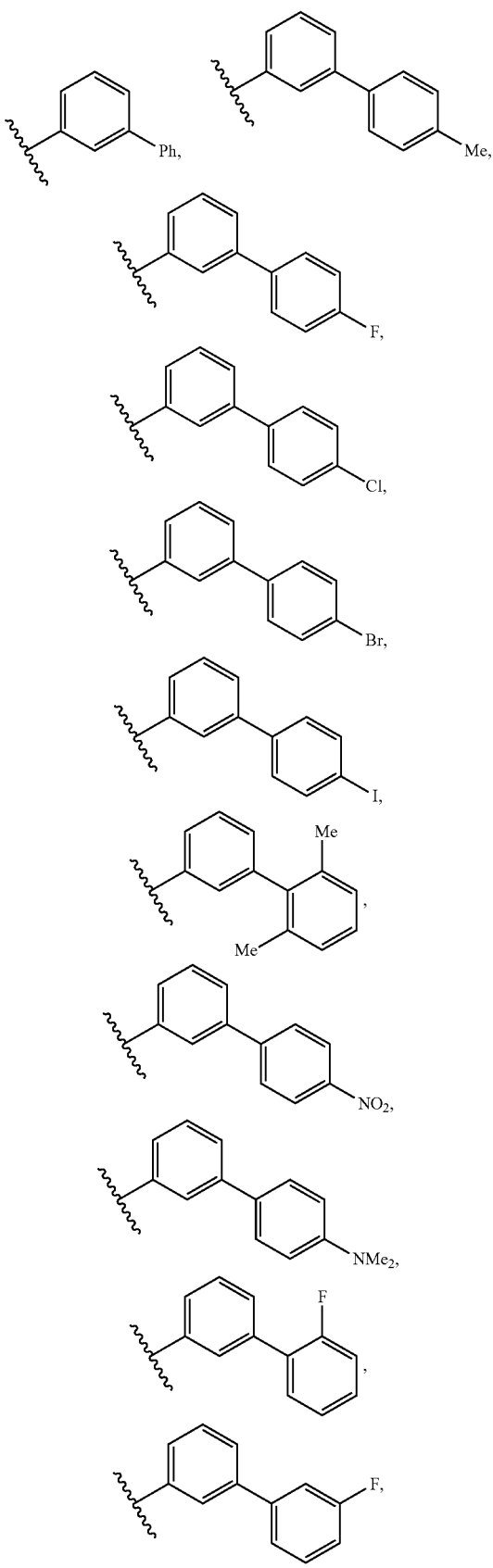

-continued
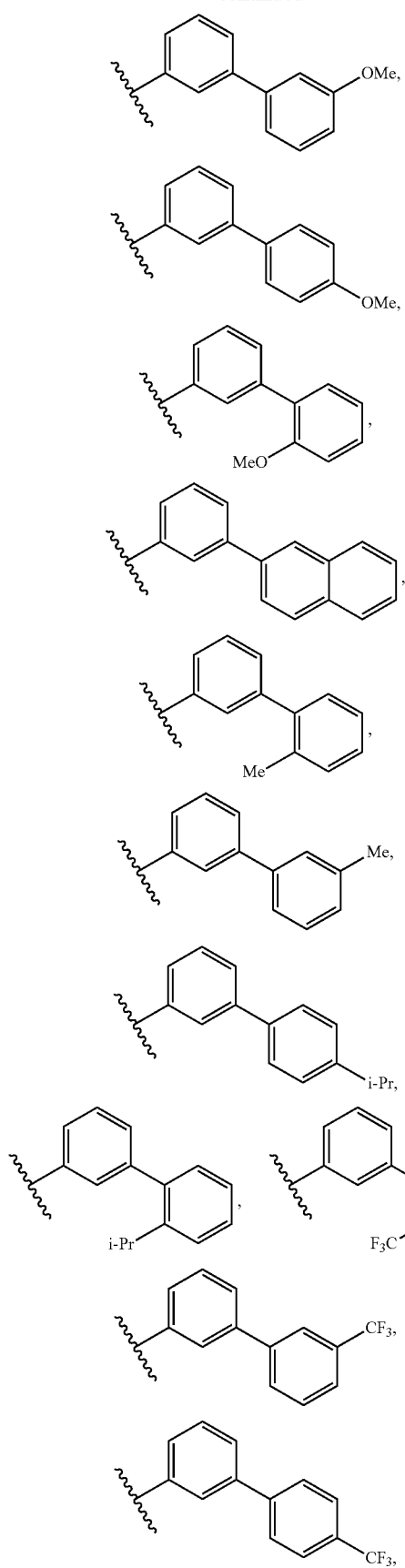
-continued
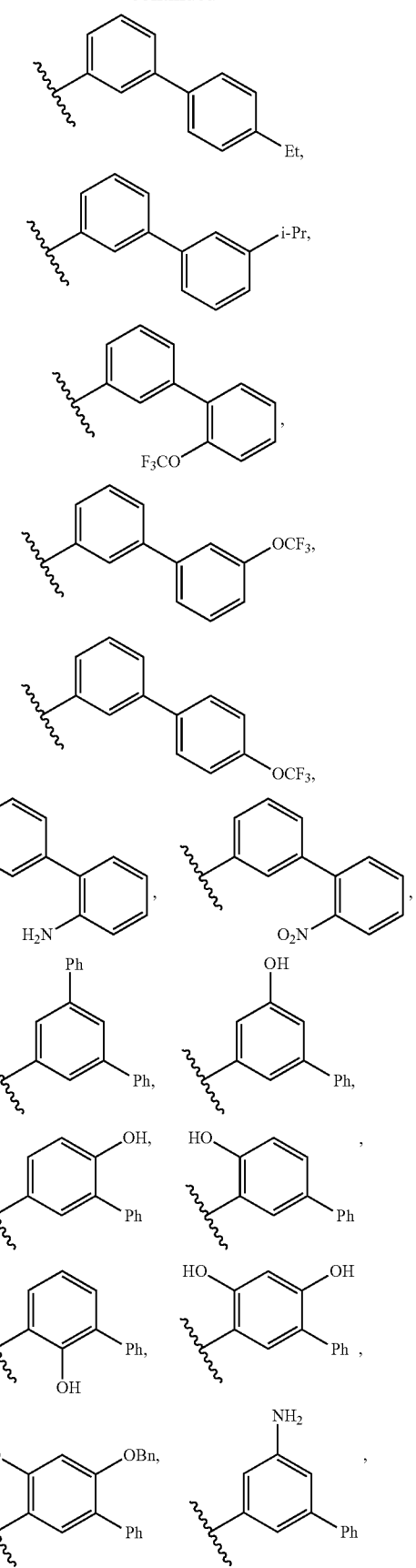

-continued
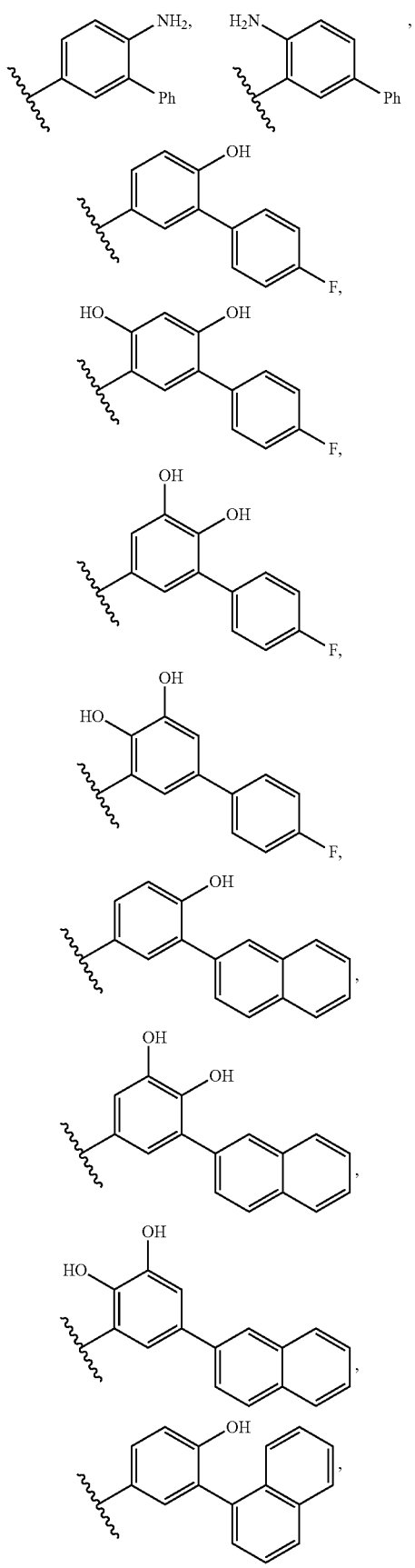
-continued
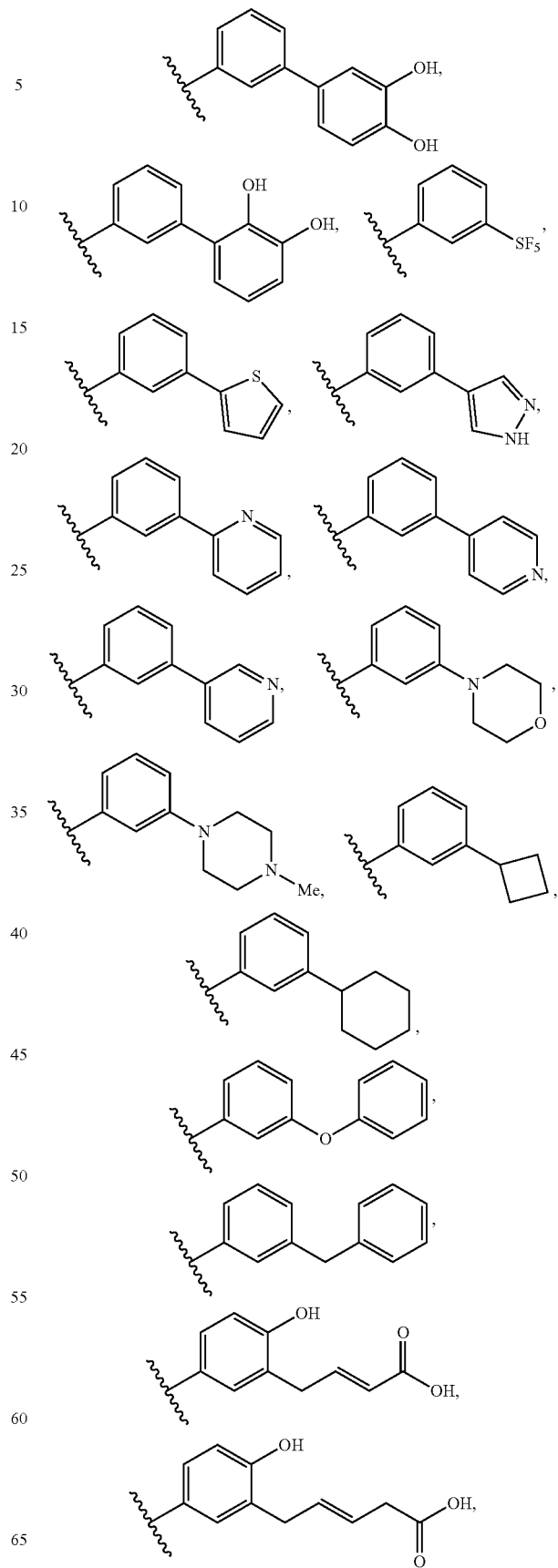

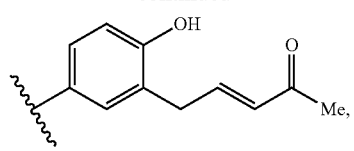
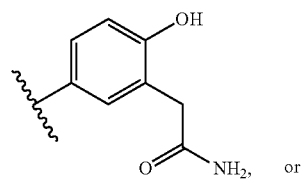 or
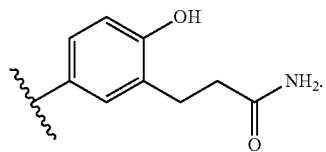
In some embodiments, $R^1$ is:
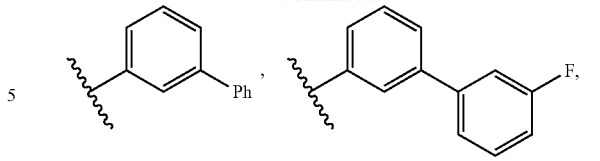
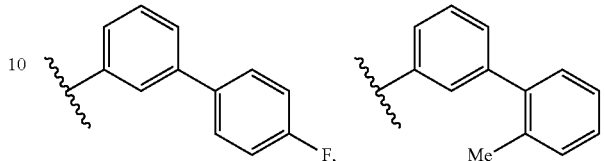
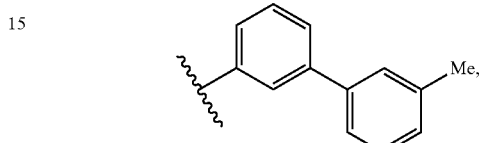
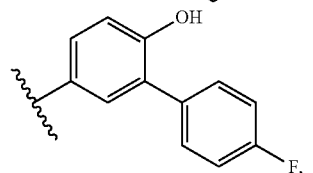
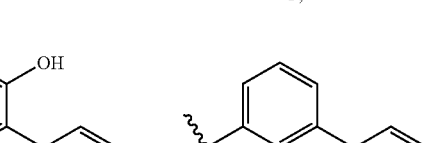
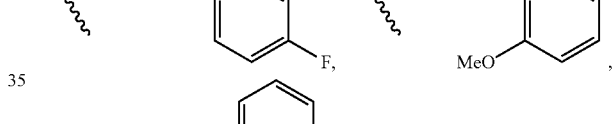
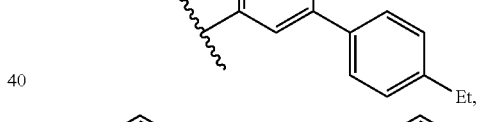
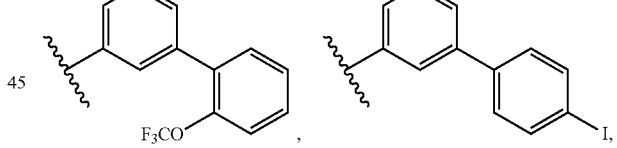
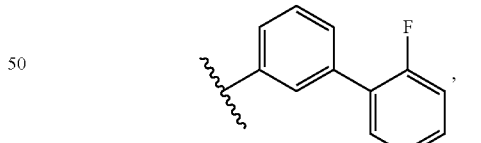
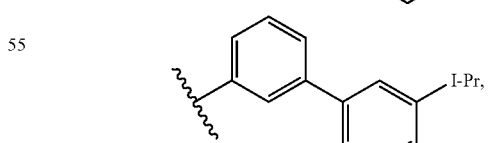
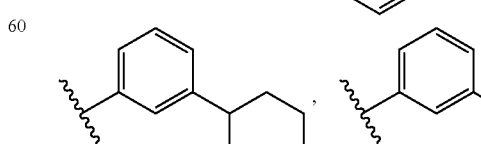
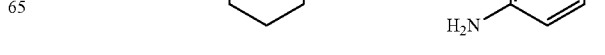

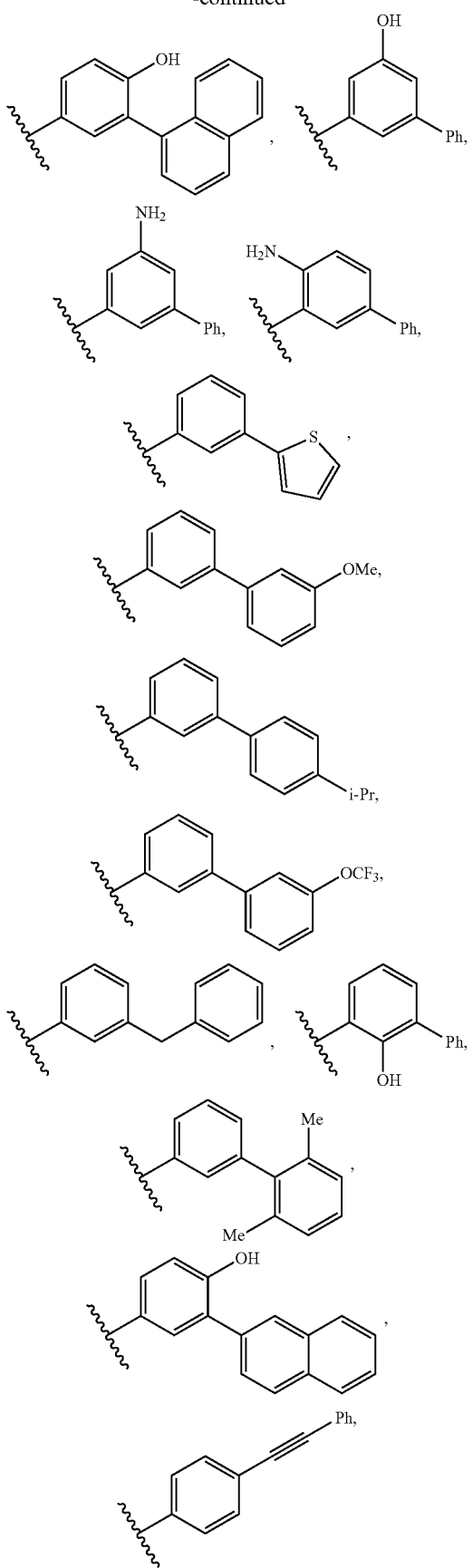
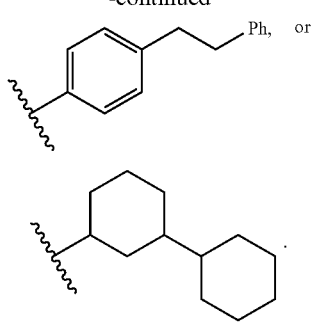
In some embodiments, $R^1$ is:
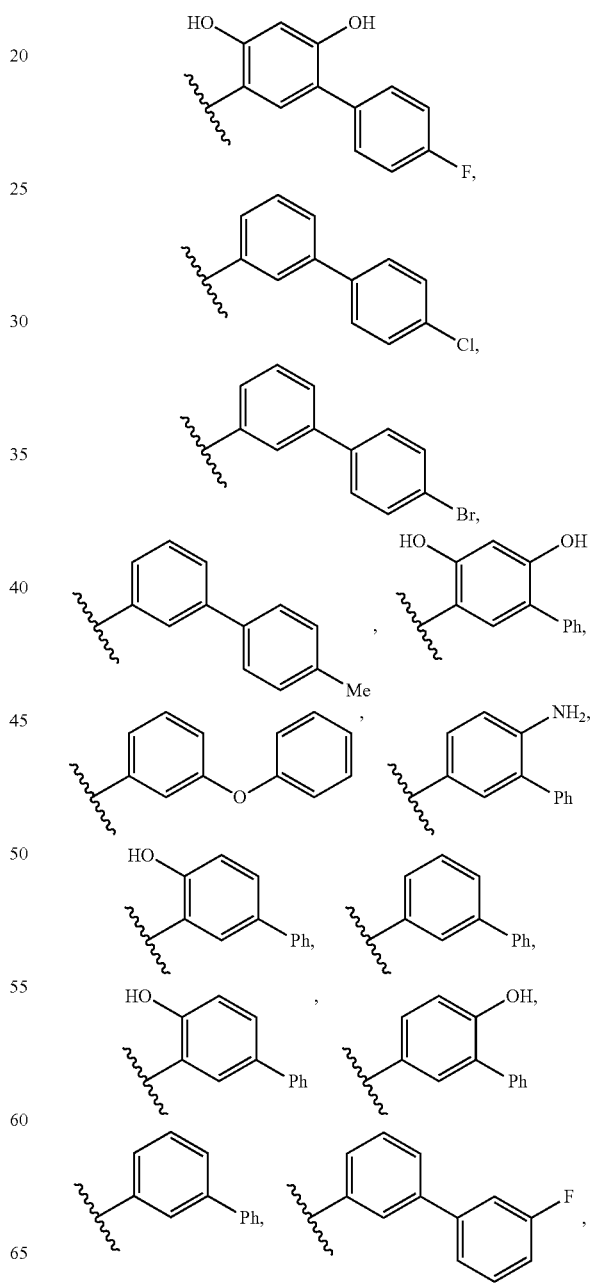

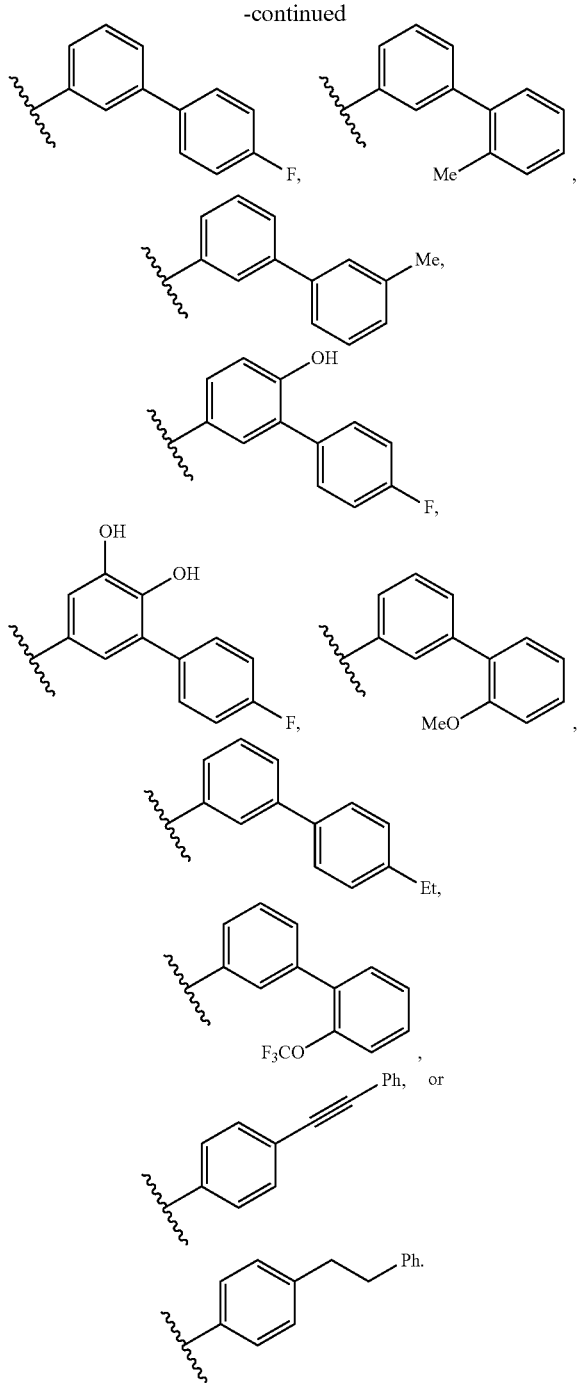

In some embodiments, $R^4$ is optionally substituted $C_{1-6}$ alkyl. In other embodiments, $R^5$ is hydroxyl.

Disclosed herein are pharmaceutical compositions comprising a compound of the invention and a pharmaceutically acceptable excipient. In some embodiments, the pharmaceutical compositions further comprise a polymyxin compound or a pharmaceutically acceptable salt thereof. In some embodiments, the polymyxin compound is polymyxin B or a salt thereof. In other embodiments, the polymyxin compound is polymyxin E or a salt thereof.

Disclosed herein are methods of treating a subject having a Gram-negative bacterial infection, the method comprising administering to the subject an effective amount of the compound or pharmaceutical composition of the invention. In some embodiments, the compound or a pharmaceutically acceptable salt thereof is administered parenterally, orally, intranasally, or topically.

In certain embodiments, the method further comprises administering an effective amount of a polymyxin or a pharmaceutically acceptable salt thereof. In some embodiments, the polymyxin or a pharmaceutically acceptable salt thereof is polymyxin B or a pharmaceutically acceptable salt thereof. In other embodiments, the polymyxin or a pharmaceutically acceptable salt thereof is polymyxin E or a pharmaceutically acceptable salt thereof. In certain embodiments, the polymyxin or a pharmaceutically acceptable salt thereof is administered parenterally, orally, intranasally, or topically.

In some embodiments, the polymyxin or pharmaceutically acceptable salt thereof is administered one or more times per day, one or more times per week, or one or more times per month. In other embodiments, the compound or a pharmaceutically acceptable salt thereof and the polymyxin or a pharmaceutically acceptable salt thereof are administered within 60 minutes of each other. In certain embodiments, the compound or a pharmaceutically acceptable salt thereof and the polymyxin or a pharmaceutically acceptable salt thereof are administered within one to 24 hours of each other.

In some embodiments, the compound or a pharmaceutically acceptable salt thereof and the polymyxin or a pharmaceutically acceptable salt thereof are administered within one to seven days of each other. In other embodiments, the compound or a pharmaceutically acceptable salt thereof and the polymyxin or a pharmaceutically acceptable salt thereof are administered within one to four weeks of each other. In certain embodiments, the compound or a pharmaceutically acceptable salt thereof and the polymyxin or a pharmaceutically acceptable salt thereof are administered by the same route of administration. In other embodiments, the compound or a pharmaceutically acceptable salt thereof and the polymyxin or a pharmaceutically acceptable salt thereof are administered by different routes of administration.

In some embodiments, the Gram-negative bacterial infection is a urinary tract infection, meningeal infection, eye infection, lung infection, or bacteremia. In other embodiments, the Gram-negative bacterial infection is caused by a non-opportunistic, pathogenic, Gram-negative bacterium. In certain embodiments, the Gram-negative bacterial infection is caused by a Gram-negative bacterium belonging to:

(i) a phylum selected from the group consisting of Acidobacteria, Aquificae, Chlamydiae, Bacteroidetes, Chlorobi, Cyanobacteria, Fibrobacteres, Verrucomicrobia, Planctomycetes, and Spirochetes;

(ii) a class selected from the group consisting of Alphaproteobacteria, Epsilonproteobacteria, Deltaproteobacteria, and Gammaproteobacteria; or (iii) an order selected from the group consisting of Hydrogenophilales, Methylophilales, Neisseriales, Nitrosomonadales, Procabacteriales, and Rhodocyclales.

In some embodiments, the Gram-negative bacterial infection is caused by *Klebsiella pneumoniae, Acinetobacter baumannii, Pseudomonas aeruginosa, Escherichia coli*, or an *Enterobacter* spp. In other embodiments, the method is effective at substantially reducing or eliminating the bacterial infection.

Disclosed herein are methods of producing a compound of formula (III) from a compound of formula (IIIA):

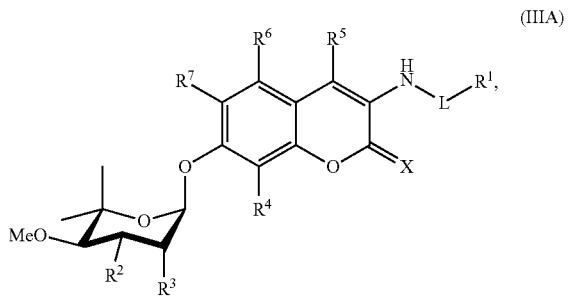

(IIIA)

or a salt thereof,
wherein
X is O or S;
L is —CO— or —SO$_2$—;
R$^1$ is substituted phenyl or benzofuryl,
  wherein the substituted phenyl is substituted:
  (i) at one and only one of its meta position relative to L, with:
    C$_{1-6}$ alkyl substituted with aryloxy, arylalkoxy, cycloalkyl, cycloalkoxy, heterocyclyl, heteroaryl, heterocyclyloxy, heteroaryloxy, nitro, thiol, =S, or —NR$^y{}_2$, where each R$^y$ is independently aryl, arylalkyl, cycloalkyl, heterocyclyl, or heteroaryl;
    C$_{3-6}$ alkenyl comprising an allylic carbon-carbon double bond and substituted with aryloxy, arylalkoxy, cycloalkyl, cycloalkoxy, heterocyclyl, heteroaryl, heterocyclyloxy, heteroaryloxy, nitro, thiol, =S, or —NR$^y{}_2$, where each R$^y$ is independently aryl, arylalkyl, cycloalkyl, heterocyclyl, or heteroaryl;
    optionally substituted C$_{6-10}$ aryloxy;
    optionally substituted (C$_{6-10}$ aryl)-C$_{1-6}$ alkoxy;
    optionally substituted C$_{3-10}$ cycloalkyl;
    optionally substituted C$_{1-9}$ heteroaryl comprising at least one nitrogen heteroatom within the heteroaryl ring system;
    optionally substituted C$_{3-9}$ heterocyclyl; or
    —SF$_5$; or
  (ii) at its para position relative to L, with optionally substituted C$_{6-10}$ aryl C$_{1-4}$ alkyl, optionally substituted C$_{6-10}$ aryl C$_{2-4}$ alkynyl, optionally substituted C$_{3-10}$ cycloalkyl, or optionally substituted (C$_{6-10}$ aryl)-C$_{1-6}$ alkoxy;
  and, valency permitting, the substituted phenyl is further optionally substituted with 1, 2, 3, or 4 substituents independently selected from the group consisting of halogen, hydroxyl, —N(R$^9$)$_2$, optionally substituted C$_{1-6}$ alkoxy, optionally substituted C$_{6-10}$ aryloxy, optionally substituted (C$_{6-10}$ aryl)-C$_{1-6}$ alkoxy, or optionally substituted C$_{6-10}$ aryl;
each of R$^2$ and R$^3$ is hydroxyl;
each of R$^4$, R$^6$, and R$^7$ is independently hydrogen, halogen, optionally substituted C$_{1-6}$ alkyl, optionally substituted C$_{1-6}$ alkoxy, or optionally substituted C$_{6-10}$ aryl;
R$^5$ is halogen, hydroxyl, or optionally substituted C$_{1-6}$ alkoxy; and
R$^8$ is optionally substituted C$_{6-10}$ aryl;
the method comprising producing a compound of formula (III) from the compound of formula (IIIA) and R$^{10}$—N=C=O, wherein R$^{10}$ is optionally substituted C$_{1-6}$ alkyl, optionally substituted C$_{3-10}$ cycloalkyl, or optionally substituted C$_{6-10}$ aryl; wherein the compound of formula (III) is:

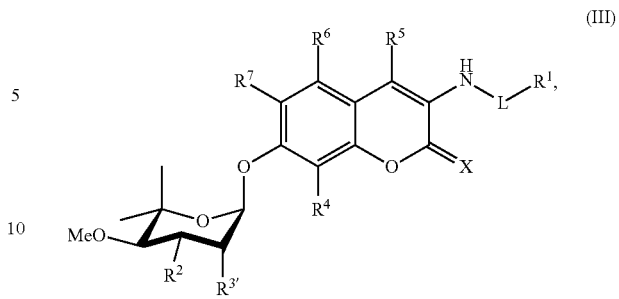

(III)

or a salt thereof,
wherein R$^{3'}$ is —O—CO—NH—R$^{10}$.

In some embodiments, the method comprises reacting the compound of formula (IIIA) with (i) MoO$_2$Cl$_2$ and (ii) optionally substituted C$_{1-6}$ alkyl isocyanate, optionally substituted C$_{3-10}$ cycloalkyl isocyanate, or optionally substituted C$_{6-10}$ aryl isocyanate.

Disclosed herein are methods of producing a compound of formula (IV) from a compound of formula (IVA):

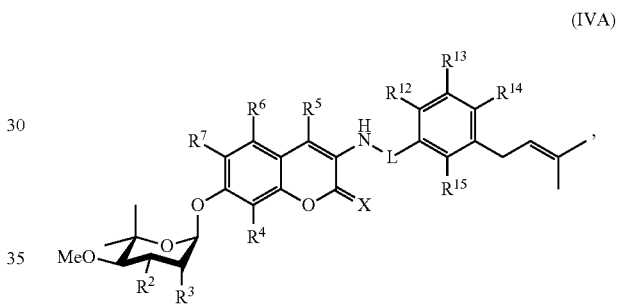

(IVA)

or a salt thereof,
wherein
X is O or S;
L is —CO— or —SO$_2$—;
each of R$^2$ and R$^3$ is independently hydroxyl, —O—CO—NH—R$^{10}$, or —O—CO—R$^{11}$;
each of R$^4$, R$^6$, and R$^7$ is independently hydrogen, halogen, optionally substituted C$_{1-6}$ alkyl, optionally substituted C$_{1-6}$ alkoxy, or optionally substituted C$_{6-10}$ aryl;
R$^5$ is halogen, hydroxyl, or optionally substituted C$_{1-6}$ alkoxy;
each R$^9$ is independently H or optionally substituted C$_{1-6}$ alkyl;
R$^{10}$, when present, is hydrogen, optionally substituted C$_{1-6}$ alkyl, optionally substituted C$_{3-10}$ cycloalkyl, or optionally substituted C$_{6-10}$ aryl;
R$^{11}$, when present, is optionally substituted C$_{1-9}$ heteroaryl or optionally substituted C$_{6-10}$ aryl;
each of R$^{12}$, R$^{14}$, and R$^{15}$ is independently hydrogen, —N(R$^9$)$_2$, hydroxyl, halogen, or C$_{1-6}$ alkoxy;
R$^{13}$ is hydrogen, —N(R$^9$)$_2$, hydroxyl, halogen, C$_{1-6}$ alkoxy, or (C$_{6-10}$ aryl)-C$_{1-6}$ alkoxy; the method comprising producing a compound of formula (IV) from the compound of formula (IVA) and R$^{20}$—CH=CH$_2$, wherein R$^{20}$ is optionally substituted C$_{1-6}$ alkyl, optionally substituted C$_{3-10}$ cycloalkyl, or optionally substituted C$_{6-10}$ aryl; wherein the compound of formula (IV) is:

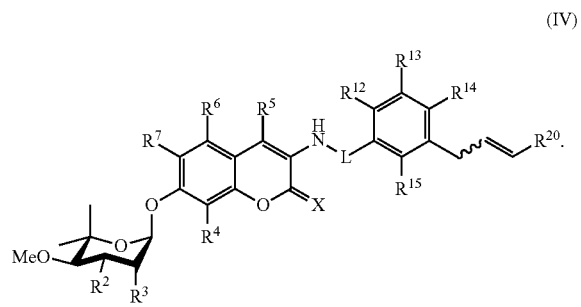

or a salt thereof.

In some embodiments, the method comprises reacting the compound of formula (IVA) with $R^{20}$—CH=$CH_2$ and an olefin metathesis catalyst. In other embodiments, the olefin metathesis catalyst is Hoveyda-Grubbs $2^{nd}$ generation catalyst or Grubbs $2^{nd}$ generation catalyst.

Exemplary aminocoumarin compounds are provided in Tables 1A and 1B.

TABLE 1A.

| Compound | $R^1$ | $R^2$ | $R^3$ |
|---|---|---|---|
| 1 | 3-Ph-phenyl | —OC(O)$NH_2$ | —OH |
| 2 | 4-Ph-phenyl | —OC(O)$NH_2$ | —OH |
| 3 | NH-(3-Ph-phenyl) | —OC(O)$NH_2$ | —OH |
| 4 | 2-naphthyl | —OC(O)$NH_2$ | —OH |
| 5 | CHPh$_2$ | —OC(O)$NH_2$ | —OH |
| 6 | benzofuran-2-yl | —OC(O)$NH_2$ | —OH |

TABLE 1A.-continued
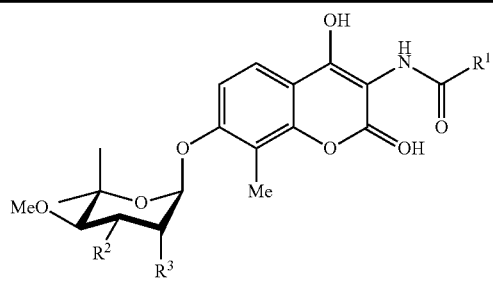
| Compound | R¹ | R² | R³ |
|---|---|---|---|
| 7 | 4-MeO-phenyl | —OC(O)NH₂ | —OH |
| 8 | Ph | —OC(O)NH₂ | —OH |
| 9 | 3,4-diMeO-phenyl | —OC(O)NH₂ | —OH |
| 10 | 2,6-diMeO-phenyl | —OC(O)NH₂ | —OH |
| 11 | 3,4,5-triMeO-phenyl | —OC(O)NH₂ | —OH |
| 12 | 5-Me-furan-2-yl | —OC(O)NH₂ | —OH |
| 13 | Cyclopropyl | —OC(O)NH₂ | —OH |
| 13A | 1-fluorocyclopropyl | —OC(O)NH₂ | —OH |
| 14 | 1-adamantyl | —OC(O)NH₂ | —OH |
| 15 | 2-pyrrolyl | —OC(O)NH₂ | —OH |
| 16 | 2-indolyl | —OC(O)NH₂ | —OH |
| 17 | 3-indolyl | —OC(O)NH₂ | —OH |
| 18 | 3-(1H-pyrazol-4-yl)phenyl | —OC(O)NH₂ | —OH |

TABLE 1A.-continued

| Compound | R¹ | R² | R³ |
|---|---|---|---|
| 20 | 4'-methyl-biphenyl-3-yl | —OC(O)NH₂ | —OH |
| 21 | 2',6'-dimethyl-biphenyl-3-yl | —OC(O)NH₂ | —OH |
| 22 | 3-(thiophen-2-yl)phenyl | —OC(O)NH₂ | —OH |
| 23 | 3-morpholinophenyl | —OC(O)NH₂ | —OH |
| 24 | 4'-nitro-biphenyl-3-yl | —OC(O)NH₂ | —OH |
| 25 | 4'-(dimethylamino)-biphenyl-3-yl | —OC(O)NH₂ | —OH |
| 26 | 3-(SF₅)phenyl | —OC(O)NH₂ | —OH |

TABLE 1A.-continued
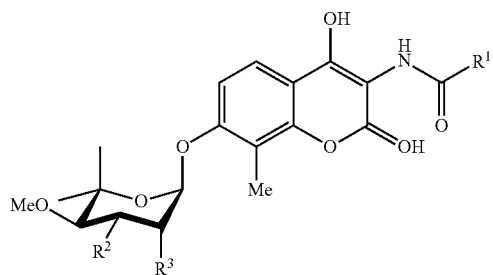
| Compound | R¹ | R² | R³ |
|---|---|---|---|
| 27 | cinnamyl (PhCH=CH-CH<) | —OC(O)NH$_2$ | —OH |
| 28 | 4'-fluoro-biphenyl-3-yl | —OC(O)NH$_2$ | —OH |
| 29 | 3-(pyridin-3-yl)phenyl | —OC(O)NH$_2$ | —OH |
| 30 | 4-hydroxyphenyl | —OC(O)NH$_2$ | —OH |
| 31 | 3-(pyridin-2-yl)phenyl | —OC(O)NH$_2$ | —OH |
| 32 | 3-(pyridin-4-yl)phenyl | —OC(O)NH$_2$ | —OH |
| 33 | 4'-chloro-biphenyl-3-yl | —OC(O)NH$_2$ | —OH |

TABLE 1A.-continued

| Compound | R¹ | R² | R³ |
|---|---|---|---|
| 34 | 3-(4-iodophenyl)phenyl | —OC(O)NH₂ | —OH |
| 35 | 3-phenoxyphenyl | —OC(O)NH₂ | —OH |
| 37 | 2'-fluorobiphenyl-3-yl | —OC(O)NH₂ | —OH |
| 38 | 3'-fluorobiphenyl-3-yl | —OC(O)NH₂ | —OH |
| 39 | 3-(naphthalen-2-yl)phenyl | —OC(O)NH₂ | —OH |
| 40 | 2-phenylphenyl | —OC(O)NH₂ | —OH |
| 41 | 4-cyclohexylphenyl | —OC(O)NH₂ | —OH |
| 42 | Benzyl | —OC(O)NH₂ | —OH |
| 43 | 2-phenethyl | —OC(O)NH₂ | —OH |

TABLE 1A.-continued

| Compound | R¹ | R² | R³ |
|---|---|---|---|
| 44 | 4-phenoxyphenyl | —OC(O)NH₂ | —OH |
| 45 | 3'-methoxy-[1,1'-biphenyl]-3-yl | —OC(O)NH₂ | —OH |
| 46 | 4'-methoxy-[1,1'-biphenyl]-3-yl | —OC(O)NH₂ | —OH |
| 47 | 2'-methyl-[1,1'-biphenyl]-3-yl | —OC(O)NH₂ | —OH |
| 48 | 4'-isopropyl-[1,1'-biphenyl]-3-yl | —OC(O)NH₂ | —OH |
| 49 | 2'-isopropyl-[1,1'-biphenyl]-3-yl | —OC(O)NH₂ | —OH |
| 50 | 2'-methoxy-[1,1'-biphenyl]-3-yl | —OC(O)NH₂ | —OH |

TABLE 1A.-continued

| Compound | R¹ | R² | R³ |
|---|---|---|---|
| 51 | 3'-methyl-biphenyl-3-yl | —OC(O)NH$_2$ | —OH |
| 52 | 3-(4-methylpiperazin-1-yl)phenyl | —OC(O)NH$_2$ | —OH |
| 53 | 3-cyclobutylphenyl | —OC(O)NH$_2$ | —OH |
| 54 | 4'-ethyl-biphenyl-3-yl | —OC(O)NH$_2$ | —OH |
| 55 | 4'-trifluoromethyl-biphenyl-3-yl | —OC(O)NH$_2$ | —OH |
| 56 | 3'-trifluoromethyl-biphenyl-3-yl | —OC(O)NH$_2$ | —OH |
| 57 | 4'-trifluoromethoxy-biphenyl-3-yl | —OC(O)NH$_2$ | —OH |

TABLE 1A.-continued

| Compound | R¹ | R² | R³ |
| --- | --- | --- | --- |
| 58 | 3-(3-trifluoromethoxyphenyl)phenyl | —OC(O)NH₂ | —OH |
| 59 | 3-(2-trifluoromethoxyphenyl)phenyl | —OC(O)NH₂ | —OH |
| 60 | 3-(2-trifluoromethylphenyl)phenyl | —OC(O)NH₂ | —OH |
| 61 | 3-(3-isopropylphenyl)phenyl | —OC(O)NH₂ | —OH |
| 62 | 3-cyclohexylphenyl | —OC(O)NH₂ | —OH |
| 63 | 3-cyclohexylcyclohexyl | —OC(O)NH₂ | —OH |
| 64 | 3-(2-nitrophenyl)phenyl | —OC(O)NH₂ | —OH |

TABLE 1A.-continued

[Structure: coumarin core with OH, NHC(=O)R¹, Me, and sugar (MeO, R², R³) substituents]

| Compound | R¹ | R² | R³ |
|---|---|---|---|
| 65 | 3-(2-aminophenyl)phenyl (biphenyl with H₂N at ortho position of distal ring) | —OC(O)NH₂ | —OH |
| 66 | 2,5-bis(benzyloxy)-4-phenylphenyl (BnO, OBn, Ph substituents) | —OC(O)NH₂ | —OH |
| 67 | 2,5-dihydroxy-4-phenylphenyl (HO, OH, Ph) | —OC(O)NH₂ | —OH |
| 68 | 3-(4-bromophenyl)phenyl (biphenyl with Br) | —OC(O)NH₂ | —OH |
| 69 | 3-benzylphenyl | —OC(O)NH₂ | —OH |
| 70 | 1-methyl-1H-indol-6-yl (N-Me) | —OC(O)NH₂ | —OH |
| 71 | 1-methyl-1H-indol-6-yl (N-Me), hydrochloride salt | —OC(O)NH₂ | —OH |
| 72 | 1-methyl-1H-indol-5-yl (N-Me) | —OC(O)NH₂ | —OH |

TABLE 1A.-continued

| Compound | R¹ | R² | R³ |
| --- | --- | --- | --- |
| 73 | 5-(1-methylindolyl), hydrochloride salt | —OC(O)NH₂ | —OH |
| 74 | 7-(1-methylindolyl) | —OC(O)NH₂ | —OH |
| 75 | 3,5-diphenylphenyl | —OC(O)NH₂ | —OH |
| 76 | 4-(phenylethynyl)phenyl | —OC(O)NH₂ | —OH |
| 77 | 4-(2-phenylethyl)phenyl | —OC(O)NH₂ | —OH |
| 78 | 3-hydroxy-5-phenylphenyl | —OC(O)NH₂ | —OH |

TABLE 1A.-continued

| Compound | R¹ | R² | R³ |
|---|---|---|---|
| 79 | 4'-fluoro-2-hydroxy-[1,1'-biphenyl]-5-yl | —OC(O)NH₂ | —OH |
| 80 | (E)-5-(2-hydroxyphenyl)pent-3-enoic acid-2-yl | —OC(O)NH₂ | —OH |
| 81 | (E)-1-(2-hydroxyphenyl)pent-3-en-4-on-2-yl (with Me ketone) | —OC(O)NH₂ | —OH |
| 82 | (E)-4-(2-hydroxyphenyl)but-2-enoic acid-4-yl | —OC(O)NH₂ | —OH |
| 83 | 2-hydroxy-3-phenylphenyl (4-yl) | —OC(O)NH₂ | —OH |
| 84 | 4'-fluoro-2,4-dihydroxy-[1,1'-biphenyl]-5-yl | —OC(O)NH₂ | —OH |
| 85 | 4-amino-3-phenylphenyl | —OC(O)NH₂ | —OH |
| 86 | 4-amino-3-phenylphenyl (isomer) | —OC(O)NH₂ | —OH |

TABLE 1A.-continued

| Compound | R¹ | R² | R³ |
|---|---|---|---|
| 87 | 2-hydroxy-5-phenylphenyl | —OC(O)NH₂ | —OH |
| 88 | 2-hydroxy-3-phenylphenyl | —OC(O)NH₂ | —OH |
| 89 | 3-amino-5-phenylphenyl | —OC(O)NH₂ | —OH |
| 90 | 4-hydroxy-3-(carbamoylmethyl)phenyl | —OC(O)NH₂ | —OH |
| 91 | 4-hydroxy-3-(2-carbamoylethyl)phenyl | —OC(O)NH₂ | —OH |
| 92 | 4-hydroxy-3-(naphthalen-2-yl)phenyl | —OC(O)NH₂ | —OH |
| 93 | 4-hydroxy-3-(naphthalen-1-yl)phenyl | —OC(O)NH₂ | —OH |

TABLE 1A.-continued

| Compound | R¹ | R² | R³ |
|---|---|---|---|
| 94 | 3'-biphenyl-3,4-diol | —OC(O)NH₂ | —OH |
| 95 | 5-(4-fluorophenyl)-2,3-dihydroxyphenyl | —OC(O)NH₂ | —OH |
| 96 | 2,3-dihydroxy-5-(naphthalen-2-yl)phenyl | —OC(O)NH₂ | —OH |
| 97 | 5-(4-fluorophenyl)-3,4-dihydroxyphenyl | —OC(O)NH₂ | —OH |
| 98 | 3,4-dihydroxy-5-(naphthalen-2-yl)phenyl | —OC(O)NH₂ | —OH |
| 99 | 3'-biphenyl-2,3-diol | —OC(O)NH₂ | —OH |

TABLE 1A.-continued

| Compound | R¹ | R² | R³ |
|---|---|---|---|
| 100 | 1-fluoroadamantyl | —OC(O)NH₂ | —OH |
| 101 | 4-fluoro-3-(3-methylbut-2-en-1-yl)phenyl | —OC(O)NH₂ | —OH |
| 102 | methyl | —OC(O)NH₂ | —OH |
| 103 | 4-hydroxy-3-(3-methylbut-2-en-1-yl)phenyl | —OH | phenylcarbamate |
| 104 | 4-hydroxy-3-(3-methylbut-2-en-1-yl)phenyl | —OH | ethylcarbamate |
| 105 | 4-hydroxy-3-(3-methylbut-2-en-1-yl)phenyl | —OH | isopropylcarbamate |
| 106 | 4-hydroxy-3-(3-methylbut-2-en-1-yl)phenyl | —OH | tert-butylcarbamate |
| 107 | 4-hydroxy-3-(3-methylbut-2-en-1-yl)phenyl | —OH | cyclopentylcarbamate |
| 108 | 4-hydroxy-3-(3-methylbut-2-en-1-yl)phenyl | cyclopentylcarbamate | —OH |

TABLE 1A.-continued

| Compound | R¹ | R² | R³ |
|---|---|---|---|
| 109 | 4-hydroxy-3-prenylphenyl | —OH | propyl-NH-C(O)-O- |
| 110 | 4-hydroxy-3-prenylphenyl | —OH | cyclohexyl-NH-C(O)-O- |
| 111 | 4-hydroxy-3-prenylphenyl | cyclohexyl-NH-C(O)-O- | —OH |
| 112 | 4-hydroxy-3-prenylphenyl | —OH | 5-methyl-1H-pyrrole-2-carboxylate |
| 112A | 4-fluoro-3-prenylphenyl | —OH | 5-methyl-1H-pyrrole-2-carboxylate |
| 113 | 4-hydroxy-3-prenylphenyl | —OH | 1H-pyrrole-2-carboxylate |
| 114 | 4-hydroxy-3-prenylphenyl | —OH | 1-methyl-1H-pyrrole-2-carboxylate |

TABLE 1B

Further exemplary aminocoumarin compounds.

| Compound Number | Structure |
|---|---|
| 200 | 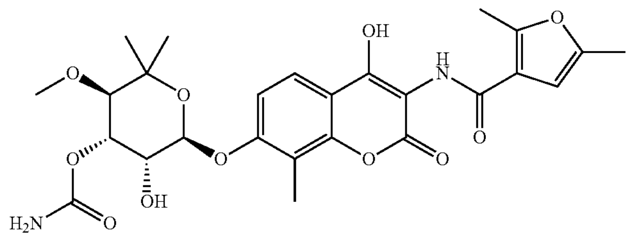 [SMILES: CO[C@@H]1[C@@H](OC(N)=O)[C@@H](O)[C@H](Oc2ccc3c(O)c(NC(=O)c4cc(C)oc4C)c(=O)oc3c2C)OC1(C)C] |
| 201 | 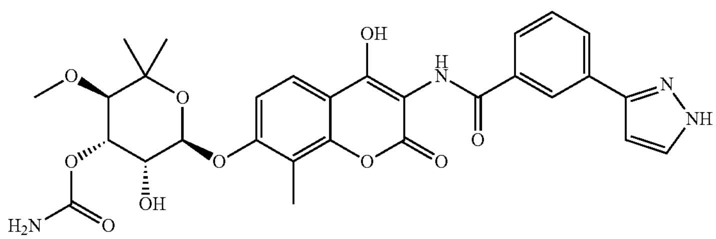 [SMILES: CO[C@@H]1[C@@H](OC(N)=O)[C@@H](O)[C@H](Oc2ccc3c(O)c(NC(=O)c4cccc(-c5cc[nH]n5)c4)c(=O)oc3c2C)OC1(C)C] |
| 202 | 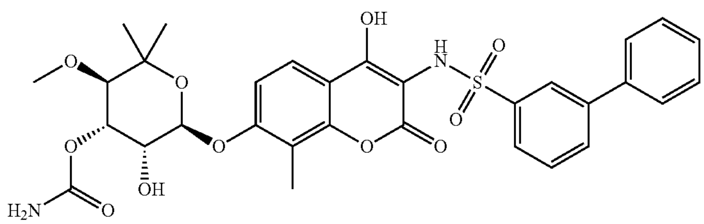 [SMILES: CO[C@@H]1[C@@H](OC(N)=O)[C@@H](O)[C@H](Oc2ccc3c(O)c(NS(=O)(=O)c4cccc(-c5ccccc5)c4)c(=O)oc3c2C)OC1(C)C] |
| 203 | 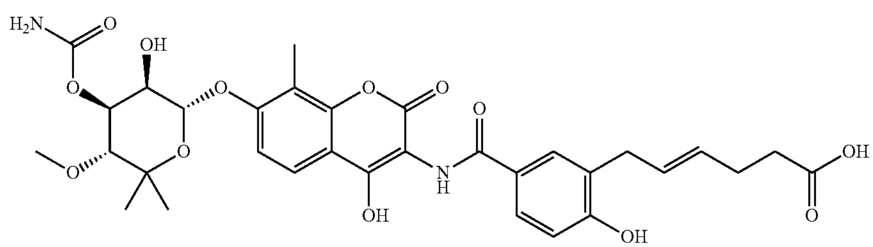 [SMILES: CO[C@@H]1[C@@H](OC(N)=O)[C@@H](O)[C@H](Oc2ccc3c(O)c(NC(=O)c4ccc(O)c(C/C=C/CCC(=O)O)c4)c(=O)oc3c2C)OC1(C)C] |
| 204 | 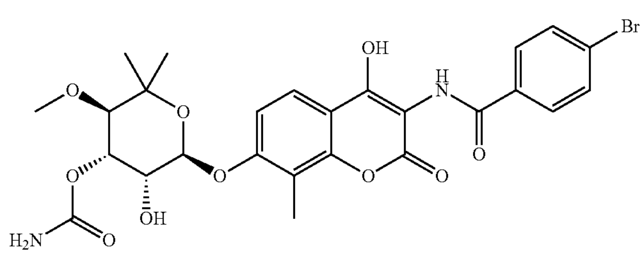 [SMILES: CO[C@@H]1[C@@H](OC(N)=O)[C@@H](O)[C@H](Oc2ccc3c(O)c(NC(=O)c4ccc(Br)cc4)c(=O)oc3c2C)OC1(C)C] |

TABLE 1B-continued
Further exemplary aminocoumarin compounds.
| Compound Number | Structure |
|---|---|
| 205 | 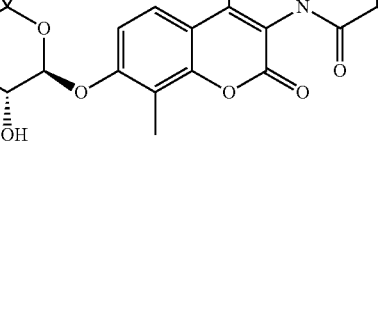 |
| 206 | 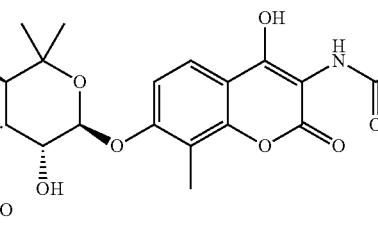 |
| 207 | 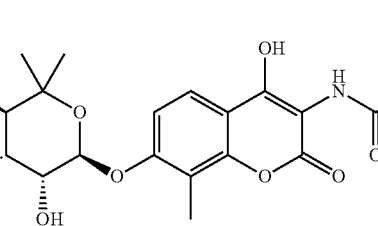 |
| 208 | 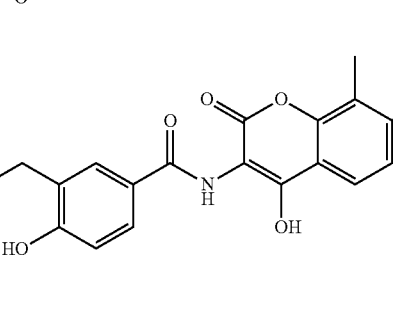 |
| 209 | 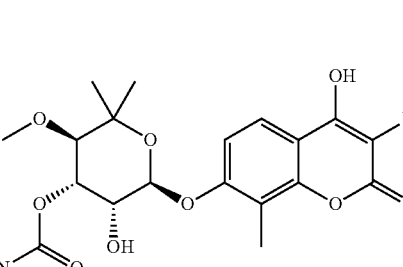 |

TABLE 1B-continued

Further exemplary aminocoumarin compounds.

| Compound Number | Structure |
|---|---|
| 210 | 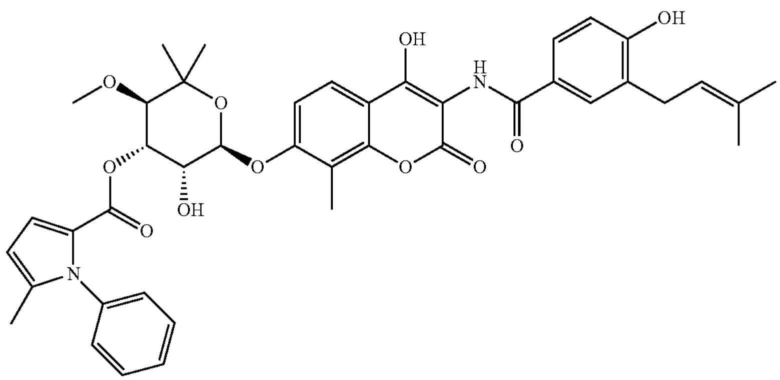 [SMILES: CO[C@@H]1[C@@H](OC(=O)c2ccc(C)n2-c2ccccc2)[C@@H](O)[C@H](Oc2ccc3c(O)c(NC(=O)c4ccc(O)c(CC=C(C)C)c4)c(=O)oc3c2C)OC1(C)C] |
| 211 | 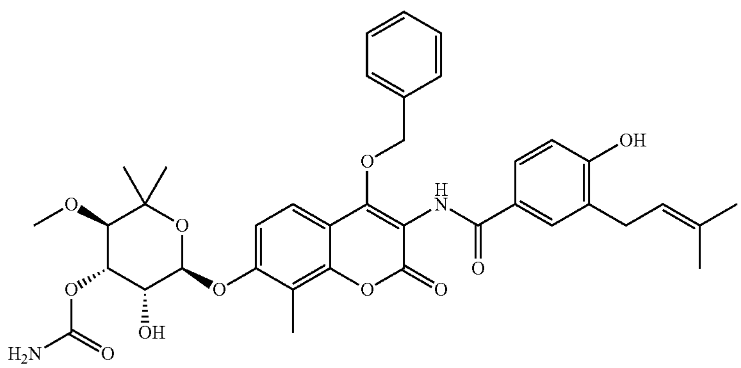 [SMILES: CO[C@@H]1[C@@H](OC(N)=O)[C@@H](O)[C@H](Oc2ccc3c(OCc4ccccc4)c(NC(=O)c4ccc(O)c(CC=C(C)C)c4)c(=O)oc3c2C)OC1(C)C] |
| 212 | 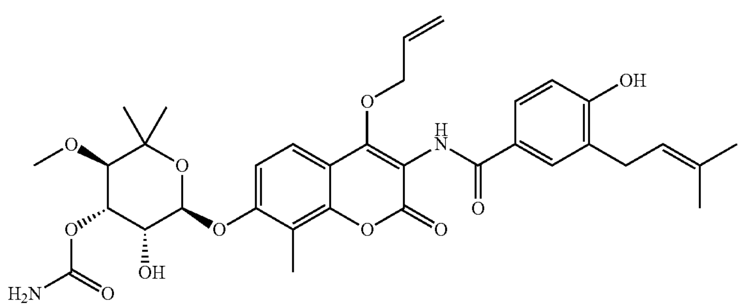 [SMILES: C=CCOc1c(NC(=O)c2ccc(O)c(CC=C(C)C)c2)c(=O)oc2c(C)c(O[C@@H]3OC(C)(C)[C@H](OC)[C@@H](OC(N)=O)[C@H]3O)ccc12] |
| 213 | 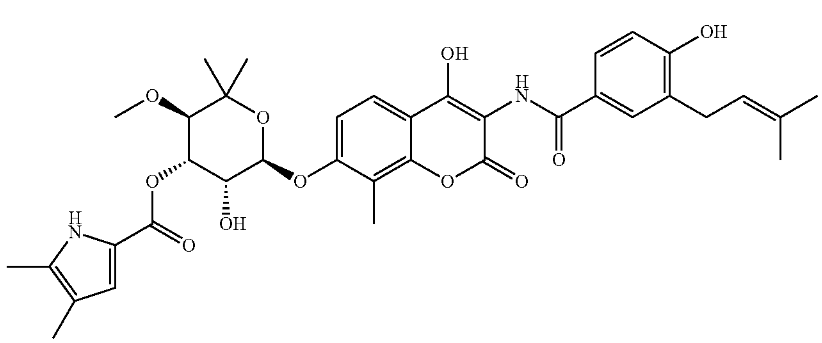 [SMILES: CO[C@@H]1[C@@H](OC(=O)c2cc(C)c(C)[nH]2)[C@@H](O)[C@H](Oc2ccc3c(O)c(NC(=O)c4ccc(O)c(CC=C(C)C)c4)c(=O)oc3c2C)OC1(C)C] |

TABLE 1B-continued

Further exemplary aminocoumarin compounds.

| Compound Number | Structure |
|---|---|
| 214 | 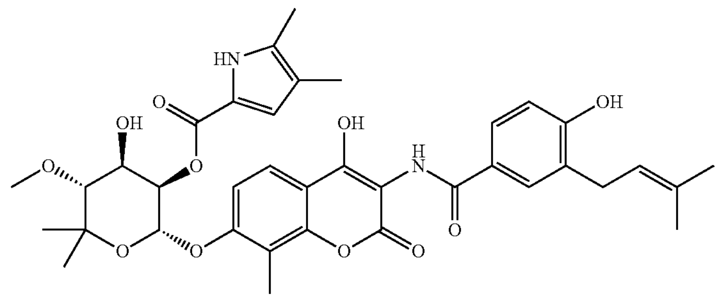 [SMILES: CO[C@@H]1[C@@H](O)[C@@H](OC(=O)c2cc(C)c(C)[nH]2)[C@H](Oc2ccc3c(O)c(NC(=O)c4ccc(O)c(CC=C(C)C)c4)c(=O)oc3c2C)OC1(C)C] |
| 215 | 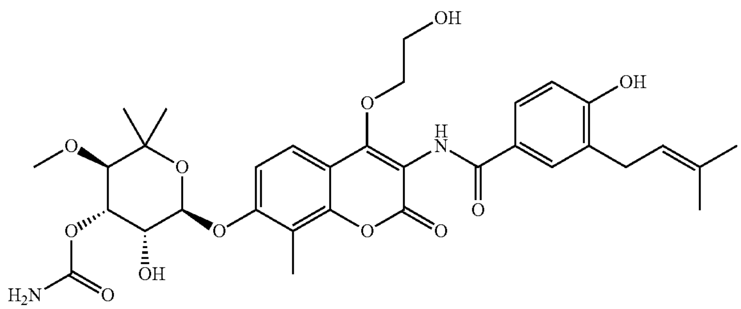 [SMILES: CO[C@@H]1[C@@H](OC(N)=O)[C@@H](O)[C@H](Oc2ccc3c(OCCO)c(NC(=O)c4ccc(O)c(CC=C(C)C)c4)c(=O)oc3c2C)OC1(C)C] |
| 216 | 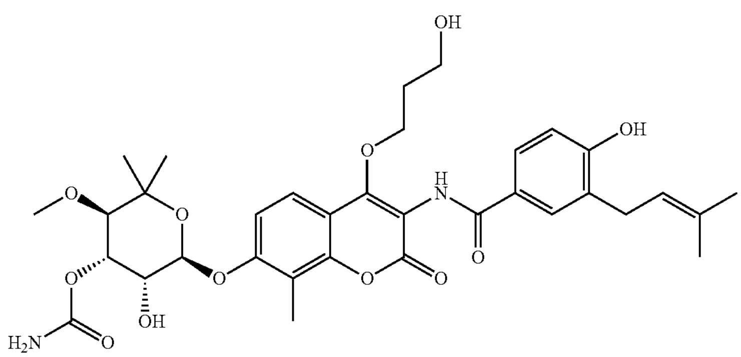 [SMILES: CO[C@@H]1[C@@H](OC(N)=O)[C@@H](O)[C@H](Oc2ccc3c(OCCCO)c(NC(=O)c4ccc(O)c(CC=C(C)C)c4)c(=O)oc3c2C)OC1(C)C] |
| 217 | 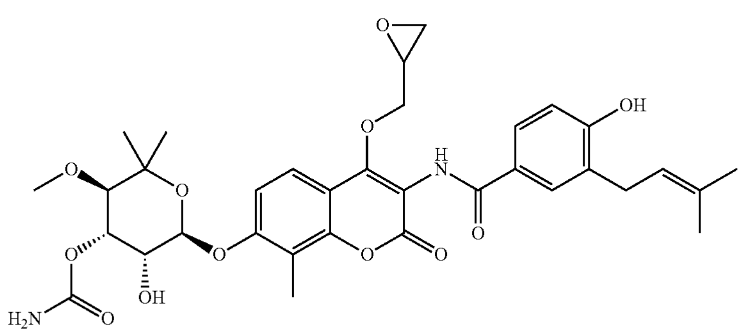 [SMILES: CO[C@@H]1[C@@H](OC(N)=O)[C@@H](O)[C@H](Oc2ccc3c(OCC4CO4)c(NC(=O)c4ccc(O)c(CC=C(C)C)c4)c(=O)oc3c2C)OC1(C)C] |
| 218 | 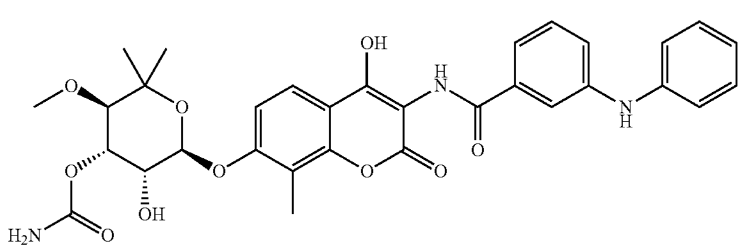 [SMILES: CO[C@@H]1[C@@H](OC(N)=O)[C@@H](O)[C@H](Oc2ccc3c(O)c(NC(=O)c4cccc(Nc5ccccc5)c4)c(=O)oc3c2C)OC1(C)C] |

TABLE 1B-continued
Further exemplary aminocoumarin compounds.
| Compound Number | Structure |
|---|---|
| 219 | 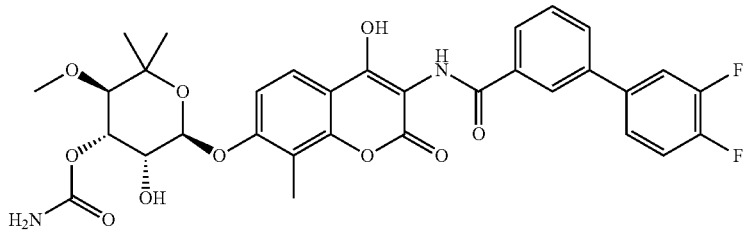 [SMILES: CO[C@@H]1[C@@H](OC(N)=O)[C@@H](O)[C@H](Oc2ccc3c(O)c(NC(=O)c4cccc(-c5ccc(F)c(F)c5)c4)c(=O)oc3c2C)OC1(C)C] |
| 220 | 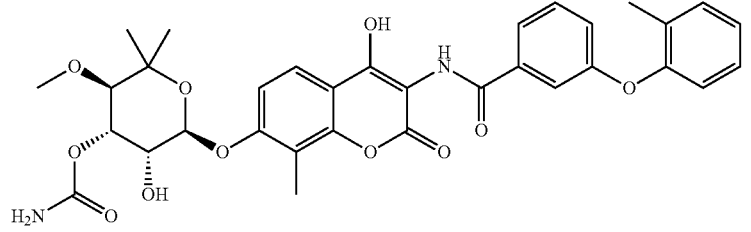 [SMILES: CO[C@@H]1[C@@H](OC(N)=O)[C@@H](O)[C@H](Oc2ccc3c(O)c(NC(=O)c4cccc(Oc5ccccc5C)c4)c(=O)oc3c2C)OC1(C)C] |
| 221 | 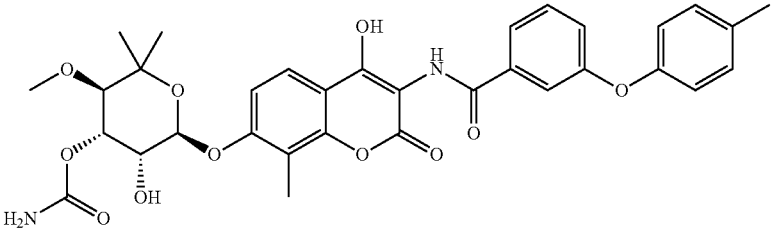 [SMILES: CO[C@@H]1[C@@H](OC(N)=O)[C@@H](O)[C@H](Oc2ccc3c(O)c(NC(=O)c4cccc(Oc5ccc(C)cc5)c4)c(=O)oc3c2C)OC1(C)C] |
| 222 | 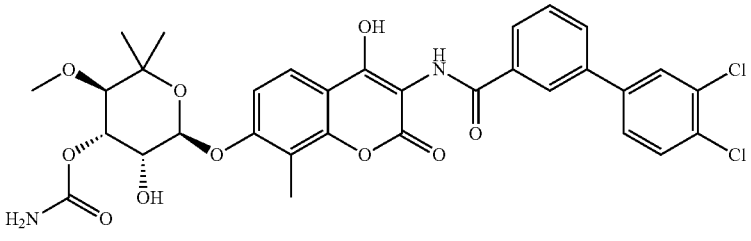 [SMILES: CO[C@@H]1[C@@H](OC(N)=O)[C@@H](O)[C@H](Oc2ccc3c(O)c(NC(=O)c4cccc(-c5ccc(Cl)c(Cl)c5)c4)c(=O)oc3c2C)OC1(C)C] |
| 223 | 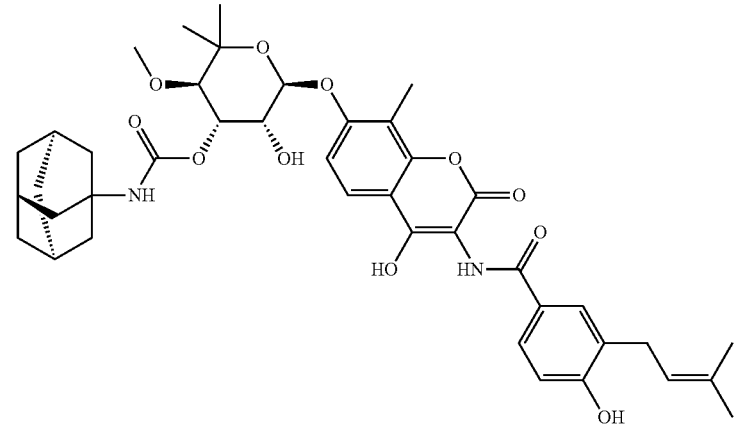 [SMILES: CO[C@@H]1[C@@H](OC(=O)NC23C[C@H]4C[C@@H](C2)C[C@@H](C3)C4)[C@@H](O)[C@H](Oc2ccc3c(O)c(NC(=O)c4ccc(O)c(CC=C(C)C)c4)c(=O)oc3c2C)OC1(C)C] |

TABLE 1B-continued

Further exemplary aminocoumarin compounds.

| Compound Number | Structure |
|---|---|
| 224 | 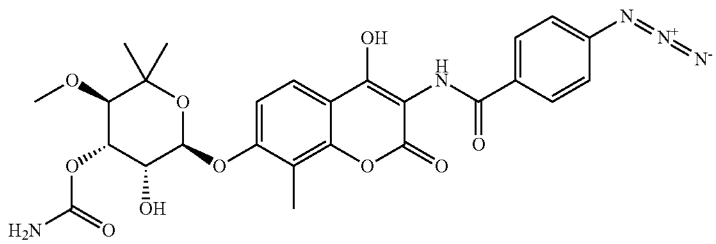 [SMILES: CO[C@@H]1[C@@H](OC(N)=O)[C@@H](O)[C@H](Oc2ccc3c(O)c(NC(=O)c4ccc(N=[N+]=[N-])cc4)c(=O)oc3c2C)OC1(C)C] |
| 225 | 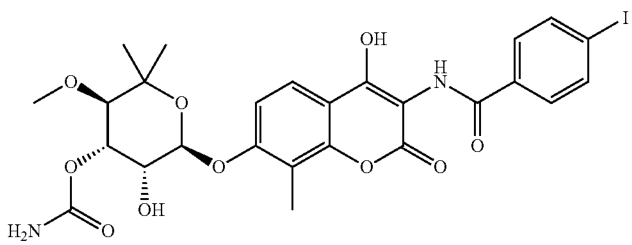 [SMILES: CO[C@@H]1[C@@H](OC(N)=O)[C@@H](O)[C@H](Oc2ccc3c(O)c(NC(=O)c4ccc(I)cc4)c(=O)oc3c2C)OC1(C)C] |
| 226 | 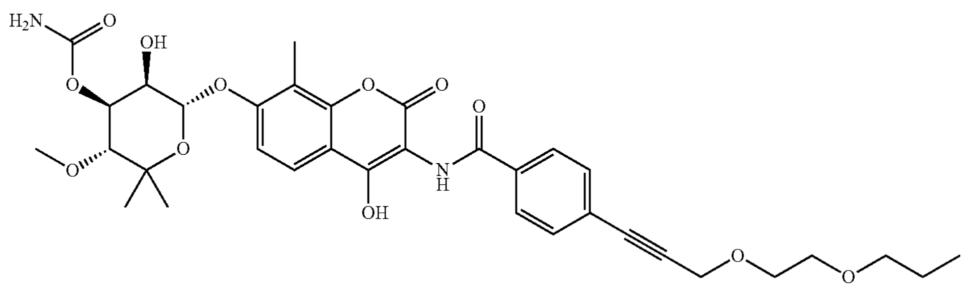 [SMILES: CCCOCCOCC#Cc1ccc(C(=O)Nc2c(O)c3ccc(O[C@@H]4OC(C)(C)[C@H](OC)[C@@H](OC(N)=O)[C@H]4O)c(C)c3oc2=O)cc1] |
| 227 | 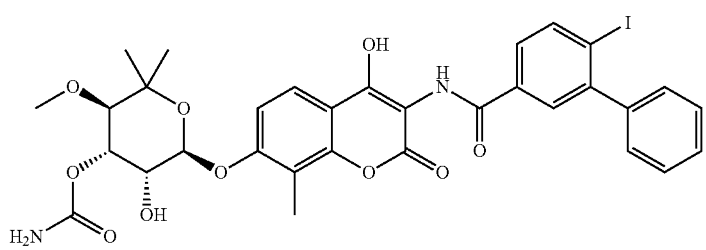 [SMILES: CO[C@@H]1[C@@H](OC(N)=O)[C@@H](O)[C@H](Oc2ccc3c(O)c(NC(=O)c4ccc(I)c(-c5ccccc5)c4)c(=O)oc3c2C)OC1(C)C] |
| 228 | 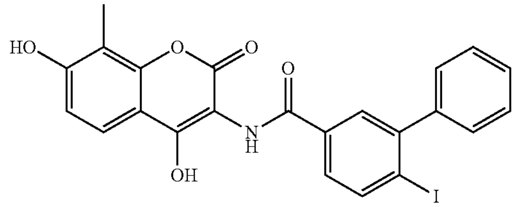 [SMILES: Cc1c(O)ccc2c(O)c(NC(=O)c3ccc(I)c(-c4ccccc4)c3)c(=O)oc12] |
| 229 | 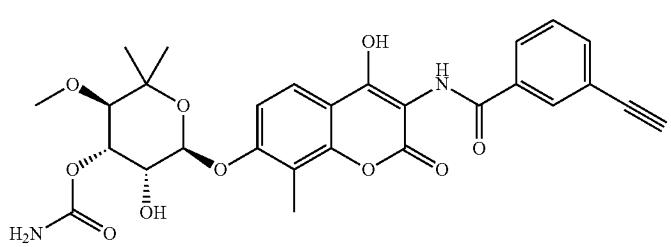 [SMILES: C#Cc1cccc(C(=O)Nc2c(O)c3ccc(O[C@@H]4OC(C)(C)[C@H](OC)[C@@H](OC(N)=O)[C@H]4O)c(C)c3oc2=O)c1] |

TABLE 1B-continued
Further exemplary aminocoumarin compounds.
| Compound Number | Structure |
|---|---|
| 230 | 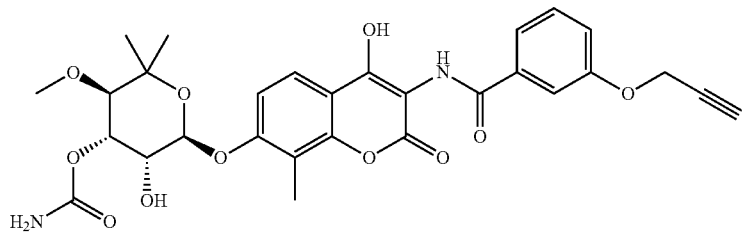 [SMILES: C#CCOc1cccc(C(=O)Nc2c(O)c3ccc(O[C@@H]4OC(C)(C)[C@H](OC)[C@@H](OC(N)=O)[C@H]4O)c(C)c3oc2=O)c1] |
| 231 | 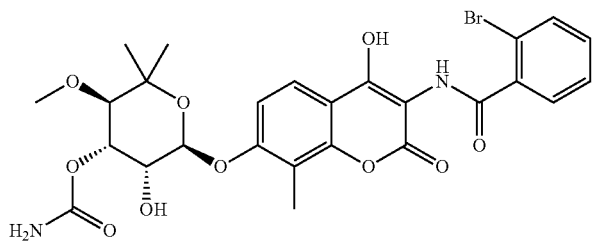 [SMILES: CO[C@@H]1[C@@H](OC(N)=O)[C@@H](O)[C@H](Oc2ccc3c(O)c(NC(=O)c4ccccc4Br)c(=O)oc3c2C)OC1(C)C] |
| 232 | 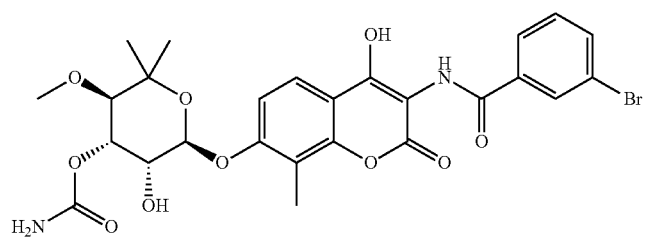 [SMILES: CO[C@@H]1[C@@H](OC(N)=O)[C@@H](O)[C@H](Oc2ccc3c(O)c(NC(=O)c4cccc(Br)c4)c(=O)oc3c2C)OC1(C)C] |
| 233 | 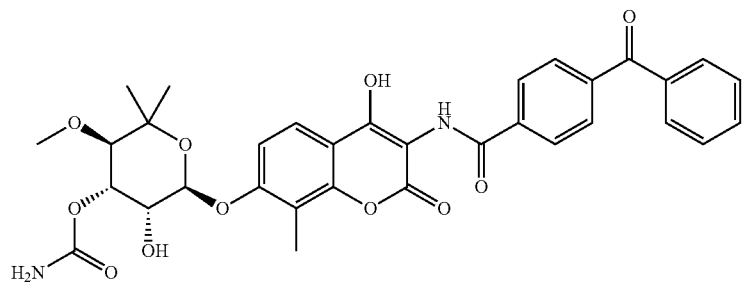 [SMILES: CO[C@@H]1[C@@H](OC(N)=O)[C@@H](O)[C@H](Oc2ccc3c(O)c(NC(=O)c4ccc(C(=O)c5ccccc5)cc4)c(=O)oc3c2C)OC1(C)C] |
| 234 | 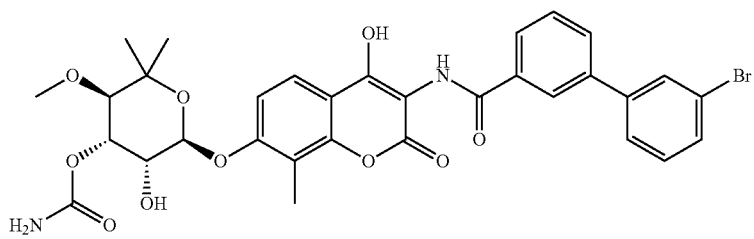 [SMILES: CO[C@@H]1[C@@H](OC(N)=O)[C@@H](O)[C@H](Oc2ccc3c(O)c(NC(=O)c4cccc(-c5cccc(Br)c5)c4)c(=O)oc3c2C)OC1(C)C] |
| 235 | 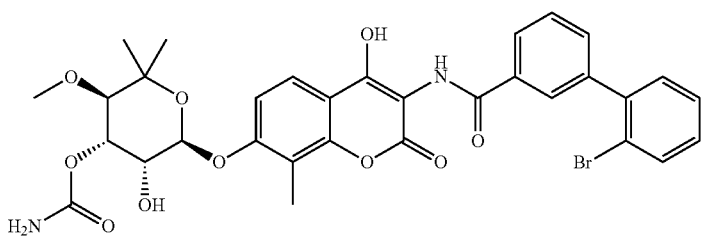 [SMILES: CO[C@@H]1[C@@H](OC(N)=O)[C@@H](O)[C@H](Oc2ccc3c(O)c(NC(=O)c4cccc(-c5ccccc5Br)c4)c(=O)oc3c2C)OC1(C)C] |

US 11,713,335 B2
135                                                                                          136
TABLE 1B-continued
Further exemplary aminocoumarin compounds.
| Compound Number | Structure |
|---|---|
| 236 | 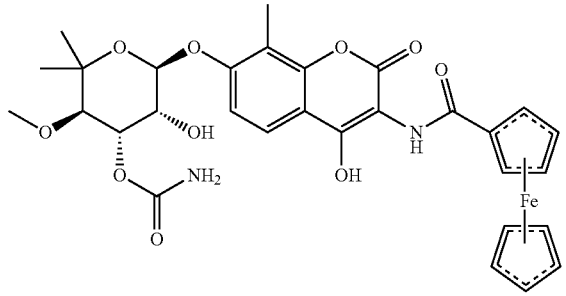 |
| 237 | 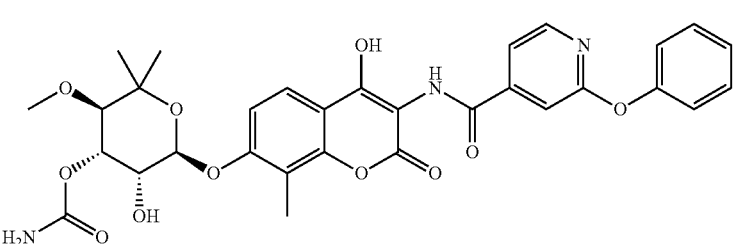 |
| 238 | 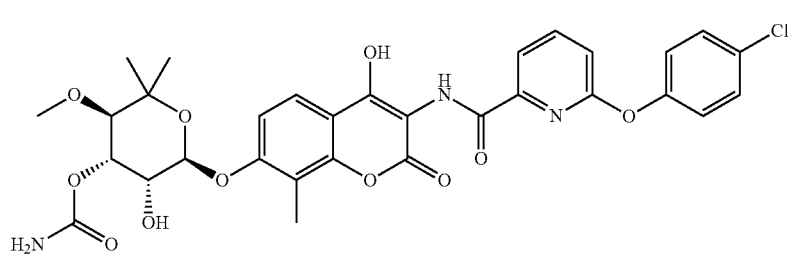 [SMILES: CO[C@@H]1[C@@H](OC(N)=O)[C@@H](O)[C@H](Oc2ccc3c(O)c(NC(=O)c4cccc(Oc5ccc(Cl)cc5)n4)c(=O)oc3c2C)OC1(C)C] |
| 239 | 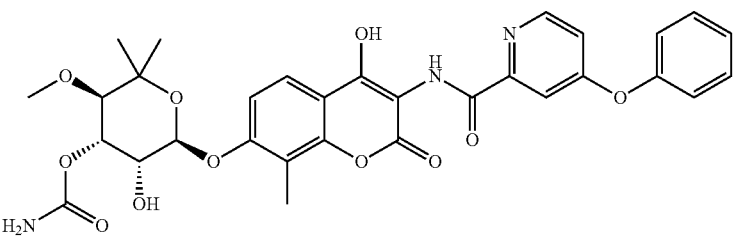 [SMILES: CO[C@@H]1[C@@H](OC(N)=O)[C@@H](O)[C@H](Oc2ccc3c(O)c(NC(=O)c4cc(Oc5ccccc5)ccn4)c(=O)oc3c2C)OC1(C)C] |
| 240 | 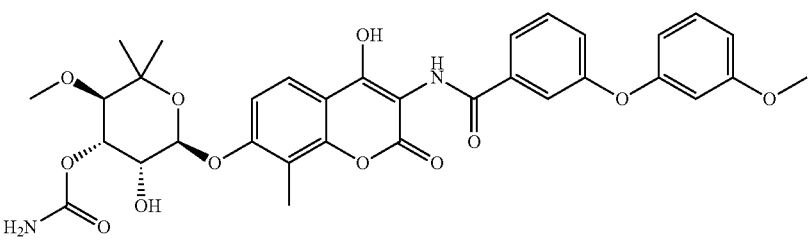 [SMILES: COc1cccc(Oc2cccc(C(=O)Nc3c(O)c4ccc(O[C@@H]5OC(C)(C)[C@H](OC)[C@@H](OC(N)=O)[C@H]5O)c(C)c4oc3=O)c2)c1] |
| 241 | 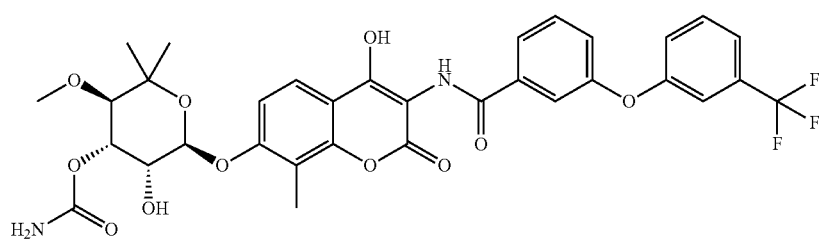 [SMILES: CO[C@@H]1[C@@H](OC(N)=O)[C@@H](O)[C@H](Oc2ccc3c(O)c(NC(=O)c4cccc(Oc5cccc(C(F)(F)F)c5)c4)c(=O)oc3c2C)OC1(C)C] |

TABLE 1B-continued
Further exemplary aminocoumarin compounds.
| Compound Number | Structure |
|---|---|
| 242 | 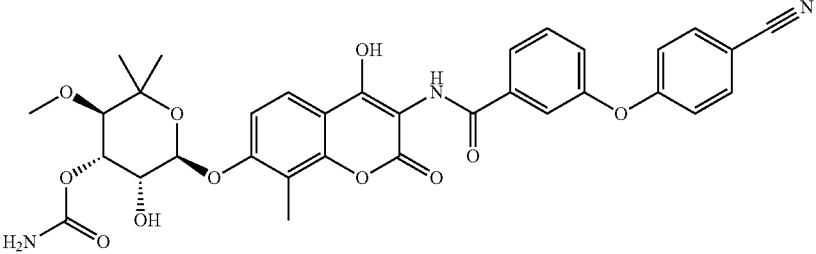 [SMILES: CO[C@@H]1[C@@H](OC(N)=O)[C@@H](O)[C@H](Oc2ccc3c(O)c(NC(=O)c4cccc(Oc5ccc(C#N)cc5)c4)c(=O)oc3c2C)OC1(C)C] |
| 243 | 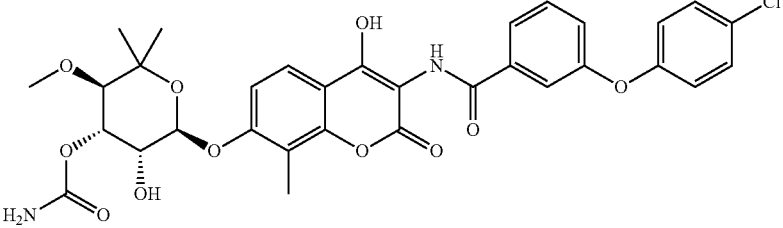 |
| 244 | 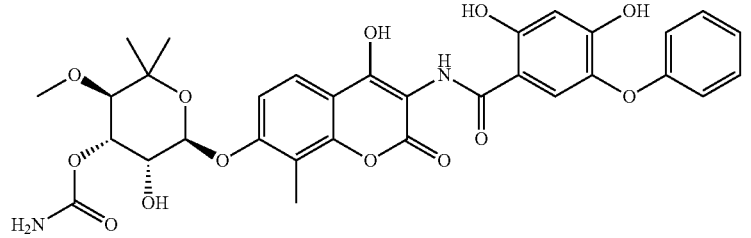 [SMILES: CO[C@@H]1[C@@H](OC(N)=O)[C@@H](O)[C@H](Oc2ccc3c(O)c(NC(=O)c4cc(Oc5ccccc5)c(O)cc4O)c(=O)oc3c2C)OC1(C)C] |
| 245 | 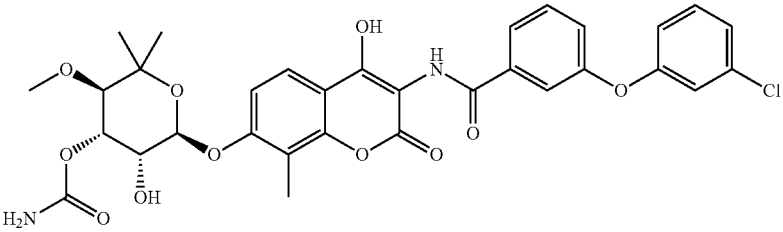 [SMILES: CO[C@@H]1[C@@H](OC(N)=O)[C@@H](O)[C@H](Oc2ccc3c(O)c(NC(=O)c4cccc(Oc5cccc(Cl)c5)c4)c(=O)oc3c2C)OC1(C)C] |
| 246 | 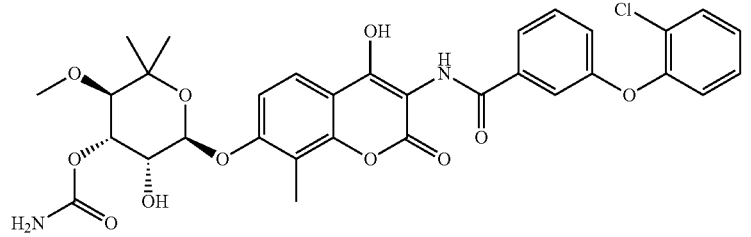 [SMILES: CO[C@@H]1[C@@H](OC(N)=O)[C@@H](O)[C@H](Oc2ccc3c(O)c(NC(=O)c4cccc(Oc5ccccc5Cl)c4)c(=O)oc3c2C)OC1(C)C] |
| 247 | 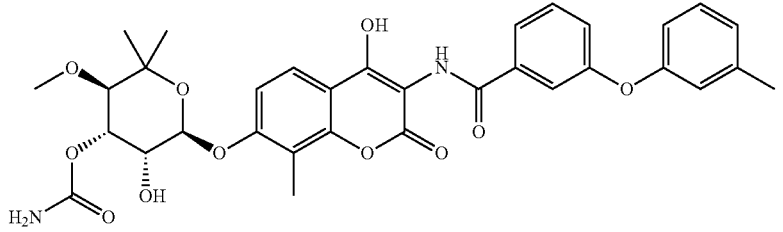 [SMILES: CO[C@@H]1[C@@H](OC(N)=O)[C@@H](O)[C@H](Oc2ccc3c(O)c(NC(=O)c4cccc(Oc5cccc(C)c5)c4)c(=O)oc3c2C)OC1(C)C] |

TABLE 1B-continued
Further exemplary aminocoumarin compounds.
| Compound Number | Structure |
|---|---|
| 248 | 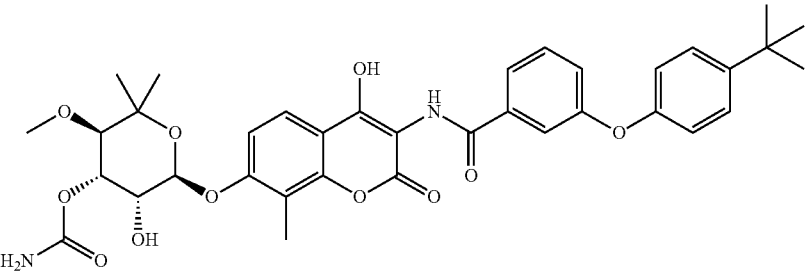 [SMILES: CO[C@@H]1[C@@H](OC(N)=O)[C@@H](O)[C@H](Oc2ccc3c(O)c(NC(=O)c4cccc(Oc5ccc(C(C)(C)C)cc5)c4)c(=O)oc3c2C)OC1(C)C] |
| 249 | 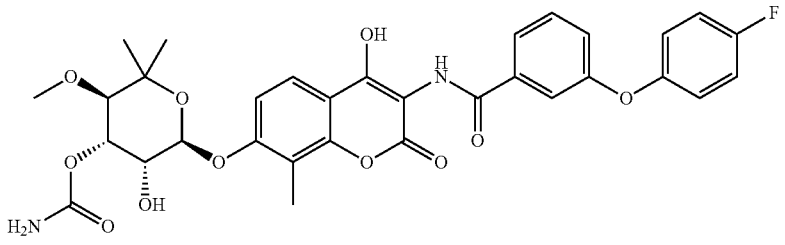 [SMILES: CO[C@@H]1[C@@H](OC(N)=O)[C@@H](O)[C@H](Oc2ccc3c(O)c(NC(=O)c4cccc(Oc5ccc(F)cc5)c4)c(=O)oc3c2C)OC1(C)C] |
| 250 | 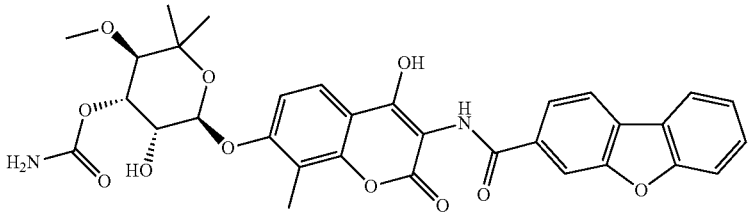 [SMILES: CO[C@@H]1[C@@H](OC(N)=O)[C@@H](O)[C@H](Oc2ccc3c(O)c(NC(=O)c4ccc5c(c4)oc4ccccc45)c(=O)oc3c2C)OC1(C)C] |
| 251 | 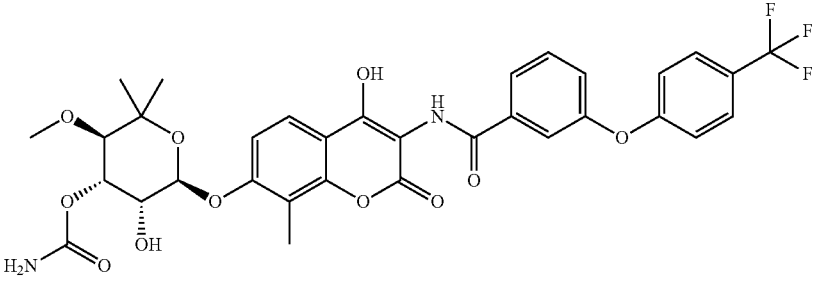 [SMILES: CO[C@@H]1[C@@H](OC(N)=O)[C@@H](O)[C@H](Oc2ccc3c(O)c(NC(=O)c4cccc(Oc5ccc(C(F)(F)F)cc5)c4)c(=O)oc3c2C)OC1(C)C] |
| 252 | 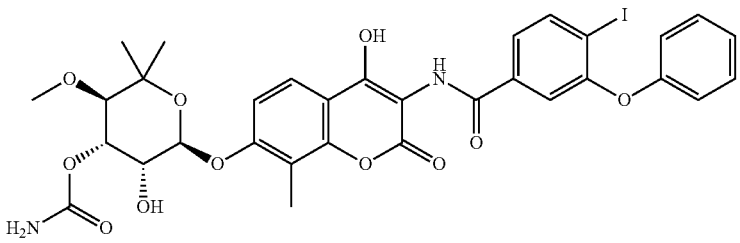 [SMILES: CO[C@@H]1[C@@H](OC(N)=O)[C@@H](O)[C@H](Oc2ccc3c(O)c(NC(=O)c4ccc(I)c(Oc5ccccc5)c4)c(=O)oc3c2C)OC1(C)C] |

TABLE 1B-continued
Further exemplary aminocoumarin compounds.
| Compound Number | Structure |
|---|---|
| 253 | 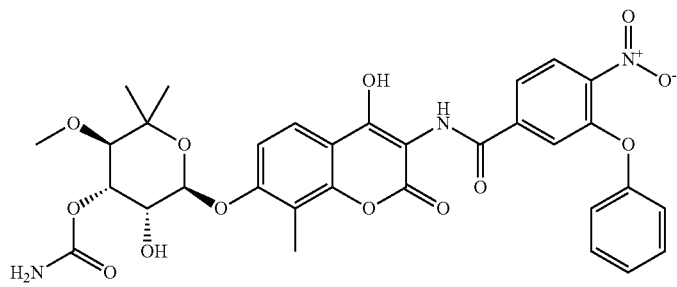 [SMILES: CO[C@@H]1[C@@H](OC(N)=O)[C@@H](O)[C@H](Oc2ccc3c(O)c(NC(=O)c4ccc([N+](=O)[O-])c(Oc5ccccc5)c4)c(=O)oc3c2C)OC1(C)C] |
| 254 | 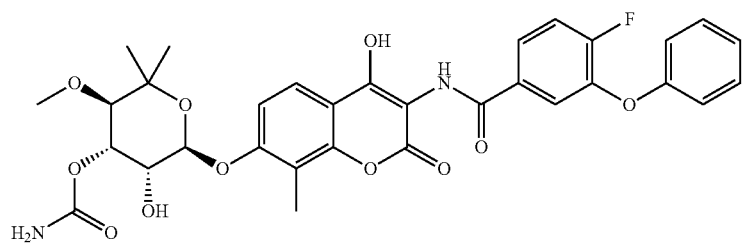 [SMILES: CO[C@@H]1[C@@H](OC(N)=O)[C@@H](O)[C@H](Oc2ccc3c(O)c(NC(=O)c4ccc(F)c(Oc5ccccc5)c4)c(=O)oc3c2C)OC1(C)C] |
| 255 | 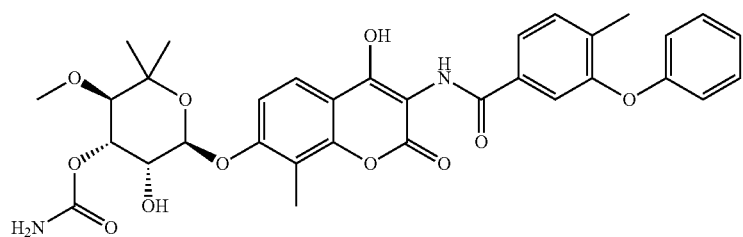 [SMILES: CO[C@@H]1[C@@H](OC(N)=O)[C@@H](O)[C@H](Oc2ccc3c(O)c(NC(=O)c4ccc(C)c(Oc5ccccc5)c4)c(=O)oc3c2C)OC1(C)C] |
| 256 | 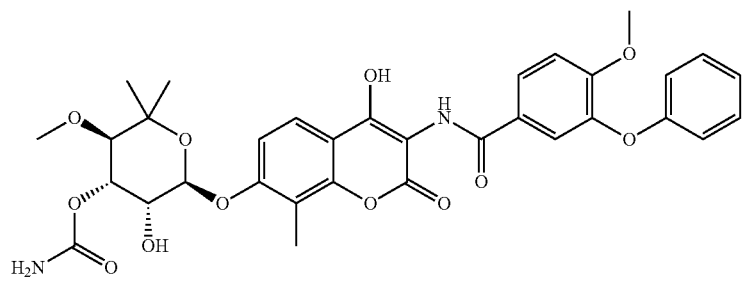 [SMILES: COc1ccc(C(=O)Nc2c(O)c3ccc(O[C@@H]4OC(C)(C)[C@H](OC)[C@@H](OC(N)=O)[C@H]4O)c(C)c3oc2=O)cc1Oc1ccccc1] |
| 257 | 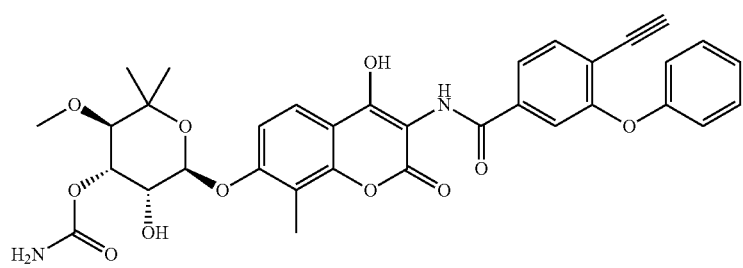 [SMILES: C#Cc1ccc(C(=O)Nc2c(O)c3ccc(O[C@@H]4OC(C)(C)[C@H](OC)[C@@H](OC(N)=O)[C@H]4O)c(C)c3oc2=O)cc1Oc1ccccc1] |

US 11,713,335 B2
TABLE 1B-continued
Further exemplary aminocoumarin compounds.
| Compound Number | Structure |
|---|---|
| 258 | 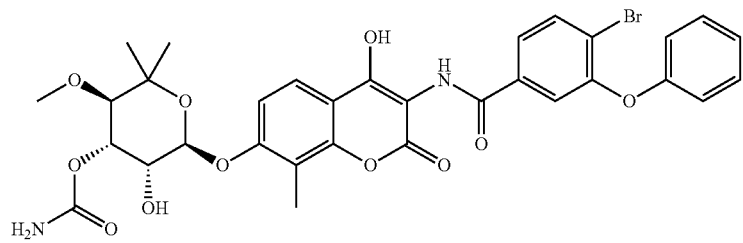 [SMILES: CO[C@@H]1[C@@H](OC(N)=O)[C@@H](O)[C@H](Oc2ccc3c(O)c(NC(=O)c4ccc(Br)c(Oc5ccccc5)c4)c(=O)oc3c2C)OC1(C)C] |
| 259 | 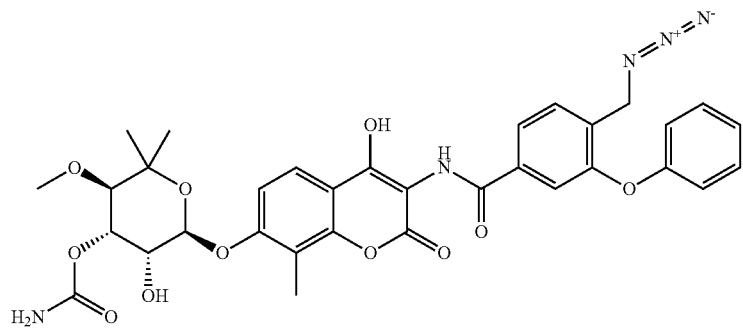 [SMILES: CO[C@@H]1[C@@H](OC(N)=O)[C@@H](O)[C@H](Oc2ccc3c(O)c(NC(=O)c4ccc(CN=[N+]=[N-])c(Oc5ccccc5)c4)c(=O)oc3c2C)OC1(C)C] |
| 260 | 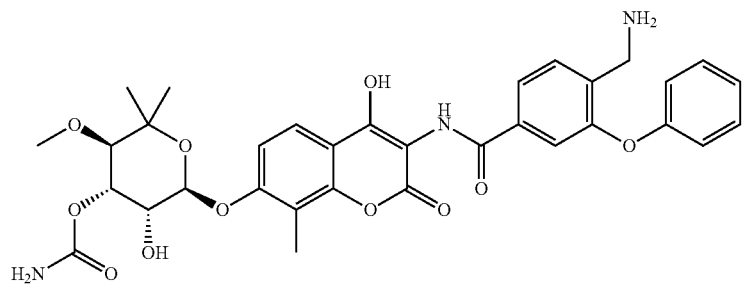 [SMILES: CO[C@@H]1[C@@H](OC(N)=O)[C@@H](O)[C@H](Oc2ccc3c(O)c(NC(=O)c4ccc(CN)c(Oc5ccccc5)c4)c(=O)oc3c2C)OC1(C)C] |
| 261 | 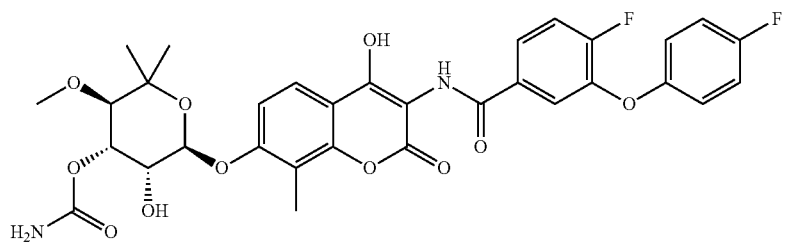 [SMILES: CO[C@@H]1[C@@H](OC(N)=O)[C@@H](O)[C@H](Oc2ccc3c(O)c(NC(=O)c4ccc(F)c(Oc5ccc(F)cc5)c4)c(=O)oc3c2C)OC1(C)C] |
| 262 | 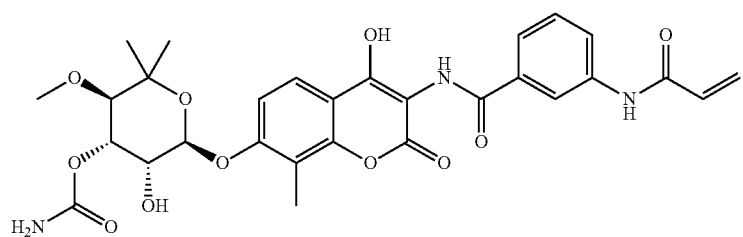 [SMILES: C=CC(=O)Nc1cccc(C(=O)Nc2c(O)c3ccc(O[C@@H]4OC(C)(C)[C@H](OC)[C@@H](OC(N)=O)[C@H]4O)c(C)c3oc2=O)c1] |

TABLE 1B-continued
Further exemplary aminocoumarin compounds.
| Compound Number | Structure |
|---|---|
| 263 | 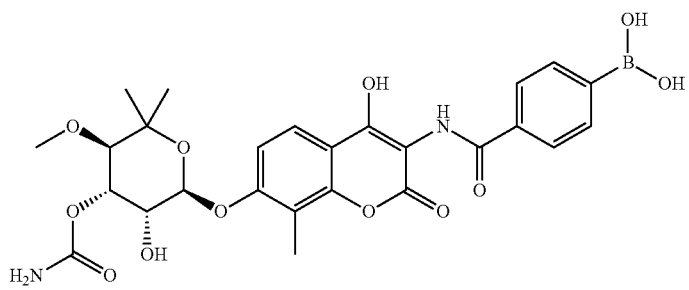 [SMILES: CO[C@@H]1[C@@H](OC(N)=O)[C@@H](O)[C@H](Oc2ccc3c(O)c(NC(=O)c4ccc(B(O)O)cc4)c(=O)oc3c2C)OC1(C)C] |
| 264 | 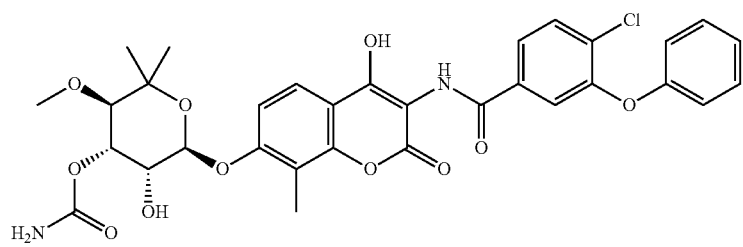 [SMILES: CO[C@@H]1[C@@H](OC(N)=O)[C@@H](O)[C@H](Oc2ccc3c(O)c(NC(=O)c4ccc(Cl)c(Oc5ccccc5)c4)c(=O)oc3c2C)OC1(C)C] |
| 265 | 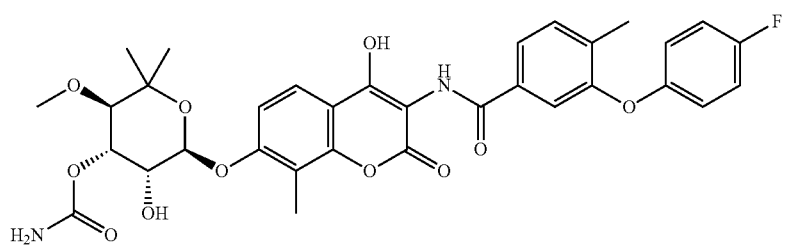 [SMILES: CO[C@@H]1[C@@H](OC(N)=O)[C@@H](O)[C@H](Oc2ccc3c(O)c(NC(=O)c4ccc(C)c(Oc5ccc(F)cc5)c4)c(=O)oc3c2C)OC1(C)C] |
| 266 | 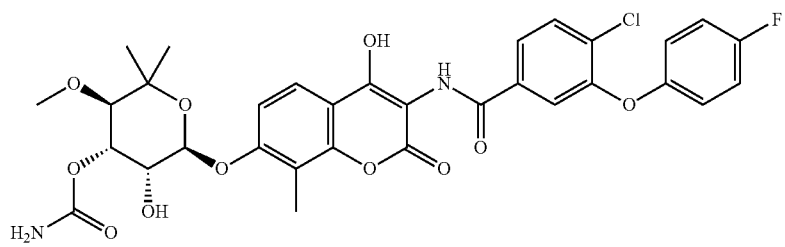 [SMILES: CO[C@@H]1[C@@H](OC(N)=O)[C@@H](O)[C@H](Oc2ccc3c(O)c(NC(=O)c4ccc(Cl)c(Oc5ccc(F)cc5)c4)c(=O)oc3c2C)OC1(C)C] |
| 267 | 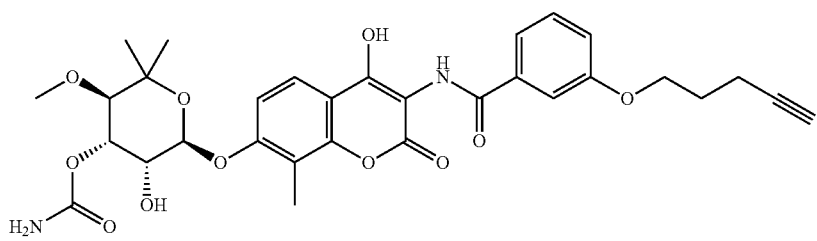 [SMILES: C#CCCCOc1cccc(C(=O)Nc2c(O)c3ccc(O[C@@H]4OC(C)(C)[C@H](OC)[C@@H](OC(N)=O)[C@H]4O)c(C)c3oc2=O)c1] |

Other exemplary aminocoumarin compounds include novenamine, e.g., novenamine hydrochloride (19), and compound 36 shown below:

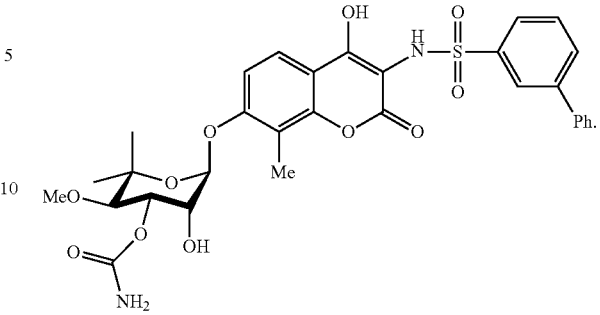

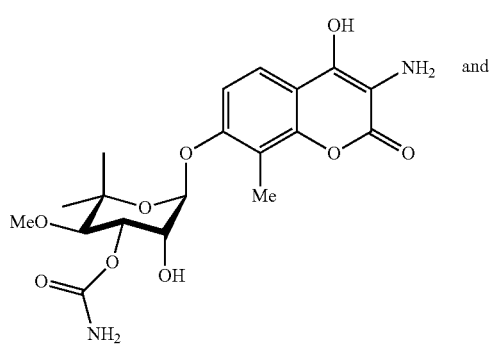

Preparation of the Aminocoumarin Compounds

An aminocoumarin compound may be prepared using methods known in the art. Novenamine may be prepared from novobiocin using USDA NRRL-B3652 heavy cell suspension in water, at about 23° C. For example, as shown in the below scheme, novenamine may be reacted with an appropriate acyl halide ($R^1COX$, where X is a halide, e.g., Cl) in the presence of a base (e.g., pyridine) to provide a compound of the invention (A). If modification of the sugar moiety is desired, the carbamate may be removed, e.g., using a strong aqueous base (e.g., 1M aq. NaOH at about 50° C.), and the desired hydroxyl group (in compound B) may be reacted with, e.g., an isocyanate compound (carbamate formation) or acid anhydride (esterification) to produce a corresponding carbamate or ester (in compound C, a compound of the invention), respectively.

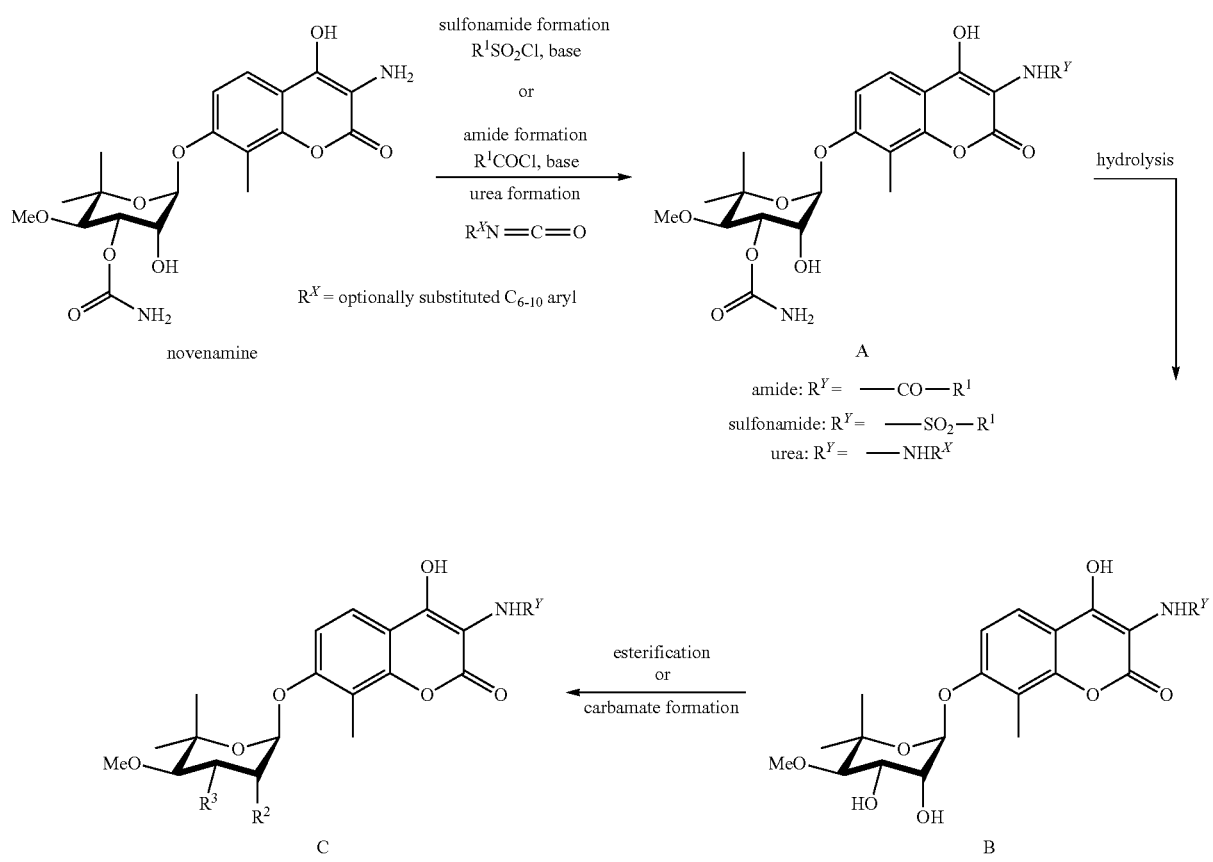

Esterification reaction conditions are known in the art. For example, an alcohol may be reacted with a carboxylic acid anhydride in the presence of a catalytic amount (e.g., about 10 mol % to about 20 mol %) of $Sc(OTf)_3$ or $Sc(NTf_2)_3$ to produce an ester. The esterification may be performed, e.g., in acetonitrile or dichloromethane. Carbamate formation may be performed in the presence of a catalytic quantities (e.g., about 0.5 mol % to about 5 mol %) of $MoO_2Cl_2$ or a solvate thereof. Advantageously, the use of $Sc(NTf_2)_3$ as a catalyst and dichloromethane as a solvent may reduce the amount of side products (e.g., may reduce the extent of the hydrolysis of compound B to its corresponding aglycone).

Alternatively, the hydrolysis step may be performed before the amide/urea formation step. One of skill in the art will recognize that certain reactive groups may need to be protected before performing one or more of the transformations described above. After the completion of the synthesis, a protecting group may be removed using reaction conditions known in the art for the removal of the protecting groups.

Another approach to the synthesis of aminocoumarin compounds includes olefin cross-metathesis of an olefinic precursor, e.g., novobiocin, with another olefin, as shown in the following scheme.

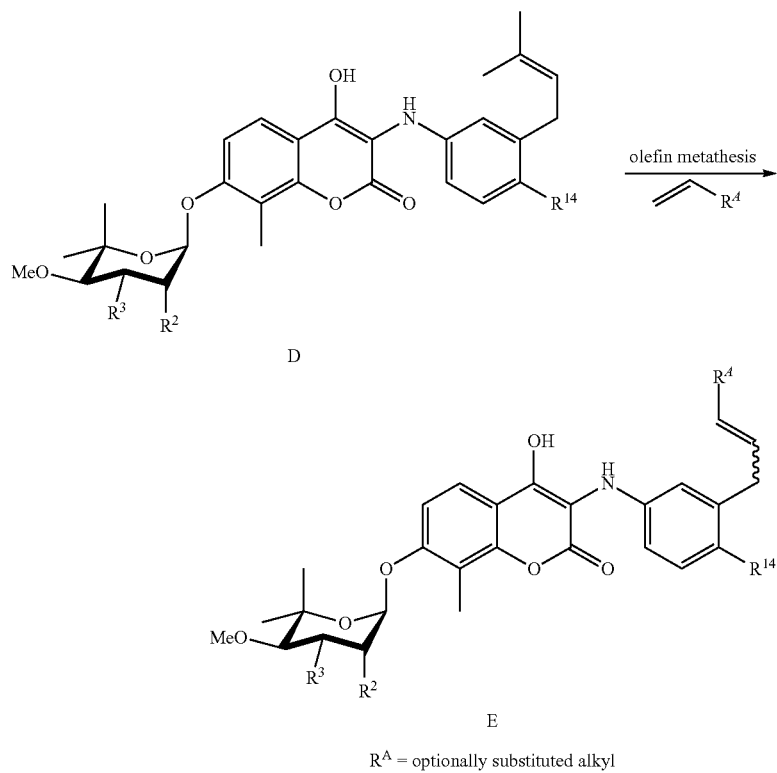

$R^A$ = optionally substituted alkyl

Olefin metathesis catalysts that may be used in the reaction converting D to E are known in the art. Non-limiting examples of the olefin metathesis catalysts include, e.g., Hoveyda-Grubbs $2^{nd}$ generation catalyst and Grubbs $2^{nd}$ generation catalyst.

Methods of Treatment

Compounds of the invention may be used for the treatment of a bacterial infection (e.g., a Gram-negative bacterial infection) in a subject by administering to the subject an effective amount of the compound of the invention. Methods of the invention may be effective at substantially reducing or eliminating the bacterial infection.

A compound of the invention is administered by a route selected from the group consisting of oral, sublingual, buccal, transdermal, intradermal, intramuscular, parenteral, intravenous, intra-arterial, intracranial, subcutaneous, intraorbital, intraventricular, intraspinal, intraperitoneal, intranasal, inhalation, and topical administration (e.g., parenterally, orally, intranasally, or topically).

A compound of the invention may be administered alone. Alternatively, a compound of the invention may be administered in combination with an effective amount of a polymyxin compound or a pharmaceutically acceptable salt thereof (e.g., polymyxin B, polymyxin E, or a pharmaceutically acceptable salt thereof). A polymyxin compound or a pharmaceutically acceptable salt thereof may be administered by a route selected from the group consisting of oral, sublingual, buccal, transdermal, intradermal, intramuscular, parenteral, intravenous, intra-arterial, intracranial, subcutaneous, intraorbital, intraventricular, intraspinal, intraperitoneal, intranasal, inhalation, and topical administration (e.g., parenterally, orally, intranasally, or topically). The polymyxin compound or pharmaceutically acceptable salt thereof can be, e.g., administered one or more times per day, one or more times per week, or one or more times per month.

A compound of the invention and the polymyxin compound or a pharmaceutically acceptable salt thereof can be, e.g., administered within 60 minutes of each other, within one to 24 hours of each other, within one to seven days of each other, or within one to four weeks of each other.

A compound of the invention and the polymyxin compound or a pharmaceutically acceptable salt thereof may be administered by the same route of administration or by different routes of administration.

Gram-negative bacteria Gram-negative bacteria are a group of bacteria characterized by their cell envelopes, which are composed of a thin peptidoglycan cell wall sandwiched between and inner cytoplasmic cell membrane and a bacterial outer membrane. The outer membrane contains LPS, which consist of lipid A, a core polysaccharide, and O antigen in its outer leaflet and phospholipids in its inner leaflet.

The compounds and methods of this invention may be used to treat any Gram-negative bacterial infection. Exemplary Gram-negative bacterial infections are those caused by proteobacteria, e.g., *Escherichia coli, Salmonella, Shigella,* and other Enterobacteriaceae, *Pseudomonas, Moraxella, Helicobacter, Stenotrophomas, Bdellovibrio,* and *Legionella.* Other medically relevant Gram-negative bacteria include *Neisseria gonorrhoeae, Neisseria meningitides, Moraxella catarrhalis, Haemophilus influenzae, Klebsiella pneumoniae, Legionella pneumophila, Pseudomonas aeruginosa, Proteus mirabilis, Enterobacter cloacae, Serratia marcescens, Helicobacter pylori, Salmonella enteritidis, Salmonella typhi, Burkholderia cenocepacia,* and *Acinetobacter baumannii.* In some embodiments, the Gram-negative bacterial infection is caused by *Klebsiella pneumoniae, Acinetobacter baumannii, Pseudomonas aeruginosa, Escherichia coli,* or an *Enterobacter* spp.

Certain bacteria that may be treated using methods and compounds of the invention include bacteria from the phyla including Acidobacteria, Aquificae, Chlamydiae, Bacteroidetes, Chlorobi, Cyanobacteria, Fibrobacteres, Verrucomicrobia, Planctomycetes, and Spirochetes, or the classes including Alphaproteobacteria, Epsilonproteobacteria, Deltaproteobacteria, and Gammaproteobacteria, or the orders including Hydrogenophilales, Methylophilales, Neisseriales, Nitrosomonadales, Procabacteriales, and Rhodocyclales, or the genus and species of *Klebsiella pneumoniae, Acinetobacter baumannii, Pseudomonas aeruginosa, Escherichia coli,* or an *Enterobacter* spp.

Indications

Gram-negative bacterial infections can be community acquired or hospital acquired. They can lead to a number of different types of infections in humans, including infection of the skin and soft tissue, urinary tract infection, bloodstream infection, or meningeal infection, eye infection, lung infection, or any other bacteremia. The methods and compositions of this invention may be used to treat or prevent any of these types of infections or at least substantially reduce the infection. In some instances, the Gram-negative bacteria may be either an opportunistic pathogen or a non-opportunistic pathogen. An opportunistic pathogen infects an individual who is immunocompromised.

Pharmaceutical Compositions

The compounds used in the methods described herein are formulated into pharmaceutical compositions for administration to subjects, preferably humans, in a biologically compatible form suitable for administration in vivo. Pharmaceutical compositions typically include a compound as described herein and a pharmaceutically acceptable excipient.

The compounds described herein can also be used in the form of the free base, in the form of salts, zwitterions, solvates, or as prodrugs, or pharmaceutical compositions thereof. All forms are within the scope of the invention. The compounds, salts, zwitterions, solvates, prodrugs, or pharmaceutical compositions thereof, may be administered to a patient in a variety of forms depending on the selected route of administration, as will be understood by those skilled in the art. The compounds used in the methods described herein may be administered, for example, by oral, parenteral, buccal, sublingual, nasal, rectal, patch, pump, or transdermal administration, and the pharmaceutical compositions formulated accordingly. Parenteral administration includes intravenous, intraperitoneal, subcutaneous, intramuscular, transepithelial, nasal, intrapulmonary, intrathecal, rectal, and topical modes of administration. Parenteral administration may be by continuous infusion over a selected period of time.

A compound of the invention can be administered alone or in admixture with a pharmaceutical carrier selected with regard to the intended route of administration and standard pharmaceutical practice. Pharmaceutical compositions for use in accordance with the present invention thus can be formulated in a conventional manner using one or more physiologically acceptable carriers comprising excipients and auxiliaries that facilitate processing of a compound of the invention into preparations which can be used pharmaceutically.

This invention also includes pharmaceutical compositions which can contain one or more pharmaceutically acceptable carriers. In making the pharmaceutical compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semisolid, or liquid material (e.g., normal saline), which acts as a vehicle, carrier or medium for the active ingredient. Thus, the compositions can be in the form of tablets, powders, lozenges, sachets, cachets, elixirs, suspensions, emulsions, solutions, syrups, and soft and hard gelatin capsules. As is known in the art, the type of diluent can vary depending upon the intended route of administration. The resulting compositions can include additional agents, e.g., preservatives.

The excipient or carrier is selected on the basis of the mode and route of administration. Suitable pharmaceutical carriers, as well as pharmaceutical necessities for use in pharmaceutical formulations, are described in *Remington: The Science and Practice of Pharmacy,* 21$^{st}$ Ed., Gennaro, Ed., Lippincott Williams & Wilkins (2005), a well-known reference text in this field, and in the USP/NF (United States Pharmacopeia and the National Formulary). Examples of suitable excipients are lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents, e.g., talc, magnesium stearate, and mineral oil; wetting agents; emulsifying and suspending agents; preserving agents, e.g., methyl- and propylhydroxy-benzoates; sweetening agents; and flavoring agents. Other exemplary excipients are described in *Handbook of Pharmaceutical Excipients,* 6$^{th}$ Edition, Rowe et al., Eds., Pharmaceutical Press (2009).

These pharmaceutical compositions can be manufactured in a conventional manner, e.g., by conventional mixing, dissolving, granulating, dragee-making, levigating, emulsifying, encapsulating, entrapping, or lyophilizing processes. Methods well known in the art for making formulations are found, for example, in *Remington: The Science and Practice of Pharmacy,* 21$^{st}$ Ed., Gennaro, Ed., Lippincott Williams & Wilkins (2005), and Encyclopedia of Pharmaceutical Technology, eds. J. Swarbrick and J. C. Boylan, 1988-1999, Marcel Dekker, New York. Proper formulation is dependent upon the route of administration chosen. The formulation and preparation of such compositions is well-known to those skilled in the art of pharmaceutical formulation. In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g., about 40 mesh.

Dosages

The dosage of the compound used in the methods described herein, or pharmaceutically acceptable salts or prodrugs thereof, or pharmaceutical compositions thereof, can vary depending on many factors, e.g., the pharmacodynamic properties of the compound; the mode of administration; the age, health, and weight of the recipient; the nature and extent of the symptoms; the frequency of the treatment, and the type of concurrent treatment, if any; and the clearance rate of the compound in the animal to be treated. One of skill in the art can determine the appropriate dosage based on the above factors. The compounds used in the methods described herein may be administered initially in a suitable dosage that may be adjusted as required, depending on the clinical response. In general, a suitable daily dose of a compound of the invention will be that amount of the compound that is the lowest dose effective to produce a therapeutic effect. Such an effective dose will generally depend upon the factors described above.

A compound of the invention may be administered to the patient in a single dose or in multiple doses. When multiple doses are administered, the doses may be separated from one another by, for example, 1-24 hours, 1-7 days, 1-4 weeks, or 1-12 months. The compound may be administered according to a schedule or the compound may be administered without a predetermined schedule. An active compound may be administered, for example, 1, 2, 3, 4, 5, 6, 7, 8, 9, 10, 11, or 12 times per day, every $2^{nd}$, $3^{rd}$, $4^{th}$, $5^{th}$, or $6^{th}$ day, 1, 2, 3, 4, 5, 6, or 7 times per week, 1, 2, 3, 4, 5, or 6 times per month, or 1, 2, 3, 4, 5, 6, 7, 8, 9, 10, 11, or 12 times per year. It is to be understood that, for any particular subject, specific dosage regimes should be adjusted over time according to the individual need and the professional judgment of the person administering or supervising the administration of the compositions.

While the attending physician ultimately will decide the appropriate amount and dosage regimen, an effective amount of a compound of the invention may be, for example, a total daily dosage of, e.g., between 0.05 mg and 3000 mg of any of the compounds described herein. Alternatively, the dosage amount can be calculated using the body weight of the patient. Such dose ranges may include, for example, between 10-1000 mg (e.g., 50-800 mg). In some embodiments, 50, 100, 150, 200, 250, 300, 350, 400, 450, 500, 550, 600, 650, 700, 750, 800, 850, 900, 950, or 1000 mg of the compound is administered.

In the methods of the invention, the time period during which multiple doses of a compound of the invention are administered to a patient can vary. For example, in some embodiments doses of the compounds of the invention are administered to a patient over a time period that is 1-7 days; 1-12 weeks; or 1-3 months. In other embodiments, the compounds are administered to the patient over a time period that is, for example, 4-11 months or 1-30 years. In other embodiments, the compounds are administered to a patient at the onset of symptoms. In any of these embodiments, the amount of compound that is administered may vary during the time period of administration. When a compound is administered daily, administration may occur, for example, 1, 2, 3, 4, 5, 6, 7, 8, 9, 10, 11, or 12 times per day.

Formulations

A compound identified as capable of treating any of the conditions described herein, using any of the methods described herein, may be administered to patients or animals with a pharmaceutically-acceptable diluent, carrier, or excipient, in unit dosage form. The chemical compounds for use in such therapies may be produced and isolated by any standard technique known to those in the field of medicinal chemistry. Conventional pharmaceutical practice may be employed to provide suitable formulations or compositions to administer the identified compound to patients suffering from a bacterial infection. Administration may begin before the patient is symptomatic.

Exemplary routes of administration of the compounds (e.g., a compound of the invention), or pharmaceutical compositions thereof, used in the present invention include oral, sublingual, buccal, transdermal, intradermal, intramuscular, parenteral, intravenous, intra-arterial, intracranial, subcutaneous, intraorbital, intraventricular, intraspinal, intraperitoneal, intranasal, inhalation, and topical administration. The compounds desirably are administered with a pharmaceutically acceptable carrier. Pharmaceutical formulations of the compounds described herein formulated for treatment of the disorders described herein are also part of the present invention.

Formulations for Oral Administration

The pharmaceutical compositions contemplated by the invention include those formulated for oral administration ("oral dosage forms"). Oral dosage forms can be, for example, in the form of tablets, capsules, a liquid solution or suspension, a powder, or liquid or solid crystals, which contain the active ingredient(s) in a mixture with non-toxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

Formulations for oral administration may also be presented as chewable tablets, as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders, granulates, and pellets may be prepared using the ingredients mentioned above under tablets and capsules in a conventional manner using, e.g., a mixer, a fluid bed apparatus or a spray drying equipment.

Controlled release compositions for oral use may be constructed to release the active drug by controlling the dissolution and/or the diffusion of the active drug substance. Any of a number of strategies can be pursued in order to obtain controlled release and the targeted plasma concentration versus time profile. In one example, controlled release is obtained by appropriate selection of various formulation parameters and ingredients, including, e.g., various types of controlled release compositions and coatings. Examples include single or multiple unit tablet or capsule compositions, oil solutions, suspensions, emulsions, microcapsules, microspheres, nanoparticles, patches, and liposomes. In certain embodiments, compositions include biodegradable, pH, and/or temperature-sensitive polymer coatings.

Dissolution or diffusion controlled release can be achieved by appropriate coating of a tablet, capsule, pellet, or granulate formulation of compounds, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

The liquid forms in which the compounds and compositions of the present invention can be incorporated for administration orally include aqueous solutions, suitably flavored syrups, aqueous or oil suspensions, and flavored emulsions with edible oils, e.g., cottonseed oil, sesame oil, coconut oil, or peanut oil, as well as elixirs and similar pharmaceutical vehicles.

Formulations for Buccal Administration

Dosages for buccal or sublingual administration typically are 0.1 to 500 mg per single dose as required. In practice, the physician determines the actual dosing regimen which is most suitable for an individual patient, and the dosage varies with the age, weight, and response of the particular patient. The above dosages are exemplary of the average case, but individual instances exist wherein higher or lower dosages are merited, and such are within the scope of this invention.

For buccal administration, the compositions may take the form of tablets, lozenges, etc. formulated in a conventional manner. Liquid drug formulations suitable for use with nebulizers and liquid spray devices and electrohydrodynamic (EHD) aerosol devices will typically include a compound of the invention with a pharmaceutically acceptable carrier. Preferably, the pharmaceutically acceptable carrier is a liquid, e.g., alcohol, water, polyethylene glycol, or a perfluorocarbon. Optionally, another material may be added to alter the aerosol properties of the solution or suspension of compounds of the invention. Desirably, this material is liquid, e.g., an alcohol, glycol, polyglycol, or a fatty acid. Other methods of formulating liquid drug solutions or suspension suitable for use in aerosol devices are known to those of skill in the art (see, e.g., Biesalski, U.S. Pat. No. 5,112,598 and Biesalski, U.S. Pat. No. 5,556,611, each of which is herein incorporated by reference).

Formulations for Nasal or Inhalation Administration

The compounds may also be formulated for nasal administration. Compositions for nasal administration also may conveniently be formulated as aerosols, drops, gels, and powders. The formulations may be provided in a single or multidose form. In the case of a dropper or pipette, dosing may be achieved by the patient administering an appropriate, predetermined volume of the solution or suspension. In the case of a spray, this may be achieved, for example, by means of a metering atomizing spray pump.

The compounds may further be formulated for aerosol administration, particularly to the respiratory tract by inhalation and including intranasal administration. The compound will generally have a small particle size for example on the order of five (5) microns or less. Such a particle size may be obtained by means known in the art, for example by micronization. The active ingredient is provided in a pressurized pack with a suitable propellant, e.g., a chlorofluorocarbon (CFC), for example, dichlorodifluoromethane, trichlorofluoromethane, or dichlorotetrafluoroethane, or carbon dioxide, or other suitable gas. The aerosol may conveniently also contain a surfactant, e.g., lecithin. The dose of drug may be controlled by a metered valve. Alternatively, the active ingredients may be provided in a form of a dry powder, e.g., a powder mix of the compound in a suitable powder base, e.g., lactose, starch, and starch derivatives, e.g., hydroxypropylmethyl cellulose, and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

Aerosol formulations typically include a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device, e.g., a single dose nasal inhaler or an aerosol dispenser fitted with a metering valve which is intended for disposal after use. Where the dosage form comprises an aerosol dispenser, it will contain a propellant, which can be a compressed gas, e.g., compressed air or an organic propellant, e.g., fluorochlorohydrocarbon. The aerosol dosage forms can also take the form of a pump-atomizer.

Formulations for Parenteral Administration

The compounds described herein for use in the methods of the invention can be administered in a pharmaceutically acceptable parenteral (e.g., intravenous or intramuscular) formulation as described herein. The pharmaceutical formulation may also be administered parenterally (intravenous, intramuscular, subcutaneous or the like) in dosage forms or formulations containing conventional, non-toxic pharmaceutically acceptable carriers and adjuvants. In particular, formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. For example, to prepare such a composition, the compounds of the invention may be dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution and isotonic sodium chloride solution. The aqueous formulation may also contain one or more preservatives, for example, methyl, ethyl, or n-propyl p-hydroxybenzoate. Additional information regarding parenteral formulations can be found, for example, in the United States Pharmacopeia-National Formulary (USP-NF), herein incorporated by reference.

The parenteral formulation can be any of the five general types of preparations identified by the USP-NF as suitable for parenteral administration:
(1) "Drug Injection:" a liquid preparation that is a drug substance (e.g., a compound of the invention), or a solution thereof,
(2) "Drug for Injection:" the drug substance (e.g., a compound of the invention) as a dry solid that will be combined with the appropriate sterile vehicle for parenteral administration as a drug injection;
(3) "Drug Injectable Emulsion:" a liquid preparation of the drug substance (e.g., a compound of the invention) that is dissolved or dispersed in a suitable emulsion medium;
(4) "Drug Injectable Suspension:" a liquid preparation of the drug substance (e.g., a compound of the invention) suspended in a suitable liquid medium; and
(5) "Drug for Injectable Suspension:" the drug substance (e.g., a compound of the invention) as a dry solid that will be combined with the appropriate sterile vehicle for parenteral administration as a drug injectable suspension.

Exemplary formulations for parenteral administration include solutions of the compound prepared in water suitably mixed with a surfactant, e.g., hydroxypropylcellulose. Dispersions can also be prepared in glycerol, liquid polyethylene glycols, DMSO and mixtures thereof with or without alcohol, and in oils. Under ordinary conditions of storage and use, these preparations may contain a preservative to prevent the growth of microorganisms. Conventional procedures and ingredients for the selection and preparation of suitable formulations are described, for example, in *Remington: The Science and Practice of Pharmacy*, 21$^{st}$ Ed., Gennaro, Ed., Lippincott Williams & Wilkins (2005) and in The United States Pharmacopeia: The National Formulary (USP 36 NF31), published in 2013.

Formulations for parenteral administration may, for example, contain excipients, sterile water, or saline, polyalkylene glycols, e.g., polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

The parenteral formulation can be formulated for prompt release or for sustained/extended release of the compound. Exemplary formulations for parenteral release of the compound include: aqueous solutions, powders for reconstitution, cosolvent solutions, oil/water emulsions, suspensions, oil-based solutions, liposomes, microspheres, and polymeric gels.

The following examples are meant to illustrate the invention. They are not meant to limit the invention in any way.

EXEMPLIFICATION

Example 1. Preparation of Reagents and Starting Materials

Example 1.1 Synthesis of Novenamine

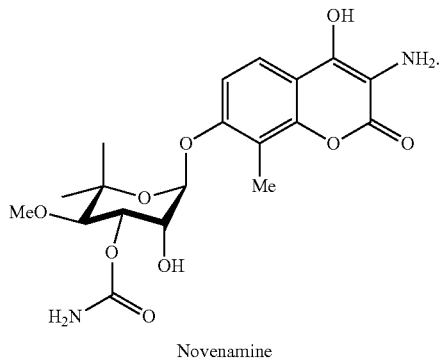

Novenamine

Novenamine HCl was prepared utilizing a modified procedure (Sebek and Hoeksema, *J. Antibiot*, 25:434, 1972). 600 mL of USDA NRRLB3652 cells were grown for 24 h at 28° C., 220 rpm. Cells were harvested by centrifugation at 5,200 g for 30 minutes, and the spent media was discarded. Using a minimal volume of distilled water, the cells were resuspended to generate 20 mL of a heavy cell suspension, which was transferred to a 100 mL round bottom flask equipped with a magnetic stir bar. The flask was fitted with a rubber septum and sparged with N2. The suspension was thoroughly stirred as 20 mL of a 20 mg/mL solution of novobiocin sodium (400 mg) was injected. The reaction was stirred for 16 h at room temperature. Once the reaction was complete, 1.2 mL of 2 M HCl were added while stirring under N2 to convert novenamine to the air-stable anilinium form. Precipitation of soluble cellular material also took place. At this point, the septum was removed, and the reaction mixture was transferred to two 50 mL Falcon centrifuge tubes and centrifuged at 10,000 g for 20 min. The supernatant was decanted into two fresh 50 mL Falcon centrifuge tubes and 10 mL of n-butyl acetate were added to each centrifuge tube. The tubes were vortexed, centrifuged at 10,000 g for 10 min in order to separate the organic layer, which was discarded. The n-butyl acetate extraction step was repeated two more times. Finally, the remaining aqueous layer was flash frozen and lyophilized to yield a pale-yellow powder (267 mg, 92%).

Example 1.2 Synthesis of Diaryl Ether Reagents

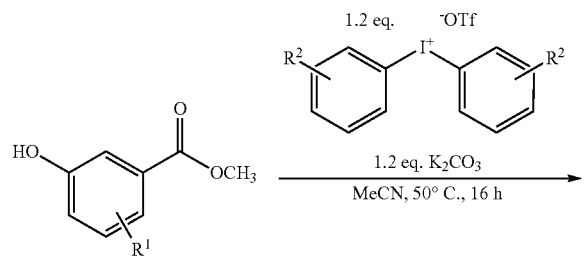

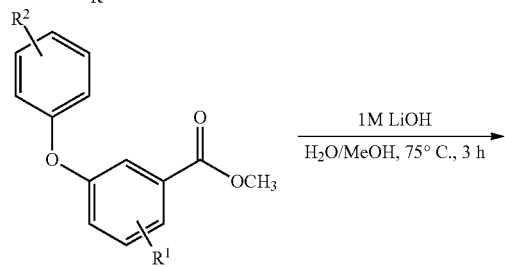

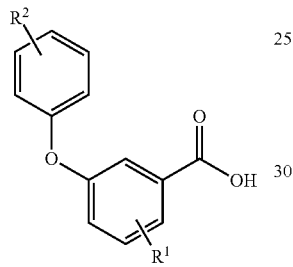

The above scheme represents a general procedure for diaryl ether-type benzoic acid reagents useful in making compounds of the invention. An exemplary synthesis follows below.

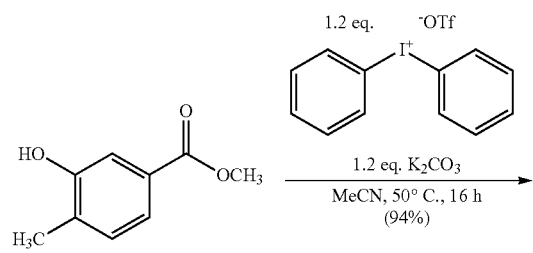

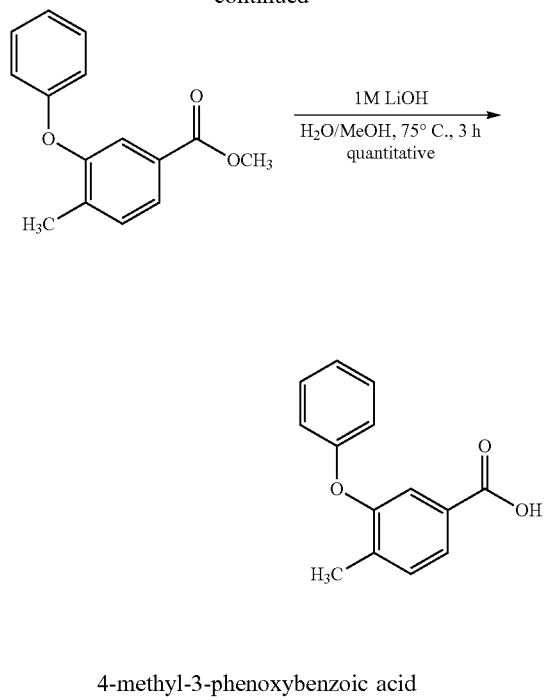

4-methyl-3-phenoxybenzoic acid

A 100 mL round bottom was fitted with a magnetic stirbar and charged with methyl 3-hydroxy-4-methylbenzoate (1.0 g, 6.0 mmol, 1.0 eq.), diphenyliodonium triflate (3.1 g, 7.2 mmol, 1.2 eq.), potassium carbonate (1 g, 7.2 mmol, 1.2 eq.) and 35 mL of acetonitrile were added. The reaction mixture was stirred at 50° C. for 16 h. The reaction mixture was then concentrated by rotary evaporation, re-dissolved in a minimal volume of toluene, and subjected to normal phase silica gel column chromatography (EtOAc/hexanes, 0 to 20% EtOAc gradient over 15 min). Fractions containing the product were concentrated and then the oil was transferred to a 2-dram vial. 1M LiOH in H₂O (2 mL) and a few drops of methanol were added. The mixture was stirred at 75° C. for 3 h. Then, the mixture was cooled and neutralized with concentrated HCl and extracted with 2× equal volume EtOAc. The organic layers were combined, dried over sodium sulfate, filtered through cotton, and concentrated by rotary evaporation to afford the title compound as a white solid (1.3 g, >99% yield).

Example 2. Preparation of Noviose O3" Esters

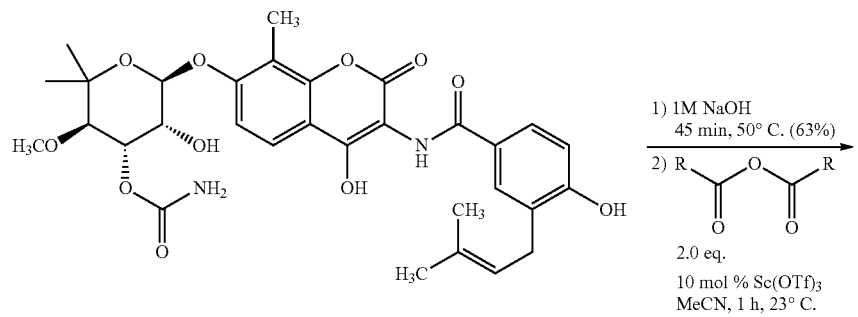

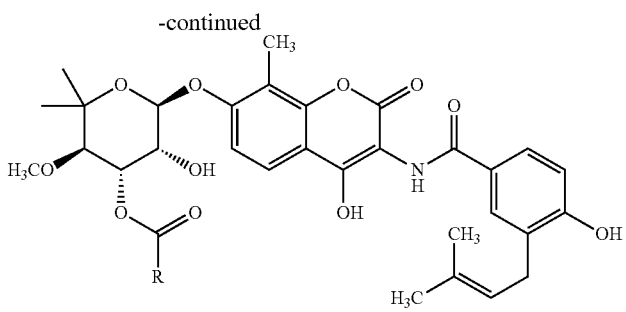
The above scheme represents a general procedure for making compounds of the invention having ester substitution (—OC(O)R) in place of the carbamate (—OC(O)NH₂). An exemplary synthetic route is described below.
Example 2.1. Synthesis of Compound 112
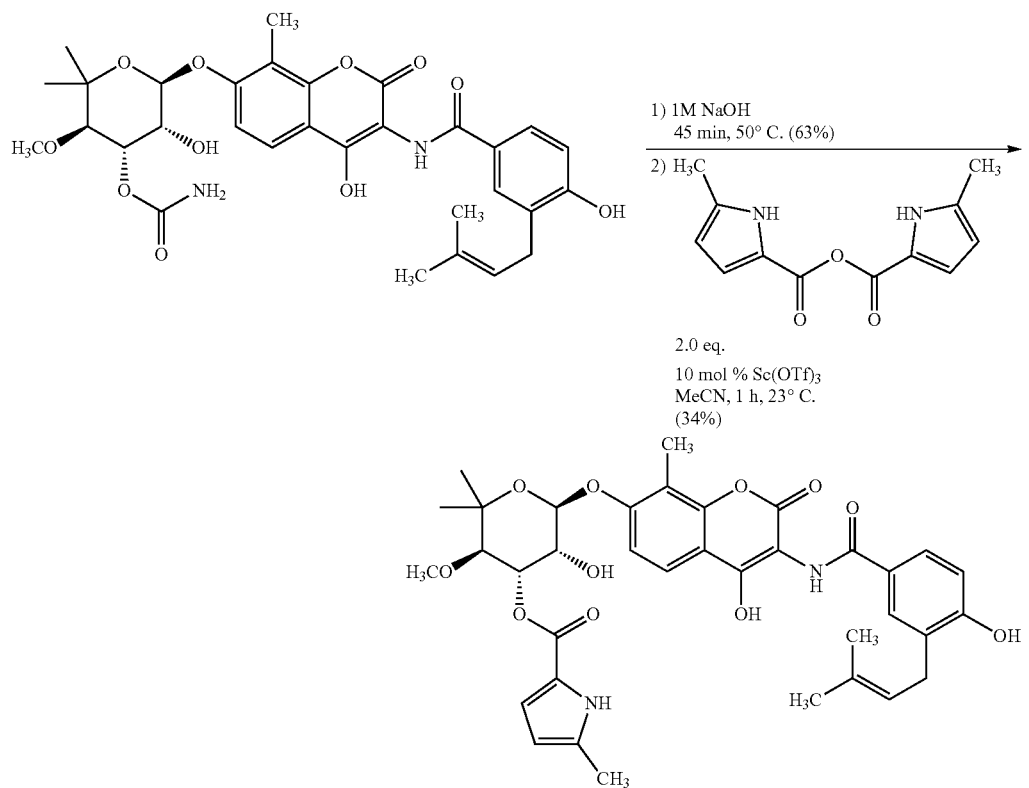
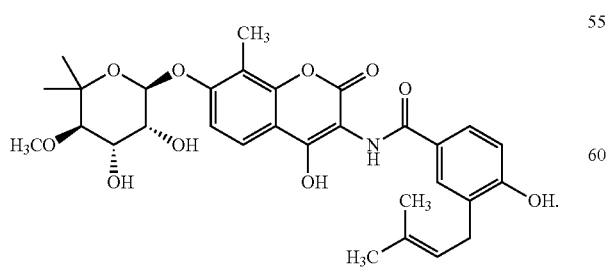
Descarbamoyl novobiocin To a 250 mL round bottom flask equipped with a magnetic stir bar was added 5 g of novobiocin as the sodium salt and 50 mL of 1 M NaOH. The flask was capped with a septum to avoid evaporation of the solution and heated at 50° C. for a total reaction time of 45 minutes. The mixture was then cooled to 0° C., neutralized with 2 M HCl, extracted with 3×50 mL dichloromethane, and the organic layer was dried over $Na_2SO_4$ with heavy stirring for 30 min. The material was concentrated by rotary evaporation and then purified by flash column chromatography with dichloromethane/MeOH as the solvent system and monitoring $A_{340}$. The desired descarbamoyl novobiocin compound eluted after novobiocin aglycone, but before unreacted novobiocin. Fractions containing the product were concentrated and dried in vacuo to afford descarbamoyl novobiocin as a pale-yellow solid (2.8 g, 63%), which was used in the next step.

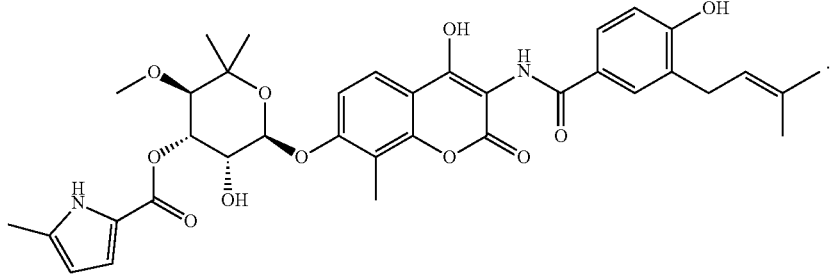

Compound 112

A 20 mL scintillation vial was charged with a magnetic stir bar, descarbamoyl novobiocin (100 mg, 0.18 mmol, 1.0 eq.), 5-methyl-1H-pyrrole-2-carboxylic anhydride (81.5 mg, 0.35 mmol, 2.0 eq.), and 5 mL of anhydrous MeCN. The reaction mixture was stirred at room temperature for 5 min. Meanwhile, a 100 mg/mL solution of $Sc(OTf)_3$ dissolved in anhydrous MeCN was prepared and injected into the reaction mixture via Hamilton syringe (86 µL, 0.018 mmol, 0.1 eq.). The reaction mixture instantly turned a bright yellow color and was allowed to react for at least 1 h or until TLC indicated the reaction was complete. The mixture was then concentrated by rotary evaporation, redissolved in a minimal volume of DMSO, and subjected to reverse-phase column chromatography. Fractions containing the product were concentrated by rotary evaporation and dried in vacuo to afford compound 112 as a tan solid (40 mg, 34%).

Example 3. Preparation of Noviose O3″ Carbamates

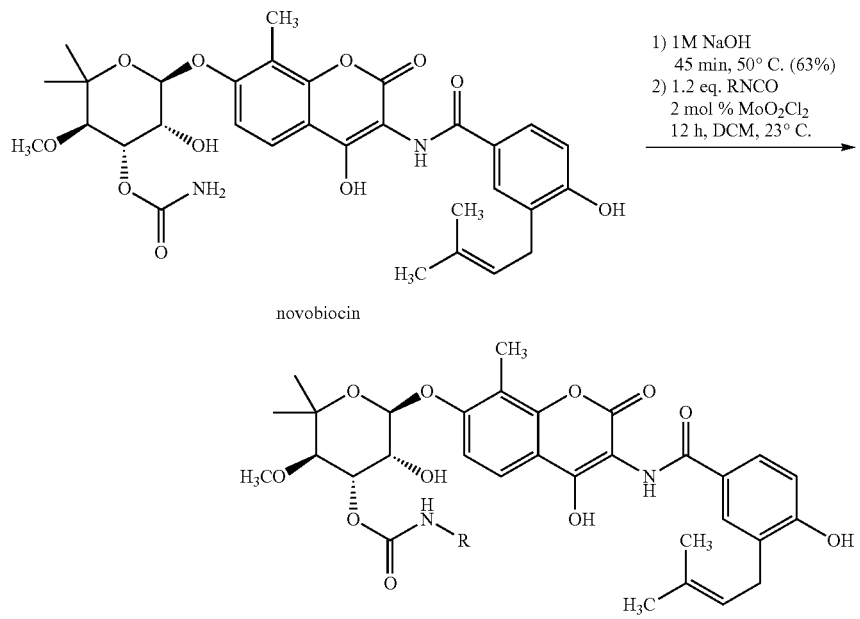

The above scheme represents a general procedure for making compounds of the invention having a substituted carbamate (—OC(O)NHR) in place of the unsubstituted carbamate (—OC(O)NH$_2$). An exemplary synthetic route is described below.

Example 3.1. Synthesis of Compound 103

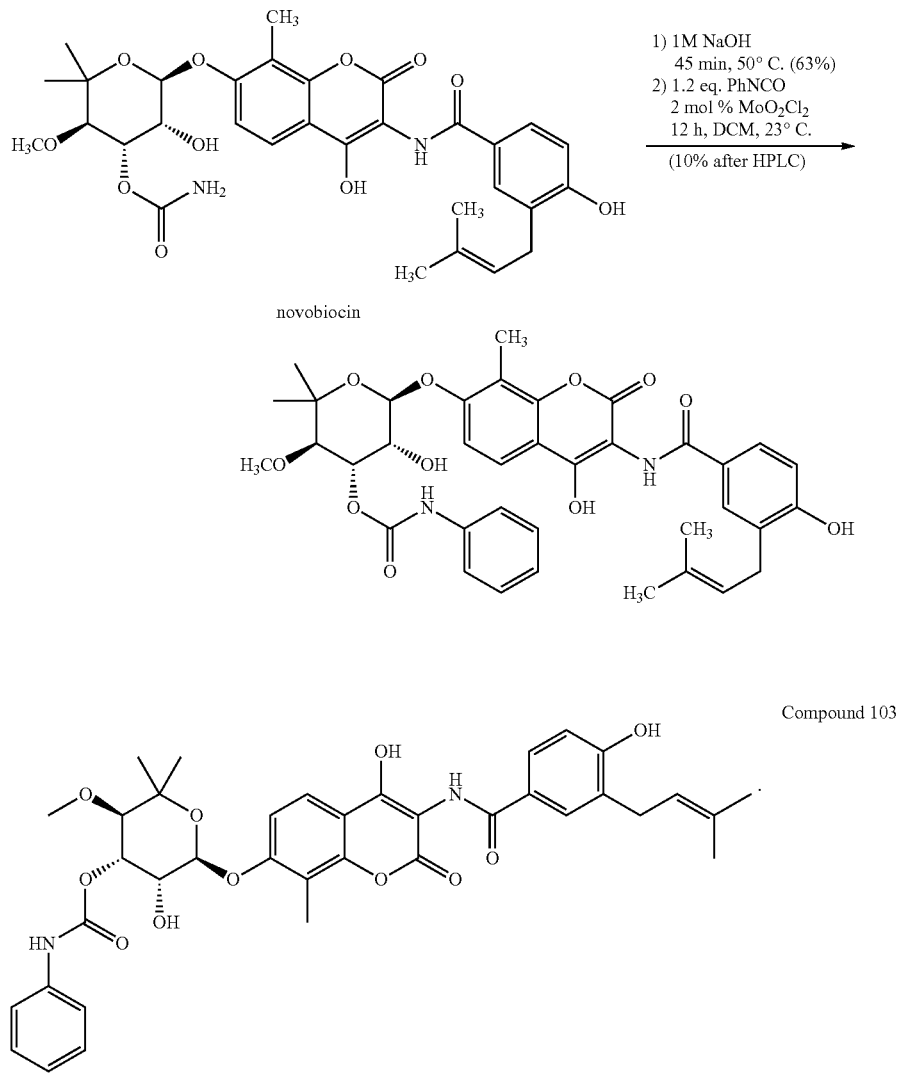

To descarbamoyl novobiocin (48 mg, 0.08 mmol; see Example 2.1) was added solid MoO$_2$Cl$_2$ (0.3 mg, 0.0016 mmol, 2 mol %), and 5 mL of anhydrous DCM were added. While stirring at room temperature (23° C.), PhNCO was delivered by Hamilton syringe (10 μL, 0.09 mmol, 1.2 eq.). The reaction was stirred for 12 h under positive N$_2$ pressure and monitored by TLC (DCM/MeOH). The solvent was subsequently removed by rotary evaporation and the material was subjected to normal phase silica gel column chromatography (DCM/MeOH) monitoring at 340 nm. Fractions containing the product were concentrated, hi-vaced, and further purified by reverse-phase HPLC with a Zorbax C18 column with acetonitrile/water as the eluent (80% MeCN to 100% MeCN over the course of 20 minutes). Fractions containing the product were concentrated by rotary evaporation and hi-vaced to yield the title compound as a white solid (5.8 mg, 10%).

Example 4. Preparation of Benzamide and Carboxamide Derivatives

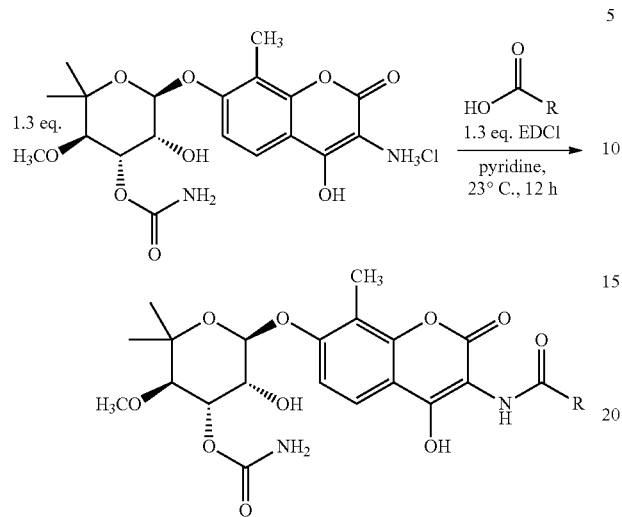

The above scheme represents a general procedure for making compounds of the invention having a benzamide or carboxamide moiety on novenamine. Several exemplary syntheses are described below.

Example 4.1. Synthesis of Compound 13

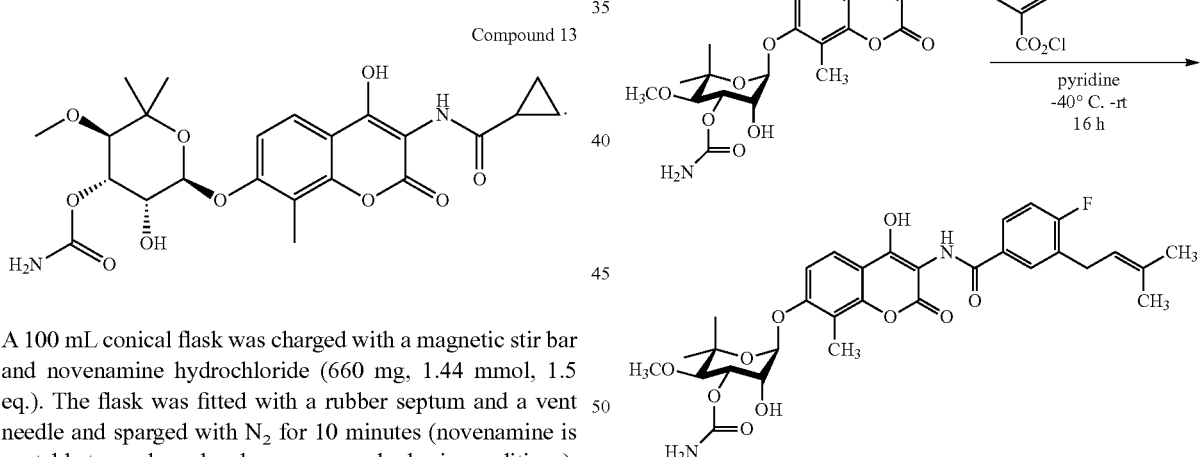

Compound 13

A 100 mL conical flask was charged with a magnetic stir bar and novenamine hydrochloride (660 mg, 1.44 mmol, 1.5 eq.). The flask was fitted with a rubber septum and a vent needle and sparged with $N_2$ for 10 minutes (novenamine is unstable towards molecular oxygen under basic conditions). While under $N_2$, 7 mL of pyridine were added via syringe and the reaction mixture was stirred at −40° C. using a dry ice/acetonitrile bath. After 5 min of stirring at −40° C., cyclopropanecarbonyl chloride (86.8 µL, 100 mg, 0.96 mmol, 1.0 eq.) was added via Hamilton syringe. The vent needle was removed after 10 minutes of stirring, and the reaction was allowed to warm to room temperature after 16 h while under $N_2$. The reaction mixture was concentrated by rotary evaporation, resuspended in dichloromethane, and subjected to normal phase silica gel column chromatography (dichloromethane/MeOH). Fractions containing the product were concentrated and dried in vacuo to afford compound 13 as a white solid (320 mg, 68%).

Example 4.2. Synthesis of Compound 101

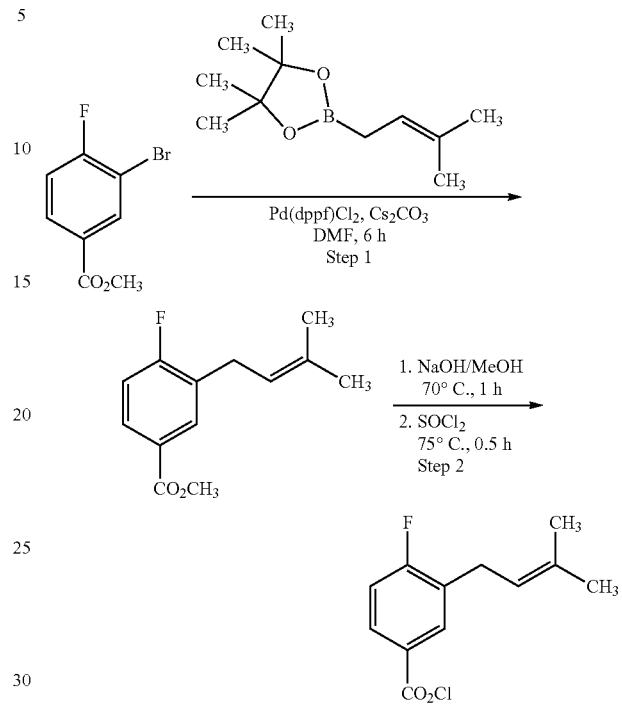

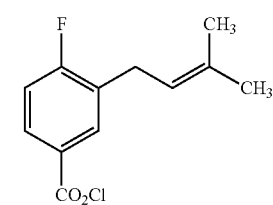

4-fluoro-3-prenylbenzoyl chloride

Step 1.

Methyl 3-bromo-4-fluorobenzoate (500 mg, 2.1 mmol, 1.0 eq.), Pd(dppf)Cl$_2$ (314 mg, 0.43 mmol, 20 mol %), Cs$_2$CO$_3$ (1.4 g, 4.3 mmol, 2.0 eq.) were charged in a 100 mL round bottom flask. 20 mL of anhydrous DMF and a magnetic stirbar were added and the flask was sealed with a rubber septum. A vent needle was inserted and the flask was sparged with N$_2$ for 5 minutes. 3-methyl-2-butenylboronic acid pinacol ester (951 µL, 4.3 mmol, 2.0 eq.) was added and the reaction was heated to 90° C. under positive N$_2$ pressure for 6 h. The reaction mixture was cooled to room temperature and filtered through a pad of Celite rinsed with EtOAc. 100 mL of water were added and the product was extracted by washing with 3×50 mL ethyl acetate. The organic layer was washed several times with water, saturated sodium chloride, and then dried over sodium sulfate. Following filtration, the extract was concentrated by rotary evaporation and subjected to flash column chromatography (hexanes/EtOAc) to afford methyl 4-fluoro-3-(3-methylbut-2-en-1-yl)benzoate as an oil (50% isolated yield), which was used immediately in the next step.

Step 2.

Methyl 4-fluoro-3-(3-methylbut-2-en-1-yl)benzoate (220 mg, 1 mmol) was added to a 15 mL scintillation vial equipped with a magnetic stirbar. 2 mL of 1M NaOH in methanol and a few drops of water were added to the vial. The reaction was heated to 70° C. for 1 h. The carboxylate product precipitated upon completion of the reaction, and the mixture was concentrated by rotary evaporation. The carboxylate salt was protonated by the dropwise addition of 1M HCl. Ethyl acetate (5 mL) and water (5 mL) were added and the acid product was extracted from the organic layer. The extract was dried over sodium sulfate, filtered, and concentrated by rotary evaporation. The carboxylic acid product was a white solid and was used without further purification. Thionyl chloride (700 µL, 14 eq.) was added and the mixture was heated to 75° C. for 0.5 h. The leftover thionyl chloride was removed by rotary evaporation and 150 mg of a sticky orange gel (88% isolated yield).

Compound 101

Novenamine hydrochloride (118 mg, 0.26 mmol, 1.0 eq.) and a magnetic stirbar were added to a 25 mL conical flask and sealed with a rubber septum. A vent needle was inserted and the flask was sparged with N$_2$ for 5 minutes. 2 mL of pyridine were added under positive N$_2$ pressure and the flask was cooled to −40° C. in a dry ice/acetonitrile bath. 4-fluoro-3-prenylbenzoyl chloride (75 mg, 0.31 mmol, 1.2 eq.) was dissolved in 0.5 mL of pyridine and added to the stirring novenamine solution. The solution was stirred for 16 h while allowing the bath to warm to room temperature. The reaction mixture was concentrated by rotary evaporation and then subjected to flash column chromatography with dichloromethane/MeOH. Compound 101 was further purified by reversed phase column chromatography with a Zorbax C18 column with acetonitrile/water as the eluent (90% MeCN to 100% MeCN over the course of 15 minutes), 12.7 mg (8% isolated yield after semi-preparative HPLC).

Example 4.3. Synthesis of Compound 35

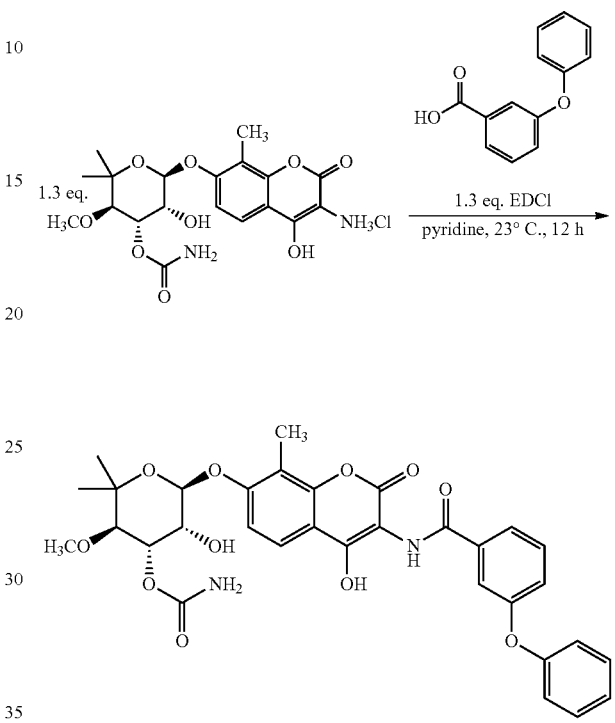

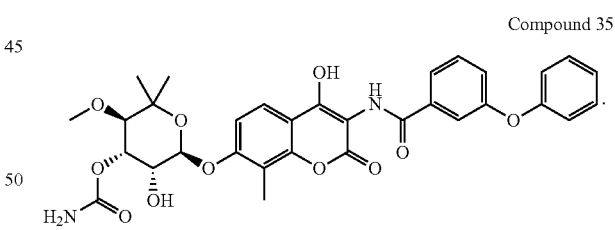

Compound 35

A 100 mL conical flask was charged with a magnetic stir bar, novenamine hydrochloride (503.4 mg, 1.09 mmol, 1.3 eq.), EDCI (209.4 mg, 1.09 mmol, 1.3 eq.), and 3-phenoxybenzoic acid (180.0 mg, 0.84 mmol, 1 eq.). The flask was fitted with a rubber septum and a vent needle and sparged with N$_2$ for 10 minutes (novenamine is unstable towards molecular oxygen under basic conditions). While under positive N$_2$ pressure and a vent needle, 5 mL of pyridine were added via syringe and the reaction mixture was stirred at 23° C. for 12 h. The reaction mixture was concentrated by rotary evaporation, resuspended in DCM, and subjected to normal phase silica gel column chromatography (DCM/MeOH). Fractions containing the product were concentrated and hi-vaced to afford the title compound as a white solid (250 mg, 48%).

Example 5. Preparation of Benzamide and Carboxamide Derivatives Having O3" Carbamate Substitution

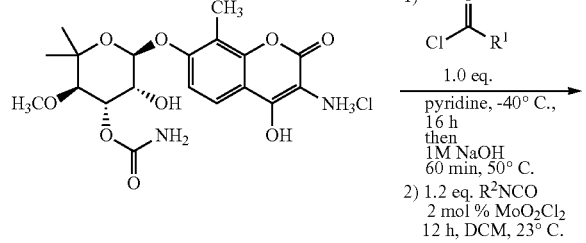

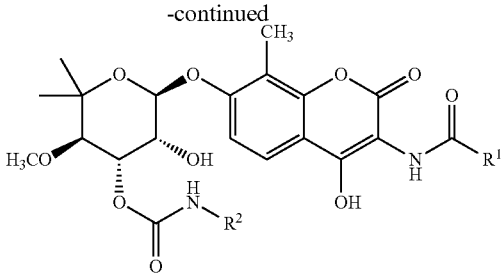

The syntheses described herein may be modular. The above scheme represents a general procedure for making compounds of the invention having benzamide or carboxamide substitution and having a substituted carbamate (—OC(O)NHR) in place of the unsubstituted carbamate (—OC(O)NH$_2$). An exemplary synthetic route is described below.

Example 5.1. Synthesis of Compound 205

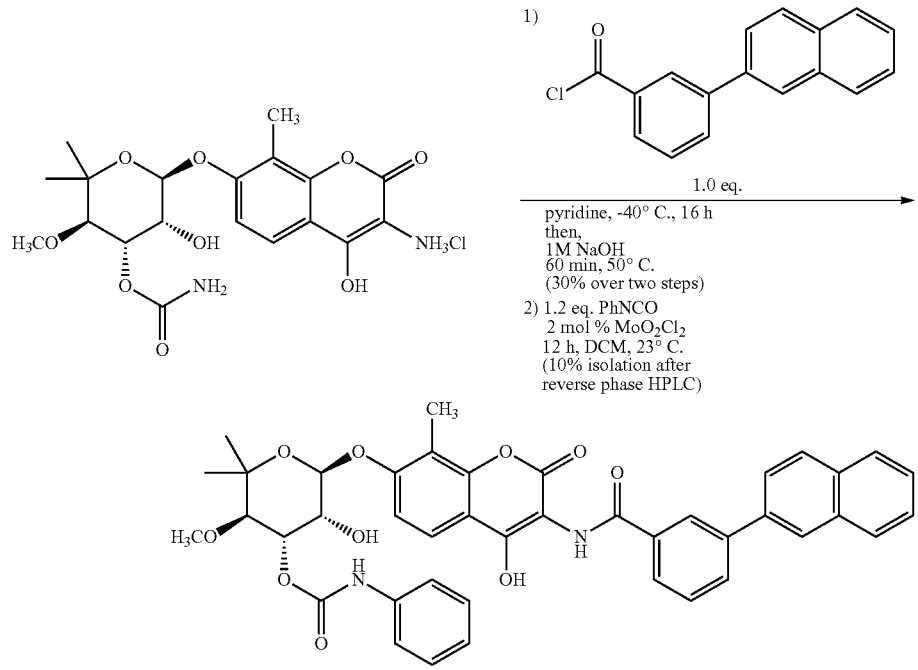

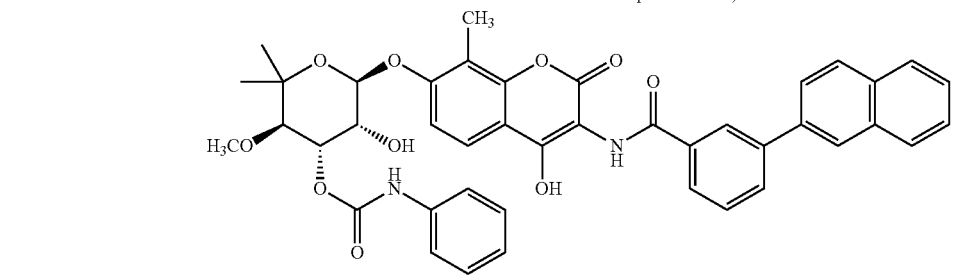

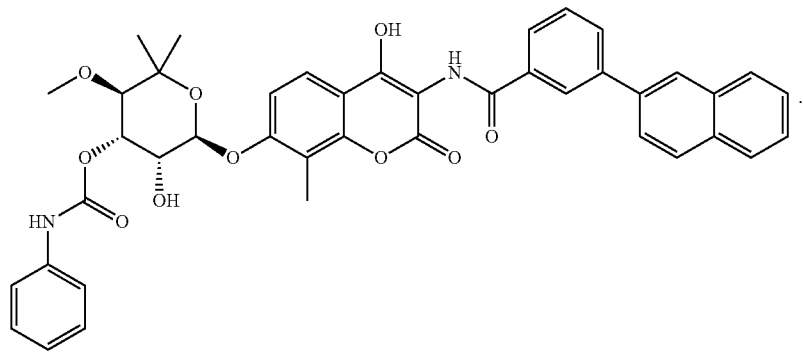

Compound 205

A 20-dram vial was charged with a magnetic stir bar, novenamine hydrochloride (160 mg, 0.35 mmol, 1.3 eq.), and solid 3-(naphthalen-2-yl)benzoyl chloride. The flask was fitted with a rubber septum and a vent needle and sparged with $N_2$ for 10 minutes (novenamine is unstable towards molecular oxygen under basic conditions). While under $N_2$, 7 mL of pyridine were added via syringe and the reaction mixture was stirred at −40° C. using a dry ice/acetonitrile bath. The vent needle was removed after 10 minutes of stirring, and the reaction was allowed to warm to room temperature after 16 h while under $N_2$. The reaction mixture was concentrated by rotary evaporation, resuspended in DCM, and subjected to an aqueous workup, in which the organic layer was subsequently evaporated and dissolved in 5 mL of 1 M NaOH. The solution was transferred to a clean 20-dram vial and heated at 50° C. for 60 minutes while sealed with a Teflon cap to prevent evaporation of the solution. The reaction was neutralized with 1 M HCl and subjected to an aqueous workup. The organic material was concentrated by rotary evaporation, resuspended in DCM, and subjected to normal phase silica gel column chromatography (DCM/MeOH) monitoring at 340 nm. Fractions containing the product were concentrated and hi-vaced before the final carbamoylation step.

To the descarbamoylated material (48 mg, 0.08 mmol) was added solid $MoO_2Cl_2$ (0.3 mg, 0.0016 mmol, 2 mol %), and 5 mL of anhydrous DCM were added. While stirring at room temperature (23° C.), PhNCO was delivered by Hamilton syringe (10 µL, 0.09 mmol, 1.2 eq.). The reaction was stirred for 12 h under positive $N_2$ pressure and monitored by TLC (DCM/MeOH). The solvent was subsequently removed by rotary evaporation and the material was subjected to normal phase silica gel column chromatography (DCM/MeOH) monitoring at 340 nm. Fractions containing the product were concentrated, hi-vaced, and further purified by reverse-phase HPLC with a Zorbax C18 column with acetonitrile/water as the eluent (80% MeCN to 100% MeCN over the course of 20 minutes). Fractions containing the product were concentrated by rotary evaporation and hi-vaced to yield the title compound as a white solid (5.8 mg, 10%).

Example 6. Synthesis of Sulfamide Derivatives

The above scheme represents a general procedure for making compounds of the invention having sulfonamide substitution. An exemplary synthetic route is described below.

Example 6.1. Synthesis of Compound 202

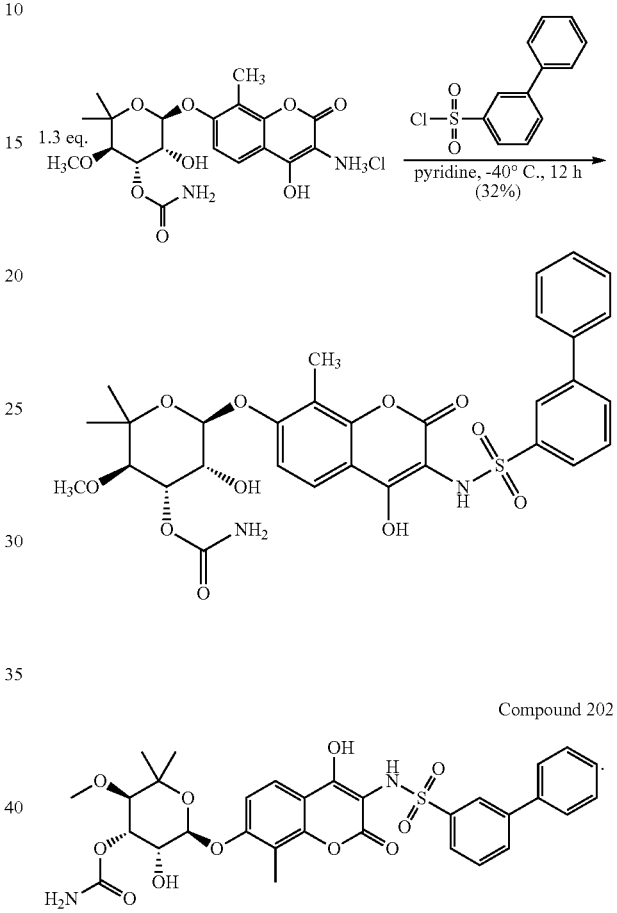

Compound 202

A 2-dram glass vial with a septum cap was fitted with a magnetic stirbar, charged with novenamine hydrochloride (30 mg, 0.06 mmol, 1.3 eq.), and sparged with positive $N_2$ pressure and a vent needle for 10 minutes. Pyridine (1 mL) was added and the mixture was cooled to −40° C. with stirring. A solution of [1,1'-biphenyl]-3-sulfonyl chloride (13.0 mg, 0.05 mmol, 1.0 eq.) in 0.5 mL of pyridine was added and the mixture was stirred under a $N_2$ atmosphere for 12 h, letting the bath warm up to 23° C. The solvent was subsequently removed by rotary evaporation and the material was subjected to normal phase silica gel column chromatography (DCM/MeOH) monitoring at 340 nm. Fractions containing the product were concentrated, hi-vaced, and further purified by reverse-phase HPLC with a Zorbax C18 column with acetonitrile/water as the eluent (80% MeCN to 100% MeCN over the course of 20 minutes). Fractions containing the product were concentrated by rotary evaporation and hi-vaced to yield the title compound as a white solid (10 mg, 32%).

Example 7. Synthesis of Prenyl-Derivatives
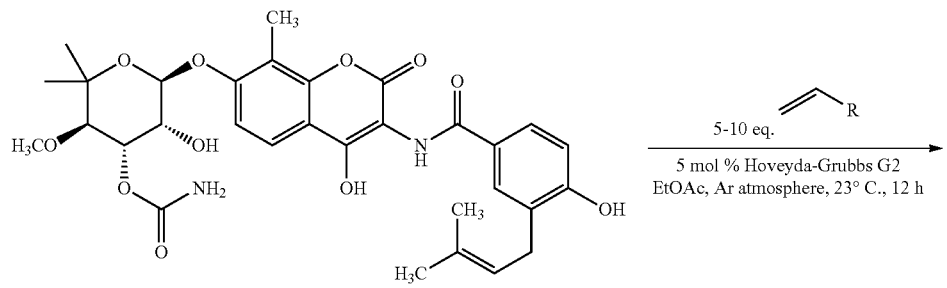
The above scheme represents a general procedure for making compounds of the invention having derivatization at the prenyl moiety. An exemplary synthetic route is described below.
Example 7.1. Synthesis of Compound 81
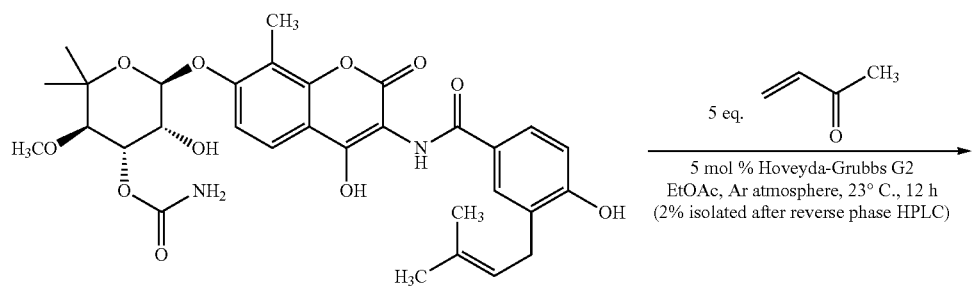
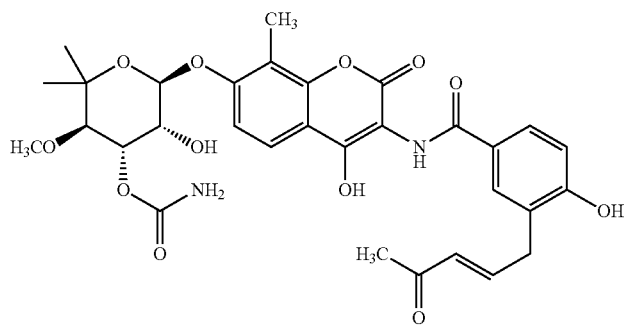

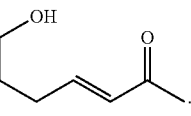

Compound 81

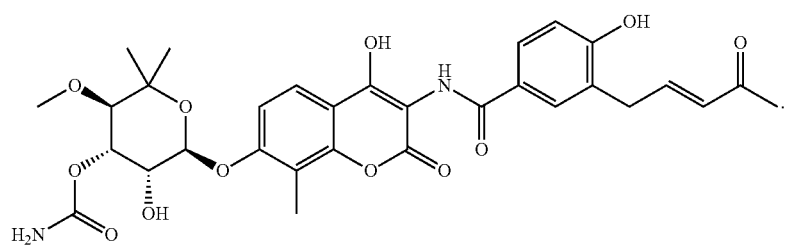

To a 100 mL round bottom flask was added novobiocin (500 mg, 0.81 mmol, 1.0 eq.), methyl vinyl ketone (0.3 mL, 4.1 mmol, 5.0 eq.), and 16 mL of EtOAc. The flask was capped with a rubber septum and parafilm and sparged with an Ar balloon and vent needle for 10 minutes. A syringe pump was used to slowly inject Hoveyda-Grubbs G2 catalyst (25 mg/3 mL $CH_2Cl_2$) over the course of 1 h. Once catalyst addition was complete, the vent needle was removed and the mixture was stirred for 12 h at room temperature. The solvent was subsequently removed by rotary evaporation and the material was subjected to normal phase silica gel column chromatography (DCM/MeOH) monitoring at 340 nm. Fractions containing the product were concentrated, hi-vaced, and further purified by reverse-phase HPLC with a Zorbax C18 column with acetonitrile/water as the eluent (80% MeCN to 100% MeCN over the course of 20 minutes). Fractions containing the product were concentrated by rotary evaporation and hi-vaced to yield the title compound as a white solid (10 mg, 2%).

Example 8. Synthesis of Urea-Derivatives

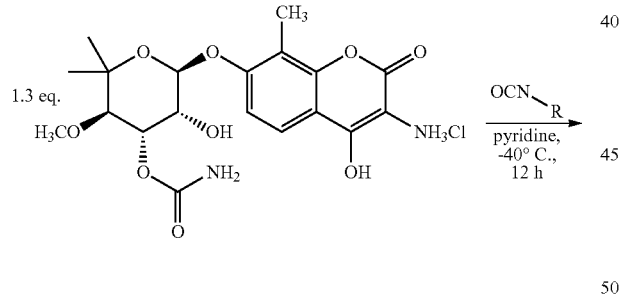

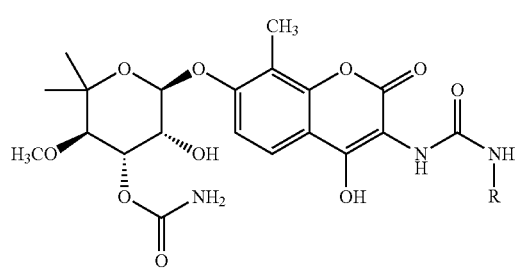

The above scheme represents a general procedure for making compounds of the invention having urea substitution. An exemplary synthetic route is described below.

Example 8.1. Synthesis of Compound 3

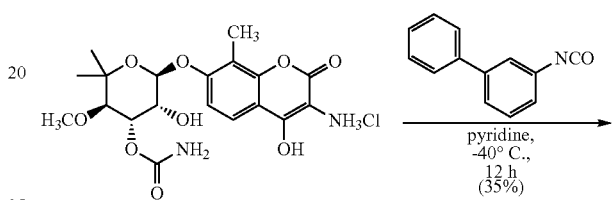

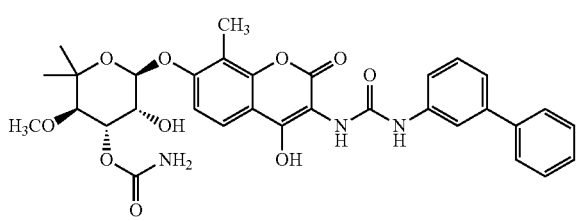

Compound 3

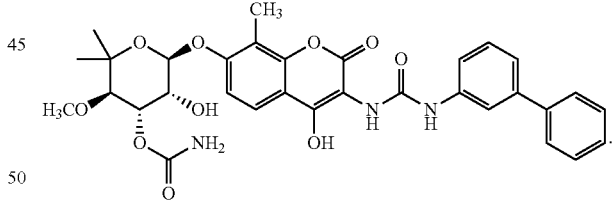

A 2-dram glass vial was charged with a magnetic stir bar and novenamine hydrochloride (46 mg, 0.10 mmol, 1.0 eq.). The vial was fitted with a septum cap and a vent needle and sparged with $N_2$ for 5 minutes. While under positive $N_2$ pressure, 1 mL of pyridine was added via syringe and the reaction mixture was cooled to −40° C. 3-isocyanato-1,1'-biphenyl (20 μL, 0.10 mmol, 1 eq.). was added and the reaction mixture was stirred for 12 h, allowing the temperature of the bath to warm to 23° C. The reaction mixture was concentrated by rotary evaporation, resuspended in DCM, and subjected to normal phase silica gel column chromatography (DCM/MeOH). Fractions containing the product were concentrated and hi-vaced to afford the title compound as a white solid (20 mg, 35%).

Example 9. Synthesis of Vinylogous Acid Derivatives
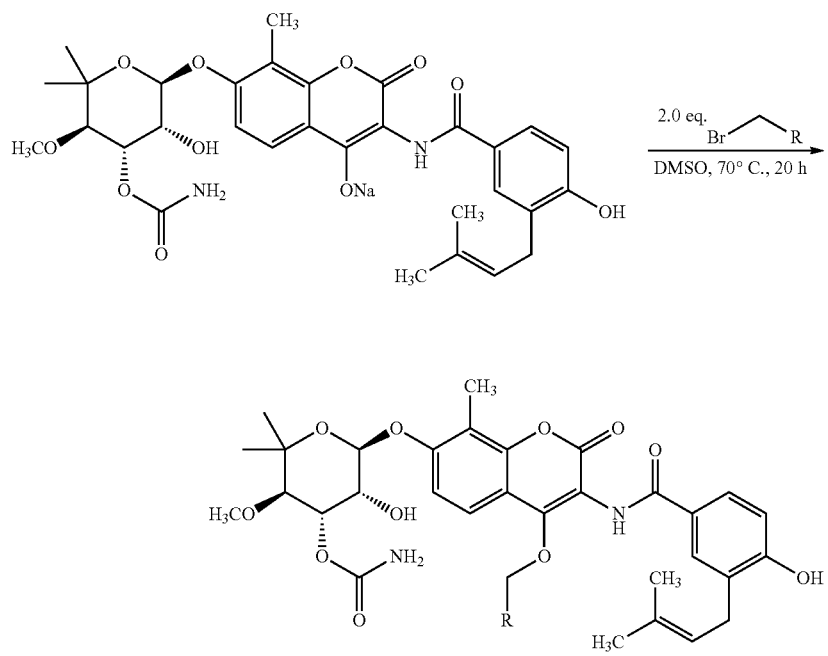
The above scheme represents a general procedure for making compounds of the invention having derivatization at the coumarin core. An exemplary synthetic route is described below.
Example 9.1 Synthesis of Compound 215
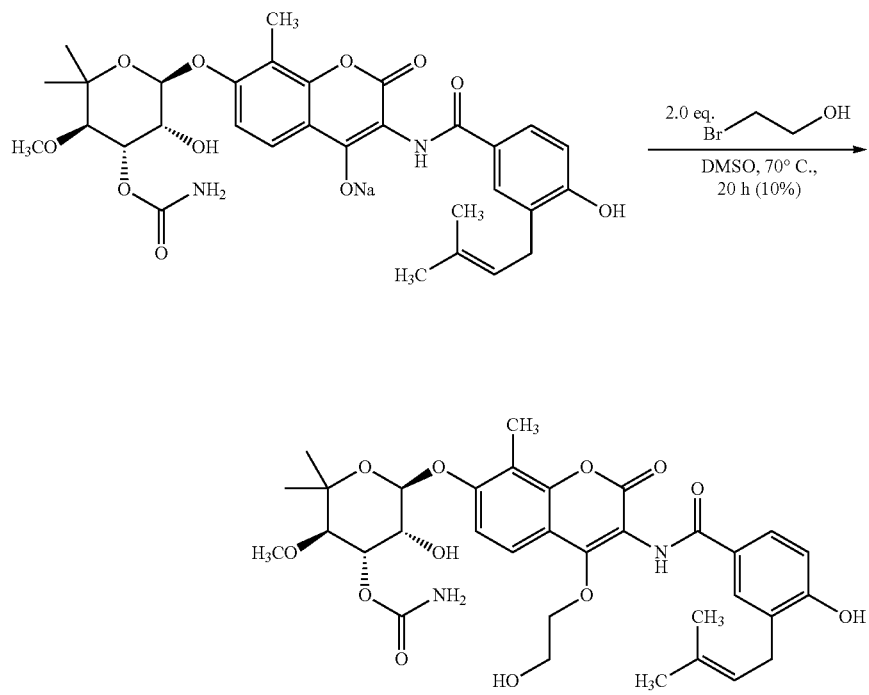

Compound 215

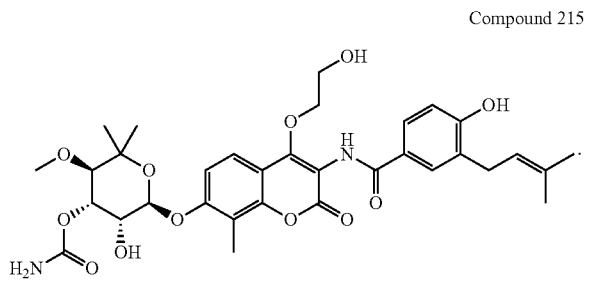 [SMILES: CO[C@@H]1[C@@H](OC(N)=O)[C@@H](O)[C@H](Oc2ccc3c(OCCO)c(NC(=O)c4ccc(O)c(CC=C(C)C)c4)c(=O)oc3c2C)OC1(C)C]

A 2-dram vial was fitted with a magnetic stirbar and charged with novobiocin sodium salt (50 mg, 0.08 mmol, 1.0 eq.) and 2-bromoethan-1-ol (11.2 µL, 0.16 mmol, 2.0 eq.). Anhydrous DMSO was added (2 mL) and the reaction was stirred at 70° C. for 20 h. The DMSO solution was cooled and then directly loaded onto Celite for column chromatography with a reverse-phase RediSep C18Aq column using acetonitrile/water as the eluent. Fractions containing the product were concentrated by rotary evaporation and hi-vaced to yield the title compound as a white solid (5 mg, 10%).

Example 10. Exemplary Characterization Data

The compounds of the invention were made according to the methods outlined in Examples 2-9. Characterization data for the compounds of the invention follows below.

Novobiocin Aglycone.

Yellow solid; TLC Rf=0.66 (DCM); 1H NMR (500 MHz, DMSO-$d_6$) δ 11.9 (s, 1H), 10.4 (s, 1H), 10.1 (s, 1H), 9.2 (s, 1H), 7.8-7.7 (m, 2H), 7.6 (d, J=8.7 Hz, 1H), 6.9 (t, J=8.8 Hz, 2H), 5.3 (t, J=7.3 Hz, 1H), 3.3 (d, J=7.3 Hz, 2H), 2.2 (s, 3H), 1.7 (comp, J=1.5 Hz, 6H); $^{13}$C NMR (126 MHz, DMSO-$d_6$) δ 167.2, 161.4, 160.1, 159.6, 158.9, 151.8, 132.0, 130.4, 128.0, 127.8, 124.7, 123.1, 122.1, 114.8, 112.4, 111.0, 108.6, 101.0, 28.6, 26.1, 18.2, 8.6; HRMS (ESI Neg) m/z calculated for C22H20NO6 [M-H]$^-$, 394.1291 found: 394.1293.

Compound 1

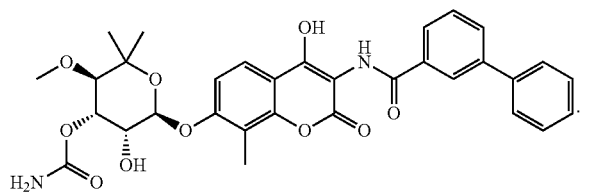

$^1$H NMR (600 MHz, DMSO-$d_6$) δ 8.3 (s, 1H), 7.9 (d, J=4.9 Hz, 1H), 7.8 (d, J=7.8 Hz, 1H), 7.8 (d, J=8.2 Hz, 2H), 7.7 (d, J=8.8 Hz, 1H), 7.6 (t, J=7.7 Hz, 1H), 7.5 (t, J=7.8 Hz, 2H), 7.4 (t, J=7.4 Hz, 1H), 7.0 (d, J=8.7 Hz, 1H), 6.6 (comp, 2H), 5.6 (d, J=5.2 Hz, 1H), 5.5 (s, 1H), 5.2 (dd, J=9.9, 3.2 Hz, 1H), 4.1-4.0 (m, 1H), 3.5 (comp, 4H), 2.2 (s, 3H), 1.3 (s, 3H), 1.1 (s, 3H).

Compound 2

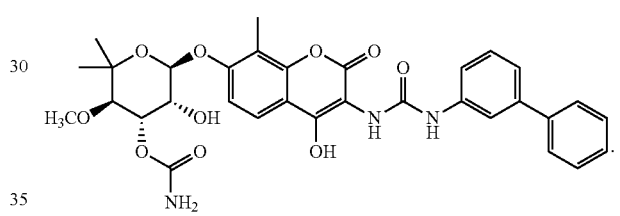

$^1$H NMR (500 MHz, DMSO-$d_6$) δ 8.6 (s, 1H), 8.2 (s, 1H), 8.1 (d, J=8.2 Hz, 2H), 7.8 (comp, J=8.0, 4.0 Hz, 4H), 7.6 (d, J=8.6 Hz, 1H), 7.5 (t, J=7.6 Hz, 2H), 7.4 (t, J=7.3 Hz, 1H), 6.9 (d, J=8.8 Hz, 1H), 6.7 (comp, 2H), 5.5 (s, 1H), 5.4 (d, J=2.5 Hz, 1H), 5.2 (dd, J=9.7, 3.2 Hz, 1H), 4.0 (s, 1H), 3.5 (comp, 4H), 2.2 (s, 3H), 1.3 (s, 3H), 1.1 (s, 3H).

Compound 3

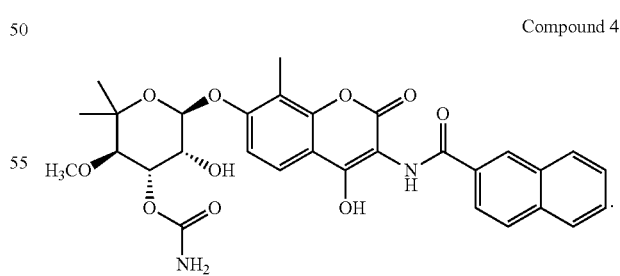

$^1$H NMR (600 MHz, DMSO-$d_6$) δ 8.1 (s, 1H), 7.7 (comp, 2H), 7.6 (comp, 2H), 7.5 (comp, 2H), 7.4 (comp, 3H), 7.2 (d, J=7.5 Hz, 1H), 7.0 (d, J=8.8 Hz, 1H), 6.6 (comp, 4H), 5.6-5.5 (m, 1H), 5.4 (d, J=2.5 Hz, 1H), 5.2 (dd, J=9.8, 3.2 Hz, 1H), 4.0 (s, 1H), 3.5 (comp, 4H), 2.2 (s, 3H), 1.3 (s, 3H), 1.1 (s, 3H).

Compound 4

$^1$H NMR (600 MHz, DMSO-$d_6$) δ 8.9 (s, 1H), 8.6 (s, 1H), 8.1 (s, 1H), 8.1 (d, J=8.6 Hz, 1H), 8.0 (d, J=7.8 Hz, 1H), 8.0 (comp, 2H), 7.6 (comp, 3H), 6.9 (d, J=8.8 Hz, 1H), 6.6 (comp, 2H), 5.6 (d, J=5.1 Hz, 1H), 5.4 (d, J=2.5 Hz, 1H), 5.2 (dd, J=9.8, 3.2 Hz, 1H), 4.1-4.0 (m, 1H), 3.5 (comp, 4H), 2.2 (s, 3H), 1.3 (s, 3H), 1.1 (s, 3H).

Compound 5

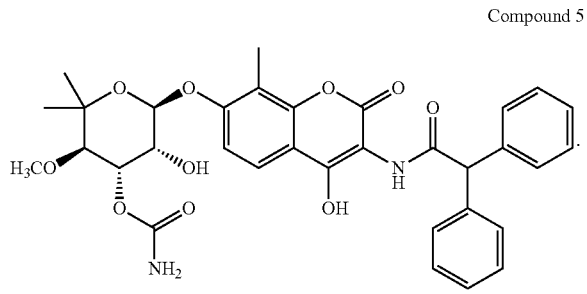 [SMILES: CO[C@@H]1[C@@H](OC(N)=O)[C@@H](O)[C@H](Oc2ccc3c(O)c(NC(=O)C(c4ccccc4)c4ccccc4)c(=O)oc3c2C)OC1(C)C]

¹H NMR (600 MHz, DMSO-d₆) δ 12.9-12.0 (m, 1H), 9.4 (s, 1H), 7.7 (d, J=8.7 Hz, 1H), 7.4 (comp, 4H), 7.3 (comp, 4H), 7.2 (comp, 2H), 7.1-7.0 (m, 1H), 6.6 (comp, 2H), 5.6 (d, J=4.7 Hz, 1H), 5.5 (d, J=2.6 Hz, 1H), 5.3 (s, 1H), 5.1 (dd, J=9.8, 3.2 Hz, 1H), 4.1-4.0 (m, 1H), 3.5 (comp, 4H), 2.2 (s, 3H), 1.2 (s, 3H), 1.0 (s, 3H).

Compound 6

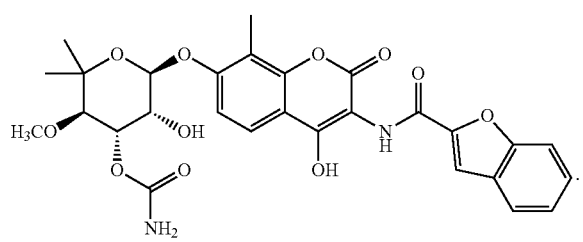

¹H NMR (600 MHz, DMSO-d₆) δ 12.8 (s, 1H), 9.0 (s, 1H), 8.1 (s, 1H), 7.8 (d, J=7.8 Hz, 1H), 7.6 (comp, 2H), 7.4 (t, J=7.6 Hz, 1H), 7.3 (t, J=7.6 Hz, 1H), 6.9 (d, J=8.8 Hz, 1H), 6.6 (comp, 2H), 5.6 (d, J=5.2 Hz, 1H), 5.5-5.4 (m, 1H), 5.2 (dd, J=9.8, 3.2 Hz, 1H), 4.1-4.0 (m, 1H), 3.5 (comp, 4H), 2.2 (s, 3H), 1.3 (s, 3H), 1.1 (s, 3H).

Compound 7

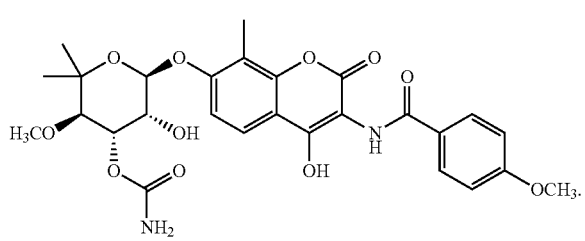

¹H NMR (500 MHz, DMSO-d₆) δ 12.1 (s, 1H), 9.2 (s, 1H), 8.0 (d, J=8.8 Hz, 2H), 7.7 (d, J=8.8 Hz, 1H), 7.1 (d, J=8.9 Hz, 1H), 7.0 (d, J=8.8 Hz, 2H), 6.6 (d, J=92.1 Hz, 2H), 5.6 (d, J=5.2 Hz, 1H), 5.5-5.5 (m, 1H), 5.2 (dd, J=9.9, 3.1 Hz, 1H), 4.1-4.1 (m, 1H), 3.8 (s, 3H), 3.5 (comp, 4H), 2.2 (s, 3H), 1.3 (s, 3H), 1.1 (s, 3H).

Compound 9

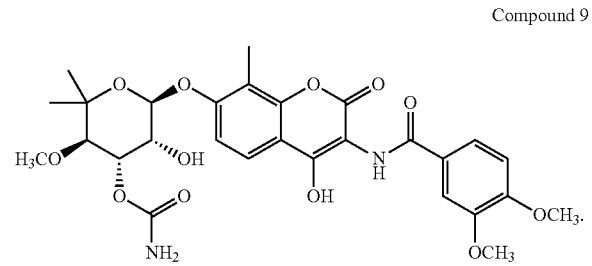 [SMILES: COc1ccc(C(=O)Nc2c(O)c3ccc(O[C@@H]4OC(C)(C)[C@H](OC)[C@@H](OC(N)=O)[C@H]4O)c(C)c3oc2=O)cc1OC]

¹H NMR (600 MHz, DMSO-d₆) δ 12.7 (s, 1H), 12.0 (s, 1H), 7.7 (d, J=8.7 Hz, 1H), 7.6 (d, J=8.7 Hz, 1H), 7.6-7.5 (m, 1H), 7.0 (d, J=8.6 Hz, 2H), 6.5 (s, 2H), 5.6-5.5 (m, 1H), 5.5-5.4 (m, 1H), 5.1 (d, J=9.9 Hz, 1H), 4.0 (s, 1H), 3.8 (comp, 6H), 3.5 (comp, J=1.7 Hz, 4H), 2.2 (s, 3H), 1.2 (s, 3H), 1.1 (s, 3H).

Compound 10

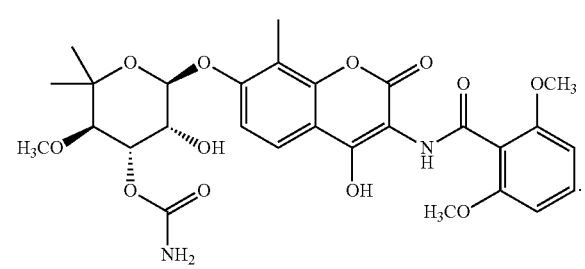

¹H NMR (600 MHz, DMSO-d₆) δ 12.5 (s, 1H), 10.0 (s, 1H), 7.8 (d, J=8.8 Hz, 1H), 7.4 (t, J=8.4 Hz, 1H), 7.2 (d, J=9.2 Hz, 1H), 6.7 (comp, J=8.4 Hz, 4H), 5.6 (d, J=4.4 Hz, 1H), 5.5 (s, 1H), 5.2 (d, J=10.2 Hz, 1H), 4.1-4.0 (m, 1H), 3.8 (comp, J=1.3 Hz, 6H), 3.5 (comp, 4H), 2.2 (s, 3H), 1.3 (s, 3H), 1.1 (s, 3H).

Compound 11

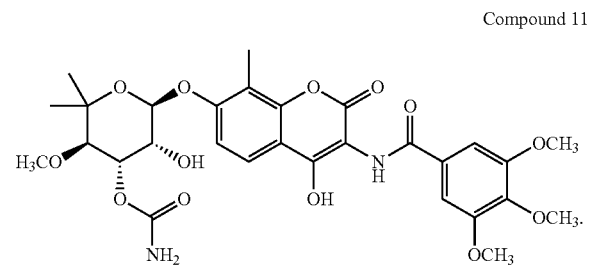 [SMILES: COc1cc(C(=O)Nc2c(O)c3ccc(O[C@@H]4OC(C)(C)[C@H](OC)[C@@H](OC(N)=O)[C@H]4O)c(C)c3oc2=O)cc(OC)c1OC]

¹H NMR (600 MHz, DMSO-d₆) δ 11.9 (s, 1H), 9.4 (s, 1H), 7.7 (d, J=8.8 Hz, 1H), 7.3 (s, 1H), 7.2 (d, J=8.9 Hz, 1H), 6.6 (comp, 2H), 5.6 (d, J=5.2 Hz, 1H), 5.6-5.5 (m, 1H), 5.2 (dd, J=9.9, 3.2 Hz, 1H), 4.1-4.0 (m, 1H), 3.9 (comp, 6H), 3.7 (s, 3H), 3.5 (comp, 4H), 2.2 (s, 3H), 1.3 (s, 3H), 1.1 (s, 3H).

3.1 Hz, 1H), 4.07 (d, J=3.0 Hz, 1H), 3.49-3.44 (comp, 4H), 3.23 (s, 1H), 2.19 (s, 3H), 1.99-1.91 (m, 3H), 1.90-1.84 (comp, 6H), 1.69-1.56 (comp, 6H), 1.25 (s, 3H), 1.04 (s, 3H).

Compound 13

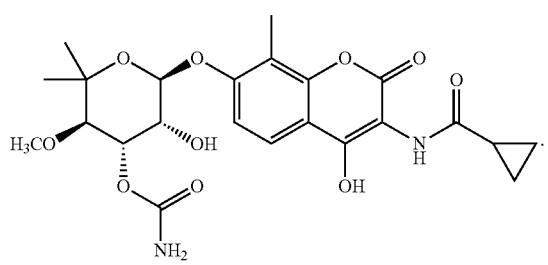

White solid; TLC Rf=0.3 (5% MeOH/DCM); $^1$H NMR (500 MHz, DMSO-$d_6$) δ 12.6 (br, 1H), 9.9 (s, 1H), 7.7 (d, J=8.9 Hz, 1H), 7.1 (d, J=9.1 Hz, 1H), 6.6 (s, 2H), 5.6 (br, 1H), 5.5 (d, J=2.4 Hz, 1H), 5.2 (dd, J=9.9, 3.1 Hz, 1H), 4.1 (t, J=2.8 Hz, 1H), 3.5 (comp, 4H), 2.2 (comp, 4H), 1.2 (s, 3H), 1.0 (s, 3H), 0.9 (comp, 4H); $^{13}$C NMR (126 MHz, DMSO-$d_6$) δ 175.0, 160.1, 156.9, 156.4, 156.1, 150.0, 121.8, 112.7, 110.4, 110.2, 102.5, 98.6, 80.8, 78.2, 70.4, 68.8, 61.0, 28.5, 22.7, 13.8, 8.3, 8.2; HRMS (ESI Neg) m/z calculated for $C_{23}H_{27}N_2O_{10}$ [M-H]$^-$, 491.1671 found: 491.1680.

Compound 13A

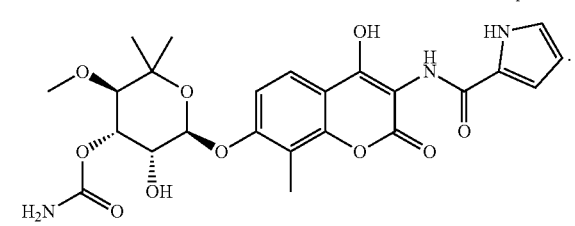

White solid; TLC Rf=0.33 (10% MeOH/DCM); $^1$H NMR (600 MHz, DMSO-$d_6$) δ 12.1 (s, 1H), 9.2 (s, 1H), 7.7 (d, J=8.9 Hz, 1H), 7.2 (d, J=9.0 Hz, 1H), 6.8-6.4 (comp, 2H), 5.6 (d, J=5.2 Hz, 1H), 5.5 (d, J=2.5 Hz, 1H), 5.2 (dd, J=9.8, 3.2 Hz, 1H), 4.1-4.0 (m, 1H), 3.5-3.4 (comp, 4H), 2.2 (s, 3H), 1.4-1.3 (m, 2H), 1.3-1.2 (comp, 5H), 1.0 (s, 3H); $^{13}$C NMR (151 MHz, DMSO-$d_6$) δ 169.9 (d, J=21.1 Hz), 161.0, 160.9, 157.5, 156.7, 151.3, 122.4, 113.3, 110.5, 110.4, 100.2, 98.9, 81.2, 79.3, 78.6, 77.8, 70.8, 69.2, 61.4, 28.9, 23.2, 13.9 (d, J=10.3 Hz), 8.7; 19F NMR (471 MHz, DMSO-$d_6$) δ −195.5; HRMS (ESI Neg) m/z calculated for $C_{23}H_{26}FN_2O_{10}$ [M-H]$^-$, 509.1571 found: 509.1585.

Compound 14

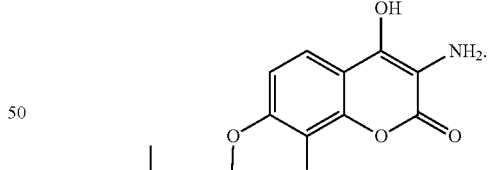

$^1$H NMR (400 MHz, DMSO-$d_6$) δ 8.21 (s, 1H), 7.70 (d, J=8.8 Hz, 1H), 7.10 (d, J=9.1 Hz, 1H), 6.62 (d, J=61.5 Hz, 2H), 5.58 (s, 1H), 5.50 (d, J=2.4 Hz, 1H), 5.15 (dd, J=9.7,

Compound 15

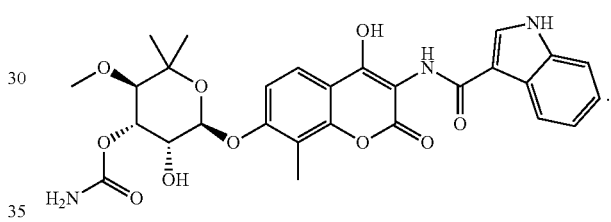

$^1$H NMR (500 MHz, DMSO-$d_6$) δ 12.1 (s, 1H), 11.6 (s, 1H), 8.9 (s, 1H), 7.7 (d, J=8.8 Hz, 1H), 7.1 (s, 1H), 7.0 (s, 1H), 6.9 (s, 1H), 6.6 (comp, 2H), 6.2-6.1 (m, 1H), 5.6 (d, J=5.1 Hz, 1H), 5.5-5.5 (m, 1H), 5.2 (dd, J=10.1, 3.2 Hz, 1H), 4.1-4.0 (m, 1H), 3.5 (comp, 4H), 2.2 (s, 3H), 1.3 (s, 3H), 1.1 (s, 3H).

Compound 17

$^1$H NMR (600 MHz, DMSO-$d_6$) δ 11.4 (s, 1H), 8.2 (comp, 2H), 8.1 (s, 1H), 7.6 (d, J=8.7 Hz, 1H), 7.4 (d, J=8.1 Hz, 1H), 7.1 (t, J=7.6 Hz, 1H), 7.1-7.0 (m, 1H), 6.9 (d, J=8.7 Hz, 1H), 6.6 (comp, 3H), 5.6-5.5 (m, 1H), 5.5-5.4 (m, 1H), 5.2 (dd, J=9.7, 3.2 Hz, 1H), 4.1-4.0 (m, 1H), 3.5 (comp, 4H), 2.2 (s, 3H), 1.3 (s, 3H), 1.1 (s, 3H).

Compound 19

$^1$H NMR (500 MHz, DMSO-$d_6$) δ 8.9 (s, 1H), 8.3 (s, 1H), 8.1 (s, 1H), 7.9 (d, J=7.8 Hz, 1H), 7.8 (d, J=7.8 Hz, 1H), 7.7 (d, J=7.8 Hz, 2H), 7.6 (d, J=8.7 Hz, 1H), 7.5 (t, J=7.7 Hz, 1H), 7.3 (d, J=7.8 Hz, 2H), 6.9 (d, J=8.8 Hz, 1H), 6.6 (comp, 2H), 5.5-5.5 (m, 1H), 5.5-5.4 (m, 1H), 5.2 (dd, J=9.8, 3.1 Hz, 1H), 4.1-4.0 (m, 1H), 3.5 (comp, 4H), 2.4 (s, 3H), 2.2 (s, 3H), 1.3 (s, 3H), 1.1 (s, 3H).

Compound 21

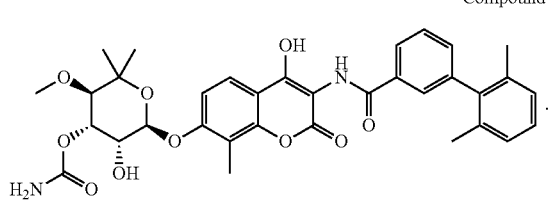

¹H NMR (600 MHz, DMSO-d₆) δ 8.8 (s, 1H), 8.3 (s, 1H), 8.1 (s, 1H), 7.9 (d, J=7.7 Hz, 1H), 7.8 (d, J=7.8 Hz, 1H), 7.6 (d, J=3.9 Hz, 2H), 7.6 (d, J=5.0 Hz, 1H), 7.5 (t, J=7.7 Hz, 1H), 7.2 (t, J=4.4 Hz, 1H), 6.9 (d, J=8.8 Hz, 1H), 6.7-6.5 (m, 2H), 5.5 (d, J=4.9 Hz, 1H), 5.4-5.4 (m, 1H), 5.2 (dd, J=9.7, 3.2 Hz, 1H), 4.1-4.0 (m, 1H), 3.5 (comp, 4H), 2.2 (s, 3H), 1.3 (s, 3H), 1.1 (s, 3H).

Compound 22

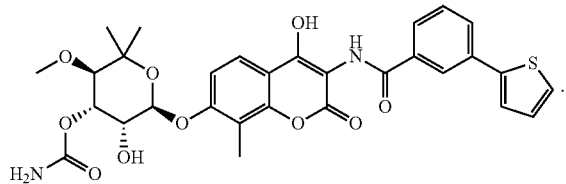

¹H NMR (600 MHz, DMSO-d₆) δ 8.7 (s, 1H), 8.1 (s, 1H), 7.6 (d, J=8.6 Hz, 1H), 7.5 (s, 1H), 7.4 (d, J=7.7 Hz, 1H), 7.3 (t, J=7.9 Hz, 1H), 7.1 (d, J=8.2 Hz, 1H), 6.9 (d, J=8.9 Hz, 1H), 6.6 (comp, 2H), 5.5 (d, J=5.2 Hz, 1H), 5.5-5.4 (m, 1H), 5.2 (dd, J=9.8, 3.0 Hz, 1H), 4.1-4.0 (m, 1H), 3.8 (comp, 4H), 3.5 (comp, 4H), 3.2 (comp, 4H), 2.2 (s, 3H), 1.3 (s, 3H), 1.1 (s, 3H).

Compound 23

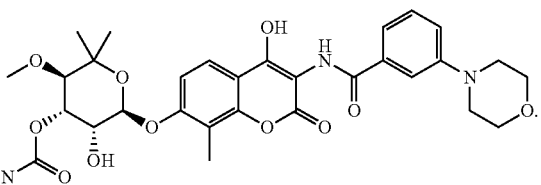

¹H NMR (500 MHz, DMSO-d₆) δ 9.1 (s, 1H), 8.4 (s, 1H), 8.3 (d, J=8.4 Hz, 2H), 8.1 (s, 1H), 8.1 (d, J=8.5 Hz, 2H), 8.0 (d, J=7.8 Hz, 1H), 7.9 (d, J=7.9 Hz, 1H), 7.6 (comp, 2H), 6.9 (d, J=8.9 Hz, 1H), 6.5 (comp, 2H), 5.5 (d, J=5.1 Hz, 1H), 5.4-5.4 (m, 1H), 5.2 (dd, J=9.8, 3.1 Hz, 1H), 4.1-4.0 (m, 1H), 3.5 (comp, 4H), 2.1 (s, 3H), 1.3 (s, 3H), 1.1 (s, 3H).

Compound 24

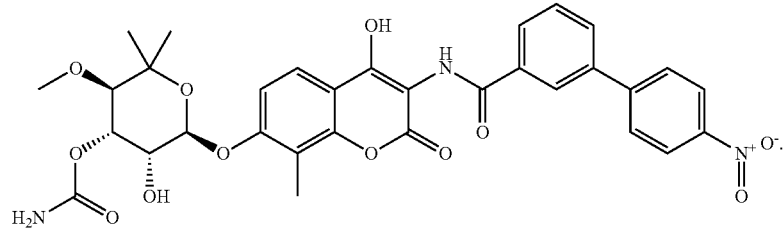

¹H NMR (500 MHz, DMSO-d₆) δ 8.2 (s, 1H), 8.1 (s, 1H), 7.8 (d, J=7.8 Hz, 1H), 7.7 (d, J=7.9 Hz, 1H), 7.7 (comp, 4H), 7.5 (t, J=7.7 Hz, 1H), 7.0-7.0 (m, 1H), 6.8 (d, J=8.9 Hz, 2H), 6.5 (comp, 2H), 5.5 (d, J=5.1 Hz, 1H), 5.5 (s, 1H), 5.2 (dd, J=9.8, 3.2 Hz, 1H), 4.1-4.0 (m, 1H), 3.5 (comp, 4H), 3.0 (comp, 6H), 2.2 (s, 3H), 1.3 (s, 3H), 1.1 (s, 3H).

Compound 25

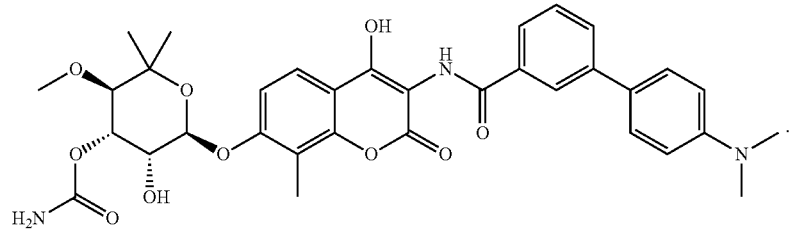

¹H NMR (500 MHz, DMSO-d₆) δ 9.5 (s, 1H), 8.4 (s, 1H), 8.3 (d, J=7.6 Hz, 1H), 8.1 (d, J=8.9 Hz, 1H), 7.7 (t, J=8.1 Hz, 1H), 7.7 (d, J=8.7 Hz, 1H), 7.0 (s, 1H), 6.5 (s, 2H), 5.6 (d, J=5.0 Hz, 1H), 5.5 (s, 1H), 5.2 (comp, 2H), 4.1-4.0 (m, 1H), 3.5 (comp, 4H), 2.2 (s, 3H), 1.3 (s, 3H), 1.1 (s, 3H).

Compound 26

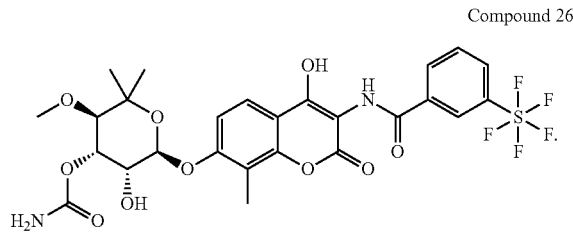 [SMILES: CO[C@@H]1[C@@H](OC(N)=O)[C@@H](O)[C@H](Oc2ccc3c(O)c(NC(=O)c4cccc(S(F)(F)(F)(F)F)c4)c(=O)oc3c2C)OC1(C)C]

¹H NMR (600 MHz, DMSO-d₆) δ 7.7 (d, J=8.8 Hz, 1H), 7.6 (d, J=7.1 Hz, 2H), 7.5 (d, J=15.8 Hz, 1H), 7.5 (comp, 2H), 7.4-7.4 (m, 1H), 7.1 (comp, 2H), 6.6 (comp, 4H), 5.6 (d, J=5.2 Hz, 1H), 5.5 (d, J=2.5 Hz, 1H), 5.2 (dd, J=9.8, 3.1 Hz, 1H), 4.1-4.0 (m, 1H), 3.5 (comp, 4H), 2.2 (s, 3H), 1.3 (s, 3H), 1.1 (s, 3H).

Compound 27

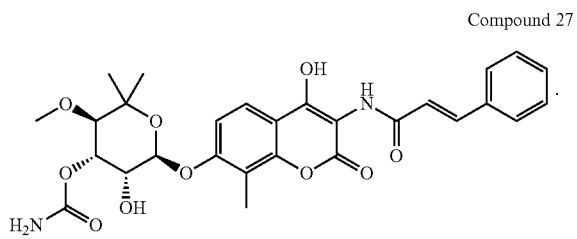 [SMILES: CO[C@@H]1[C@@H](OC(N)=O)[C@@H](O)[C@H](Oc2ccc3c(O)c(NC(=O)/C=C/c4ccccc4)c(=O)oc3c2C)OC1(C)C]

¹H NMR (600 MHz, DMSO-d₆) δ 9.3 (s, 1H), 8.3 (d, J=2.0 Hz, 1H), 7.9 (d, J=7.6 Hz, 1H), 7.8 (dt, J=11.9, 4.3 Hz, 3H), 7.6 (d, J=8.8 Hz, 1H), 7.5 (t, J=7.7 Hz, 1H), 7.3 (comp, 3H), 7.0 (d, J=8.8 Hz, 1H), 6.7 (s, 2H), 5.6 (d, J=5.1 Hz, 1H), 5.5 (s, 1H), 5.2 (dd, J=10.1, 3.2 Hz, 1H), 4.1 (d, J=4.5 Hz, 1H), 3.5 (comp, 4H), 2.2 (s, 3H), 1.3 (s, 3H), 1.1 (s, 3H).

Compound 28

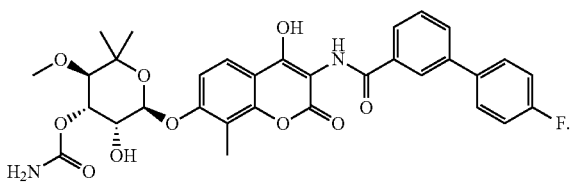

¹H NMR (600 MHz, DMSO-d₆) δ 9.0 (s, 1H), 8.8 (s, 1H), 8.6 (d, J=4.7 Hz, 1H), 8.4 (s, 2H), 8.3 (s, 1H), 8.2-8.2 (m, 1H), 8.0 (d, J=7.8 Hz, 1H), 7.9 (d, J=7.7 Hz, 1H), 7.6 (d, J=8.6 Hz, 1H), 7.6 (t, J=7.7 Hz, 1H), 7.5 (dd, J=8.0, 4.8 Hz, 1H), 6.9 (d, J=8.8 Hz, 1H), 6.3 (s, 1H), 5.5 (s, 1H), 5.4 (d, J=2.5 Hz, 1H), 5.2 (dd, J=9.7, 3.1 Hz, 1H), 4.0 (s, 1H), 3.5 (comp, 4H), 2.2 (s, 3H), 1.3 (s, 3H), 1.1 (s, 3H).

Compound 29

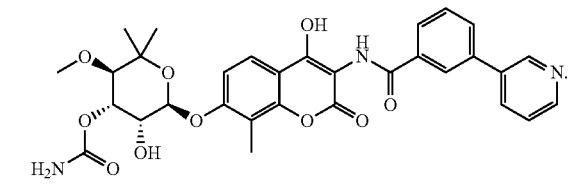

¹H NMR (500 MHz, DMSO-d₆) δ 9.9 (s, 1H), 8.7 (s, 1H), 7.8 (d, J=8.4 Hz, 2H), 7.6 (d, J=8.8 Hz, 1H), 7.0 (d, J=8.9 Hz, 1H), 6.8 (d, J=8.3 Hz, 2H), 6.5 (comp, 3H), 5.5 (d, J=5.1 Hz, 1H), 5.5 (d, J=2.5 Hz, 1H), 5.2 (dd, J=9.8, 3.2 Hz, 1H), 4.1-4.0 (m, 1H), 3.5 (comp, 4H), 2.2 (s, 3H), 1.3 (s, 3H), 1.1 (s, 3H).

Compound 30

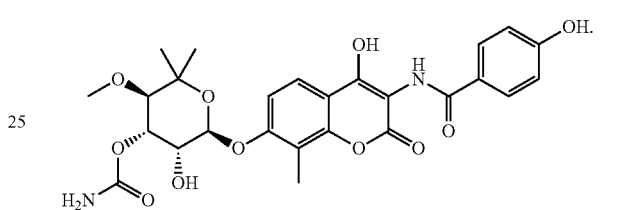

¹H NMR (600 MHz, DMSO-d₆) δ 8.9 (s, 1H), 8.7 (d, J=4.7 Hz, 1H), 8.7 (s, 1H), 8.2 (d, J=7.8 Hz, 1H), 8.1 (d, J=8.0 Hz, 1H), 8.0 (d, J=7.7 Hz, 1H), 7.9 (t, J=7.7 Hz, 1H), 7.6 (d, J=8.6 Hz, 1H), 7.6 (t, J=7.7 Hz, 1H), 7.4 (dd, J=7.4, 4.8 Hz, 1H), 6.9 (d, J=8.8 Hz, 1H), 6.5 (s, 3H), 5.5 (d, J=5.0 Hz, 1H), 5.4 (d, J=2.5 Hz, 1H), 5.2 (dd, J=9.8, 3.2 Hz, 1H), 4.1-4.0 (m, 1H), 3.5 (comp, 4H), 2.2 (s, 3H), 1.3 (s, 3H), 1.1 (s, 3H).

Compound 31

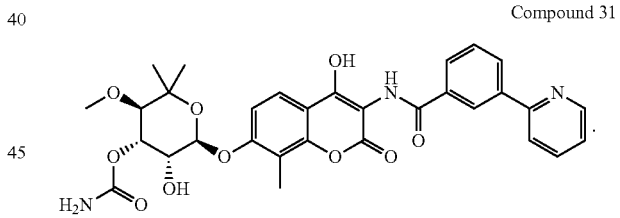

¹H NMR (600 MHz, DMSO-d₆) δ 9.3 (s, 1H), 8.7-8.6 (m, 2H), 8.4-8.4 (m, 1H), 8.0 (d, J=7.7 Hz, 1H), 7.9 (d, J=7.8 Hz, 1H), 7.8 (d, J=6.2 Hz, 2H), 7.6 (comp, 2H), 7.0 (d, J=8.7 Hz, 1H), 6.5 (s, 2H), 5.6 (d, J=5.1 Hz, 1H), 5.4 (d, J=2.6 Hz, 1H), 5.2 (dd, J=9.8, 3.1 Hz, 1H), 4.1 (comp, 2H), 3.5 (comp, 4H), 2.2 (s, 3H), 1.3 (s, 3H), 1.1 (s, 3H).

Compound 32

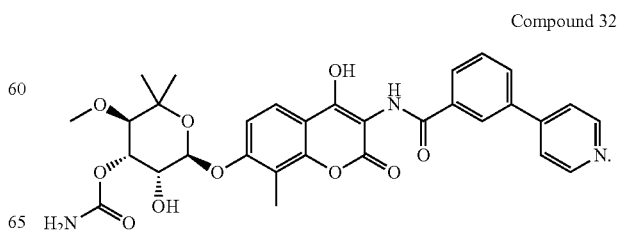

¹H NMR (600 MHz, DMSO-d₆) δ 9.4 (s, 1H), 8.3 (s, 1H), 7.9 (d, J=7.7 Hz, 1H), 7.8 (comp, 3H), 7.6 (d, J=8.8 Hz, 1H), 7.5 (comp, 3H), 7.0 (d, J=8.8 Hz, 1H), 6.6 (comp, 3H), 5.6 (d, J=5.2 Hz, 1H), 5.5-5.5 (m, 1H), 5.2 (dd, J=9.9, 3.1 Hz, 1H), 4.1-4.0 (m, 1H), 3.5 (comp, 4H), 2.2 (s, 3H), 1.3 (s, 3H), 1.1 (s, 3H).

Compound 33

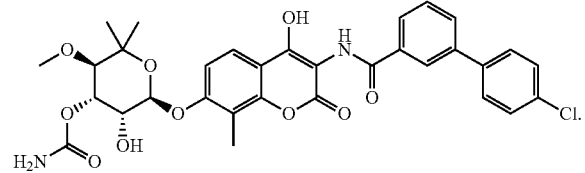

¹H NMR (600 MHz, DMSO-d₆) δ 9.1 (s, 1H), 8.3 (s, 1H), 7.9 (d, J=7.7 Hz, 1H), 7.8 (d, J=8.1 Hz, 2H), 7.8 (d, J=7.8 Hz, 1H), 7.6 (comp, 3H), 7.5 (t, J=7.7 Hz, 1H), 6.9 (d, J=8.8 Hz, 1H), 6.5 (comp, 2H), 5.6 (d, J=5.1 Hz, 1H), 5.5-5.4 (m, 1H), 5.2 (dd, J=9.8, 3.1 Hz, 1H), 4.1 (s, 1H), 4.1-4.0 (m, 1H), 3.5 (comp, 4H), 2.2 (s, 3H), 1.3 (s, 3H), 1.1 (s, 3H).

Compound 34

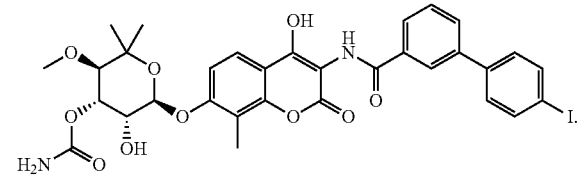

¹H NMR (600 MHz, DMSO-d₆) δ 9.2 (s, 1H), 7.8 (d, J=7.7 Hz, 1H), 7.7 (d, J=8.8 Hz, 1H), 7.6 (d, J=2.3 Hz, 1H), 7.5 (t, J=7.9 Hz, 1H), 7.4 (comp, 2H), 7.2 (dt, J=14.8, 7.8 Hz, 2H), 7.0 (comp, 3H), 6.5 (s, 3H), 5.6 (d, J=5.2 Hz, 1H), 5.5 (s, 1H), 5.2 (dd, J=9.9, 3.1 Hz, 1H), 4.1-4.0 (m, 1H), 3.5 (comp, J=1.6 Hz, 4H), 2.2 (s, 3H), 1.3 (s, 3H), 1.1 (s, 3H).

Compound 36

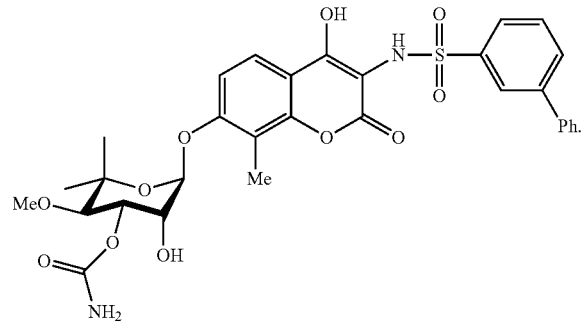

¹H NMR (600 MHz, DMSO-d₆) δ 9.3 (s, 1H), 8.2 (s, 1H), 8.0 (d, J=7.8 Hz, 1H), 7.7 (d, J=7.7 Hz, 1H), 7.6 (d, J=8.8 Hz, 1H), 7.6-7.6 (m, 1H), 7.6 (t, J=7.7 Hz, 1H), 7.5-7.4 (m, 1H), 7.3 (comp, 2H), 7.0 (d, J=8.9 Hz, 1H), 6.5 (comp, 3H), 5.6 (d, J=5.1 Hz, 1H), 5.5-5.5 (m, 1H), 5.2 (dd, J=9.8, 3.2 Hz, 1H), 4.1-4.1 (m, 1H), 3.5 (comp, 4H), 2.2 (s, 3H), 1.3 (s, 3H), 1.1 (s, 3H).

Compound 37

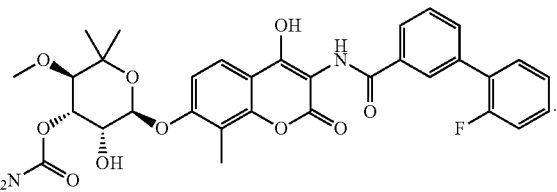

¹H NMR (600 MHz, DMSO-d₆) δ 9.1 (s, 1H), 8.3 (s, 1H), 8.0 (d, J=7.6 Hz, 1H), 7.8 (d, J=7.7 Hz, 1H), 7.6 (comp, 3H), 7.5 (comp, 2H), 7.2 (td, J=8.6, 2.5 Hz, 1H), 7.0 (d, J=8.7 Hz, 1H), 6.5 (comp, 3H), 5.5 (d, J=5.2 Hz, 1H), 5.5-5.4 (m, 1H), 5.2 (dd, J=9.8, 3.2 Hz, 1H), 4.1-4.0 (m, 1H), 3.5 (comp, 4H), 2.2 (s, 3H), 1.3 (s, 3H), 1.1 (s, 3H).

Compound 38

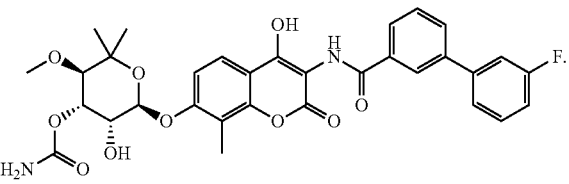

¹H NMR (600 MHz, DMSO-d₆) δ 8.9 (s, 1H), 8.4 (s, 1H), 8.4 (s, 1H), 8.1 (s, 1H), 8.0 (comp, 2H), 8.0 (comp, 4H), 7.6 (d, J=8.6 Hz, 1H), 7.6 (comp, 3H), 6.9 (d, J=8.7 Hz, 1H), 6.5 (comp, 2H), 5.5 (d, J=5.1 Hz, 1H), 5.4-5.4 (m, 1H), 5.2 (dd, J=9.9, 3.1 Hz, 1H), 4.1 (d, J=3.9 Hz, 1H), 3.5 (comp, 4H), 2.2 (s, 3H), 1.3 (s, 3H), 1.1 (s, 3H).

Compound 40

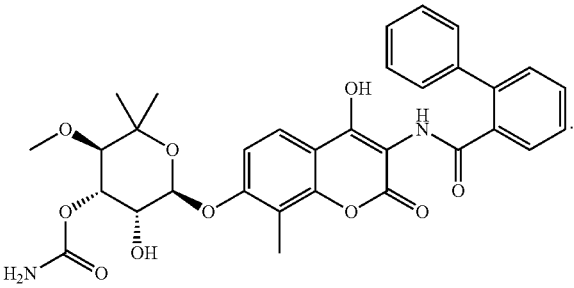

¹H NMR (600 MHz, DMSO-d₆) δ 9.1 (s, 1H), 7.9 (s, 1H), 7.8 (d, J=6.7 Hz, 1H), 7.6 (d, J=8.7 Hz, 1H), 7.3 (comp, 2H), 7.0 (d, J=8.9 Hz, 1H), 6.5 (comp, 2H), 5.6 (d, J=5.1 Hz, 1H), 5.5-5.5 (m, 1H), 5.2 (dd, J=9.9, 3.2 Hz, 1H), 4.1-4.0 (m, 1H), 3.6 (comp, 2H), 3.5 (comp, 4H), 2.3 (comp, 2H), 2.2 (s, 2H), 2.2-2.1 (m, 2H), 2.0-1.9 (m, 1H), 1.8 (dd, J=10.7, 8.2 Hz, 1H), 1.3 (s, 3H), 1.1 (s, 3H).

Compound 41

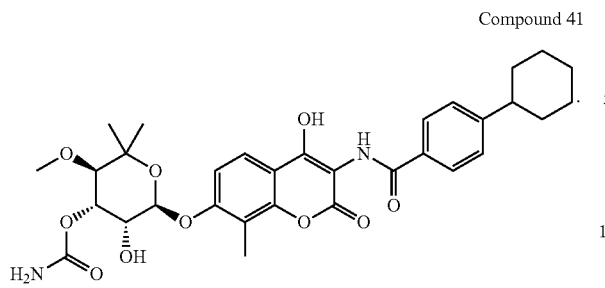

¹H NMR (600 MHz, DMSO-d₆) δ 9.0 (s, 1H), 8.3 (s, 1H), 7.9 (d, J=7.7 Hz, 1H), 7.8 (d, J=7.7 Hz, 1H), 7.7 (d, J=7.9 Hz, 2H), 7.6 (d, J=8.7 Hz, 1H), 7.5 (t, J=7.7 Hz, 1H), 7.3 (d, J=7.9 Hz, 2H), 6.9 (comp, 1H), 6.6 (d, J=112.4 Hz, 3H), 5.6 (d, J=5.1 Hz, 1H), 5.5-5.4 (m, 1H), 5.2 (dd, J=9.8, 3.2 Hz, 1H), 4.1-4.0 (m, 1H), 3.5 (comp, 4H), 2.7 (q, J=7.6 Hz, 2H), 2.2 (s, 3H), 1.3 (s, 3H), 1.2 (comp, 3H), 1.1 (s, 3H).

Compound 43

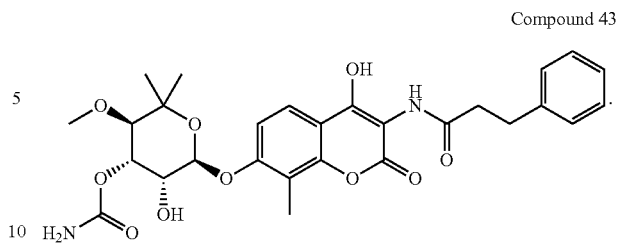

¹H NMR (600 MHz, DMSO-d₆) δ 12.5 (s, 1H), 10.1 (s, 1H), 8.9 (s, 1H), 7.7 (comp, 2H), 7.7 (d, J=8.8 Hz, 1H), 7.0 (d, J=8.9 Hz, 1H), 7.0 (comp, 1H), 6.8 (d, J=8.3 Hz, 1H), 6.6 (comp, 2H), 6.0 (d, J=15.8 Hz, 1H), 5.6 (s, 1H), 5.5 (d, J=2.5 Hz, 1H), 5.2 (dd, J=9.8, 3.1 Hz, 1H), 4.1-4.0 (m, 1H), 3.5 (comp, 6H), 2.2 (s, 6H), 1.3 (s, 3H), 1.1 (s, 3H).

Compound 45

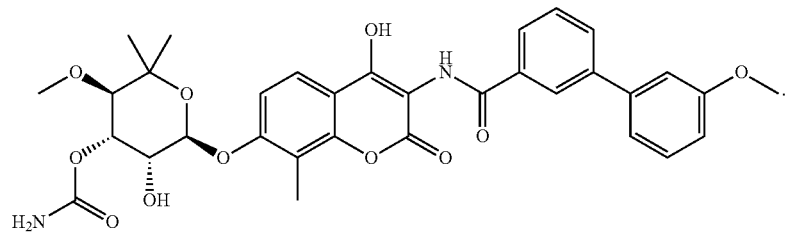

¹H NMR (600 MHz, DMSO-d₆) δ 10.0 (s, 1H), 9.8 (s, 1H), 9.1 (s, 1H), 7.7 (comp, 4H), 7.5 (comp, 2H), 7.3 (comp, 2H), 7.1 (d, J=9.1 Hz, 1H), 7.0 (t, J=7.4 Hz, 1H), 6.8 (d, J=8.3 Hz, 1H), 5.8 (d, J=5.2 Hz, 1H), 5.6 (d, J=2.4 Hz, 1H), 5.3 (comp, 2H), 4.2-4.2 (m, 1H), 3.6 (d, J=9.9 Hz, 1H), 3.5 (s, 3H), 3.3 (d, J=7.4 Hz, 2H), 2.2 (s, 3H), 1.7 (comp, 6H), 1.3 (s, 3H), 1.1 (s, 3H).

Compound 46

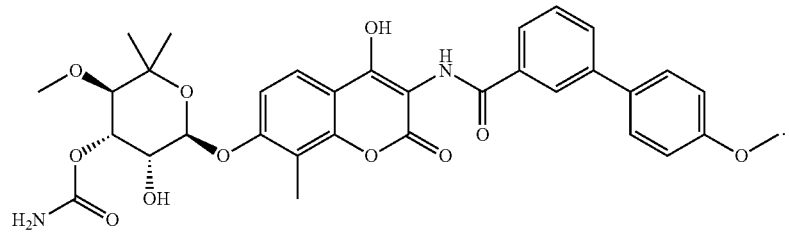

¹H NMR (600 MHz, DMSO-d₆) δ 9.8 (s, 1H), 8.4 (s, 1H), 7.7 (s, 1H), 7.6 (comp, 3H), 7.3 (t, J=5.6 Hz, 1H), 6.9 (s, 1H), 6.8 (d, J=8.3 Hz, 1H), 5.5 (s, 1H), 5.4 (s, 1H), 5.3-5.3 (m, 1H), 5.2-5.2 (m, 1H), 4.1 (s, 1H), 3.5 (comp, 4H), 3.3 (d, J=7.5 Hz, 2H), 3.1 (comp, 2H), 2.2 (s, 3H), 1.7 (comp, 6H), 1.3 (s, 3H), 1.1 (comp, 6H).

Compound 47

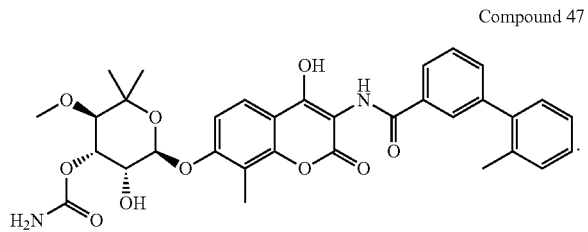 [SMILES: CO[C@@H]1[C@@H](OC(N)=O)[C@@H](O)[C@H](Oc2ccc3c(O)c(NC(=O)c4cccc(-c5ccccc5C)c4)c(=O)oc3c2C)OC1(C)C]

¹H NMR (600 MHz, DMSO-d₆) δ 9.9 (s, 1H), 8.9 (s, 1H), 7.7 (comp, 3H), 7.2 (d, J=7.8 Hz, 1H), 7.1 (d, J=8.9 Hz, 1H), 6.8 (d, J=8.3 Hz, 1H), 5.6 (d, J=5.0 Hz, 1H), 5.5 (d, J=2.5 Hz, 1H), 5.3 (t, J=7.6 Hz, 1H), 5.2-5.2 (m, 1H), 4.1 (comp, 2H), 3.7-3.6 (m, 1H), 3.5 (comp, 4H), 3.2 (d, J=7.3 Hz, 2H), 2.2 (s, 3H), 1.7 (comp, 6H), 1.3 (s, 3H), 1.1 (comp, 9H).

Compound 52

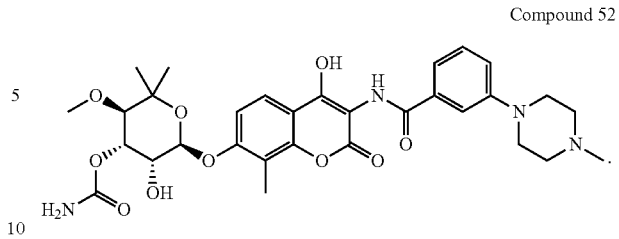

¹H NMR (400 MHz, DMSO-d₆) δ 11.6 (s, 1H), 9.7 (s, 1H), 8.3-8.2 (m, 1H), 7.7 (s, 1H), 7.6-7.6 (comp, 2H), 6.9 (d, J=8.8 Hz, 1H), 6.8-6.7 (comp, 2H), 5.9 (m, 1H), 5.6-5.5 (m, 1H), 5.5-5.4 (m, 2H), 5.3 (t, J=7.7 Hz, 1H), 4.1 (s, 1H), 3.6 (d, J=9.8 Hz, 1H), 3.4 (s, 3H), 3.2 (d, J=7.6 Hz, 2H), 2.2 (s, 3H), 2.2 (s, 3H), 1.7 (comp, 6H), 1.3 (s, 3H), 1.1 (s, 3H)

Compound 48

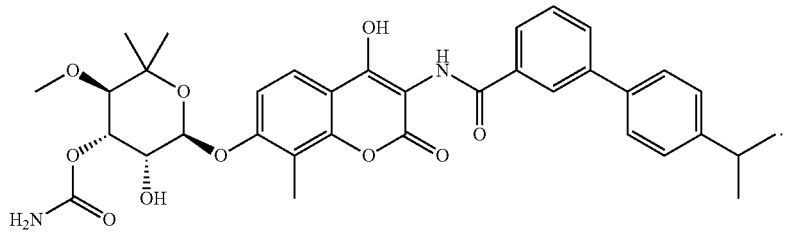

¹H NMR (500 MHz, DMSO-d₆) δ 9.9 (s, 1H), 8.8 (s, 1H), 7.7-7.7 (m, 1H), 7.7 (comp, J=8.5, 5.9 Hz, 2H), 7.0 (comp, 2H), 6.8 (d, J=8.3 Hz, 1H), 5.5 (d, J=5.0 Hz, 1H), 5.5 (d, J=2.6 Hz, 1H), 5.3 (t, J=7.4 Hz, 1H), 5.2 (dd, J=9.6, 3.1 Hz, 1H), 4.1-4.0 (m, 1H), 3.5 (comp, 4H), 3.3 (d, J=7.3 Hz, 2H), 2.2 (s, 3H), 1.7 (comp, 6H), 1.3 (comp, 12H), 1.1 (s, 3H).

Compound 51

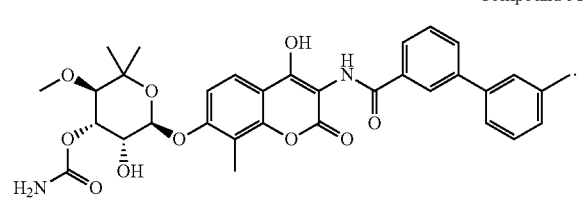

¹H NMR (600 MHz, DMSO-d₆) δ 12.2 (s, 1H), 9.4 (s, 1H), 7.7 (d, J=8.9 Hz, 1H), 7.1 (d, J=9.0 Hz, 1H), 6.6 (comp, J=114.2 Hz, 2H), 5.6 (d, J=5.2 Hz, 1H), 5.5 (d, J=2.5 Hz, 1H), 5.1 (dd, J=9.9, 3.1 Hz, 1H), 4.1-4.1 (m, 1H), 3.5 (comp, 4H), 2.2 (s, 3H), 2.1 (s, 3H), 1.3 (s, 3H), 1.0 (s, 3H).

Compound 68

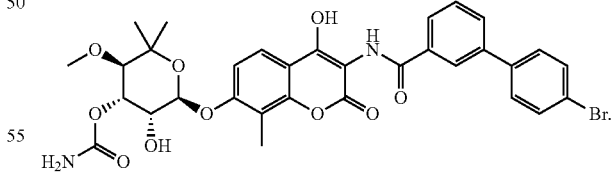

¹H NMR (400 MHz, DMSO-d₆) δ 11.90 (s, 1H), 9.65 (s, 1H), 8.38-8.27 (m, 1H), 7.99 (d, J=7.8 Hz, 1H), 7.91 (d, J=7.8 Hz, 1H), 7.74 (comp, 5H), 7.62 (t, J=7.8 Hz, 1H), 7.18 (d, J=8.9 Hz, 1H), 6.62 (comp, 2H), 5.60 (d, J=5.2 Hz, 1H), 5.57-5.53 (m, 1H), 5.16 (dd, J=9.9, 3.0 Hz, 1H), 4.13-4.03 (m, 1H), 3.48 (comp, 4H), 2.24 (d, J=1.8 Hz, 3H), 1.27 (s, 3H), 1.06 (s, 3H).

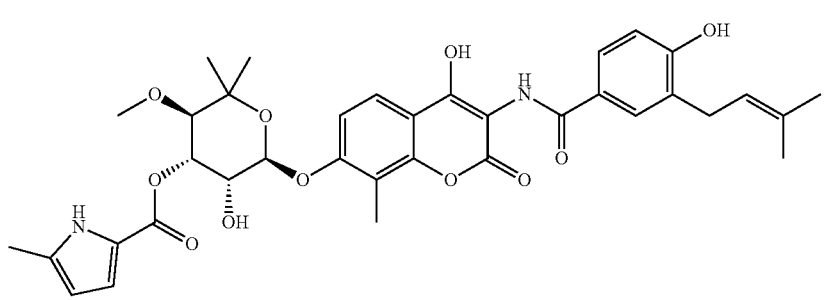

Compound 112

Tan solid (white solid after recrystallization from EtOAc); TLC Rf=0.3 (5% MeOH/DCM); $^1$H NMR (400 MHz, DMSO-d$_6$) δ 11.6 (s, 1H), 9.7 (s, 1H), 8.3-8.2 (m, 1H), 7.7 (s, 1H), 7.6-7.6 (comp, 2H), 6.9 (d, J=8.8 Hz, 1H), 6.8-6.7 (comp, 2H), 5.9 (m, 1H), 5.6-5.5 (m, 1H), 5.5-5.4 (m, 2H), 5.3 (t, J=7.7 Hz, 1H), 4.1 (s, 1H), 3.6 (d, J=9.8 Hz, 1H), 3.4 (s, 3H), 3.2 (d, J=7.6 Hz, 2H), 2.2 (s, 3H), 2.2 (s, 3H), 1.7 (s, 6H), 1.3 (s, 3H), 1.1 (s, 3H); $^{13}$C NMR (101 MHz, DMSO-d$_6$) δ 170.5, 165.7, 162.8, 160.4, 157.6, 155.7, 152.5, 135.2, 131.6, 129.9, 127.3, 127.2, 127.0, 123.4, 123.1, 121.0, 118.6, 116.7, 114.5, 112.0, 108.9, 108.1, 98.9, 97.2, 81.3, 78.4, 71.0, 69.4, 61.5, 29.1, 28.6, 26.1, 23.4, 18.2, 13.3, 9.0; HRMS (ESI Neg) m/z calculated for C$_{36}$H$_{40}$N$_2$O$_{10}$ [M-H]$^-$, 675.2554 found: 675.2571.

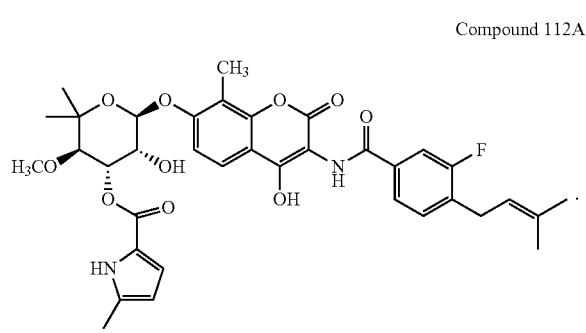 [SMILES: CO[C@@H]1[C@@H](OC(=O)c2ccc(C)[nH]2)[C@@H](O)[C@H](Oc2ccc3c(O)c(NC(=O)c4ccc(CC=C(C)C)c(F)c4)c(=O)oc3c2C)OC1(C)C]

Compound 112A

Off-white solid; TLC Rf=0.3 (5% MeOH/DCM); 1H NMR (600 MHz, DMSO-d$_6$) δ 12.1 (br, 1H), 11.6 (s, 1H), 9.4 (s, 1H), 7.9 (comp, 2H), 7.7 (d, J=8.8 Hz, 1H), 7.3 (t, J=9.2 Hz, 1H), 7.2 (d, J=9.0 Hz, 1H), 6.8 (dd, J=3.6, 2.5 Hz, 1H), 5.9 (t, J=3.0 Hz, 1H), 5.7 (d, J=5.0 Hz, 1H), 5.6 (d, J=2.5 Hz, 1H), 5.5 (dd, J=9.8, 3.1 Hz, 1H), 5.3 (t, 1H), 4.2 (m, 1H), 3.7 (d, J=9.8 Hz, 1H), 3.5 (s, 3H), 3.4 (d, J=7.3 Hz, 2H), 2.3 (comp, J=4.3 Hz, 6H), 1.7 (comp, 6H), 1.3 (s, 3H), 1.1 (s, 3H); $^{13}$C NMR (126 MHz, DMSO-d$_6$) δ 166.0, 162.6 (d, J=248.4 Hz), 161.2, 160.3, 157.4, 151.3, 135.2, 133.4, 131.1 (d, J=5.7 Hz), 130.9, 128.5 (d, J=9.5 Hz), 128.3 (d, J=16.7 Hz; two signals obscured due to overlap), 122.4, 121.7, 120.9, 116.7, 115.4 (d, J=22.3 Hz), 113.2, 110.3, 108.9, 100.9, 98.8, 81.1, 78.6, 70.8, 69.2, 61.5, 28.9, 27.5, 25.9, 23.3, 18.1, 13.2, 8.7. $^{19}$F NMR (471 MHz, DMSO-d$_6$) δ −114.4; HRMS (ESI Neg) m/z calculated for C$_{36}$H$_{38}$FN$_2$O$_{10}$, 677.2516 found 677.2500.

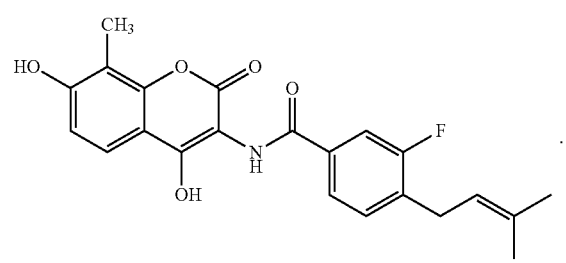

Compound 112A aglycone

Off-white solid; TLC Rf=0.3 (5% MeOH/DCM); $^1$H NMR (600 MHz, DMSO-d$_6$) δ 11.9 (br, 1H), 10.4 (s, 1H), 9.3 (s, 1H), 7.9 (comp, 2H), 7.5 (d, J=8.5 Hz, 1H), 7.2 (t, J=9.0 Hz, 1H), 6.9 (d, J=8.6 Hz, 1H), 5.3 (t, J=6.5 Hz, 1H), 3.4 (m, 2H), 2.2 (s, 3H), 1.7 (comp, 6H); $^{13}$C NMR (151 MHz, DMSO-d$_6$) δ 166.0, 163.5, 162.6 (d, J=248.6 Hz), 161.5, 159.4, 152.0, 133.3, 131.1 (d, J=5.9 Hz), 130.9, 128.4 (d, J=9.4 Hz), 128.3 (d, J=16.5 Hz), 122.1, 121.7, 115.4 (d, J=23.0 Hz), 112.1, 110.8, 108.9, 99.9, 27.5, 26.0, 18.1, 8.6; $^{19}$F NMR (564 MHz, DMSO-d$_6$) δ −114.5; HRMS (ESI Neg) m/z calculated for C$_{22}$H$_{19}$FNO$_5$ [M-H]$^-$, 396.1247 found: 396.1256.

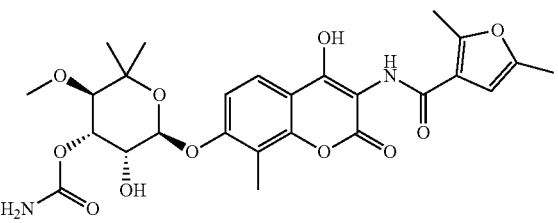

Compound 200

$^1$H NMR (600 MHz, DMSO-d$_6$) δ 12.0 (s, 1H), 8.9 (s, 1H), 7.7 (d, J=8.8 Hz, 1H), 7.2-7.1 (m, 1H), 6.6 (s, 3H), 5.6 (d, J=5.2 Hz, 1H), 5.5 (d, J=2.4 Hz, 1H), 5.2 (dd, J=9.9, 3.2 Hz, 1H), 4.1-4.0 (m, 1H), 3.5 (comp, 4H), 2.5 (s, 3H), 2.3 (s, 3H), 2.2 (s, 3H), 1.3 (s, 3H), 1.0 (s, 3H).

Compound 201

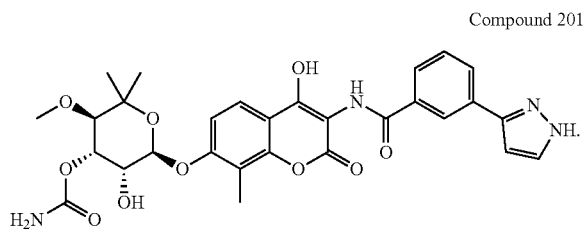 [SMILES: CO[C@@H]1[C@@H](OC(N)=O)[C@@H](O)[C@H](Oc2ccc3c(O)c(NC(=O)c4cccc(-c5cc[nH]n5)c4)c(=O)oc3c2C)OC1(C)C]

¹H NMR (600 MHz, DMSO-d₆) δ 13.0 (s, 1H), 9.1 (s, 1H), 8.4 (s, 1H), 8.1 (s, 1H), 8.0 (s, 1H), 7.9 (d, J=7.7 Hz, 1H), 7.8 (s, 1H), 7.7 (d, J=8.7 Hz, 1H), 7.5 (t, J=7.7 Hz, 1H), 7.0 (s, 1H), 6.8 (s, 1H), 6.6 (comp, 2H), 5.6 (d, J=5.1 Hz, 1H), 5.5 (s, 1H), 5.2 (dd, J=9.8, 3.1 Hz, 1H), 4.1 (s, 1H), 3.5 (comp, 4H), 2.2 (s, 3H), 1.3 (s, 3H), 1.1 (s, 3H).

Compound 204

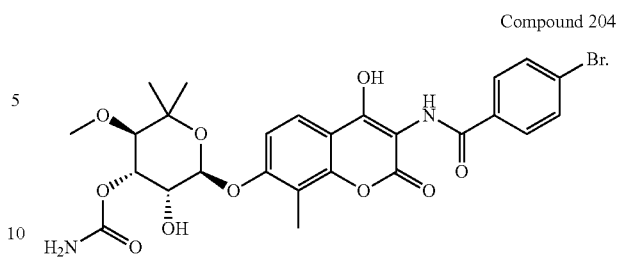

¹H NMR (400 MHz, DMSO-d₆) δ 11.93 (s, 1H), 9.57 (s, 1H), 7.95 (comp, 2H), 7.75 (comp, 3H), 7.17 (d, J=9.0 Hz, 1H), 6.60 (comp, 2H), 5.63-5.56 (m, 1H), 5.56-5.52 (m, 1H), 5.16 (dd, J=9.8, 3.0 Hz, 1H), 4.08 (s, 1H), 3.47 (comp, 4H), 2.22 (s, 3H), 1.27 (s, 3H), 1.05 (s, 3H).

Compound 205

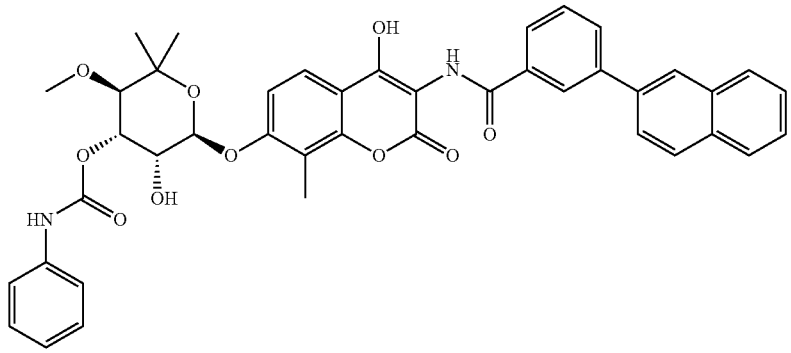

¹H NMR (500 MHz, DMSO-d₆) δ 9.8 (s, 1H), 9.3 (s, 1H), 8.5 (s, 1H), 8.3 (s, 1H), 8.0 (t, J=8.0 Hz, 2H), 8.0 (comp, 4H), 7.7-7.6 (m, 1H), 7.6 (comp, 6H), 7.3 (t, J=7.7 Hz, 2H), 7.0 (q, J=7.3 Hz, 2H), 5.7 (s, 1H), 5.5 (s, 1H), 5.3 (d, J=9.8 Hz, 1H), 4.2 (s, 1H), 3.5 (comp, 4H), 2.2 (s, 3H), 1.3 (s, 3H), 1.1 (s, 3H).

Compound 237

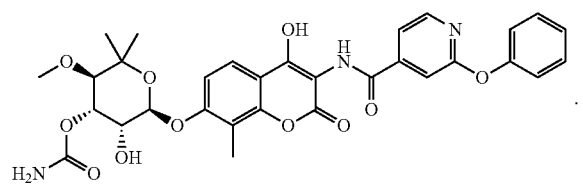

¹H NMR (500 MHz, DMSO-d₆) δ 8.29 (d, J=5.2 Hz, 1H), 7.67 (s, 1H), 7.63 (d, J=5.2 Hz, 1H), 7.50 (s, 1H), 7.44 (t, J=7.8 Hz, 2H), 7.24 (t, J=7.4 Hz, 1H), 7.16 (d, J=7.9 Hz, 2H), 7.03 (br, 1H), 6.72 (comp, 2H), 5.56 (d, J=5.1 Hz, 1H), 5.48 (s, 1H), 5.16 (dd, J=9.8, 3.1 Hz, 1H), 4.10-4.04 (m, 1H), 3.46 (comp, 4H), 2.19 (s, 3H), 1.26 (s, 3H), 1.07 (s, 3H).

Compound 206

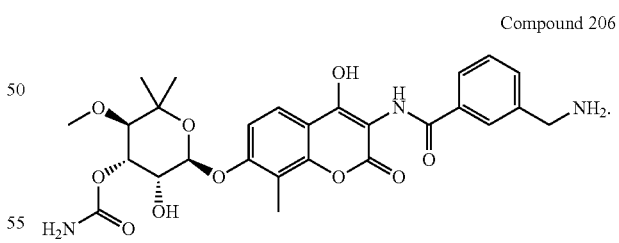

¹H NMR (400 MHz, DMSO-d₆) δ 8.50 (s, 1H), 8.23 (s, 2H), 8.04 (s, 1H), 7.95 (d, J=7.6 Hz, 1H), 7.61 (d, J=8.6 Hz, 1H), 7.53 (d, J=7.7 Hz, 1H), 7.47 (t, J=7.6 Hz, 1H), 6.88 (d, J=8.8 Hz, 1H), 6.60 (comp, 2H), 5.50 (s, 1H), 5.44-5.40 (m, 1H), 5.16 (dd, J=9.7, 3.1 Hz, 1H), 4.03 (s, 3H), 3.45 (comp, 4H), 2.16 (s, 3H), 1.26 (s, 3H), 1.09 (s, 3H).

Compound 208

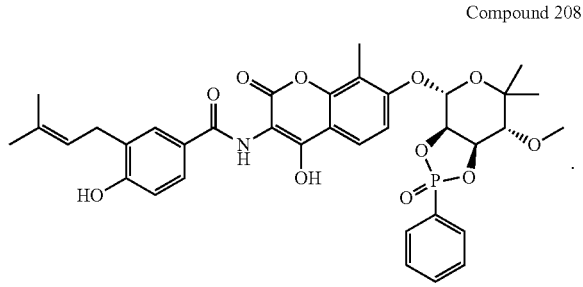

¹H NMR (400 MHz, DMSO-d₆) δ 9.96 (s, 1H), 8.93 (s, 1H), 7.95 (comp, 2H), 7.71 (comp, 4H), 7.62 (comp, 2H), 7.15 (d, J=9.0 Hz, 1H), 6.82 (d, J=8.3 Hz, 1H), 6.53 (s, 1H), 6.04 (d, J=3.7 Hz, 1H), 5.30 (t, J=7.3 Hz, 1H), 5.20 (comp, 2H), 3.72 (d, J=8.0 Hz, 1H), 3.58 (s, 3H), 3.26-3.23 (m, 1H), 2.54 (s, 1H), 2.22 (s, 3H), 1.69 (comp, 6H), 1.38 (s, 3H), 1.17 (s, 3H).

Compound 209

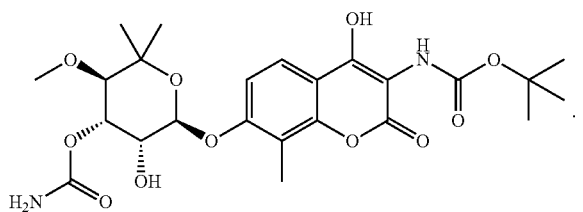

¹H NMR (400 MHz, DMSO-d₆) δ 11.79 (s, 1H), 7.87 (s, 1H), 7.69 (d, J=9.4 Hz, 1H), 7.13 (d, J=9.1 Hz, 1H), 6.61 (comp, J=50.7 Hz, 2H), 5.58 (s, 1H), 5.53-5.48 (m, 1H), 5.14 (dd, J=9.8, 3.0 Hz, 1H), 4.09-4.04 (m, 1H), 3.46 (comp, 4H), 2.19 (s, 3H), 1.43 (s, 9H), 1.26 (s, 3H), 1.04 (s, 3H).

Compound 211

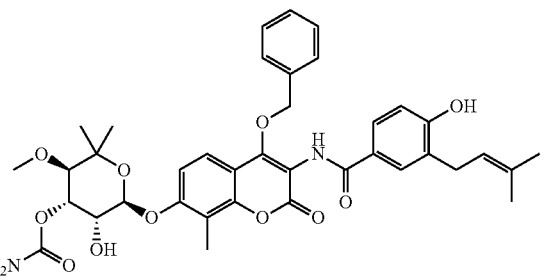

¹H NMR (400 MHz, DMSO-d₆) δ 10.16 (s, 1H), 9.66 (d, J=2.5 Hz, 1H), 7.63 (comp, 3H), 7.07 (comp, 3H), 6.96 (comp, 3H), 6.86 (dd, J=8.5, 2.0 Hz, 1H), 6.73 (comp, 2H), 5.65-5.56 (m, 1H), 5.49 (s, 1H), 5.33-5.22 (m, 1H), 5.07 (dd, J=10.0, 3.0 Hz, 1H), 4.02 (s, 1H), 3.73 (t, J=1.6 Hz, 1H), 3.45 (comp, 4H), 3.25 (d, J=7.5 Hz, 2H), 2.54 (d, J=2.0 Hz, 1H), 1.89 (d, J=2.4 Hz, 3H), 1.68 (comp, 6H), 1.22 (s, 3H), 0.98 (d, J=2.4 Hz, 3H).

Compound 213

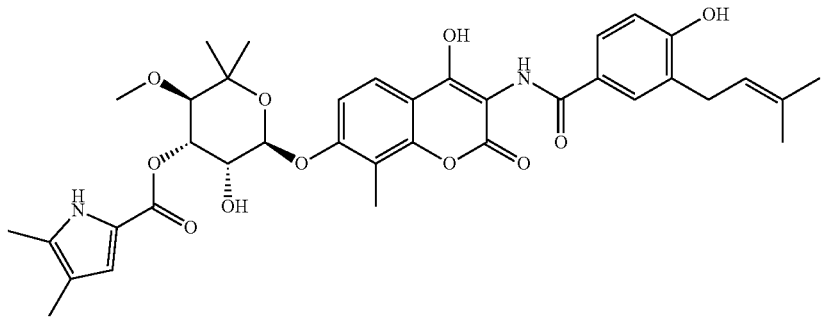

¹H NMR (400 MHz, DMSO-d₆) δ 11.43 (s, 1H), 9.81 (s, 1H), 7.80-7.58 (m, 3H), 7.00 (s, 1H), 6.81 (d, J=8.3 Hz, 1H), 6.64 (s, 1H), 6.52 (s, 2H), 5.57 (d, J=4.9 Hz, 1H), 5.52 (s, 1H), 5.48 (d, J=9.7 Hz, 1H), 5.37-5.24 (m, 1H), 4.13 (s, 1H), 3.62 (d, J=9.8 Hz, 1H), 3.47 (s, 3H), 2.21 (s, 3H), 2.16 (s, 3H), 1.96 (s, 3H), 1.70 (s, 6H), 1.30 (s, 3H), 1.12 (s, 3H). (methylene protons obscured).

Compound 215

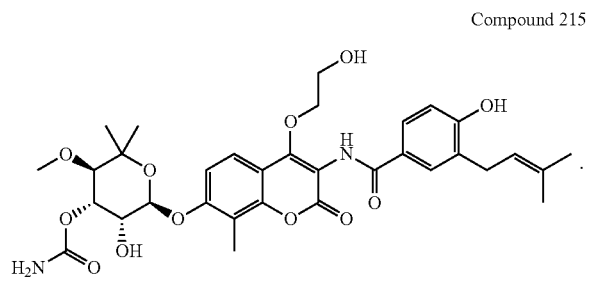 [SMILES: CO[C@@H]1[C@@H](OC(N)=O)[C@@H](O)[C@H](Oc2ccc3c(OCCO)c(NC(=O)c4ccc(O)c(CC=C(C)C)c4)c(=O)oc3c2C)OC1(C)C]

¹H NMR (400 MHz, DMSO-d₆) δ 10.07 (s, 1H), 9.44 (s, 1H), 7.82 (d, J=9.0 Hz, 1H), 7.70 (comp, 2H), 7.17 (d, J=9.1 Hz, 1H), 6.87 (d, J=8.5 Hz, 1H), 6.59 (comp, 2H), 5.60 (d, J=4.6 Hz, 1H), 5.57-5.54 (m, 1H), 5.35-5.27 (m, 1H), 5.15 (dd, J=10.5, 2.3 Hz, 1H), 4.98 (t, J=5.6 Hz, 1H), 4.36 (comp, 2H), 4.11-4.06 (m, 1H), 3.68 (comp, 2H), 3.48 (comp, 4H), 3.26 (comp, 2H), 2.22 (s, 3H), 1.72-1.66 (m, 6H), 1.27 (s, 3H), 1.05 (s, 3H).

Compound 216

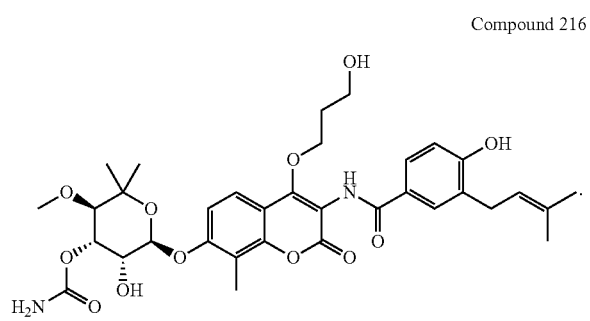 [SMILES: CO[C@@H]1[C@@H](OC(N)=O)[C@@H](O)[C@H](Oc2ccc3c(OCCCO)c(NC(=O)c4ccc(O)c(CC=C(C)C)c4)c(=O)oc3c2C)OC1(C)C]

¹H NMR (400 MHz, DMSO-d₆) δ 10.08 (s, 1H), 9.45 (s, 1H), 7.72 (s, 2H), 7.19 (s, 1H), 6.88 (comp, 2H), 6.69 (comp, 2H), 5.60 (comp, 3H), 5.35-5.28 (m, 1H), 5.16 (d, J=11.2 Hz, 1H), 4.50 (comp, 2H), 4.08 (comp, 2H), 3.47 (comp, 8H), 3.29-3.24 (m, 1H), 2.22 (s, 3H), 2.04-1.99 (m, 1H), 1.86 (q, J=5.8 Hz, 1H), 1.69 (s, 4H), 1.27 (s, 3H), 1.05 (s, 3H).

Compound 217

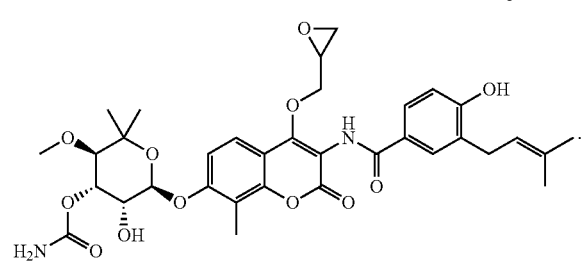

¹H NMR (500 MHz, DMSO-d₆) δ 10.13-10.06 (m, 1H), 9.46 (s, 1H), 7.71 (comp, 3H), 7.20 (d, J=9.1 Hz, 1H), 6.87 (d, J=8.2 Hz, 1H), 6.63 (comp, 2H), 5.62 (d, J=5.1 Hz, 1H), 5.55 (dd, J=8.0, 2.6 Hz, 1H), 5.31 (t, J=7.6 Hz, 1H), 5.19-5.11 (m, 1H), 4.64 (dd, J=11.4, 2.6 Hz, 1H), 4.42-4.34 (m, 1H), 4.25-4.18 (m, 1H), 4.08 (d, J=5.6 Hz, 1H), 3.47 (comp, 4H), 3.26 (comp, 2H), 2.82-2.78 (m, 1H), 2.69-2.66 (m, 1H), 2.22 (s, 3H), 1.70 (comp, 6H), 1.27 (s, 3H), 1.04 (s, 3H).

Compound 218

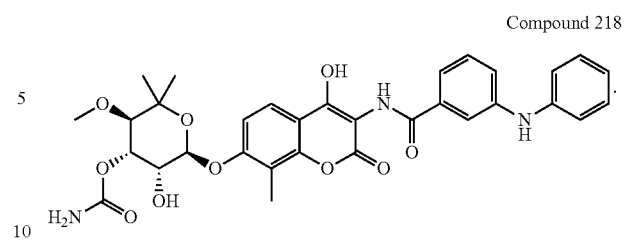

¹H NMR (400 MHz, DMSO-d₆) δ 11.93 (s, 1H), 9.40 (s, 1H), 8.36 (s, 1H), 7.75 (d, J=8.9 Hz, 1H), 7.71-7.66 (m, 1H), 7.48 (d, J=7.7 Hz, 1H), 7.39-7.33 (m, 1H), 7.26 (comp, 3H), 7.15 (comp, 3H), 6.86 (t, J=7.3 Hz, 1H), 6.62 (comp, 2H), 5.60 (s, 1H), 5.56-5.53 (m, 1H), 5.16 (dd, J=10.6, 2.3 Hz, 1H), 4.13-4.06 (m, 1H), 3.48 (comp, 4H), 2.23 (s, 3H), 1.27 (s, 3H), 1.06 (s, 3H).

Compound 219

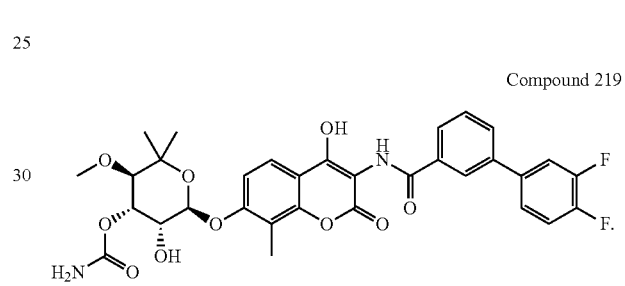

¹H NMR (400 MHz, DMSO-d₆) δ 11.95 (s, 1H), 9.61 (s, 1H), 8.34 (s, 1H), 7.98 (d, J=7.8 Hz, 1H), 7.91 (t, J=8.2 Hz, 2H), 7.76 (d, J=8.9 Hz, 1H), 7.62 (comp, 3H), 7.16 (d, J=9.0 Hz, 1H), 6.68 (comp, 2H), 5.60 (d, J=5.2 Hz, 1H), 5.54 (d, J=2.4 Hz, 1H), 5.16 (dd, J=9.9, 3.1 Hz, 1H), 4.12-4.06 (m, 1H), 3.48 (comp, 4H), 2.23 (s, 3H), 1.27 (s, 3H), 1.06 (s, 3H).

Compound 220

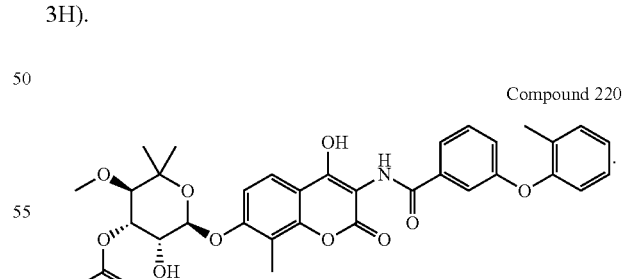

¹H NMR (400 MHz, DMSO-d₆) δ 9.50 (s, 1H), 8.59 (d, J=3.9 Hz, 1H), 7.83-7.71 (m, 2H), 7.50 (comp, 2H), 7.43-7.38 (m, 1H), 7.37-7.33 (m, 1H), 7.26 (comp, 1H), 7.15 (comp, 2H), 6.95 (dd, J=8.0, 1.2 Hz, 1H), 6.62 (comp, 2H), 5.63-5.57 (m, 1H), 5.54 (d, J=2.5 Hz, 1H), 5.16 (dd, J=9.8, 3.2 Hz, 1H), 4.11-4.06 (m, 1H), 3.48 (comp, 4H), 2.21 (comp, 6H), 1.27 (s, 3H), 1.05 (s, 3H).

Compound 221

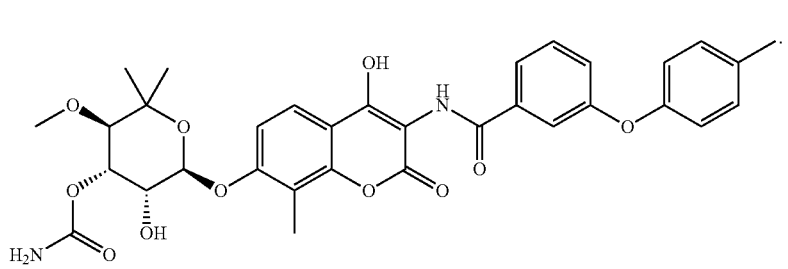

¹H NMR (400 MHz, DMSO-d₆) δ 11.88 (s, 1H), 9.50 (s, 1H), 7.75 (comp, 2H), 7.61-7.56 (m, 1H), 7.51 (t, J=7.9 Hz, 1H), 7.20 (comp, 4H), 6.99-6.94 (m, 2H), 6.67 (comp, 2H), 5.63-5.57 (m, 1H), 5.54 (d, J=2.4 Hz, 1H), 5.16 (dd, J=9.9, 3.1 Hz, 1H), 4.08 (s, 1H), 3.48 (comp, 4H), 2.30 (s, 3H), 2.22 (s, 3H), 1.27 (s, 3H), 1.05 (s, 3H).

(t, J=7.4 Hz, 1H), 5.18 (dd, J=9.6, 3.1 Hz, 1H), 4.01 (s, 1H), 3.44 (comp, 4H), 3.24 (d, J=7.4 Hz, 2H), 2.17 (s, 3H), 2.02 (comp, 4H), 1.90 (comp, 6H), 1.69 (comp, 6H), 1.62 (comp, 6H), 1.25 (s, 3H), 1.07 (s, 3H).

Compound 222

¹H NMR (400 MHz, DMSO-d₆) δ 11.92 (s, 1H), 9.63 (s, 1H), 8.38 (s, 1H), 8.15-8.05 (m, 1H), 7.98 (comp, 2H), 7.79 (comp, 3H), 7.63 (t, J=7.7 Hz, 1H), 7.17 (d, J=9.0 Hz, 1H), 6.58 (comp, 2H), 5.60 (d, J=5.2 Hz, 1H), 5.54 (d, J=2.5 Hz, 1H), 5.16 (dd, J=9.8, 3.1 Hz, 1H), 4.09 (s, 1H), 3.48 (comp, 4H), 2.23 (s, 3H), 1.27 (s, 3H), 1.06 (s, 3H).

Compound 224

¹H NMR (400 MHz, DMSO-d₆) δ 11.92 (s, 1H), 9.48 (s, 1H), 8.05 (comp, 2H), 7.75 (d, J=8.8 Hz, 1H), 7.26 (comp, 2H), 7.16 (d, J=9.0 Hz, 1H), 6.64 (comp, 2H), 5.59 (d, J=5.2 Hz, 1H), 5.56-5.51 (m, 1H), 5.16 (dd, J=9.9, 3.2 Hz, 1H), 4.12-4.05 (m, 1H), 3.47 (comp, 4H), 2.22 (s, 3H), 1.27 (s, 3H), 1.06 (s, 3H).

Compound 223

¹H NMR (600 MHz, DMSO-d₆) δ 9.82 (s, 1H), 8.46 (s, 1H), 7.70-7.67 (m, 1H), 7.64 (comp, 2H), 6.92 (comp, 2H), 6.79 (d, J=8.3 Hz, 1H), 5.51 (s, 1H), 5.44 (d, J=2.6 Hz, 1H), 5.31

Compound 225

¹H NMR (400 MHz, DMSO-d₆) δ 11.91 (s, 1H), 9.51 (s, 1H), 7.91 (comp, 2H), 7.76 (comp, 3H), 7.16 (d, J=9.0 Hz, 1H), 6.68 (comp, 2H), 5.59 (d, J=5.2 Hz, 1H), 5.56-5.50 (m, 1H), 5.16 (dd, J=9.8, 3.1 Hz, 1H), 4.11-4.04 (m, 1H), 3.48 (comp, 4H), 2.22 (s, 3H), 1.27 (s, 3H), 1.05 (s, 3H).

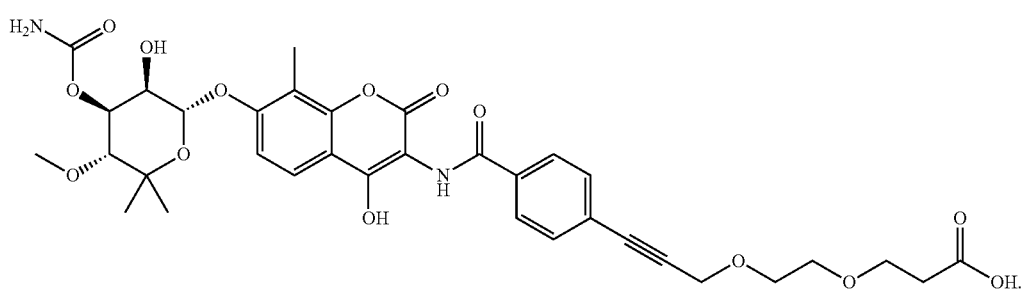

Compound 226

¹H NMR (400 MHz, DMSO-d₆) δ 8.71 (s, 1H), 7.97 (d, J=8.1 Hz, 1H), 7.62 (d, J=8.5 Hz, 1H), 7.52 (d, J=8.0 Hz, 1H), 6.89 (d, J=8.8 Hz, 1H), 6.66 (comp, 2H), 5.49 (d, J=5.2 Hz, 1H), 5.45-5.36 (m, 1H), 5.16 (dd, J=9.9, 2.5 Hz, 1H), 4.43 (s, 2H), 4.07-4.02 (m, 1H), 3.63 (comp, 5H), 3.57 (comp, 3H), 3.45 (comp, 4H), 2.16 (s, 3H), 1.26 (s, 3H), 1.09 (comp, 6H).

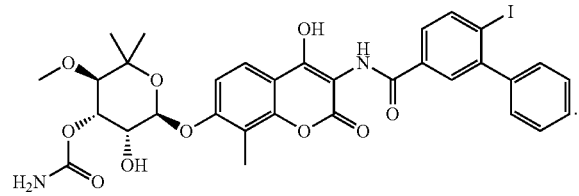

Compound 227

¹H NMR (400 MHz, DMSO-d₆) δ 9.61 (s, 1H), 8.14 (d, J=8.2 Hz, 1H), 7.97 (d, J=2.1 Hz, 1H), 7.71 (comp, 2H), 7.45 (comp, 7H), 6.63 (comp, 2H), 5.59 (d, J=5.2 Hz, 1H), 5.54 (d, J=2.4 Hz, 1H), 5.15 (dd, J=9.8, 3.1 Hz, 1H), 4.11-4.01 (m, 1H), 3.48 (comp, 4H), 2.22 (s, 3H), 1.26 (s, 3H), 1.05 (s, 3H).

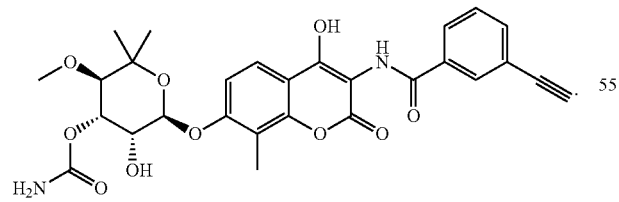

Compound 229

¹H NMR (400 MHz, DMSO-d₆) δ 11.89 (s, 1H), 9.59 (s, 1H), 8.14 (s, 1H), 8.01 (d, J=8.0 Hz, 1H), 7.72 (comp, 2H), 7.55 (t, J=7.8 Hz, 1H), 7.17 (d, J=9.1 Hz, 1H), 6.66 (comp, 2H), 5.60 (d, J=5.0 Hz, 1H), 5.54 (d, J=2.4 Hz, 1H), 5.16 (dd, J=9.9, 3.2 Hz, 1H), 4.31 (s, 1H), 4.12-4.04 (m, 1H), 3.47 (comp, 4H), 2.23 (s, 3H), 1.27 (s, 3H), 1.05 (s, 3H).

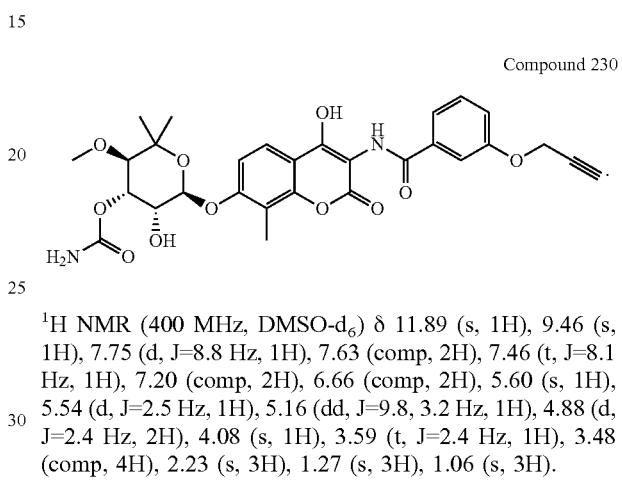

Compound 230

¹H NMR (400 MHz, DMSO-d₆) δ 11.89 (s, 1H), 9.46 (s, 1H), 7.75 (d, J=8.8 Hz, 1H), 7.63 (comp, 2H), 7.46 (t, J=8.1 Hz, 1H), 7.20 (comp, 2H), 6.66 (comp, 2H), 5.60 (s, 1H), 5.54 (d, J=2.5 Hz, 1H), 5.16 (dd, J=9.8, 3.2 Hz, 1H), 4.88 (d, J=2.4 Hz, 2H), 4.08 (s, 1H), 3.59 (t, J=2.4 Hz, 1H), 3.48 (comp, 4H), 2.23 (s, 3H), 1.27 (s, 3H), 1.06 (s, 3H).

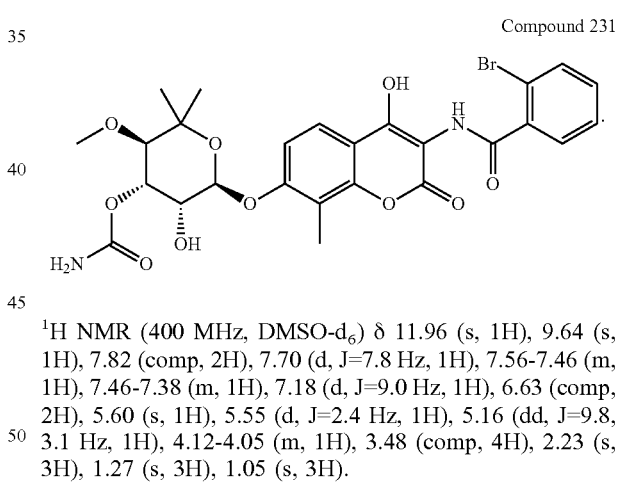

Compound 231

¹H NMR (400 MHz, DMSO-d₆) δ 11.96 (s, 1H), 9.64 (s, 1H), 7.82 (comp, 2H), 7.70 (d, J=7.8 Hz, 1H), 7.56-7.46 (m, 1H), 7.46-7.38 (m, 1H), 7.18 (d, J=9.0 Hz, 1H), 6.63 (comp, 2H), 5.60 (s, 1H), 5.55 (d, J=2.4 Hz, 1H), 5.16 (dd, J=9.8, 3.1 Hz, 1H), 4.12-4.05 (m, 1H), 3.48 (comp, 4H), 2.23 (s, 3H), 1.27 (s, 3H), 1.05 (s, 3H).

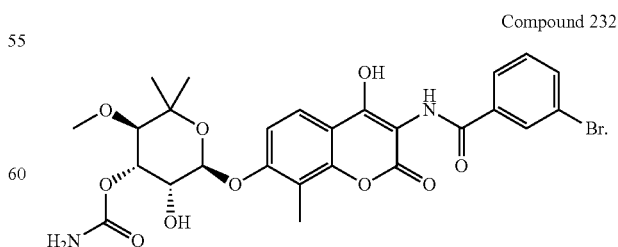

Compound 232

¹H NMR (400 MHz, DMSO-d₆) δ 11.94 (s, 1H), 9.59 (s, 1H), 8.25-8.17 (m, 1H), 7.98 (d, J=7.8 Hz, 1H), 7.77 (comp, 2H), 7.49 (t, J=7.9 Hz, 1H), 7.17 (d, J=8.9 Hz, 1H), 6.62

(comp, 2H), 5.59 (d, J=5.2 Hz, 1H), 5.56-5.52 (m, 1H), 5.16 (dd, J=9.9, 3.1 Hz, 1H), 4.14-4.03 (m, 1H), 3.47 (comp, 4H), 2.22 (s, 3H), 1.27 (s, 3H), 1.06 (s, 3H).

Compound 233

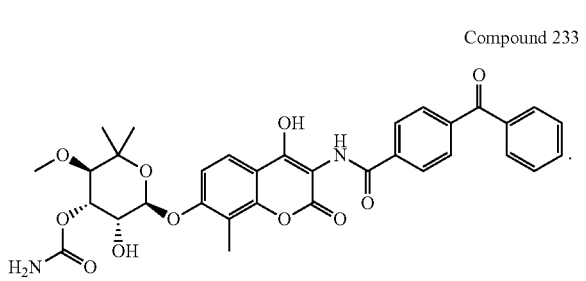 [SMILES: CO[C@@H]1[C@@H](OC(N)=O)[C@@H](O)[C@H](Oc2ccc3c(O)c(NC(=O)c4ccc(C(=O)c5ccccc5)cc4)c(=O)oc3c2C)OC1(C)C]

$^1$H NMR (400 MHz, DMSO-$d_6$) δ 12.03 (s, 1H), 9.65 (s, 1H), 8.16 (comp, 2H), 7.85 (comp, 2H), 7.75 (comp, 4H), 7.60 (comp, 2H), 7.16 (d, J=9.0 Hz, 1H), 6.68 (comp, 2H), 5.60 (d, J=5.2 Hz, 1H), 5.54 (d, J=2.4 Hz, 1H), 5.16 (dd, J=9.8, 3.1 Hz, 1H), 4.12-4.06 (m, 1H), 3.47 (comp, 4H), 2.23 (s, 3H), 1.27 (s, 3H), 1.06 (s, 3H).

Compound 234

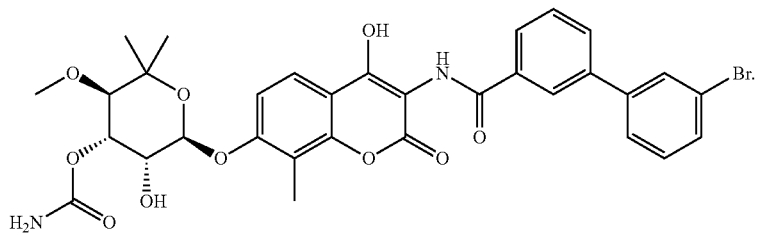

$^1$H NMR (400 MHz, DMSO-$d_6$) δ 9.65 (s, 1H), 8.36 (d, J=2.1 Hz, 1H), 8.02 (d, J=1.9 Hz, 1H), 7.95 (comp, 2H), 7.79 (comp, 2H), 7.62 (comp, 2H), 7.49 (comp, 1H), 7.18 (d, J=9.0 Hz, 1H), 6.58 (comp, 2H), 5.61 (d, J=5.2 Hz, 1H), 5.55 (d, J=2.4 Hz, 1H), 5.16 (dd, J=9.9, 3.1 Hz, 1H), 4.12-4.04 (m, 1H), 3.48 (comp, 4H), 2.23 (s, 3H), 1.27 (s, 3H), 1.06 (s, 3H).

Compound 235

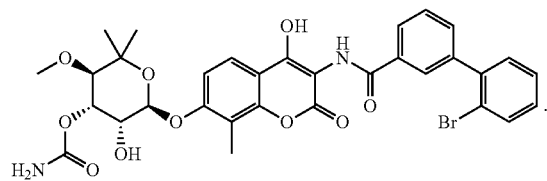

$^1$H NMR (400 MHz, DMSO-$d_6$) δ 11.90 (s, 1H), 9.57 (s, 1H), 8.04 (comp, 2H), 7.77 (comp, 3H), 7.62 (comp, 2H), 7.50 (comp, 3H), 7.37 (td, J=7.6, 2.0 Hz, 1H), 7.17 (d, J=9.1 Hz, 1H), 5.59 (s, 1H), 5.54 (d, J=2.5 Hz, 1H), 5.16 (dd, J=9.9, 3.2 Hz, 1H), 4.08 (s, 1H), 3.48 (comp, 4H), 2.23 (s, 3H), 1.27 (s, 3H), 1.06 (s, 3H).

Compound 236

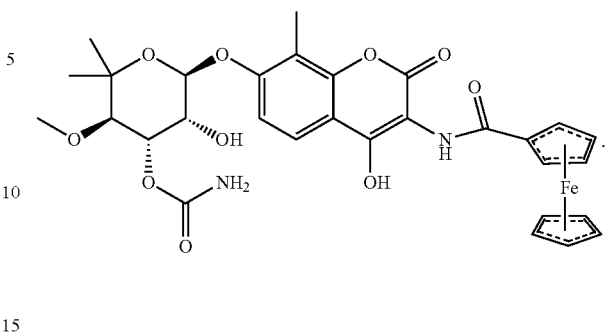

$^1$H NMR (400 MHz, DMSO-$d_6$) δ 11.88 (s, 1H), 8.59 (s, 1H), 7.72 (d, J=9.1 Hz, 1H), 7.11 (s, 1H), 6.67 (comp, 2H), 5.57 (d, J=5.2 Hz, 1H), 5.51 (s, 1H), 5.16 (d, J=9.6 Hz, 1H), 4.94 (s, 2H), 4.41 (s, 2H), 4.33 (comp, 5H), 4.08 (s, 1H), 3.48 (comp, 4H), 2.22 (s, 3H), 1.27 (s, 3H), 1.06 (s, 3H).

Compound 237

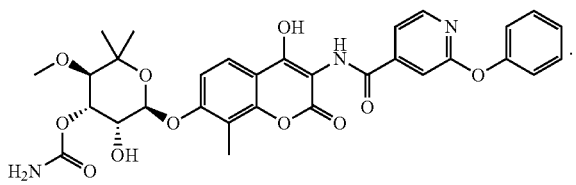

$^1$H NMR (400 MHz, DMSO-$d_6$) δ 12.13 (s, 1H), 9.45 (s, 1H), 8.30 (d, J=5.1 Hz, 1H), 7.69 (d, J=8.9 Hz, 1H), 7.63 (d, J=5.2 Hz, 1H), 7.50 (s, 1H), 7.45 (comp, 2H), 7.24 (t, J=7.4 Hz, 1H), 7.17 (comp, 2H), 7.00 (d, J=34.3 Hz, 1H), 6.66 (comp, 2H), 5.55 (d, J=5.1 Hz, 1H), 5.49 (s, 1H), 5.16 (dd, J=9.8, 3.1 Hz, 1H), 4.11-4.03 (m, 1H), 3.46 (comp, 4H), 2.19 (s, 3H), 1.26 (s, 3H), 1.07 (s, 3H).

Compound 238

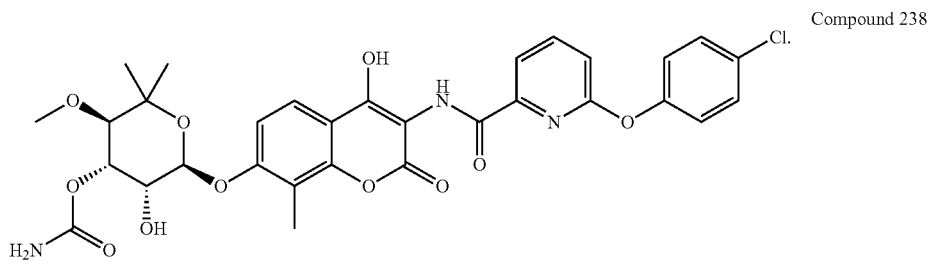 [SMILES: CO[C@@H]1[C@@H](OC(N)=O)[C@@H](O)[C@H](Oc2ccc3c(O)c(NC(=O)c4cccc(Oc5ccc(Cl)cc5)n4)c(=O)oc3c2C)OC1(C)C]

¹H NMR (500 MHz, DMSO-d$_6$) δ 12.86 (s, 1H), 9.43 (s, 1H), 8.17-8.08 (m, 1H), 7.91 (d, J=7.3 Hz, 1H), 7.72 (d, J=9.0 Hz, 1H), 7.52 (comp, 2H), 7.32 (comp, 3H), 7.15 (d, J=9.1 Hz, 1H), 6.63 (comp, 2H), 5.61 (d, J=5.2 Hz, 1H), 5.52 (d, J=2.5 Hz, 1H), 5.15 (dd, J=9.9, 3.1 Hz, 1H), 4.07 (dt, J=5.4, 2.8 Hz, 1H), 3.47 (comp, 4H), 2.21 (s, 3H), 1.26 (s, 3H), 1.04 (s, 3H).

Compound 239

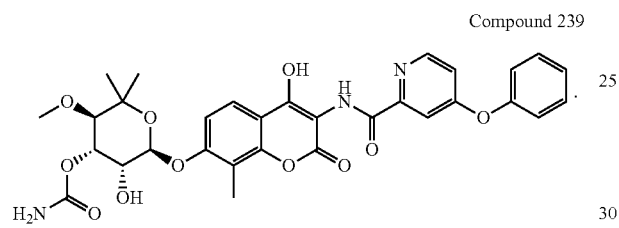

¹H NMR (500 MHz, DMSO-d$_6$) δ 12.43 (s, 1H), 9.91 (s, 1H), 8.64 (d, J=5.6 Hz, 1H), 7.73 (d, J=8.9 Hz, 1H), 7.55 (comp, J=7.9 Hz, 2H), 7.46 (d, J=2.5 Hz, 1H), 7.37 (t, J=7.4 Hz, 1H), 7.27 (comp, 3H), 7.16 (d, J=9.0 Hz, 1H), 6.73 (comp, 2H), 5.61 (d, J=5.2 Hz, 1H), 5.53 (d, J=2.4 Hz, 1H), 5.15 (dd, J=9.9, 3.2 Hz, 1H), 4.10-4.03 (m, 1H), 3.47 (comp, 4H), 2.21 (s, 3H), 1.26 (s, 3H), 1.04 (s, 3H).

Compound 240

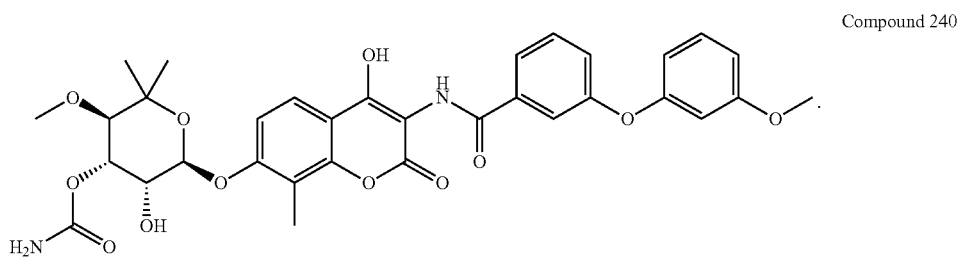

¹H NMR (500 MHz, DMSO-d$_6$) δ 11.89 (s, 1H), 9.52 (s, 1H), 7.80 (d, J=7.8 Hz, 1H), 7.74 (d, J=8.8 Hz, 1H), 7.65 (d, J=2.1 Hz, 1H), 7.62-7.52 (m, 3H), 7.32 (t, J=8.2 Hz, 1H), 7.19-7.14 (m, 1H), 6.76 (dd, J=8.2, 2.7 Hz, 1H), 6.63 (t, J=2.4 Hz, 1H), 6.61-6.58 (m, 1H), 5.61 (d, J=5.3 Hz, 1H), 5.54 (d, J=2.5 Hz, 1H), 5.15 (dd, J=9.9, 3.2 Hz, 1H), 4.10-4.06 (m, 1H), 3.75 (s, 3H), 3.73 (d, J=2.7 Hz, 1H), 3.47 (comp, 4H), 2.22 (s, 3H), 1.26 (s, 3H), 1.05 (s, 3H).

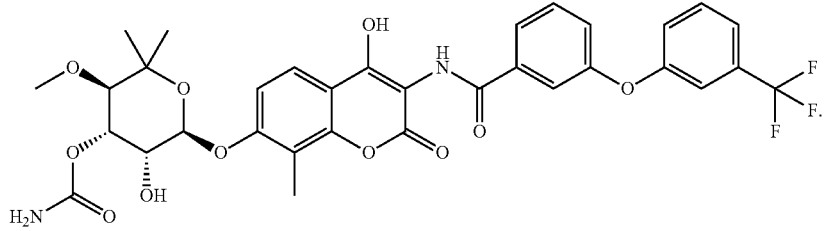
Compound 241
¹H NMR (500 MHz, DMSO-d₆) δ 11.89 (s, 1H), 9.55 (s, 1H), 7.93-7.84 (m, 1H), 7.78-7.72 (m, 1H), 7.70-7.63 (m, 1H), 7.56 (comp, 3H), 7.36 (comp, 3H), 7.17 (d, J=8.9 Hz, 1H), 6.64 (comp, 2H), 5.62 (dd, J=13.0, 5.2 Hz, 1H), 5.54 (d, J=2.4 Hz, 1H), 5.15 (dd, J=9.8, 3.1 Hz, 1H), 4.08 (s, 1H), 3.47 (comp, 4H), 2.22 (s, 3H), 1.26 (s, 3H), 1.05 (s, 3H).
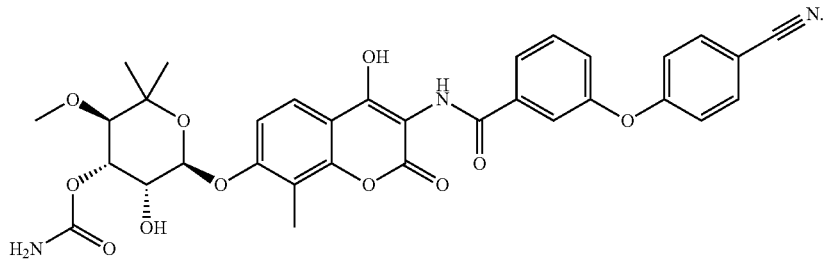
Compound 242
¹H NMR (500 MHz, DMSO-d₆) δ 11.90 (s, 1H), 9.55 (s, 1H), 7.90 (comp, J=10.6, 8.1 Hz, 3H), 7.76 (comp, 2H), 7.63 (t, J=7.9 Hz, 1H), 7.42-7.38 (m, 1H), 7.17 (comp, 3H), 6.54 (comp, 2H), 5.60 (d, J=5.2 Hz, 1H), 5.53 (d, J=2.4 Hz, 1H), 5.15 (dd, J=9.9, 3.1 Hz, 1H), 4.11-4.04 (m, 1H), 3.48 (comp, 4H), 2.22 (s, 3H), 1.26 (s, 3H), 1.05 (s, 3H).
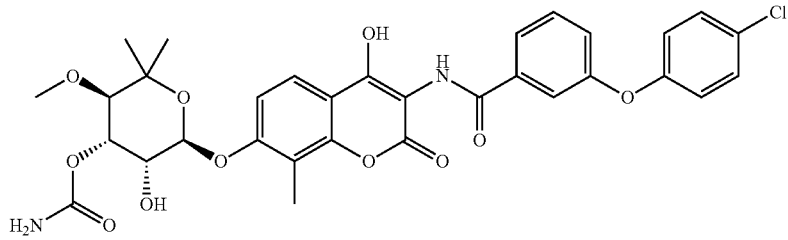
Compound 243
¹H NMR (500 MHz, DMSO-d₆) δ 11.89 (s, 1H), 9.52 (s, 1H), 7.82 (d, J=7.7 Hz, 1H), 7.74 (d, J=8.9 Hz, 1H), 7.67-7.64 (m, 1H), 7.56 (t, J=8.0 Hz, 1H), 7.47 (comp, 2H), 7.29 (dd, J=8.4, 2.5 Hz, 1H), 7.16 (d, J=9.0 Hz, 1H), 7.09 (comp, 2H), 6.73 (comp, 2H), 5.61 (d, J=5.2 Hz, 1H), 5.53 (d, J=2.4 Hz, 1H), 5.15 (dd, J=9.9, 3.2 Hz, 1H), 4.10-4.06 (m, 1H), 3.48 (comp, 4H), 2.22 (s, 3H), 1.26 (s, 3H), 1.05 (s, 3H).

Compound 244
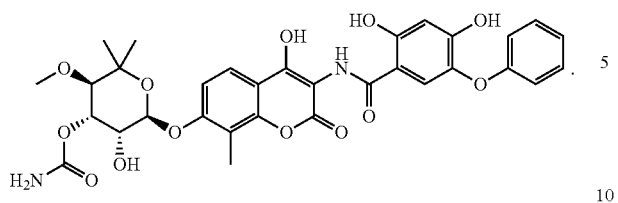
¹H NMR (500 MHz, DMSO-d₆) δ 13.69 (s, 1H), 12.39 (s, 1H), 10.63 (s, 1H), 7.80-7.61 (m, 2H), 7.31 (t, J=7.9 Hz, 2H), 7.17 (s, 1H), 7.01 (t, J=7.3 Hz, 1H), 6.86 (d, J=8.1 Hz, 2H), 6.57 (d, J=42.7 Hz, 3H), 5.60 (d, J=5.2 Hz, 1H), 5.52 (s, 1H), 5.15 (dd, J=9.8, 3.1 Hz, 1H), 4.10-4.03 (m, 1H), 3.47 (comp, 4H), 2.22 (s, 3H), 1.26 (s, 3H), 1.04 (s, 3H).
Compound 245
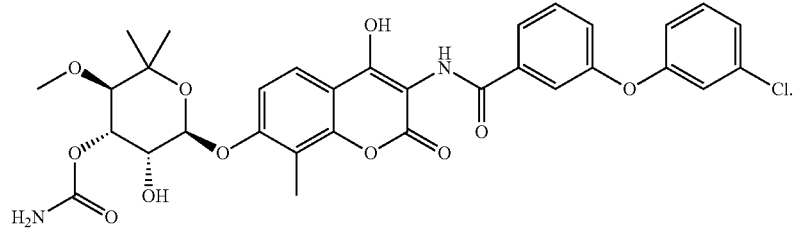
¹H NMR (400 MHz, DMSO-d₆) δ 11.89 (s, 1H), 9.53 (s, 1H), 8.37 (s, 1H), 7.97 (dd, J=14.6, 7.9 Hz, 1H), 7.85 (d, J=7.9 Hz, 1H), 7.74 (d, J=8.9 Hz, 1H), 7.69 (s, 1H), 7.58 (t, J=8.0 Hz, 1H), 7.45 (s, 1H), 7.28 (dd, J=33.5, 8.0 Hz, 1H), 7.21-6.99 (m, 2H), 6.68 (s, 2H), 5.59 (d, J=5.1 Hz, 1H), 5.53 (s, 1H), 5.15 (d, J=10.0 Hz, 1H), 4.11-4.04 (m, 1H), 3.48 (comp, 4H), 2.22 (s, 3H), 1.27 (s, 3H), 1.05 (s, 3H).
Compound 246
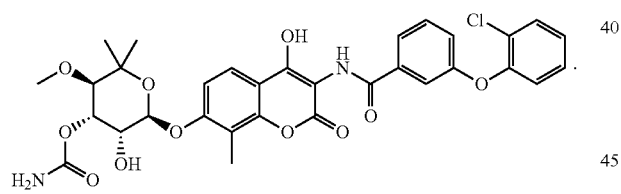
¹H NMR (400 MHz, DMSO-d₆) δ 11.88 (s, 1H), 9.50 (s, 1H), 7.79 (d, J=7.9 Hz, 1H), 7.73 (d, J=8.8 Hz, 1H), 7.64 (d, J=8.2 Hz, 1H), 7.56 (d, J=2.2 Hz, 1H), 7.52 (d, J=7.9 Hz, 1H), 7.42 (t, J=7.7 Hz, 1H), 7.27 (t, J=7.8 Hz, 1H), 7.17 (q, J=9.8, 8.5 Hz, 2H), 6.67 (comp, 2H), 5.58 (d, J=5.2 Hz, 1H), 5.55-5.50 (m, 1H), 5.15 (dd, J=9.9, 3.2 Hz, 1H), 4.11-4.05 (m, 1H), 3.46 (comp, 4H), 2.21 (s, 3H), 1.26 (s, 3H), 1.05 (s, 3H).
Compound 247
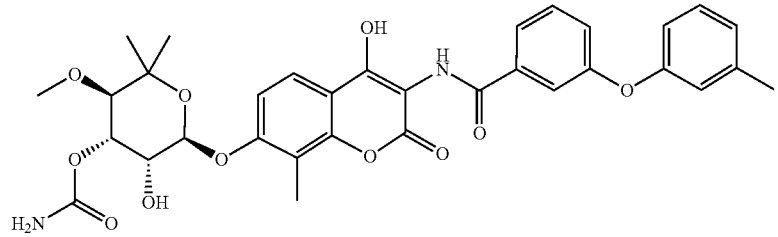

¹H NMR (400 MHz, DMSO-d$_6$) δ 11.97 (s, 1H), 9.11 (s, 1H), 7.78 (d, J=7.8 Hz, 1H), 7.67 (d, J=8.8 Hz, 1H), 7.58 (s, 1H), 7.49 (t, J=7.9 Hz, 1H), 7.29 (t, J=7.8 Hz, 1H), 7.19 (d, J=8.2 Hz, 1H), 6.98 (comp, 2H), 6.86 (comp, 2H), 6.66 (comp, 2H), 5.54 (d, J=3.8 Hz, 1H), 5.48 (s, 1H), 5.15 (dd, J=9.5, 2.9 Hz, 1H), 4.10-4.03 (m, 1H), 3.47 (comp, 4H), 2.31 (s, 3H), 2.18 (s, 3H), 1.26 (s, 3H), 1.07 (s, 3H).

Compound 248

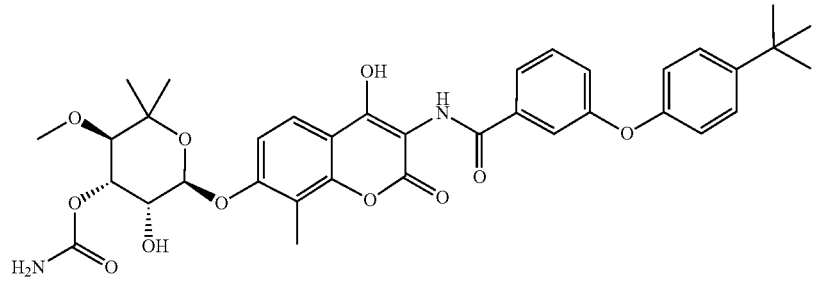

¹H NMR (400 MHz, DMSO-d$_6$) δ 11.90 (s, 1H), 9.35 (s, 1H), 7.77 (d, J=7.8 Hz, 1H), 7.70 (d, J=8.8 Hz, 1H), 7.59 (s, 1H), 7.50 (t, J=8.0 Hz, 1H), 7.46-7.40 (m, 2H), 7.21 (d, J=8.2 Hz, 1H), 7.14-7.06 (m, 1H), 6.98 (d, J=8.5 Hz, 2H), 6.69 (comp, 2H), 5.57 (d, J=5.1 Hz, 1H), 5.51 (s, 1H), 5.15 (dd, J=9.7, 2.9 Hz, 1H), 4.10-4.03 (m, 1H), 3.47 (comp, 4H), 2.20 (s, 3H), 1.29 (s, 9H), 1.26 (s, 3H), 1.06 (s, 3H).

Compound 249

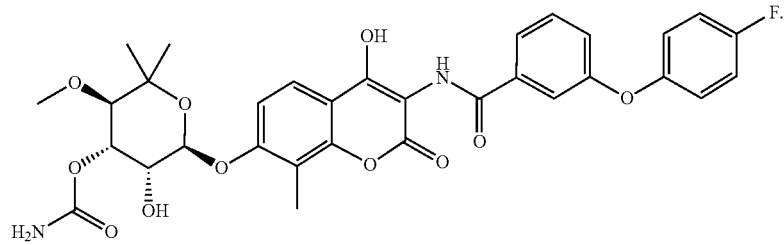

¹H NMR (400 MHz, DMSO-d$_6$) δ 11.87 (s, 1H), 9.50 (s, 1H), 7.76 (comp, 2H), 7.63-7.58 (m, 1H), 7.53 (t, J=7.9 Hz, 1H), 7.25 (comp, 3H), 7.14 (comp, 3H), 6.67 (comp, 2H), 5.59 (d, J=5.2 Hz, 1H), 5.53 (d, J=2.5 Hz, 1H), 5.15 (dd, J=9.9, 3.1 Hz, 1H), 4.10-4.05 (m, 1H), 3.48 (comp, 4H), 2.22 (s, 3H), 1.26 (s, 3H), 1.05 (s, 3H).

Compound 250

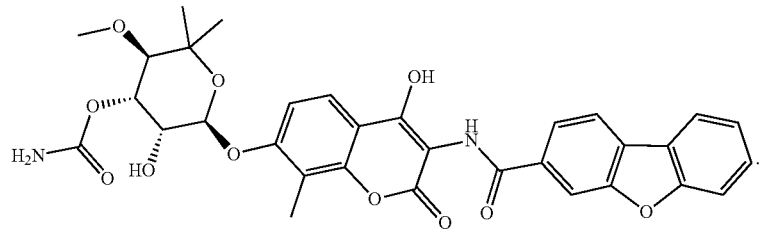

¹H NMR (400 MHz, DMSO-d$_6$) δ 11.97 (s, 1H), 9.66 (s, 1H), 8.30 (comp, 3H), 8.09 (dd, J=8.1, 1.4 Hz, 1H), 7.78 (comp, 2H), 7.66-7.56 (m, 1H), 7.47 (t, J=7.6 Hz, 1H), 7.19 (d, J=9.1 Hz, 1H), 6.69 (comp, 2H), 5.67-5.58 (m, 1H), 5.58-5.52 (m, 1H), 5.17 (dd, J=10.1, 2.7 Hz, 1H), 4.14-4.04 (m, 1H), 3.48 (comp, 4H), 2.24 (s, 3H), 1.28 (s, 3H), 1.07 (s, 3H).

Compound 251

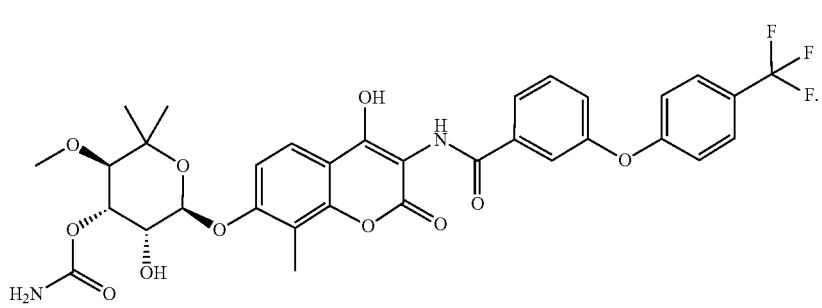

¹H NMR (400 MHz, DMSO-d₆) δ 11.88 (s, 1H), 9.53 (s, 1H), 7.89 (d, J=7.8 Hz, 1H), 7.76 (comp, 4H), 7.62 (d, J=8.5 Hz, 1H), 7.39 (d, J=8.0 Hz, 1H), 7.18 (comp, 3H), 6.64 (comp, 2H), 5.59 (d, J=4.1 Hz, 1H), 5.56-5.50 (m, 1H), 5.15 (dd, J=9.7, 3.0 Hz, 1H), 4.11-4.04 (m, 1H), 3.47 (comp, 4H), 2.22 (s, 3H), 1.26 (s, 3H), 1.05 (s, 3H).

Compound 252

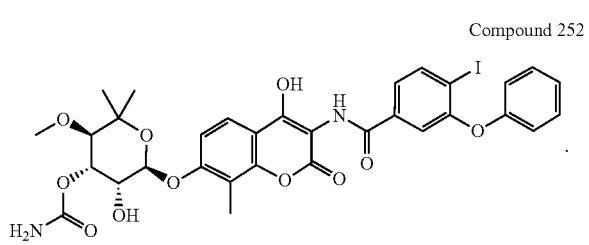 [SMILES: CO[C@@H]1[C@@H](OC(N)=O)[C@@H](O)[C@H](Oc2ccc3c(O)c(NC(=O)c4ccc(I)c(Oc5ccccc5)c4)c(=O)oc3c2C)OC1(C)C]

¹H NMR (400 MHz, DMSO-d₆) δ 11.92 (d, J=17.8 Hz, 1H), 9.49 (s, 1H), 8.07 (d, J=8.2 Hz, 1H), 7.75-7.54 (m, 3H), 7.42 (t, J=7.7 Hz, 1H), 7.08 (comp, 4H), 6.65 (comp, 2H), 5.57 (d, J=5.2 Hz, 1H), 5.51 (s, 1H), 5.15 (dd, J=9.8, 3.1 Hz, 1H), 4.33 (d, J=4.2 Hz, 1H), 4.09-4.03 (m, 1H), 3.46 (comp, 4H), 2.19 (s, 3H), 1.26 (s, 3H), 1.05 (s, 3H).

Compound 253

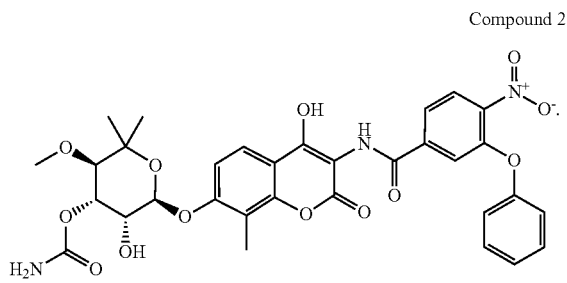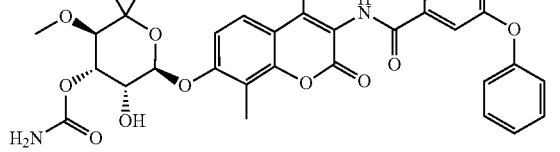

¹H NMR (400 MHz, DMSO-d₆) δ 11.94 (s, 1H), 9.68 (s, 1H), 8.18 (d, J=8.5 Hz, 1H), 7.90 (d, J=8.5 Hz, 1H), 7.72-7.63 (m, 2H), 7.44 (t, J=7.8 Hz, 2H), 7.25-7.18 (m, 1H), 7.11 (d, J=8.0 Hz, 3H), 6.57 (comp, 2H), 5.54 (d, J=5.2 Hz, 1H), 5.51-5.46 (m, 1H), 5.11 (dd, J=9.8, 3.1 Hz, 1H), 4.07-4.00 (m, 1H), 3.44 (comp, 4H), 2.16 (s, 3H), 1.22 (s, 3H), 1.01 (s, 3H).

Compound 254

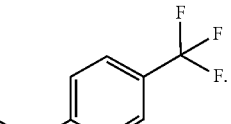

¹H NMR (400 MHz DMSO-d₆) δ 11.87 (s, 1H), 9.54 (s, 1H), 7.89 (d, J=8.5 Hz, 1H), 7.80 (d, J=8.0 Hz, 1H), 7.73 (d, J=8.9 Hz, 1H), 7.60-7.52 (m, 1H), 7.42 (t, J=7.7 Hz, 2H), 7.16 (comp, 2H), 7.05 (comp, 2H), 6.61 (comp, 2H), 5.59 (s, 1H), 5.53 (s, 1H), 5.19-5.10 (m, 1H), 4.10-4.05 (m, 1H), 3.47 (comp, 4H), 2.21 (s, 3H), 1.26 (s, 3H), 1.04 (s, 3H).

Compound 255

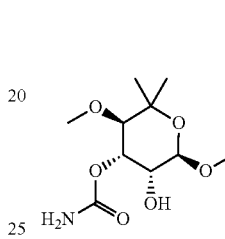

¹H NMR (600 MHz, DMSO-d₆) δ 11.84 (s, 1H), 9.45 (s, 1H), 7.75 (comp, 2H), 7.56 (s, 1H), 7.48 (d, J=7.9 Hz, 1H), 7.39 (comp, 2H), 7.14 (comp, 2H), 6.95 (comp, 2H), 6.72 (comp, 2H), 5.59 (s, 1H), 5.53 (d, J=2.8 Hz, 1H), 5.15 (d, J=9.4 Hz, 1H), 4.10-4.04 (m, 1H), 3.46 (comp, 4H), 2.26 (s, 3H), 2.21 (s, 3H), 1.26 (s, 3H), 1.04 (s, 3H).

Compound 256

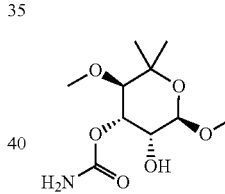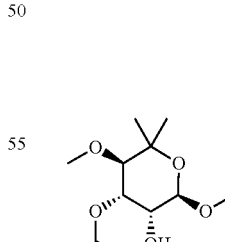

¹H NMR (400 MHz, DMSO-d₆) δ 11.84 (s, 1H), 9.40 (s, 1H), 7.92 (dd, J=8.6, 2.2 Hz, 1H), 7.73 (comp, 2H), 7.33 (comp, 3H), 7.16 (d, J=9.1 Hz, 1H), 7.07 (d, J=7.4 Hz, 1H), 6.89 (comp, 2H), 6.66 (comp, 2H), 5.59 (d, J=5.2 Hz, 1H), 5.53 (d, J=2.4 Hz, 1H), 5.15 (dd, J=9.9, 3.1 Hz, 1H), 4.11-4.05 (m, 1H), 3.84 (s, 3H), 3.47 (comp, 4H), 2.22 (s, 3H), 1.26 (s, 3H), 1.05 (s, 3H).

Compound 257

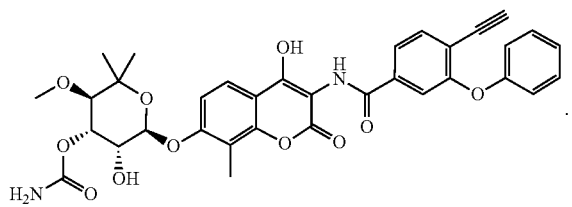

¹H NMR (400 MHz, DMSO-d₆) δ 11.87 (s, 1H), 9.58 (s, 1H), 7.82 (d, J=8.7 Hz, 1H), 7.73 (d, J=8.4 Hz, 2H), 7.58 (s, 1H), 7.43 (t, J=7.9 Hz, 2H), 7.17 (t, J=9.1 Hz, 2H), 7.04 (d, J=8.0 Hz, 2H), 6.59 (comp, 2H), 5.53 (comp, 2H), 5.15 (d, J=9.7 Hz, 1H), 4.48 (s, 1H), 4.08 (s, 1H), 3.48 (comp, 4H), 2.21 (s, 3H), 1.26 (s, 3H), 1.05 (s, 3H).

Compound 259

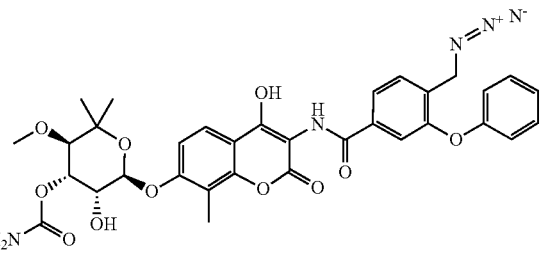

¹H NMR (400 MHz, DMSO-d₆) δ 11.86 (s, 1H), 9.53 (s, 1H), 7.85 (d, J=8.1 Hz, 1H), 7.73 (d, J=9.0 Hz, 1H), 7.65 (d, J=8.0 Hz, 1H), 7.52 (s, 1H), 7.45 (comp, 2H), 7.18 (comp, 2H), 7.06 (comp, 2H), 6.63 (comp, 2H), 5.59 (s, 1H), 5.53 (s, 1H), 5.15 (d, J=9.8 Hz, 1H), 4.58 (s, 2H), 4.11-4.05 (m, 1H), 3.47 (comp, 4H), 2.21 (s, 3H), 1.26 (s, 3H), 1.05 (s, 3H).

Compound 258

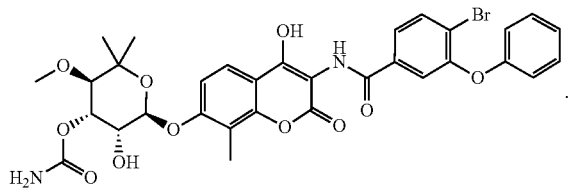

¹H NMR (400 MHz, DMSO-d₆) δ 9.59 (s, 1H), 8.60 (s, 1H), 7.94-7.81 (m, 1H), 7.80-7.65 (m, 3H), 7.44 (d, J=8.0 Hz, 2H), 7.17 (comp, 2H), 7.02 (d, J=8.1 Hz, 2H), 6.61 (comp, 2H), 5.59 (s, 1H), 5.53 (s, 1H), 5.19-5.10 (m, 1H), 4.10-4.06 (m, 1H), 3.48 (comp, 4H), 2.21 (s, 3H), 1.26 (s, 3H), 1.05 (s, 3H).

Compound 260

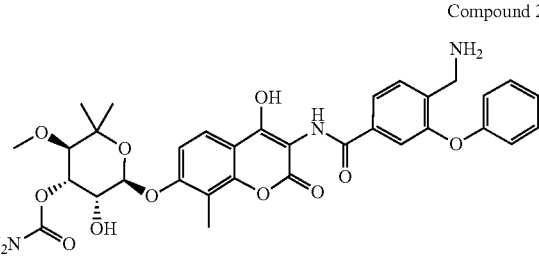

¹H NMR (400 MHz, DMSO-d₆) δ 8.66 (s, 1H), 7.83 (d, J=8.0 Hz, 1H), 7.59 (comp, 2H), 7.43 (comp, 3H), 7.18 (t, J=7.4 Hz, 1H), 7.07 (comp, 2H), 6.86 (comp, 2H), 6.60 (comp, 2H), 5.49 (d, J=5.1 Hz, 1H), 5.40 (d, J=2.6 Hz, 1H), 5.15 (dd, J=9.7, 3.2 Hz, 1H), 4.03 (s, 3H), 3.44 (comp, 4H), 2.14 (s, 3H), 1.25 (s, 3H), 1.08 (s, 3H). (missing two signals, likely those of the primary amine NH₂).

Compound 261

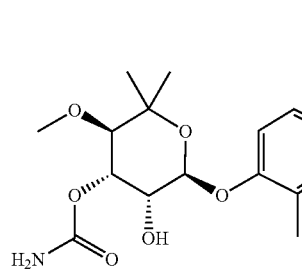

¹H NMR (400 MHz, DMSO-d₆) δ 11.87 (s, 1H), 9.53 (s, 1H), 7.74 (comp, 2H), 7.55 (comp, 2H), 7.19 (comp, 4H), 7.09-7.01 (m, 1H), 6.65 (comp, 2H), 5.59 (br, 1H), 5.53 (d, J=2.4 Hz, 1H), 5.15 (dd, J=9.9, 3.1 Hz, 1H), 4.08 (s, 1H), 3.46 (comp, 4H), 2.21 (s, 3H), 1.26 (s, 3H), 1.05 (s, 3H).

Compound 262

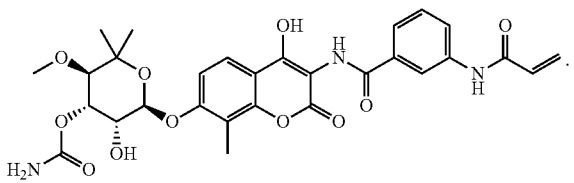

¹H NMR (400 MHz, DMSO-d₆) δ 11.93 (s, 1H), 10.33 (d, J=2.6 Hz, 1H), 9.44 (s, 1H), 8.16 (s, 1H), 7.94 (dd, J=24.3, 8.4 Hz, 1H), 7.75 (comp, 2H), 7.47 (t, J=8.0 Hz, 1H), 7.16 (d, J=8.7 Hz, 1H), 6.65 (comp, 2H), 6.51-6.36 (m, 1H), 6.29 (d, J=17.1 Hz, 1H), 5.78 (d, J=10.0 Hz, 1H), 5.62-5.56 (m, 1H), 5.54 (s, 1H), 5.16 (d, J=9.9 Hz, 1H), 4.11-4.04 (m, 1H), 3.47 (comp, 4H), 2.23 (s, 3H), 1.27 (s, 3H), 1.06 (s, 3H).

Compound 263

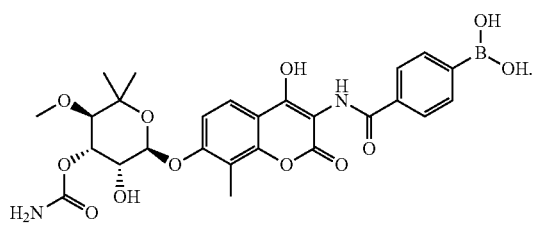

¹H NMR (400 MHz, DMSO-d₆) δ 11.91 (s, 1H), 9.46 (s, 1H), 8.23 (d, J=5.3 Hz, 2H), 7.97 (d, J=7.8 Hz, 2H), 7.90 (comp, 2H), 7.75 (d, J=8.9 Hz, 1H), 7.17 (d, J=9.0 Hz, 1H), 6.60 (comp, 2H), 5.59 (d, J=5.2 Hz, 1H), 5.56-5.52 (m, 1H), 5.16 (dd, J=9.8, 3.1 Hz, 1H), 4.10-4.05 (m, 1H), 3.47 (comp, 4H), 2.23 (s, 3H), 1.27 (s, 3H), 1.06 (d, J=1.6 Hz, 3H).

Compound 264

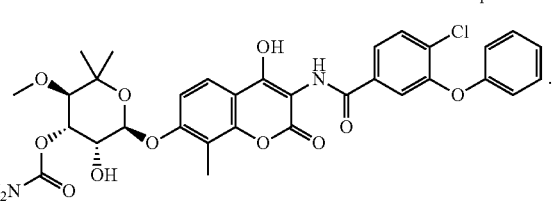

¹H NMR (400 MHz, DMSO-d₆) δ 11.89 (s, 1H), 9.56 (s, 1H), 7.77 (comp, 4H), 7.41 (comp, 2H), 7.16 (comp, 2H), 7.03 (comp, 2H), 6.62 (comp, 2H), 5.62-5.55 (m, 1H), 5.53 (s, 1H), 5.15 (dd, J=9.5, 2.8 Hz, 1H), 4.10-4.03 (m, 1H), 3.47 (comp, 4H), 2.21 (s, 3H), 1.26 (s, 3H), 1.04 (s, 3H).

Compound 265

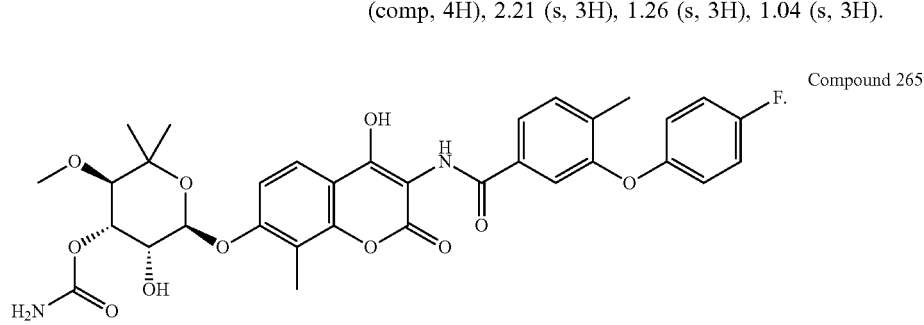

¹H NMR (400 MHz, DMSO-d₆) δ 11.85 (s, 1H), 9.42 (s, 1H), 8.58 (s, 1H), 7.75 (dd, J=18.6, 8.7 Hz, 2H), 7.49 (d, J=11.8 Hz, 2H), 7.41-7.36 (m, 1H), 7.27-7.22 (m, 1H), 7.15 (comp, 1H), 7.01 (d, J=6.5 Hz, 1H), 6.67 (comp, 2H), 5.58 (d, J=5.2 Hz, 1H), 5.56-5.47 (m, 1H), 5.15 (dd, J=10.8, 2.0 Hz, 1H), 4.11-4.03 (m, 1H), 3.47 (comp, 4H), 2.28 (s, 3H), 2.21 (s, 3H), 1.26 (s, 3H), 1.05 (s, 3H).

Compound 266

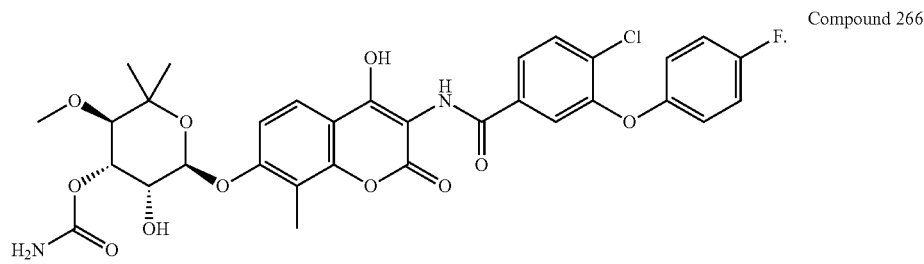 [SMILES: CO[C@@H]1[C@@H](OC(N)=O)[C@@H](O)[C@H](Oc2ccc3c(O)c(NC(=O)c4ccc(Cl)c(Oc5ccc(F)cc5)c4)c(=O)oc3c2C)OC1(C)C]

$^1$H NMR (400 MHz, DMSO-d$_6$) δ 11.90 (s, 1H), 9.54 (s, 1H), 8.58 (d, J=4.8 Hz, 1H), 7.87-7.78 (m, 1H), 7.76-7.70 (m, 1H), 7.65 (s, 1H), 7.39 (dd, J=7.6, 5.0 Hz, 1H), 7.27 (comp, 2H), 7.14 (d, J=9.0 Hz, 1H), 7.11-7.07 (m, 1H), 6.66 (comp, 2H), 5.58 (d, J=5.1 Hz, 1H), 5.54-5.49 (m, 1H), 5.15 (dd, J=10.0, 3.1 Hz, 1H), 4.10-4.05 (m, 1H), 3.48 (comp, 4H), 2.21 (s, 3H), 1.26 (s, 3H), 1.05 (s, 3H).

Compound 267

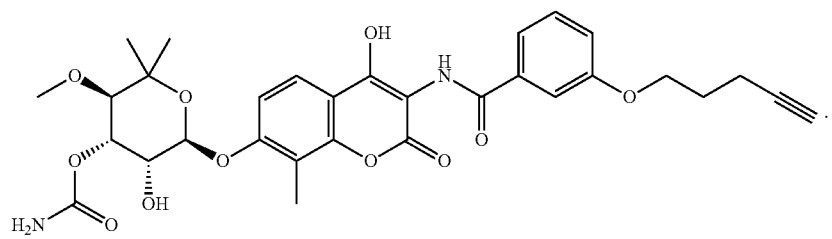

$^1$H NMR (500 MHz, DMSO-d$_6$) δ 11.88 (s, 1H), 9.46 (s, 1H), 7.75 (d, J=8.8 Hz, 1H), 7.58 (comp, 2H), 7.42 (t, J=8.1 Hz, 1H), 7.16 (comp, 2H), 6.54 (comp, 2H), 5.60 (d, J=5.2 Hz, 1H), 5.54 (d, J=2.5 Hz, 1H), 5.16 (dd, J=9.8, 3.1 Hz, 1H), 4.11 (comp, 3H), 3.48 (comp, 4H), 2.83 (t, J=2.7 Hz, 1H), 2.36 (dd, J=7.0, 2.7 Hz, 2H), 2.22 (s, 3H), 1.93 (q, J=6.5 Hz, 2H), 1.27 (s, 3H), 1.06 (s, 3H).

Example 11. Antibacterial Inhibitory Activity, Lipopolysaccharide Release, and Synergistic Activity with Polymyxin B Compounds described herein were tested for antibacterial inhibitory activity in wild-type *E. coli*, for lipopolysaccharide release, and for synergistic activity with polymyxin B. The assays are described below. The results of both assays are provided in Table 2.

General Procedure for Determination of Minimal Inhibitory Concentrations

Overnight cultures (5 mL) of bacterial strains were grown in LB media or TSA media (for *S. aureus*) at 37° C. and with shaking at 220 rpm until saturation. The overnight culture was diluted serially 1:100 (50 μL in 5 mL sterile media) and then 1:100 (250 μL in 25 mL sterile media). The 25 mL of diluted culture was then dispensed to a sterile 96 well plate (Corning #3370). 198 μL of culture were dispensed into row A and 100 μL of this culture were dispensed into rows B-H. Aminocoumarin compound (DMSO stock) were added to the first row and then the row was mixed by pipetting. 100 μL of culture from row A were transferred to row B and the serial dilution continued until the final 100 μL from row H were discarded. The plate was incubated without shaking in a 37° C. for 16 hours and then read by visible light spectrophotometer (Molecular Devices) at 600 nm. The minimal inhibitory concentration (MIC) was determined as the lowest concentration of compound concentration that inhibited the growth of bacteria.

General Procedure for In Cell UV Photocrosslinking for Measuring the Effect of Aminocoumarin Derivatives on Lipopolysaccharide Transport BL21(λDE3) *E. coli* were transformed with plasmid pBAD18HisA-LptC(T47Am)-Thrombin-His7 along with pCDFduet-LptB-LptFG (encoding wild-type *E. coli* proteins) and pSup-BpaRS-6TRN (encoding a tRNA synthetase capable of charging p-benzoylphenylalanine to a tRNA that can recognize UAG codon). Overnight cultures were diluted 1:50 into 50 mL of LB Miller media containing 50 μg/mL carbenicillin, 50 μg/mL spectinomycin, 35 μg/mL of chloramphenicol and grown at 37° C., 220 rpm to OD600~0.7. Expression was induced by addition of 0.02% L-arabinose and 20 μM Isopropyl β-D-1-thiogalactopyranoside (IPTG) and shaking was resumed at 37° C., 220 rpm for 30 min. The main culture was split into 5 mL sterile culture tubes and aminocoumarin derivative was added. The tubes were incubated at 37° C., 220 rpm for 90 min. Cells were transferred to 6 well plates, on ice, and UV irradiation was performed for 10 min with a 365 nm light source. Samples were transferred to 5 mL Eppendorf tubes and centrifuged at 4,000 g for 20 min to pellet cells. Cell pellets were resuspended in 20 mM Tris, pH 8.0, 300 mM NaCl, 5 mM MgCl$_2$ supplemented with 100 μg/mL lysozyme, 100 μg/mL DNase I, and 1 mM PMSF and freeze-thawed twice to lyse. Supplemented each tube with Anzergent 3-14 (1% final concentration), vortexed, and centrifuged at 4,000 g for 30 min. The supernatant was poured into a 10 mL disposable affinity column containing 500 μL of Ni-NTA resin (pre-equilibrated with water and then 20 mM Tris, pH 8.0, 300 mM NaCl, 20 mM imidazole, 0.02% Anzergent 3-14). The columns were gently rocked at 4° C. for 1 h before flowing through. The columns were washed with 5 mL of 20 mM Tris, pH 8.0, 300 mM NaCl, 20 mM imidazole, 0.02% Anzergent 3-14 and then eluted into 1.5 mL Eppendorf tubes with 900 μL of 20 mM Tris, pH 8.0, 300 mM NaCl, 200 mM imidazole, 0.02% Anzergent 3-14. Trichloroacetic acid (100 μL of a 100% solution) was added to each Eppendorf tube. Tubes were mixed and placed on ice for 30 min to induce precipitation of the Lpt proteins. The tubes were centrifuged at 20,000 g for 15 min at 4° C. and the supernatant discarded. The pellets were resuspended in a 1:1 mixture of 2×SDS loading dye (100 mM Tris-HCl pH 6.8, 4% w/v SDS, 0.05% w/v bromothymol blue, 20% glycerol+5% β-mercaptoethanol) and 1 M Tris pH 8.0, and boiled for 10 minutes. Immunoblotting was used to assess LptC-LPS levels in each sample. Boiled samples were run on homemade 4% to 20% polyacrylamide gradient gels at 150 V for about 75 min until the 15 kDa ladder band (BioRad Precision Plus all Blue standards) had run out of the gel, transferred to PVDF, and immunoblotted with mouse anti-LPS core antiserum (HyCult Biotechnology) followed by sheep-anti-mouse IgG horseradish peroxidase conjugate (GE Healthcare). LptC levels were assessed similarly, using rabbit anti-LptC antiserum followed by donkey anti-rabbit horseradish peroxidase conjugate (GE Amersham). ECL Prime Western Blotting Detection Reagent (GE Amersham) was used to visualize antibody-label bands in conjunction with an Azure c400 imaging system (Azure Biosystems).

LPS Release Assay

Right-Side-Out Vesicle Preparation

Right-side-out (RSO) vesicles were prepared as described in Okuda et al., Science, 338:1214, 2012; May et al., *J. Am. Chem. Soc.,* 139:17221, 2017, with minor modifications. BL21(λDE3) *E. coli* were transformed with plasmid pBAD18HisA-LptC along with pCDFduet-LptB-LptFG (encoding wild-type *E. coli* proteins). Overnight cultures were diluted 1:100 into 50 mL of LB Miller media containing 50 μg/mL carbenicillin and 50 μg/mL spectinomycin and grown at 24° C. to OD600~1. Growth temperature was then increased to 37° C. and expression induced by addition of 0.02% L-arabinose and 10 μM Isopropyl β-D-1-thiogalactopyranoside (IPTG). After two hours, cells were pelleted, resuspended in 5 mL 50 mM Tris-HCl (pH 7.4) 250 mM sucrose, 300 μg/mL lysozyme and 150 μg/mL DNaseI, and converted to spheroplasts by dropwise addition of 5 mL buffer containing 50 mM Tris-HCl (pH 7.4), 250 mM sucrose and 3 mM EDTA followed by incubation on ice for 30 minutes. To convert spheroplasts to RSO-vesicles, spheroplasts were pelleted, 6000 g×10 minutes, resuspended in 5 mL lysis buffer (20 mM Tris (pH 8), 150 mM NaCl, 0.1 mM EDTA, 5 mM $MgCl_2$, and 5 mM sodium-ATP (pH ~7)), pelleted at 10,000 g×15 minutes, and resuspended in the supernatant to complete lysis. RSO-vesicles were collected by centrifugation at 200,000 g×30 minutes and resuspended in 1 mL of 10% v/v glycerol, 20 mM Tris (pH 8.0), 150 mM NaCl, 5 mM $MgCl_2$, and 5 mM sodium-ATP (pH ~7). Total protein concentration in RSO-vesicle samples was determined by DC-protein assay (BioRad), and samples were either used immediately in LPS release assays or flash-frozen and stored at −80° C.

LPS Release Assay

The in vitro LPS-transport experiments were set-up as described in May et al., *J. Am. Chem. Soc.,* 139:17221, 2017, with some modifications. RSO-vesicles (50 g total protein) were diluted into 100 μL reaction buffer (10% v/v glycerol, 20 mM Tris (pH 8.0), 150 mM NaCl, 5 mM sodium-ATP, 5 mM MgCl2), and incubated on ice with compounds listed in Table 2, or no compound for 15 minutes (50× compound stocks in water were used for each concentration). To start the assay, 3 μg of LptA* was added to each sample, with each time-point its own 100 μL sample, and samples were then incubated at 30° C. for the stated time. To cross-link LptA* to LPS, samples were transferred to a 96-well plate and irradiated with 365 nm UV-light for 5 minutes. Cross-linked samples were then mixed 1:1 with 2×SDS loading dye (100 mM Tris-HCl pH 6.8, 4% w/v SDS, 0.05% w/v bromothymol blue, 20% glycerol) with 5% β-mercaptoethanol, and boiled for 10 minutes.

Immunoblotting was used to assess LptA*-LPS levels in each sample. Boiled samples were run on homemade 4%/15% polyacrylamide stacking gels at 0.02 A constant-current until the 15 kDa ladder band (BioRad Precision Plus all Blue standards) had run out of the gel, transferred to PVDF, and immunoblotted with mouse anti-LPS core antiserum (HyCult Biotechnology) followed by sheep-anti-mouse IgG horseradish peroxidase conjugate (GE Healthcare). LptA levels were assessed similarly, using rabbit anti-LptA antiserum (see Chng et al., Biochemistry, 49:4565, 2010) followed by donkey anti-rabbit horseradish peroxidase conjugate (GE Amersham). ECL Prime Western Blotting Detection Reagent (GES11Amersham) was used to visualize antibody-label bands in conjunction with an Azure c400 imaging system (Azure Biosystems).

Results are shown in FIG. 1, and LPS release to LptA for selected compounds is shown qualitatively in Table 2.

Microdilution Assays

Checkerboard microdilution assays between polymyxin B and the compounds in Table 2 were performed in wild-type *Escherichia coli* at 37° C. for 24 h. The data indicate that compounds in Table 2 may synergize with polymyxin B to kill Gram-negative pathogens in vitro. Table 2 shown above also shows the minimal inhibitory concentrations (MIC) of aminocoumarin compounds and polymyxin B.

TABLE 2

| Compound | LPS Release | MIC (μM) in WT *E. coli* | Polymyxin B Synergy |
|---|---|---|---|
| Novobiocin | + | 59 | − |
| 1 | | 26 | 2 |
| 2 | | >300 | 2 |
| 3 | | >300 | 1 |
| 4 | | >300 | 1 |
| 5 | | >300 | 0 |
| 6 | | >300 | 0 |
| 7 | | >300 | 0 |
| 8 | | >300 | 0 |
| 9 | | >300 | 0 |
| 10 | | >300 | 0 |
| 11 | | >300 | 0 |
| 12 | | >300 | 0 |
| 13 | − | >300 | 0 |
| 13A | − | | |
| 14 | + | >300 | 2 |
| 15 | | >300 | 0 |
| 16 | | >300 | 1 |
| 17 | | >300 | 1 |
| 18 | | >300 | 1 |
| 19 | | >300 | 0 |
| 20 | | 26 | 2 |
| 21 | | 133 | 0 |
| 22 | | 89 | 2 |
| 23 | | >300 | 0 |
| 24 | | >300 | 1 |
| 25 | | >300 | 2 |
| 26 | | >300 | 0 |
| 27 | | >300 | 1 |
| 28 | ++ | 26 | 3 |
| 29 | | >300 | 0 |
| 30 | | >300 | 0 |
| 31 | | >300 | 0 |
| 32 | | >300 | 0 |
| 33 | +++ | 18 | 2 |
| 34 | +++ | 59 | 3 |
| 35 | | 8 | 2 |
| 36 | + | >300 | 0 |
| 37 | | 59 | 2 |
| 38 | | 26 | 2 |
| 39 | +++ | >300 | 2 |
| 40 | | >300 | — |
| 41 | | >300 | — |
| 42 | | >300 | — |
| 43 | | >300 | — |
| 44 | | >300 | 0 |
| 45 | | 89 | 1 |
| 46 | | >300 | 1 |
| 47 | | 26 | 1 |
| 48 | | 89 | 2 |
| 49 | | >300 | 3 |
| 50 | | 40 | 2 |
| 51 | | 26 | 2 |
| 52 | | >300 | 0 |
| 53 | | >300 | 1 |
| 54 | | 40 | 2 |
| 55 | | >300 | 1 |
| 56 | | >300 | 1 |
| 57 | | >300 | 2 |
| 58 | | 89 | 1 |
| 59 | | 40 | 1 |
| 60 | | >300 | |
| 61 | | 59 | |
| 62 | | 59 | |
| 63 | | 300 | |
| 64 | | >300 | |

TABLE 2-continued

| Compound | LPS Release | MIC (µM) in WT E. coli | Polymyxin B Synergy |
|---|---|---|---|
| 65 | | 59 | |
| 66 | | >300 | |
| 67 | | 18 | |
| 68 | | 18 | |
| 69 | | 89 | |
| 70 | | >300 | |
| 71 | | >300 | |
| 72 | | >300 | |
| 73 | | >300 | |
| 74 | | >300 | |
| 75 | | >300 | |
| 76 | | 40 | |
| 77 | | 40 | |
| 78 | | 59 | |
| 79 | | 26 | |
| 80 | | >300 | |
| 81 | | >300 | |
| 82 | | >300 | |
| 83 | | 26 | |
| 84 | + | 8 | |
| 85 | | 59 | |
| 86 | | 18 | |
| 87 | | 18 | |
| 88 | | 89 | |
| 89 | | 59 | |
| 90 | | >300 | |
| 91 | | >300 | |
| 92 | | 150 | |
| 93 | | 75 | |
| 94 | | >300 | |
| 95 | | 38 | |
| 96 | | >300 | |
| 97 | | >300 | |
| 98 | | >300 | |
| 99 | | >300 | |
| 101 | + | | |
| 103 | +++ | | |
| 104 | + | | |
| 105 | + | | |
| 106 | + | | |
| 112 | ++ | | 3 |
| 112A | ++ | | |
| 113 | ++ | | |
| 114 | ++ | | |

Example 12. Antibacterial Inhibitory Activity

The compounds of the invention were assessed for activities against the pathogens *S. aureus* RN4220 and MW2, *E. cloacae* 13047, *A. baumannii* 19606, *K. pneumoniae* 700721, *E. coli* MC4100, 25922. All activities are reported in micromolar (uM) and are 16 hour minimal inhibitory concentrations at 37° C. The assay is detailed in Example 11 and is titled "General Procedure for Determination of Minimal Inhibitory Concentrations."

| Compound # | MIC (µM) E. coli MC4100 ara+ | MIC (µM) E. coli 25922 | MIC (µM) S. aureus RN4220 | MIC (µM) S. aureus MW2 (MRSA) | MIC (µM) A. baumannii 19606 | MIC (µM) E. cloacae 13047 | MIC (µM) K. pneumoniae 700721 |
|---|---|---|---|---|---|---|---|
| Novobiocin | 59 | 40 | 0.2 | 0.25 | 1.27 | >100 | >100 |
| 1 | 26 | 41 | 5 | 5 | >50 | >100 | >100 |
| 2 | >200 | >200 | 21 | 21 | >50 | >100 | >100 |
| 3 | >200 | >200 | 81 | 81 | >50 | >100 | >100 |
| 4 | >200 | >200 | 22 | 22 | >50 | >100 | >100 |
| 5 | >200 | >200 | >100 | 80 | >50 | >100 | >100 |
| 6 | >200 | >200 | 88 | 88 | >50 | >100 | >100 |
| 7 | >200 | >200 | 45 | 45 | >50 | >100 | >100 |
| 8 | >200 | >200 | >100 | >100 | >50 | >100 | >100 |
| 9 | >200 | >200 | 85 | 43 | >50 | >100 | >100 |
| 10 | >200 | >200 | >100 | 85 | >50 | >100 | >100 |
| 11 | >200 | >200 | >100 | >100 | >50 | >100 | >100 |
| 200 | >200 | >200 | 91 | 91 | >50 | >100 | >100 |
| 13 | >200 | >200 | >100 | >100 | >50 | >100 | >100 |
| 14 | >200 | >200 | 43 | 21 | >50 | >100 | >100 |
| 15 | >200 | >200 | >100 | >100 | >50 | >100 | >100 |
| 16 | >200 | >200 | >100 | >100 | >50 | >100 | >100 |
| 17 | >200 | >200 | 44 | 22 | >50 | >100 | >100 |
| 201 | >200 | >200 | 42 | 42 | >50 | >100 | >100 |
| 20 | 26 | 40 | 2.5 | 3 | 40 | >100 | >100 |
| 21 | 133 | >200 | 10 | 10 | >50 | >100 | >100 |
| 22 | 89 | 164 | 10 | 10 | >50 | >100 | >100 |
| 23 | >200 | >200 | 82 | 82 | >50 | >100 | >100 |
| 24 | >200 | 154 | 5 | 5 | >50 | >100 | >100 |
| 25 | >200 | >200 | 0.96 | 0.96 | 19 | >100 | >100 |
| 26 | >200 | >200 | >100 | >100 | >50 | >100 | >100 |
| 27 | >200 | >200 | 45 | 23 | >50 | >100 | >100 |
| 28 | 26 | 40 | 5 | 5 | >50 | 161 | 80 |
| 29 | >200 | >200 | 83 | 83 | >50 | >100 | >100 |
| 30 | >200 | >200 | 46 | 46 | >50 | >100 | >100 |
| 31 | >200 | >200 | 41 | 41 | >50 | >100 | >100 |
| 32 | >200 | >200 | 83 | 41 | >50 | >100 | >100 |
| 33 | 18 | 20 | 1.96 | 0.98 | 39 | >100 | >100 |
| 34 | 59 | 68 | 0.43 | 0.43 | 9 | >100 | >100 |
| 35 | 8 | 10 | 40 | 20 | >50 | >100 | >100 |
| 202 | >200 | >200 | >100 | >100 | >50 | >100 | >100 |
| 37 | 59 | 80 | 10 | 10 | >50 | >100 | >100 |
| 38 | 26 | 40 | 5 | 10 | >50 | >100 | >100 |
| 39 | >200 | 153 | 0.19 | 0.1 | 5 | >100 | >100 |

-continued

| Compound # | MIC (μM) E. coli MC4100 ara+ | MIC (μM) E. coli 25922 | MIC (μM) S. aureus RN4220 | MIC (μM) S. aureus MW2 (MRSA) | MIC (μM) A. baumannii 19606 | MIC (μM) E. cloacae 13047 | MIC (μM) K. pneumoniae 700721 |
|---|---|---|---|---|---|---|---|
| 52 | >200 | 160 | >100 | >100 | >50 | >100 | >100 |
| 53 | >200 | >200 | 11 | 11 | >50 | >100 | >100 |
| 54 | 40 | 79 | 0.99 | 0.99 | 20 | >100 | 79 |
| 203 | >200 | >200 | >100 | >100 | >50 | >100 | >100 |
| 81 | >200 | >200 | 40 | 40 | >50 | >100 | >100 |
| 82 | >200 | >200 | >100 | >100 | >50 | >100 | >100 |
| 103 | >200 | >200 | 36 | 36 | 9 | >100 | >100 |
| 104 | >200 | 156 | 2 | 2 | 10 | >100 | >100 |
| 105 | >200 | >200 | >100 | >100 | >50 | >100 | >100 |
| 106 | >200 | >200 | >100 | >100 | >50 | >100 | >100 |
| 100 | >200 | >200 | 83 | 41 | >50 | >100 | >100 |
| 101 | 20 | 20 | 2 | 1 | 41 | >100 | 81 |
| 102 | >200 | >200 | >100 | >100 | >50 | >100 | >100 |
| 112 | 74 | 18.5 | <0.01 | <0.01 | <0.11 | >100 | 37 |
| 113 | >200 | >200 | 0.5 | 0.24 | 2 | >100 | >100 |
| 114 | >200 | >200 | 74 | 74 | >50 | >100 | >100 |
| 204 | >200 | >200 | 82 | 82 | >50 | >100 | >100 |
| 205 | >200 | >200 | 9 | 9 | >50 | >100 | >100 |
| 206 | >200 | >200 | >100 | >100 | >50 | >100 | >100 |
| 207 | >200 | >200 | >100 | >100 | >50 | >100 | >100 |
| 208 | >200 | >200 | >100 | >100 | >50 | >100 | >100 |
| 209 | >200 | >200 | >100 | >100 | >50 | >100 | >100 |
| 210 | >200 | >200 | 33 | 33 | >50 | >100 | >100 |
| 211 | >200 | >200 | >100 | >100 | >50 | >100 | >100 |
| 212 | >200 | >200 | >100 | >100 | >50 | >100 | >100 |
| 213 | >200 | >200 | 1.8 | 0.45 | 4.5 | >100 | >100 |
| 214 | >200 | >200 | 5 | 5 | >50 | >100 | >100 |
| 215 | >200 | >200 | 38 | 19 | >50 | >100 | >100 |
| 216 | >200 | >200 | 19 | 19 | >50 | >100 | >100 |
| 217 | >200 | >200 | 19 | 9 | >50 | >100 | >100 |
| 218 | 80 | 161 | 10 | 10 | >50 | >100 | >100 |
| 219 | 39 | 20 | 5 | 5 | >50 | >100 | 78 |
| 220 | 158 | 160 | 10 | 10 | >50 | >100 | >100 |
| 221 | 10 | 5 | 10 | 10 | >50 | >100 | >100 |
| 222 | 37 | 37 | 0.46 | 0.23 | 9 | >100 | >100 |
| 223 | | | | | | | |
| 224 | | >200 | 88 | >100 | >50 | >100 | >100 |
| 225 | | >200 | 38 | 38 | >50 | >100 | >100 |
| 226 | >200 | >200 | >100 | >100 | >50 | >100 | >100 |
| 227 | 9 | 34 | 4 | 4 | >50 | >100 | 34 |
| 228 | >200 | >200 | 97 | 97 | >50 | >100 | >100 |
| 229 | >200 | >200 | 90 | 90 | >50 | >100 | >100 |
| 230 | 86 | 172 | 86 | 86 | >50 | >100 | >100 |
| 231 | >200 | >200 | >100 | >100 | >50 | >100 | >100 |
| 232 | >200 | >200 | 82 | 82 | >50 | >100 | >100 |
| 233 | >200 | >200 | 40 | 40 | >50 | >100 | >100 |
| 68 | 18 | 18 | 0.91 | 0.91 | 18 | >100 | >100 |
| 234 | 18 | 18 | 0.73 | 0.46 | 18 | >100 | >100 |
| 235 | 18 | 18 | 9 | 5 | >50 | >100 | >100 |
| 236 | | | | | | | |
| 237 | >100 | >200 | >100 | >100 | >50 | >100 | >100 |
| 238 | 152 | >200 | 10 | 10 | >50 | >100 | >100 |
| 239 | >200 | >200 | 20 | 20 | >50 | >100 | >100 |
| 240 | 4.5 | 38 | 19.2 | 19.2 | >50 | >100 | >100 |
| 241 | 155 | 145 | 9.08 | 9.08 | >50 | >100 | >100 |
| 242 | 153 | 154 | >100 | 77 | >50 | >100 | >100 |
| 243 | 4.8 | 38 | 10 | 10 | >50 | >100 | >100 |
| 244 | 4.8 | 38 | 19 | 19 | >50 | >100 | 38 |
| 245 | 38 | 76 | 10 | 19 | >50 | >100 | >100 |
| 246 | 79 | 76 | 10 | 5 | >50 | >100 | >100 |
| 247 | 18 | 39 | 10 | 5 | >50 | >100 | >100 |
| 248 | >200 | 148 | 2.3 | 2.3 | >50 | >100 | >100 |
| 249 | 5 | <1.563 | 20 | 20 | >50 | >100 | 20 |
| 250 | >100 | >200 | 10 | 10 | >50 | >100 | >100 |
| 251 | 4.5 | 9 | 9 | 9 | >50 | >100 | >100 |
| 252 | 17 | 33 | 2.3 | 2 | >50 | >100 | 38 |
| 253 | 75 | 75 | 38 | 38 | >50 | >100 | >100 |
| 254 | 2.4 | 5 | 10 | 10 | >50 | 79 | 20 |
| 255 | 2.4 | 5 | 5 | 5 | >50 | 77 | 10 |
| 256 | 10 | 10 | 19 | 19 | >50 | >100 | 19 |
| 257 | 39 | 19 | 5 | 5 | >50 | >100 | 71 |
| 258 | 4.5 | 18 | 5 | 4.5 | >50 | >100 | 20 |
| 40 | >100 | >200 | 41 | 41 | >50 | >100 | >100 |
| 41 | >200 | >200 | 20 | 20 | >50 | >100 | >100 |

-continued

| Compound # | MIC (μM) E. coli MC4100 ara+ | MIC (μM) E. coli 25922 | MIC (μM) S. aureus RN4220 | MIC (μM) S. aureus MW2 (MRSA) | MIC (μM) A. baumannii 19606 | MIC (μM) E. cloacae 13047 | MIC (μM) K. pneumoniae 700721 |
|---|---|---|---|---|---|---|---|
| 42 | >200 | >200 | >100 | >100 | >50 | >100 | >100 |
| 43 | >200 | >200 | >100 | >100 | >50 | >100 | >100 |
| 44 | >200 | >200 | 45 | 40 | >50 | >100 | >100 |
| 45 | 89 | 79 | 5 | 3 | >50 | >100 | >100 |
| 46 | >200 | >200 | 5 | 3 | >50 | >100 | >100 |
| 47 | 26 | 40 | 20 | 10 | >50 | >100 | >100 |
| 48 | 89 | 77 | 0.77 | 0.48 | 19 | >100 | 77 |
| 49 | >200 | >200 | 10 | 5 | >50 | >100 | >100 |
| 50 | 40 | 39 | 19 | 10 | >50 | >100 | >100 |
| 51 | 26 | 81 | 1.62 | 1 | 40 | >100 | >100 |
| 55 | >200 | >200 | 1.49 | 0.93 | 37 | >100 | >100 |
| 56 | >200 | >200 | 0.74 | 0.46 | 37 | >100 | >100 |
| 57 | >200 | >200 | 1.45 | 0.91 | 18 | >100 | >100 |
| 58 | 89 | >200 | 0.36 | 0.18 | 18 | >100 | >100 |
| 59 | 40 | >200 | 9 | 5 | >50 | >100 | >100 |
| 60 | >200 | >200 | 9 | 5 | >50 | >100 | >100 |
| 61 | 59 | 77 | 0.39 | 0.19 | 10 | >100 | >100 |
| 62 | 59 | 82 | 5 | 3 | >50 | >100 | 82 |
| 63 | >200 | >200 | 10 | 5 | >50 | >100 | >100 |
| 64 | >200 | >200 | 77 | 39 | >50 | >100 | >100 |
| 65 | 59 | >200 | 81 | 40 | >50 | >100 | >100 |
| 66 | >200 | >200 | >100 | >100 | >50 | >100 | >100 |
| 67 | 18 | 5 | 10 | 5 | >50 | >100 | 79 |
| 69 | 89 | 81 | 5 | 3 | >50 | >100 | >100 |
| 70 | >200 | >200 | 86 | 43 | >50 | >100 | >100 |
| 71 | >200 | >200 | 81 | 41 | >50 | >100 | >100 |
| 72 | >200 | >200 | 86 | 43 | >50 | >100 | >100 |
| 73 | >200 | >200 | >100 | 81 | >50 | >100 | >100 |
| 74 | >200 | >200 | >100 | >100 | >50 | >100 | >100 |
| 75 | >200 | >200 | 18 | 9 | >50 | >100 | >100 |
| 76 | 40 | 80 | 5 | 3 | 40 | >100 | >100 |
| 77 | 40 | 40 | 10 | 5 | >50 | >100 | >100 |
| 78 | 59 | 40 | 5 | 4 | 40 | >100 | >100 |
| 79 | 26 | 20 | 2 | 0.98 | 20 | >100 | 78 |
| 83 | 26 | 40 | 3 | 2.5 | 20 | >100 | >100 |
| 84 | 8 | 10 | 5 | 5 | >50 | 81 | 40 |
| 85 | 59 | 40 | 5 | 2.5 | >50 | >100 | >100 |
| 86 | 18 | 20 | 20 | 20 | >50 | >100 | 40 |
| 87 | 18 | 20 | 20 | 20 | >50 | >100 | 40 |
| 88 | 89 | 161 | >100 | 81 | >50 | >100 | >100 |
| 89 | 59 | 81 | 20 | 10 | >50 | >100 | >100 |
| 90 | >200 | >200 | >100 | >100 | >50 | >100 | >100 |
| 91 | >200 | >200 | >100 | >100 | >50 | >100 | >100 |
| 92 | 150 | >200 | 0.09 | 0.09 | 1.16 | >100 | >100 |
| 93 | 75 | >200 | 37 | 19 | >50 | >100 | >100 |
| 94 | >200 | >200 | 20 | 20 | >50 | >100 | >100 |
| 95 | 38 | 38 | 38 | 38 | >50 | >100 | >100 |
| 96 | >200 | 146 | 9 | 9 | 18 | >100 | 76 |
| 97 | >200 | 153 | 76 | 38 | >50 | >100 | >100 |
| 98 | >200 | >200 | 18 | 18 | 36 | >100 | >100 |
| 99 | >200 | >200 | 79 | 79 | >50 | >100 | >100 |
| 107 | >200 | >200 | 73 | 73 | 9 | >100 | >100 |
| 108 | >200 | >200 | >100 | >100 | >50 | >100 | >100 |
| 109 | >200 | >200 | 1.53 | 1.53 | 10 | >100 | >100 |
| 110 | >200 | >200 | >100 | >100 | >50 | >100 | >100 |

Other Embodiments

Embodiment 1. A compound of formula (I):

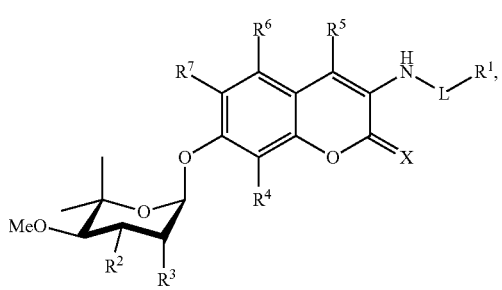

or a pharmaceutically acceptable salt thereof,
wherein
X is O or S;
L is —CO— or —SO$_2$—;
R$^1$ is unsubstituted phenyl, substituted phenyl, optionally substituted C$_{6-10}$ aryl C$_{1-4}$ alkyl, optionally substituted C$_{6-10}$ aryl C$_{2-4}$ alkenyl, o-phenylphenyl, optionally substituted C$_{3-10}$ cycloalkyl, optionally substituted C$_{1-9}$ heteroaryl comprising at least one nitrogen heteroatom within the heteroaryl ring system, benzofuryl, optionally substituted furyl, or —NHR$^8$,
wherein the substituted phenyl is substituted:
(i) at one and only one of its meta position relative to L, with optionally substituted C$_{6-10}$ aryl, optionally substituted C$_{1-6}$ alkyl, optionally substituted C$_{3-6}$ alkenyl comprising an allylic carbon-carbon double bond, optionally substituted C$_{6-10}$ aryl C$_{1-4}$ alkyl, optionally substituted C$_{1-6}$ alkoxy, optionally substituted C$_{6-10}$ aryloxy, optionally substituted (C$_{6-10}$ aryl)-C$_{1-6}$ alkoxy, optionally substituted C$_{3-10}$ cycloalkyl, optionally substituted C$_{1-9}$ heteroaryl comprising at least one nitrogen heteroatom within the heteroaryl ring system, optionally substituted C$_{3-9}$ heterocyclyl, or —SF$_5$; or
(ii) at its para position relative to L with hydroxyl, optionally substituted C$_{6-10}$ aryl C$_{1-4}$ alkyl, optionally substituted C$_{6-10}$ aryl C$_{2-4}$ alkynyl, optionally substituted C$_{6-10}$ aryl, optionally substituted C$_{3-10}$ cycloalkyl, optionally substituted C$_{1-6}$ alkoxy, optionally substituted C$_{6-10}$ aryloxy, or optionally substituted (C$_{6-10}$ aryl)-C$_{1-6}$ alkoxy;
and, valency permitting, the substituted phenyl is further optionally substituted with 1, 2, 3, or 4 substituents independently selected from the group consisting of halogen, hydroxyl, —N(R$^9$)$_2$, optionally substituted C$_{1-6}$ alkoxy, optionally substituted C$_{6-10}$ aryloxy, or optionally substituted C$_{6-10}$ aryl;
each of R$^2$ and R$^3$ is independently hydroxyl, —O—CO—NH—R$^{10}$, or —O—CO—R$^{11}$;
each of R$^4$, R$^6$, and R$^7$ is independently hydrogen, halogen, optionally substituted C$_{1-6}$ alkyl, optionally substituted C$_{1-6}$ alkoxy, or optionally substituted C$_{6-10}$ aryl;
R$^5$ is halogen, hydroxyl, or optionally substituted C$_{1-6}$ alkoxy;
R$^8$ is optionally substituted C$_{6-10}$ aryl;
each R$^9$ is independently H or optionally substituted C$_{1-6}$ alkyl;
R$^{10}$, when present, is hydrogen, optionally substituted C$_{1-6}$ alkyl, optionally substituted C$_{3-10}$ cycloalkyl, or optionally substituted C$_{6-10}$ aryl; and R$^{11}$, when present, is optionally substituted C$_{1-9}$ heteroaryl or optionally substituted C$_{6-10}$ aryl;
and
wherein, when R$^5$ is hydroxyl,
R$^1$ is substituted phenyl, optionally substituted C$_{6-10}$ aryl C$_{1-4}$ alkyl, optionally substituted C$_{6-10}$ aryl C$_{2-4}$ alkenyl, o-phenylphenyl, optionally substituted C$_{3-10}$ cycloalkyl, optionally substituted C$_{1-9}$ heteroaryl comprising at least one nitrogen heteroatom within the heteroaryl ring system, benzofuryl, or optionally substituted furyl,
wherein the substituted phenyl is substituted,
(i) at one and only one of its meta position relative to L, with optionally substituted C$_{6-10}$ aryl, substituted C$_{1-6}$ alkyl, substituted C$_{3-6}$ alkenyl comprising an allylic carbon-carbon double bond, optionally substituted C$_{6-10}$ aryl C$_{1-4}$ alkyl, optionally substituted C$_{1-6}$ alkoxy, optionally substituted C$_{6-10}$ aryloxy, optionally substituted (C$_{6-10}$ aryl)-C$_{1-6}$ alkoxy, optionally substituted C$_{3-10}$ cycloalkyl, optionally substituted C$_{1-9}$ heteroaryl comprising at least one nitrogen heteroatom within the heteroaryl ring system, optionally substituted C$_{3-9}$ heterocyclyl, or —SF$_5$; or
(ii) at its para position relative to L, with hydroxyl, optionally substituted C$_{6-10}$ aryl C$_{1-4}$ alkyl, optionally substituted C$_{6-10}$ aryl C$_{2-4}$ alkynyl, optionally substituted C$_{6-10}$ aryl, optionally substituted C$_{3-10}$ cycloalkyl, optionally substituted C$_{1-6}$ alkoxy, optionally substituted C$_{6-10}$ aryloxy, or optionally substituted (C$_{6-10}$ aryl)-C$_{1-6}$ alkoxy;
and, valency permitting, the substituted phenyl is further optionally substituted with 1, 2, 3, or 4 substituents independently selected from the group consisting of halogen, hydroxyl, —N(R$^9$)$_2$, optionally substituted C$_{1-6}$ alkoxy, optionally substituted C$_{6-10}$ aryloxy, optionally substituted (C$_{6-10}$ aryl)-C$_{1-6}$ alkoxy, or optionally substituted C$_{6-10}$ aryl.

Embodiment 2. The compound of Embodiment 1, wherein L is —CO—.

Embodiment 3. The compound of Embodiments 1 or 2, wherein X is O.

Embodiment 4. The compound of Embodiment 1, wherein the compound is of formula (IA).

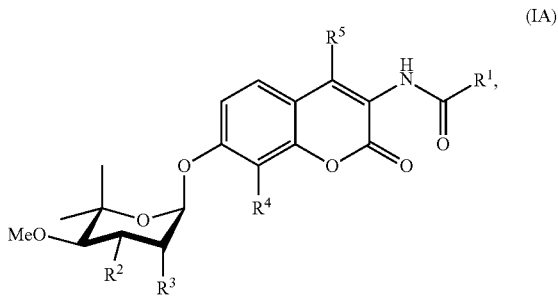

or a pharmaceutically acceptable salt thereof.

Embodiment 5. The compound of any one of any one of Embodiments 1-4, wherein R$^{11}$, when present, is optionally substituted C$_{1-9}$ heteroaryl.

Embodiment 6. A compound of formula (II):

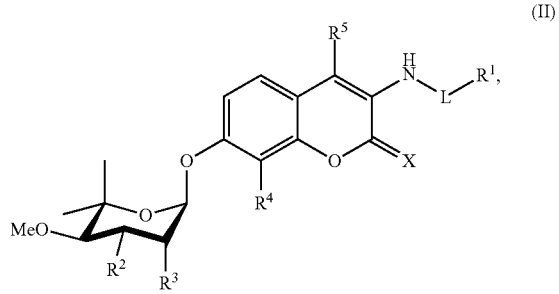

or a pharmaceutically acceptable salt thereof,
wherein
X is O or S;
L is —CO— or —SO$_2$—;
R$^1$ is unsubstituted phenyl, substituted phenyl, optionally substituted C$_{6-10}$ aryl C$_{1-4}$ alkyl, optionally substituted C$_{6-10}$ aryl C$_{2-4}$ alkenyl, o-phenylphenyl, optionally substituted C$_{3-10}$ cycloalkyl, optionally substituted C$_{1-9}$ heteroaryl comprising at least one nitrogen heteroatom within the heteroaryl ring system, benzofuryl, optionally substituted furyl, or —NHR$^8$,
wherein the substituted phenyl is substituted:
(i) at one and only one of its meta position relative to L, with optionally substituted C$_{6-10}$ aryl, optionally substituted C$_{1-6}$ alkyl, optionally substituted C$_{3-6}$ alkenyl comprising an allylic carbon-carbon double bond, optionally substituted C$_{6-10}$ aryl C$_{1-4}$ alkyl, optionally substituted C$_{1-6}$ alkoxy, optionally substituted C$_{6-10}$ aryloxy, optionally substituted (C$_{6-10}$ aryl)-C$_{1-6}$ alkoxy, optionally substituted C$_{3-10}$ cycloalkyl, optionally substituted C$_{1-9}$ heteroaryl comprising at least one nitrogen heteroatom within the heteroaryl ring system, optionally substituted C$_{3-9}$ heterocyclyl, or —SF$_5$; or
(ii) at its para position relative to L with hydroxyl, optionally substituted C$_{6-10}$ aryl C$_{1-4}$ alkyl, optionally substituted C$_{6-10}$ aryl C$_{2-4}$ alkynyl, optionally substituted C$_{6-10}$ aryl, optionally substituted C$_{3-10}$ cycloalkyl, optionally substituted C$_{1-6}$ alkoxy, or optionally substituted C$_{6-10}$ aryloxy;
and, valency permitting, the substituted phenyl is further optionally substituted with 1, 2, 3, or 4 substituents independently selected from the group consisting of halogen, hydroxyl, —N(R$^9$)$_2$, optionally substituted C$_{1-6}$ alkoxy, optionally substituted C$_{6-10}$ aryloxy, or optionally substituted C$_{6-10}$ aryl;
each of R$^2$ and R$^3$ is independently hydroxyl, —O—CO—NH—R$^{10}$, or —O—CO—R$^{11}$, provided that at least one of R$^2$ and R$^3$ is —O—CO—NH—R$^{10}$ or —O—CO—R$^{11}$;
R$^4$ is hydrogen, halogen, optionally substituted C$_{1-6}$ alkyl, optionally substituted C$_{1-6}$ alkoxy, or optionally substituted C$_{6-10}$ aryl;
R$^5$ is halogen, hydroxyl, or optionally substituted C$_{1-6}$ alkoxy;
R$^8$ is optionally substituted C$_{6-10}$ aryl;
each R$^9$ is independently H or optionally substituted C$_{1-6}$ alkyl;
R$^{10}$, when present, is hydrogen, optionally substituted C$_{2-6}$ alkyl, optionally substituted C$_{3-10}$ cycloalkyl; or optionally substituted C$_{6-10}$ aryl; and R$^{11}$, when present, is optionally substituted C$_{1-9}$ heteroaryl that is not 5-methyl-pyrrol-2-yl, 2-indolyl, or 3-indolyl.
Embodiment 7. The compound of Embodiment 6, wherein L is —CO—.
Embodiment 8. The compound of Embodiment 6 or 7, wherein X is O.
Embodiment 9. The compound of any one of Embodiments 1-8, wherein one and only one of R$^2$ and R$^3$ is —O—CO—NH—R$^{10}$ or —O—CO—R$^{11}$.
Embodiment 10. The compound of any one of Embodiments 1-9, wherein R$^3$ is —O—CO—NH—R$^{10}$ or —O—CO—R$^{11}$.
Embodiment 11. The compound of any one of Embodiments 1-10, wherein R$^{10}$, when present, is hydrogen, optionally substituted C$_{3-10}$ cycloalkyl; or optionally substituted C$_{6-10}$ aryl.
Embodiment 12. The compound of any one of Embodiments 1-5, wherein one and only one of R$^2$ and R$^3$ is:

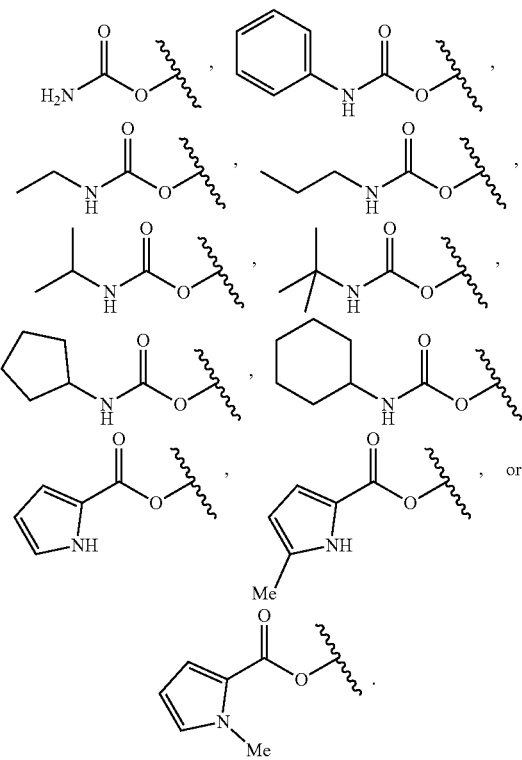

Embodiment 13. The compound of any one of Embodiments 6-8, wherein one and only one of R$^2$ and R$^3$ is:

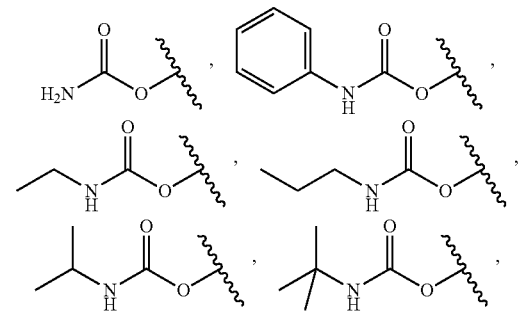

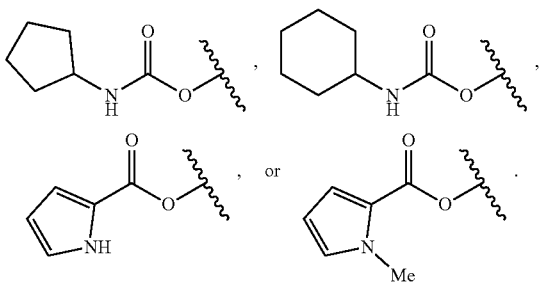

Embodiment 14. The compound of Embodiment 12 or 13, wherein $R^3$ is:

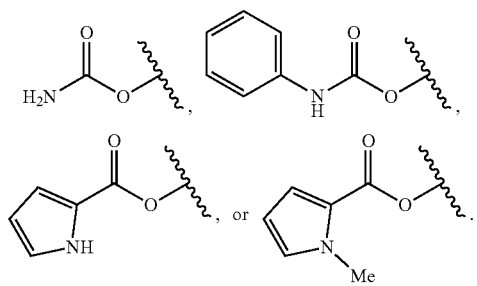

Embodiment 15. The compound of Embodiment 12 or 13, wherein $R^2$ is:

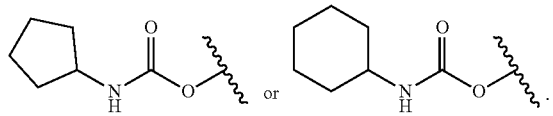 [SMILES: *OC(=O)NC1CCCC1 ; *OC(=O)NC1CCCCC1]

Embodiment 16. The compound of any one of Embodiments 1-14, wherein $R^2$ is hydroxyl.

Embodiment 17. The compound of any one of Embodiments 1-16, wherein $R^1$ is a substituted phenyl.

Embodiment 18. The compound of any one of Embodiments 1-17, wherein the substituted phenyl is substituted at one and only one of its meta position relative to L, with optionally substituted $C_{6-10}$ aryl, optionally substituted $C_{1-6}$ alkyl, optionally substituted $C_{3-6}$ alkenyl comprising an allylic carbon-carbon double bond, optionally substituted $C_{6-10}$ aryl $C_{1-4}$ alkyl, optionally substituted $C_{1-6}$ alkoxy, optionally substituted $C_{6-10}$ aryloxy, optionally substituted ($C_{6-10}$ aryl)-$C_{1-6}$ alkoxy, optionally substituted $C_{3-10}$ cycloalkyl, optionally substituted $C_{1-9}$ heteroaryl comprising at least one nitrogen heteroatom within the heteroaryl ring system, optionally substituted $C_{3-9}$ heterocyclyl, or —$SF_5$; and, valency permitting, the substituted phenyl is further optionally substituted with 1, 2, 3, or 4 substituents independently selected from the group consisting of halogen, hydroxyl, —N(R')$_2$, optionally substituted $C_{1-6}$ alkoxy, optionally substituted $C_{6-10}$ aryloxy, optionally substituted ($C_{6-10}$ aryl)-$C_{16}$ alkoxy, or optionally substituted $C_{6-10}$ aryl.

19. The compound of any one of Embodiments 1-18, wherein $R^1$ is:

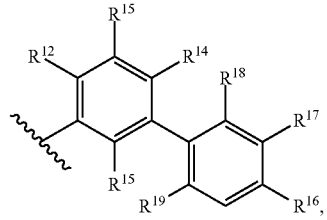

wherein
each of $R^{12}$, $R^{14}$ and $R^{15}$ is independently hydrogen, —N(R$^9$)$_2$, hydroxyl, halogen, or $C_{1-6}$ alkoxy;
$R^{13}$ is hydrogen, —N(R$^9$)$_2$, hydroxyl, halogen, $C_{1-6}$ alkoxy, or ($C_{6-10}$ aryl)-$C_{1-6}$ alkoxy;
$R^{19}$ is hydrogen, hydrogen, —N(R$^9$)$_2$, hydroxyl, halogen, nitro, optionally substituted $C_{1-6}$ alkyl, or optionally substituted $C_{1-6}$ alkoxy; and (iii) $R^{16}$ is hydrogen, —N(R$^9$)$_2$, hydroxyl, halogen, nitro, optionally substituted $C_{1-6}$ alkyl, or optionally substituted $C_{1-6}$ alkoxy; and
each of $R^{17}$ and $R^{18}$ is independently hydrogen, —N(R$^9$)$_2$, hydroxyl, halogen, optionally substituted $C_{1-6}$ alkyl, or optionally substituted $C_{1-6}$ alkoxy; or $R^{17}$ and $R^{18}$, together with the ring to which they are attached, combine to form:

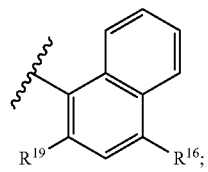

or
(iv) $R^8$ is hydrogen, —N(R$^9$)$_2$, hydroxyl, halogen, nitro, optionally substituted $C_{1-6}$ alkyl, or optionally substituted $C_{1-6}$ alkoxy; and
$R^{16}$ and $R^{17}$, together with the ring to which they are attached, combine to form:

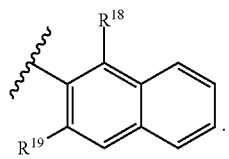

Embodiment 20. The compound of Embodiment 19, wherein $R^{12}$ is hydrogen or hydroxyl.

Embodiment 21. The compound of Embodiment 19 or 20, wherein $R^{13}$ is hydrogen or hydroxyl.

Embodiment 22. The compound of any one of Embodiments 19-21, wherein $R^{14}$ is hydrogen, hydroxyl, or —N(R$^9$)$_2$.

Embodiment 23. The compound of any one of Embodiments 19-22, wherein $R^{15}$ is hydrogen or hydroxyl.

Embodiment 24. The compound of any one of Embodiments 19-23, wherein $R^{16}$ is hydrogen, —N(R$^9$)$_2$, hydroxyl, halogen, optionally substituted $C_{1-6}$ alkyl, or optionally substituted $C_{1-6}$ alkoxy.

Embodiment 25. The compound of any one of Embodiments 19-24, wherein $R^{17}$ is hydrogen, halogen, optionally substituted $C_{1-6}$ alkyl, or optionally substituted $C_{1-6}$ alkoxy.

Embodiment 26. The compound of any one of Embodiments 19-24, wherein $R^{18}$ is hydrogen, halogen, optionally substituted $C_{1-6}$ alkyl, or optionally substituted $C_{1-6}$ alkoxy.

Embodiment 27. The compound of any one of Embodiments 19-24, wherein $R^{16}$ and $R^{17}$, together with the ring to which they are attached, combine to form:

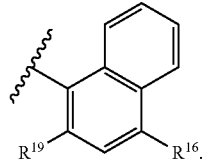

Embodiment 28. The compound of any one of Embodiments 19-24, wherein $R^{17}$ and $R^{18}$, together with the ring to which they are attached, combine to form:

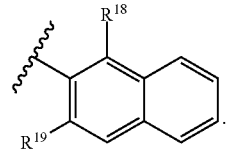

Embodiment 29. The compound of any one of Embodiments 19-28, wherein $R^{19}$ is hydrogen, halogen, nitro, or optionally substituted $C_{1-6}$ alkyl.

Embodiment 30. The compound of any one of Embodiments 1-18, wherein $R^1$ is:

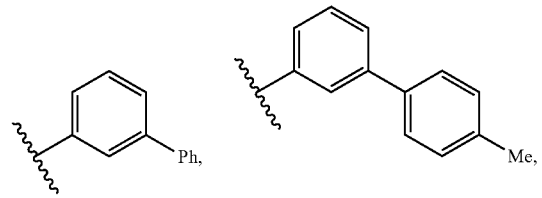

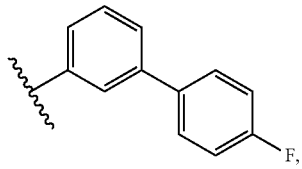

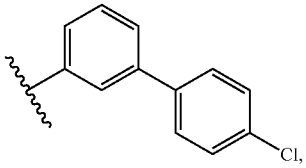

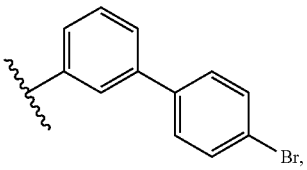

-continued

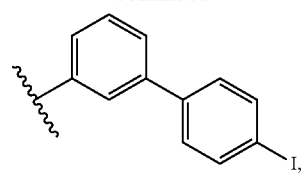

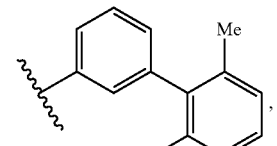

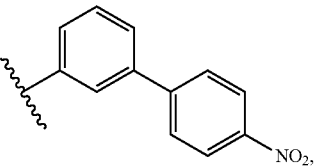

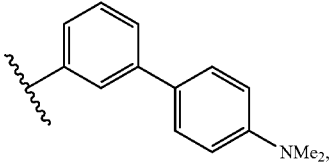

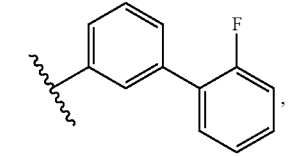

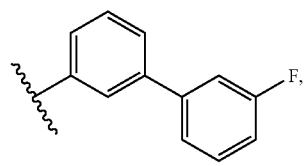

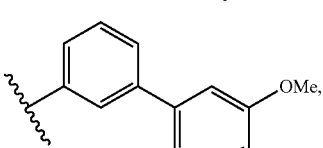

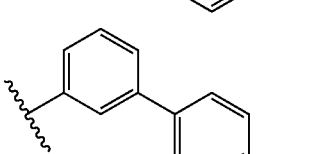

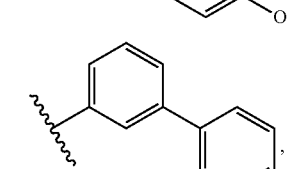

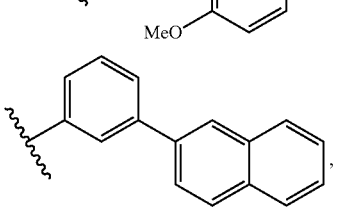

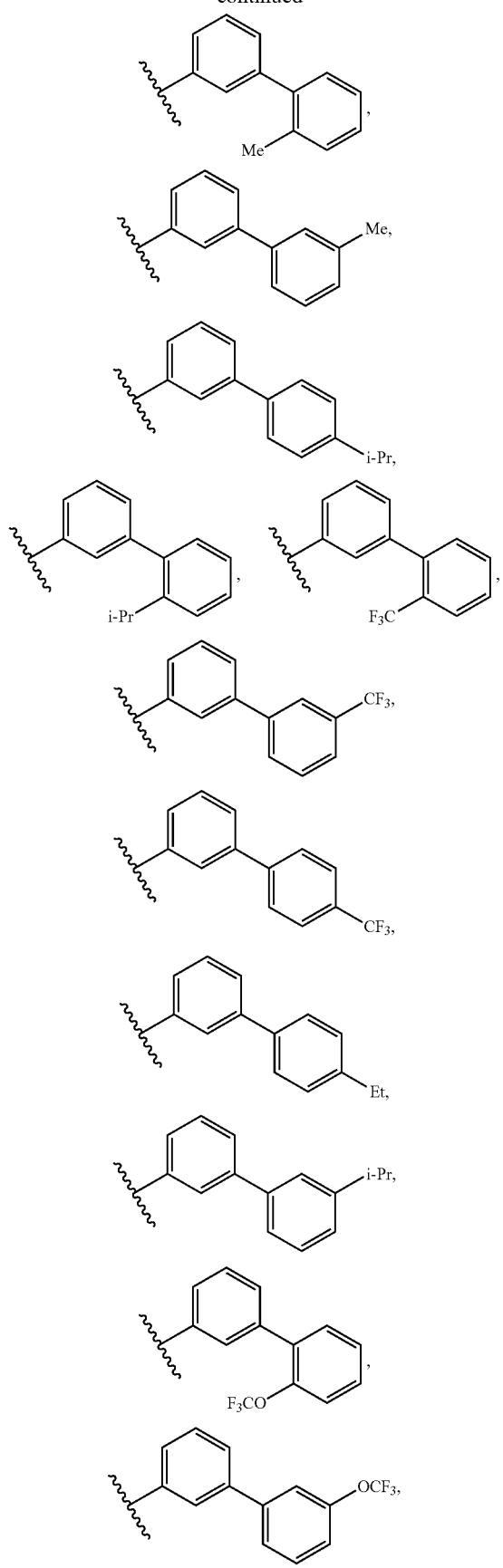
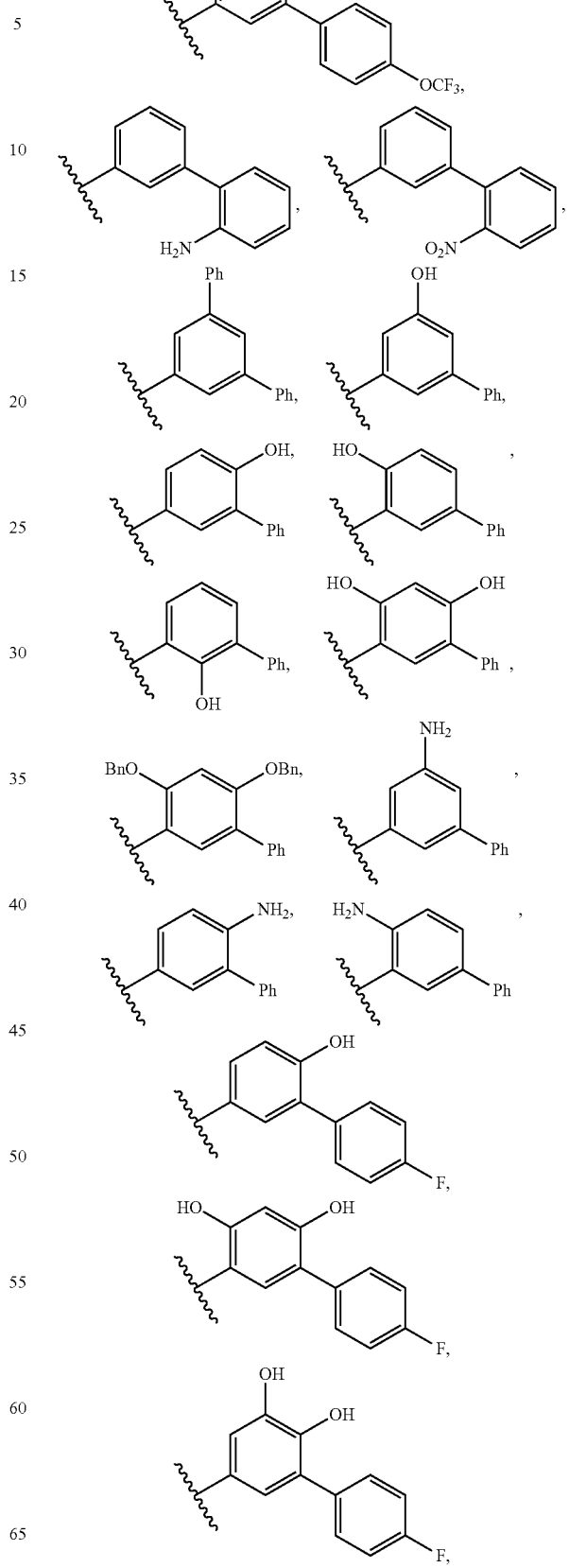

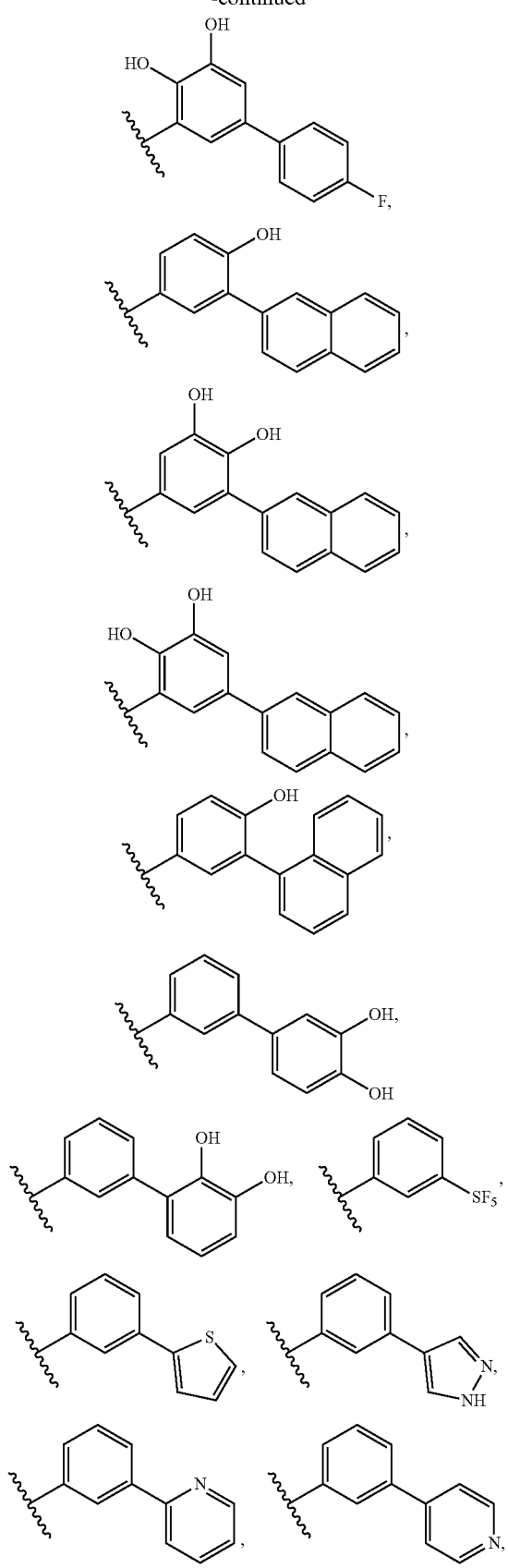
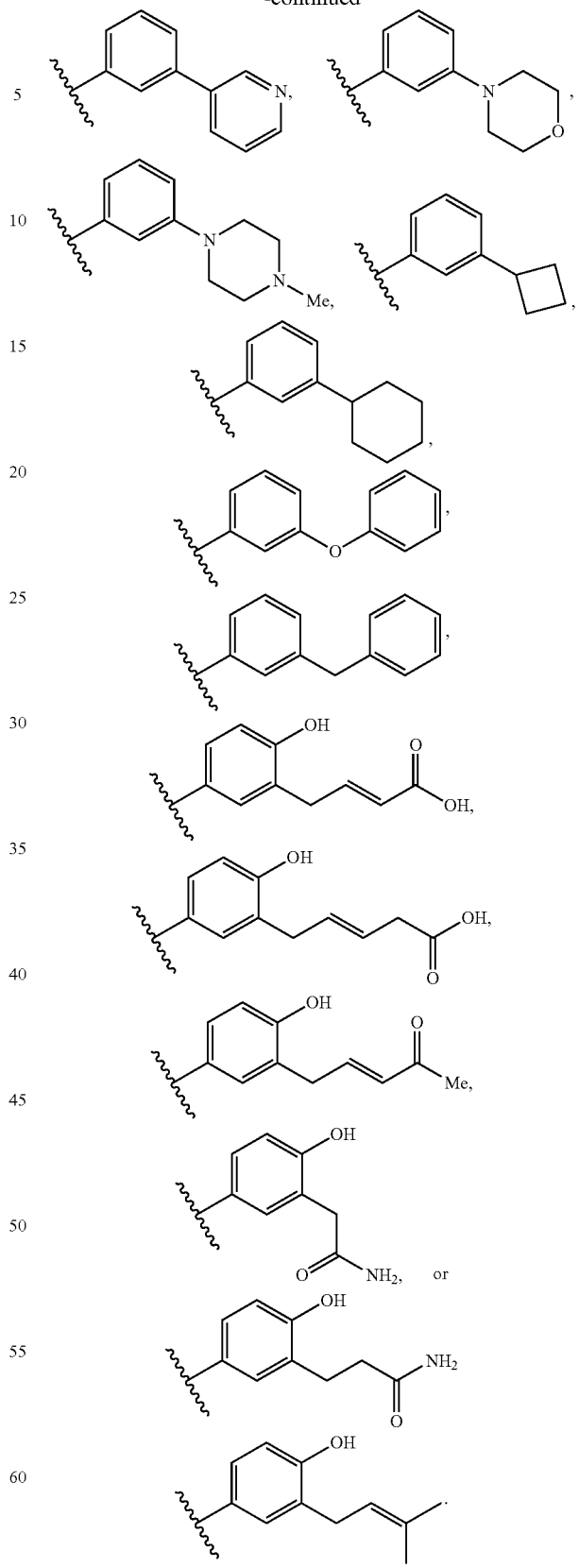
Embodiment 31. The compound of any one of Embodiments 1-18, wherein $R^1$ is:

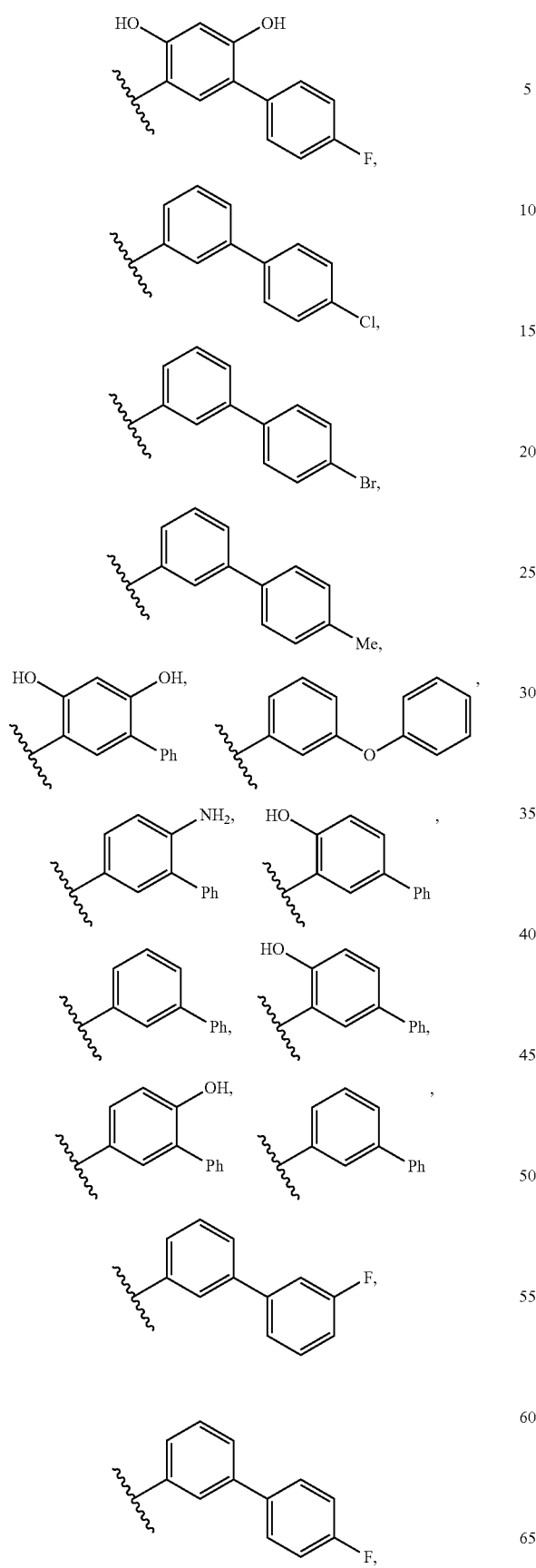
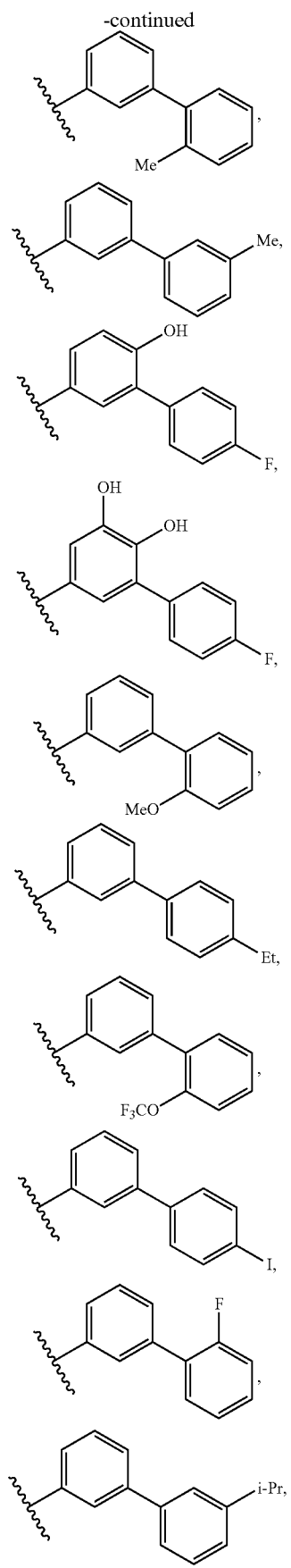

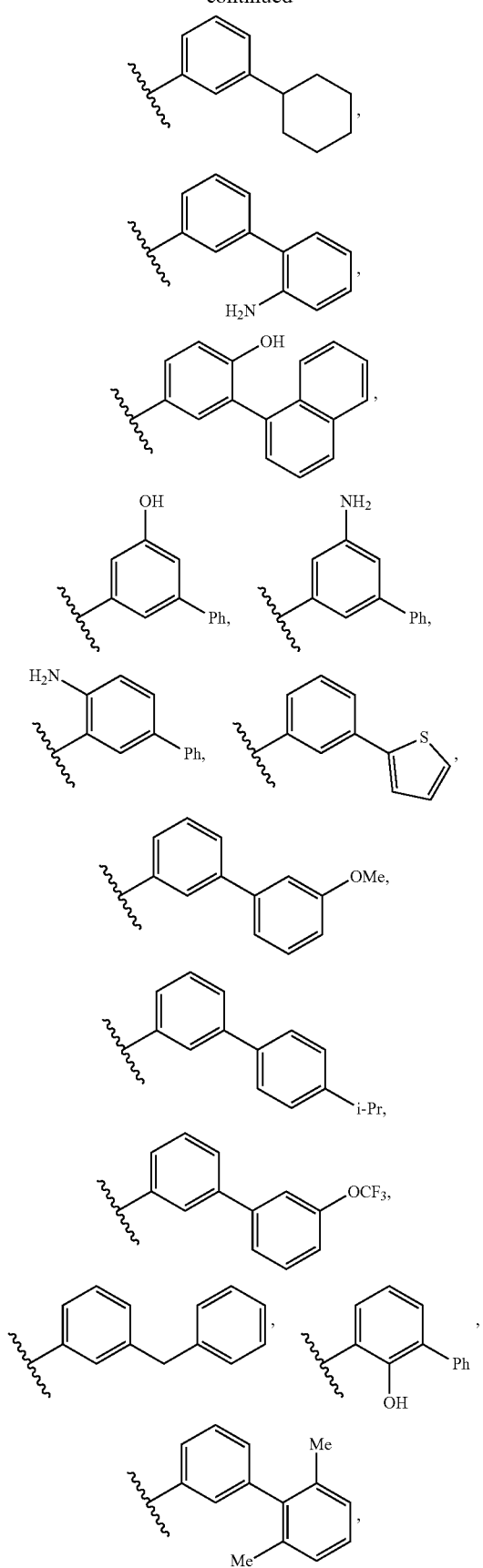
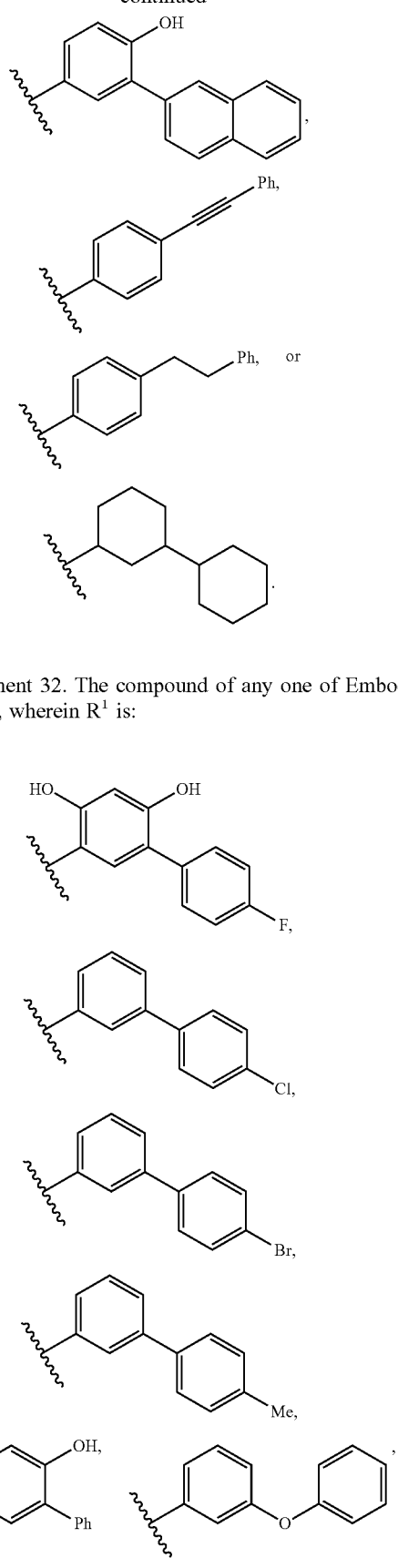
Embodiment 32. The compound of any one of Embodiments 1-18, wherein $R^1$ is:

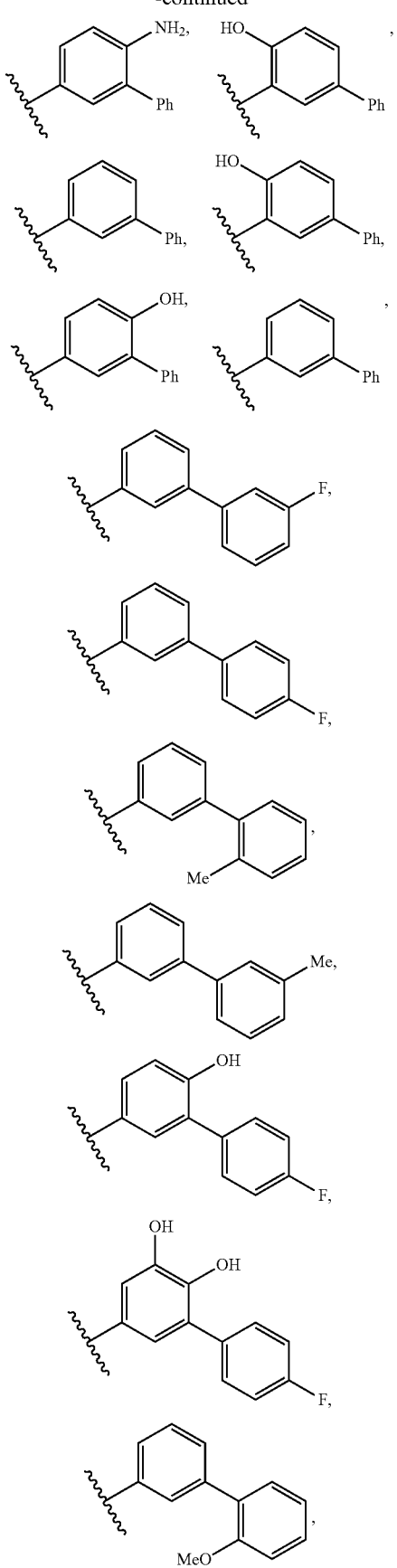

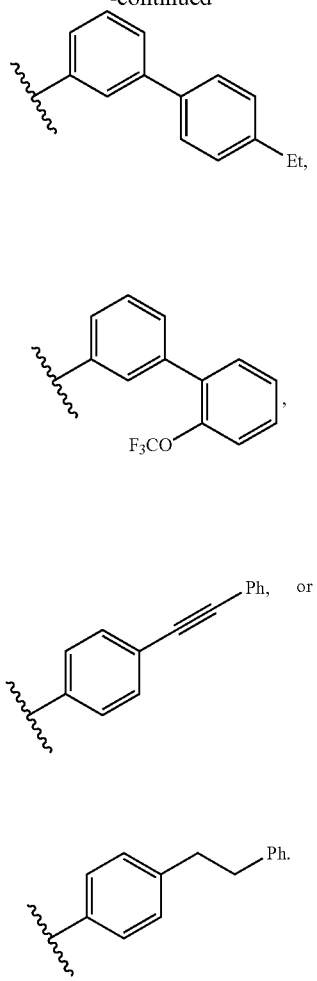

Embodiment 33. The compound of any one of Embodiments 1-32, wherein $R^4$ is optionally substituted $C_{1-6}$ alkyl.

Embodiment 34. The compound of any one of Embodiments 1-33, wherein $R^5$ is hydroxyl.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below.

The full scope of the invention should be determined by reference to the claims, along with their full scope of equivalents, and the specification, along with such variations.

What is claimed is:

1. A compound of formula (XX):

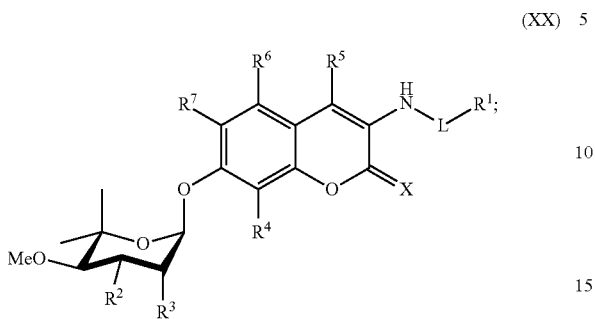

(XX)

or a pharmaceutically acceptable salt thereof,
wherein
X is O or S;
L is —CO— or —SO$_2$—;
R$^1$ is unsubstituted phenyl, substituted phenyl, optionally substituted C$_{6-10}$ aryl C$_{1-4}$ alkyl, optionally substituted C$_{6-10}$ aryl C$_{2-4}$ alkenyl, o-phenylphenyl, optionally substituted C$_{3-10}$ cycloalkyl, optionally substituted C$_{1-9}$ heteroaryl comprising at least one nitrogen heteroatom within the heteroaryl ring system, benzofuryl, optionally substituted furyl, or —NHR$^8$,
wherein the substituted phenyl is substituted:
(i) at one and only one of its meta position relative to L, with optionally substituted C$_{6-10}$ aryl, optionally substituted C$_{1-6}$ alkyl, optionally substituted C$_{3-6}$ alkenyl comprising an allylic carbon-carbon double bond, optionally substituted C$_{6-10}$ aryl C$_{1-4}$ alkyl, optionally substituted C$_{1-6}$ alkoxy, optionally substituted C$_{6-10}$ aryloxy, optionally substituted (C$_{6-10}$ aryl)-C$_{1-6}$ alkoxy, optionally substituted C$_{3-10}$ cycloalkyl, optionally substituted C$_{1-9}$ heteroaryl comprising at least one nitrogen heteroatom within the heteroaryl ring system, optionally substituted C$_{3-9}$ heterocyclyl, or —SF$_5$; or
(ii) at its para position relative to L with hydroxyl, optionally substituted C$_{6-10}$ aryl C$_{1-4}$ alkyl, optionally substituted C$_{6-10}$ aryl C$_{2-4}$ alkynyl, optionally substituted C$_{6-10}$ aryl, optionally substituted C$_{3-10}$ cycloalkyl, optionally substituted C$_{1-6}$ alkoxy, optionally substituted C$_{6-10}$ aryloxy, or optionally substituted (C$_{6-10}$ aryl)-C$_{1-6}$ alkoxy;
and, valency permitting, the substituted phenyl is further optionally substituted with 1, 2, 3, or 4 substituents independently selected from the group consisting of halogen, hydroxyl, —N(R$^9$)$_2$, optionally substituted C$_{1-6}$ alkoxy, optionally substituted C$_{6-10}$ aryloxy, or optionally substituted C$_{6-10}$ aryl;
each of R$^2$ and R$^3$ is independently hydroxyl, —O—CO—NH—R$^{10}$, or —O—CO—R$^{11}$;
each of R$^4$, R$^6$, and R$^7$ is independently hydrogen, halogen, optionally substituted C$_{1-6}$ alkyl, optionally substituted C$_{1-6}$ alkoxy, or optionally substituted C$_{6-10}$ aryl;
R$^5$ is halogen, hydroxyl, or optionally substituted C$_{1-6}$ alkoxy;
R$^8$ is optionally substituted C$_{6-10}$ aryl;
each R$^9$ is independently H or optionally substituted C$_{1-6}$ alkyl;
R$^{10}$, when present, is hydrogen, optionally substituted C$_{1-6}$ alkyl, optionally substituted C$_{3-10}$ cycloalkyl, or optionally substituted C$_{6-10}$ aryl; and
R$^{11}$, when present, is optionally substituted C$_{1-9}$ heteroaryl or optionally substituted C$_{6-10}$ aryl; and
wherein, when R$^5$ is hydroxyl, then R$^1$ is substituted phenyl or benzofuryl,
wherein the substituted phenyl is substituted:
(i) at one and only one of its meta position relative to L, with:
C$_{1-6}$ alkyl substituted with aryloxy, arylalkoxy, cycloalkyl, cycloalkoxy, heterocyclyl, heteroaryl, heterocyclyloxy, heteroaryloxy, nitro, thiol, =S, or —NR$^y$$_2$, where each R$^y$ is independently aryl, arylalkyl, cycloalkyl, heterocyclyl, or heteroaryl;
C$_{3-6}$ alkenyl comprising an allylic carbon-carbon double bond and substituted with aryloxy, arylalkoxy, cycloalkyl, cycloalkoxy, heterocyclyl, heteroaryl, heterocyclyloxy, heteroaryloxy, nitro, thiol, =S, or —NR$^y$$_2$, where each R$^y$ is independently aryl, arylalkyl, cycloalkyl, heterocyclyl, or heteroaryl;
optionally substituted C$_{6-10}$ aryloxy;
optionally substituted (C$_{6-10}$ aryl)-C$_{1-6}$ alkoxy;
optionally substituted C$_{3-10}$ cycloalkyl;
optionally substituted C$_{1-9}$ heteroaryl comprising at least one nitrogen heteroatom within the heteroaryl ring system;
optionally substituted C$_{3-9}$ heterocyclyl; or
—SF$_5$; or
(ii) at its para position relative to L, with optionally substituted C$_{6-10}$ aryl C$_{1-4}$ alkyl, optionally substituted C$_{6-10}$ aryl C$_{2-4}$ alkynyl, optionally substituted C$_{3-10}$ cycloalkyl, or optionally substituted (C$_{6-10}$ aryl)-C$_{1-6}$ alkoxy;
and, valency permitting, the substituted phenyl is further optionally substituted with 1, 2, 3, or 4 substituents independently selected from the group consisting of halogen, hydroxyl, —N(R$^9$)$_2$, optionally substituted C$_{1-6}$ alkoxy, optionally substituted C$_{6-10}$ aryloxy, optionally substituted (C$_{6-10}$ aryl)-C$_{1-6}$ alkoxy, or optionally substituted C$_{6-10}$ aryl.

2. A compound of formula (XX-II):

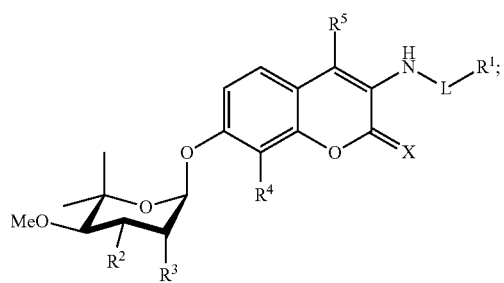

(XX-II)

or a pharmaceutically acceptable salt thereof,
wherein
X is O or S;
L is —CO— or —SO$_2$—;
R$^1$ is substituted phenyl or benzofuryl, wherein the substituted phenyl is substituted:
(i) at one and only one of its meta position relative to L, with:
- $C_{1-6}$ alkyl substituted with aryloxy, arylalkoxy, cycloalkyl, cycloalkoxy, heterocyclyl, heteroaryl, heterocyclyloxy, heteroaryloxy, nitro, thiol, =S, or —$NR^y{}_2$, where each $R^y$ is independently aryl, arylalkyl, cycloalkyl, heterocyclyl, or heteroaryl;
- $C_{3-6}$ alkenyl comprising an allylic carbon-carbon double bond and substituted with aryloxy, arylalkoxy, cycloalkyl, cycloalkoxy, heterocyclyl, heteroaryl, heterocyclyloxy, heteroaryloxy, nitro, thiol, =S, or —$NR^y{}_2$, where each $R^y$ is independently aryl, arylalkyl, cycloalkyl, heterocyclyl, or heteroaryl;
- optionally substituted $C_{6-10}$ aryloxy;
- optionally substituted ($C_{6-10}$ aryl)-$C_{1-6}$ alkoxy;
- optionally substituted $C_{3-10}$ cycloalkyl;
- optionally substituted $C_{1-9}$ heteroaryl comprising at least one nitrogen heteroatom within the heteroaryl ring system;
- optionally substituted $C_{3-9}$ heterocyclyl; or
- —$SF_5$; or (ii) at its para position relative to L, with optionally substituted $C_{6-10}$ aryl $C_{1-4}$ alkyl, optionally substituted $C_{6-10}$ aryl $C_{2-4}$ alkynyl, optionally substituted $C_{3-10}$ cycloalkyl, or optionally substituted ($C_{6-10}$ aryl)-$C_{1-6}$ alkoxy;

and, valency permitting, the substituted phenyl is further optionally substituted with 1, 2, 3, or 4 substituents independently selected from the group consisting of halogen, hydroxyl, —$N(R^9)_2$, optionally substituted $C_{1-6}$ alkoxy, optionally substituted $C_{6-10}$ aryloxy, optionally substituted ($C_{6-10}$ aryl)-$C_{1-6}$ alkoxy, or optionally substituted $C_{6-10}$ aryl;

each of $R^2$ and $R^3$ is independently hydroxyl, —O—CO—NH—$R^{10}$, or —O—CO—$R^{11}$, provided that at least one of $R^2$ and $R^3$ is —O—CO—NH—$R^{10}$ or —O—CO—$R^{11}$;

$R^4$ is hydrogen, halogen, optionally substituted $C_{1-6}$ alkyl, optionally substituted $C_{1-6}$ alkoxy, or optionally substituted $C_{6-10}$ aryl;

$R^5$ is halogen, hydroxyl, or optionally substituted $C_{1-6}$ alkoxy;

$R^8$ is optionally substituted $C_{6-10}$ aryl;

each $R^9$ is independently H or optionally substituted $C_{1-6}$ alkyl;

$R^{10}$, when present, is hydrogen, optionally substituted $C_{2-6}$ alkyl, optionally substituted $C_{3-10}$ cycloalkyl; or optionally substituted $C_{6-10}$ aryl; and $R^{11}$, when present, is optionally substituted $C_{1-9}$ heteroaryl.

3. A compound, or a pharmaceutically acceptable salt thereof, selected from the following table:

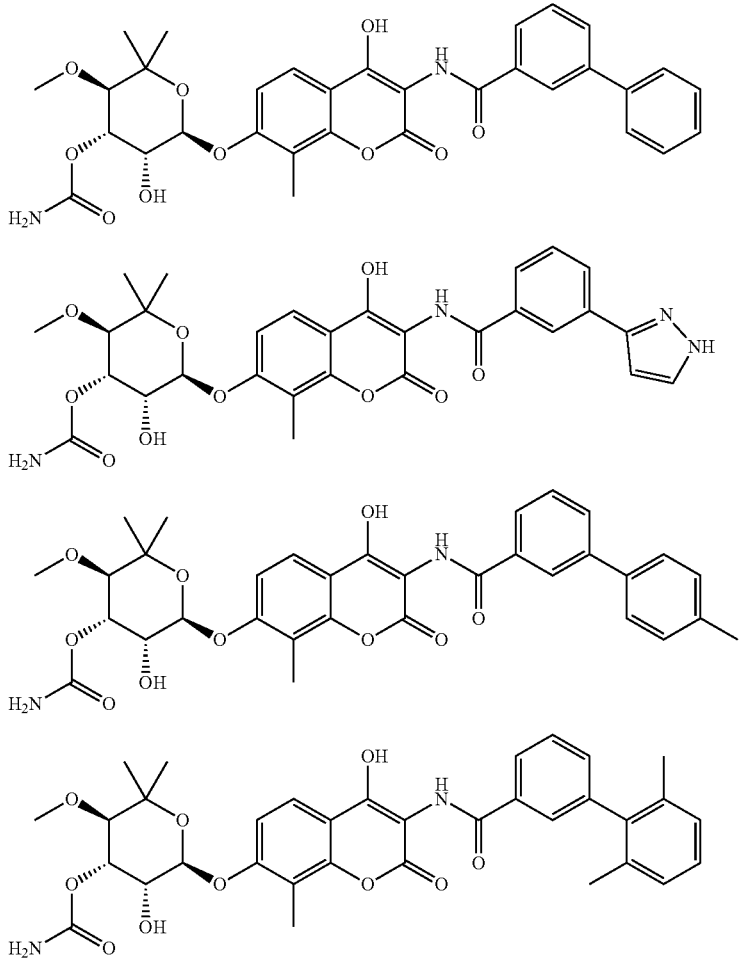

-continued
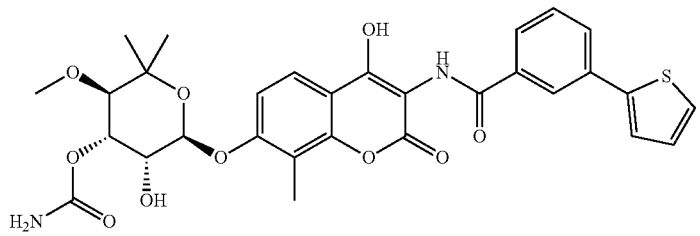
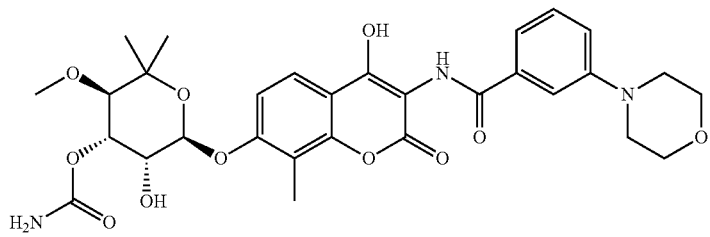
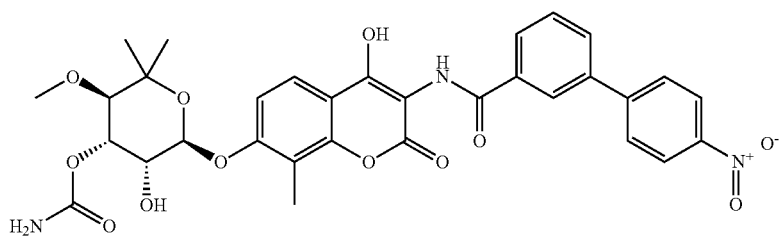
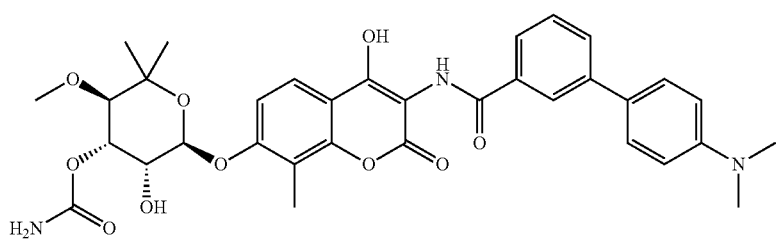
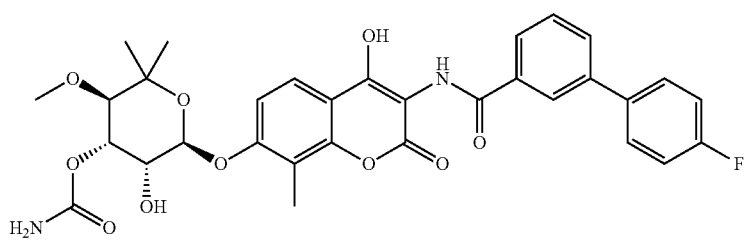
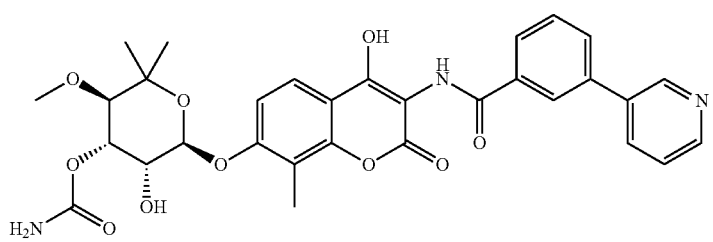
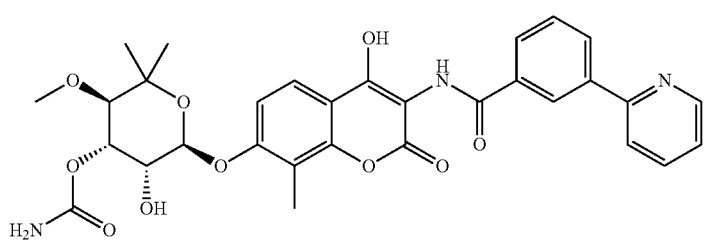

-continued
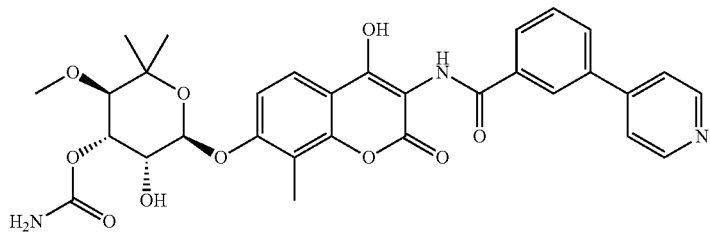
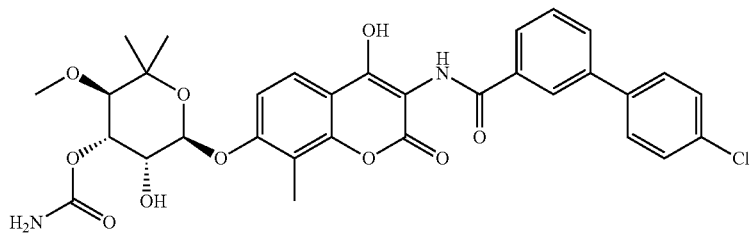
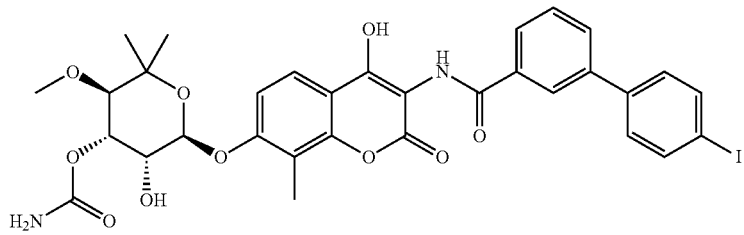
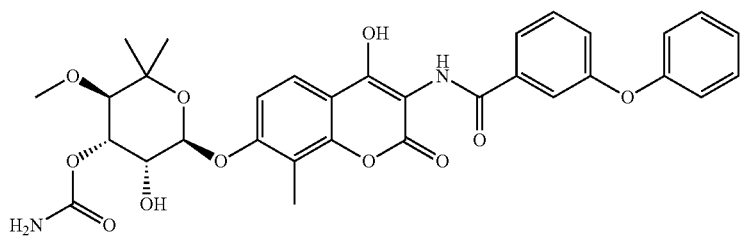
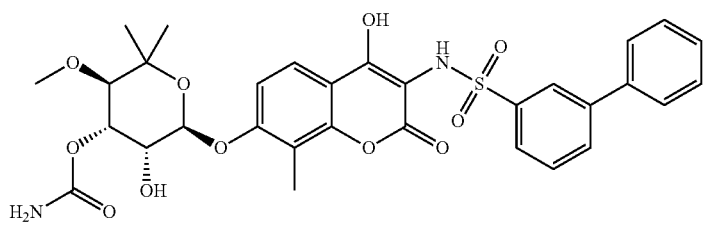
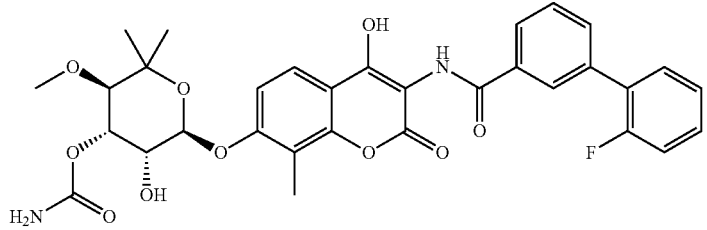
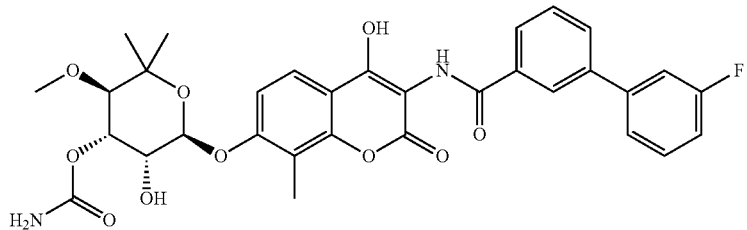

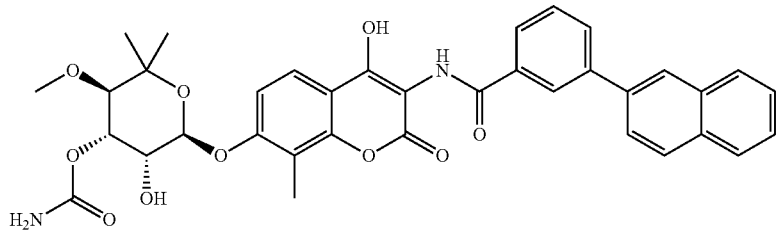
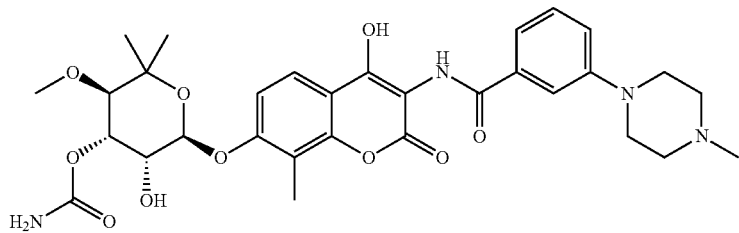
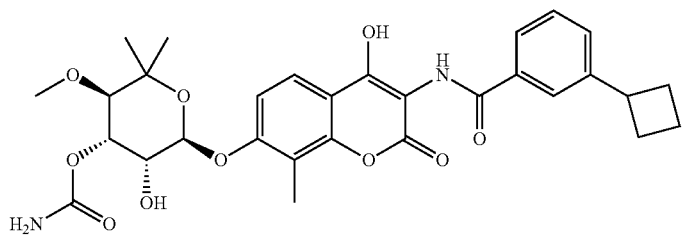
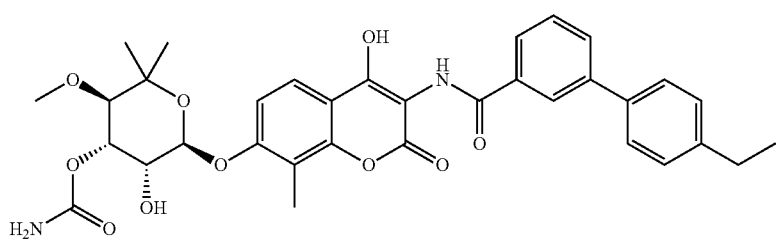
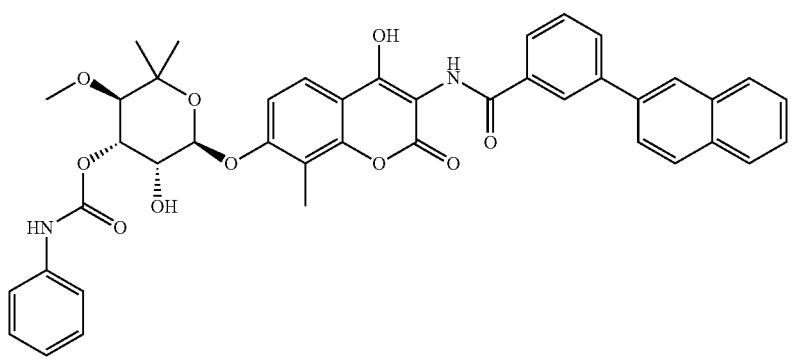
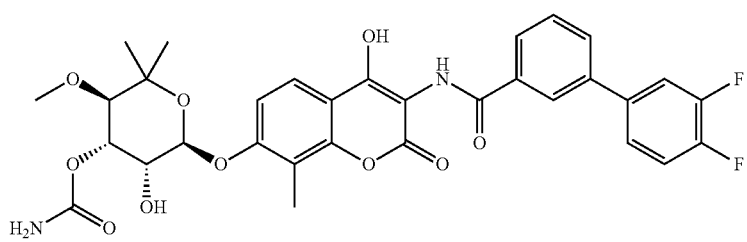

-continued
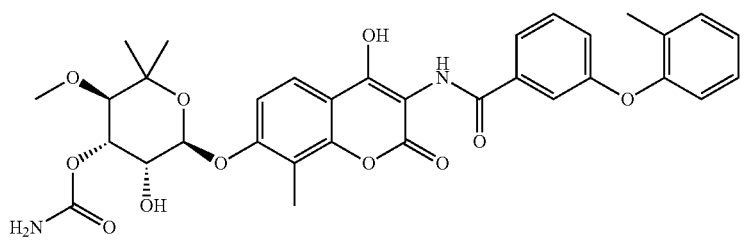
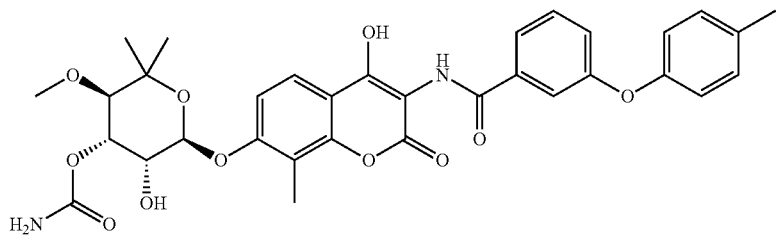
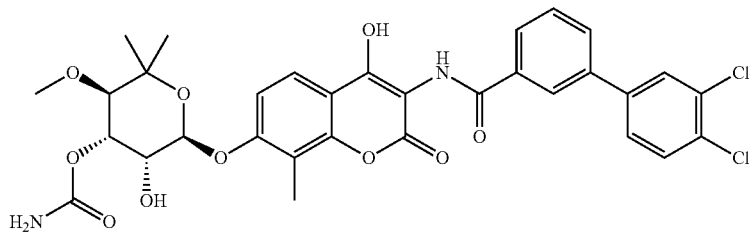
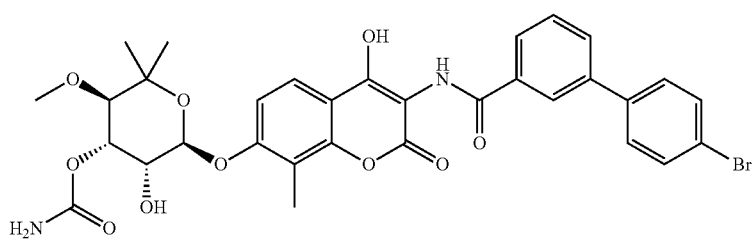
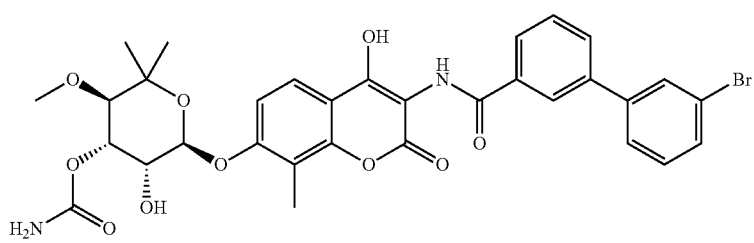
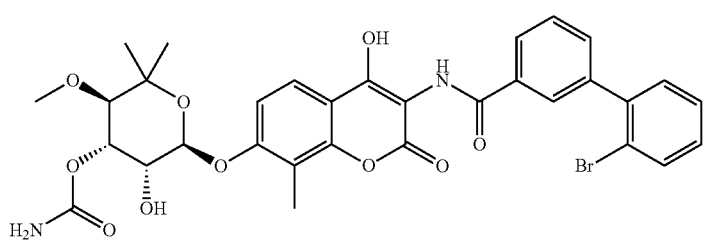
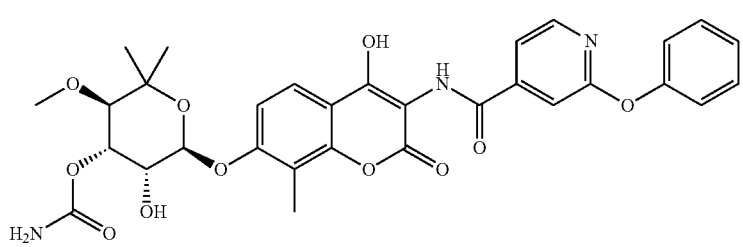

-continued
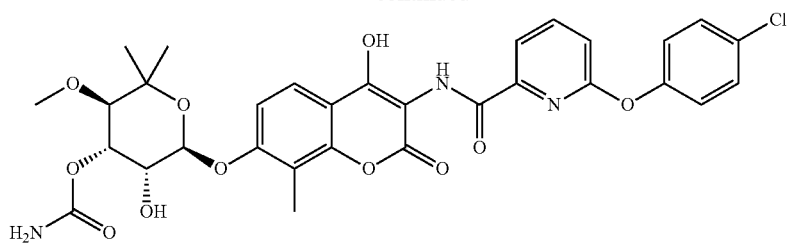
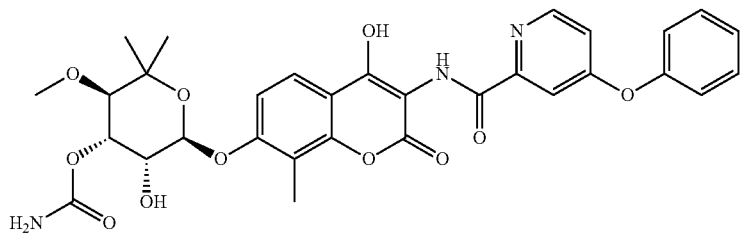
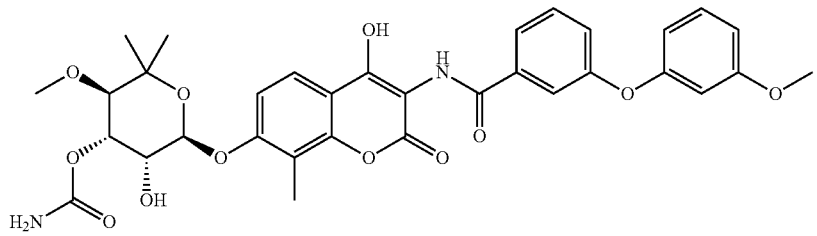
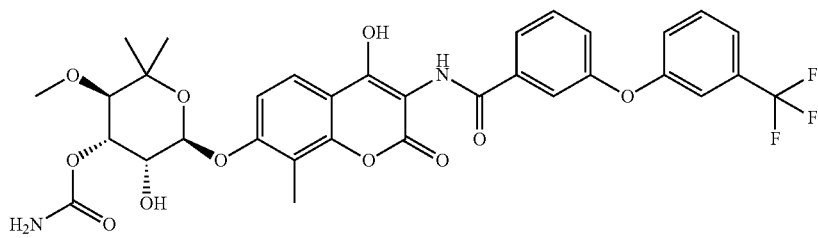
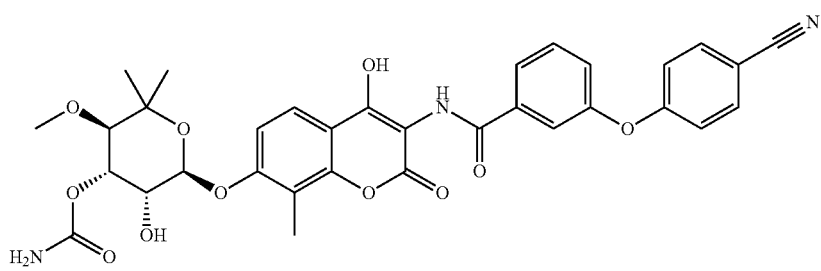
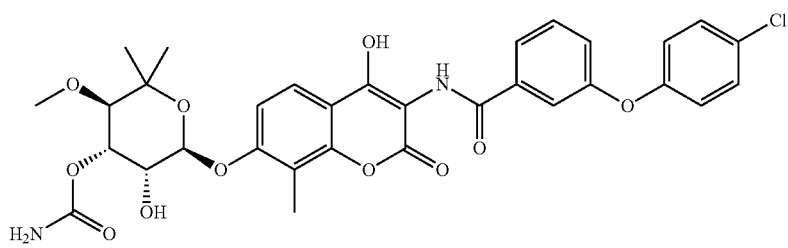
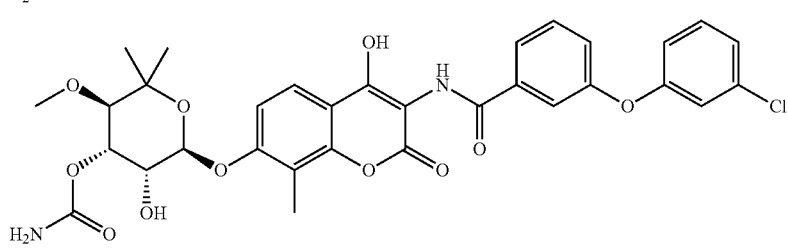

-continued
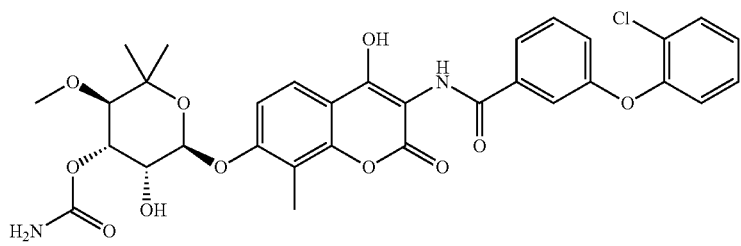
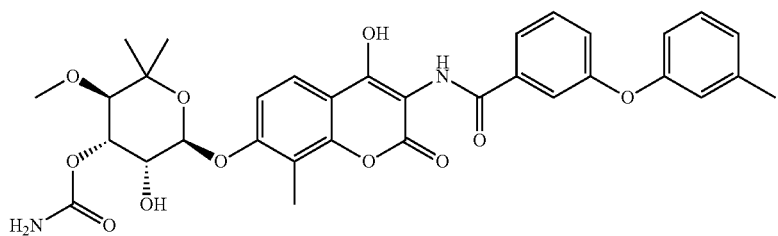
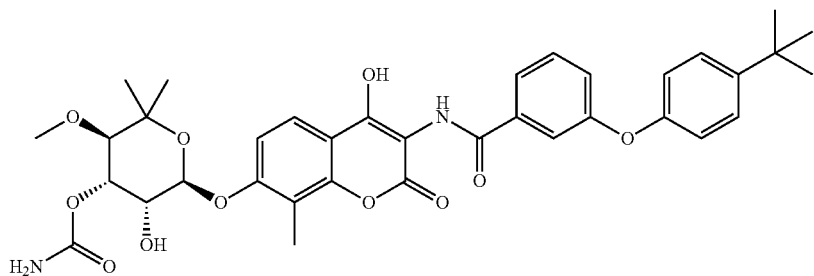
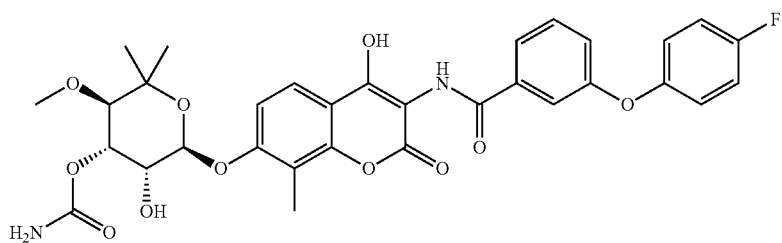
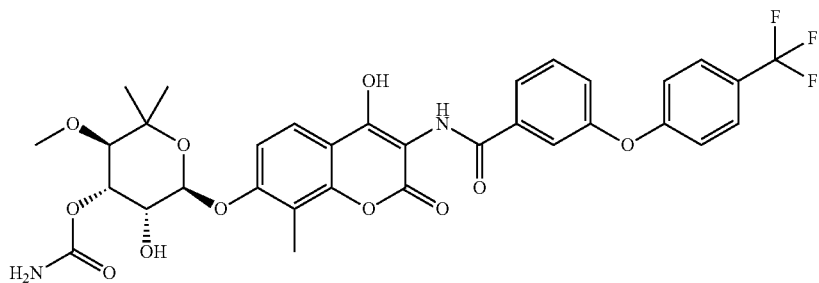
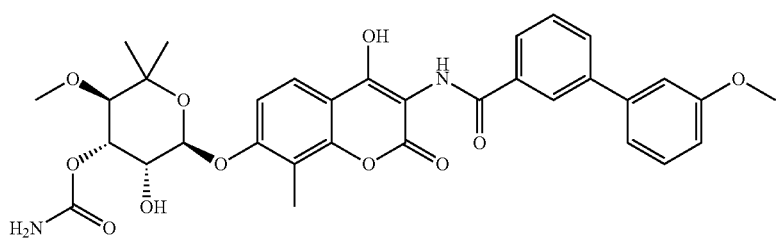

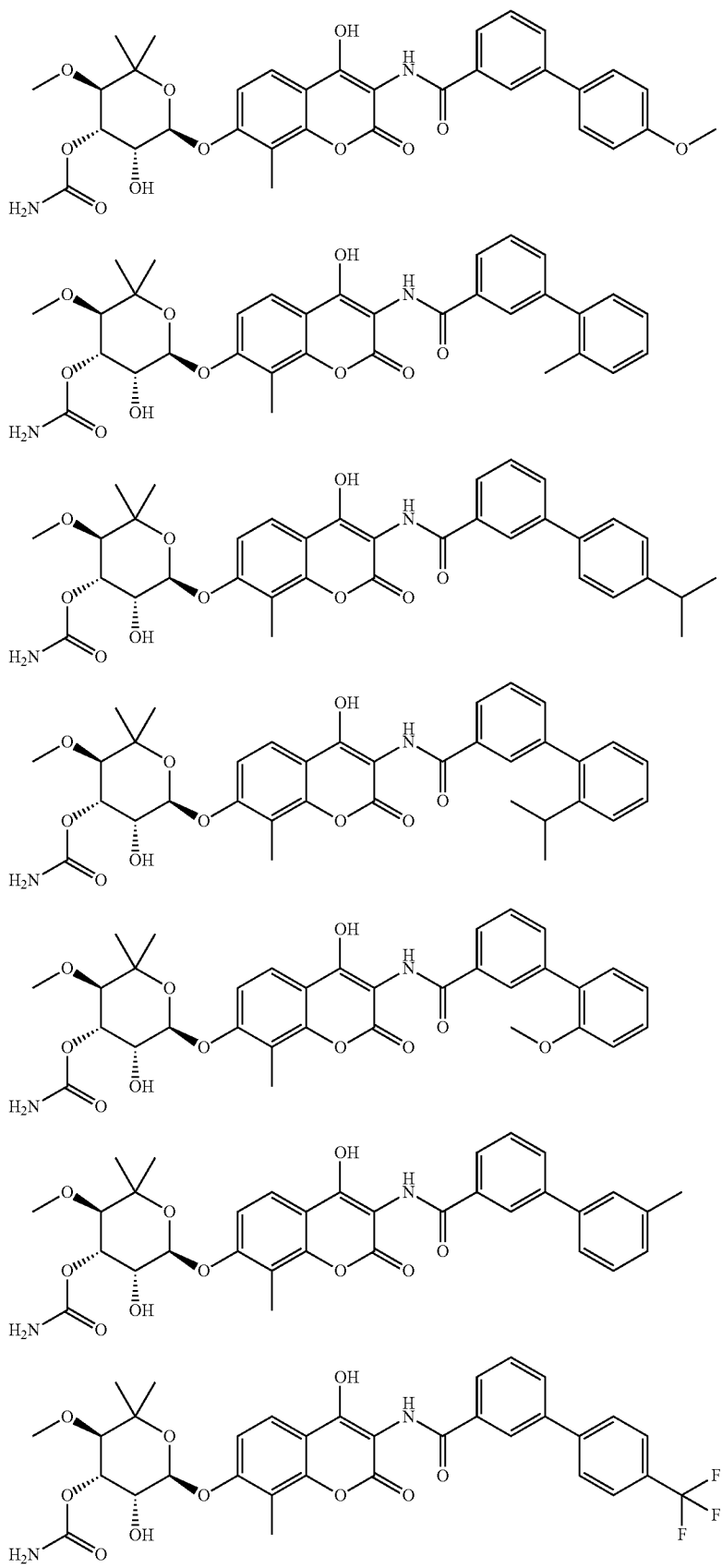

-continued
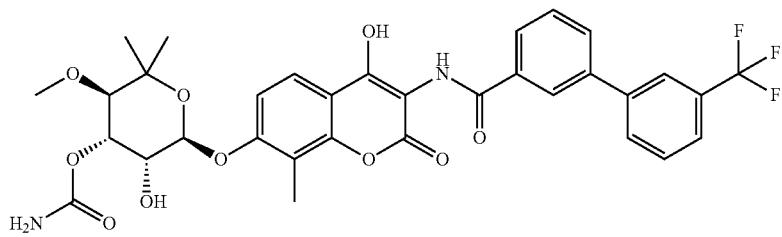
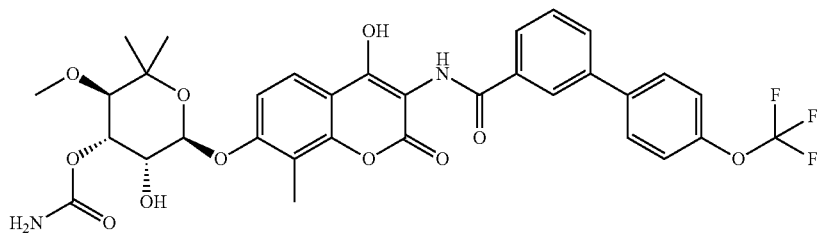
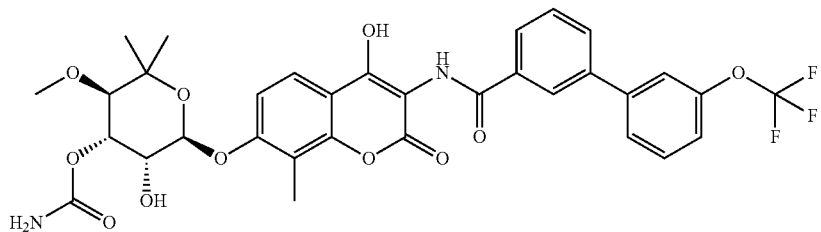
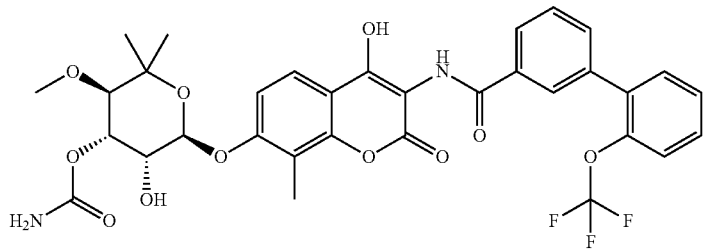
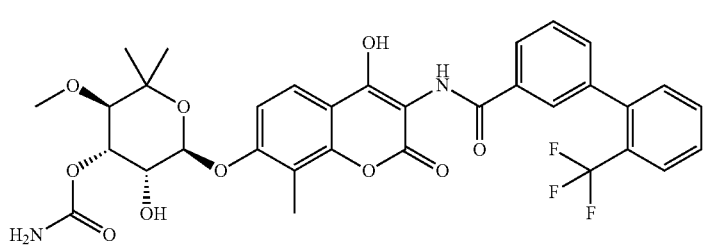
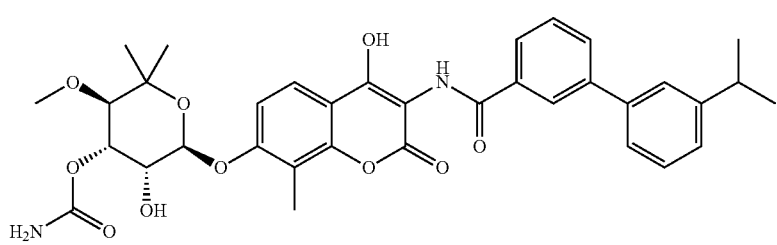
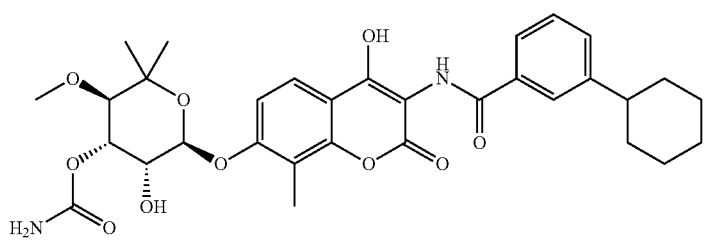

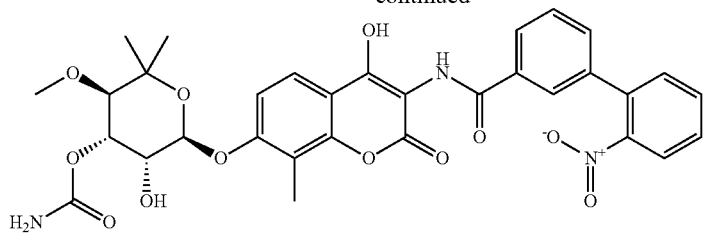
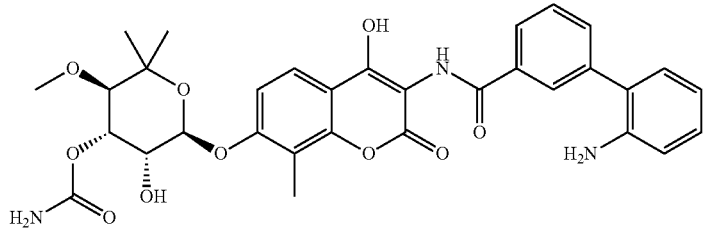
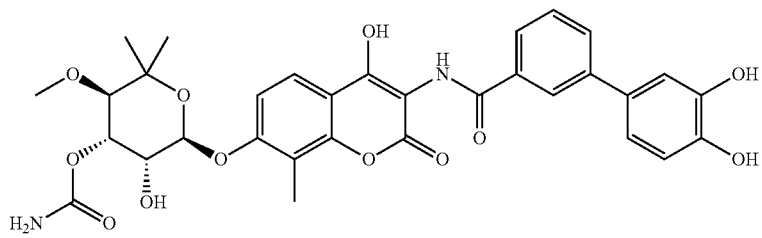
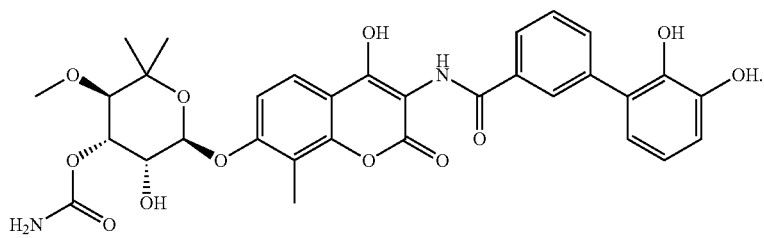
4. The compound of claim 3, selected from the following table:
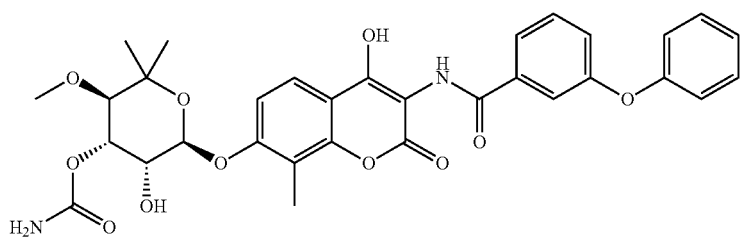
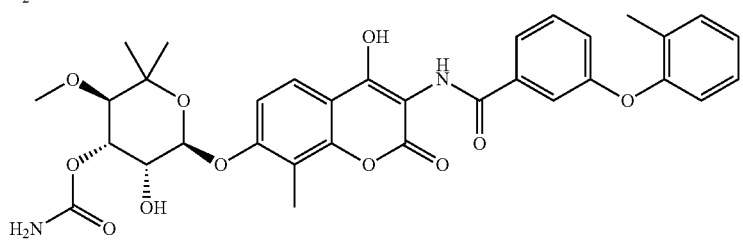

-continued
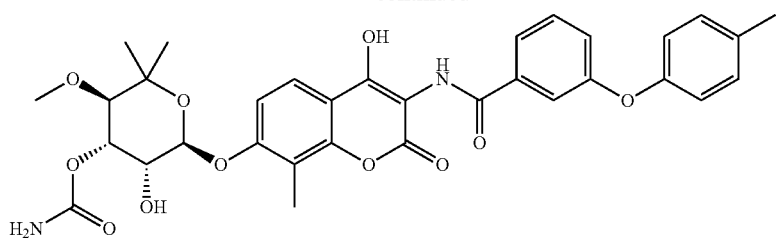
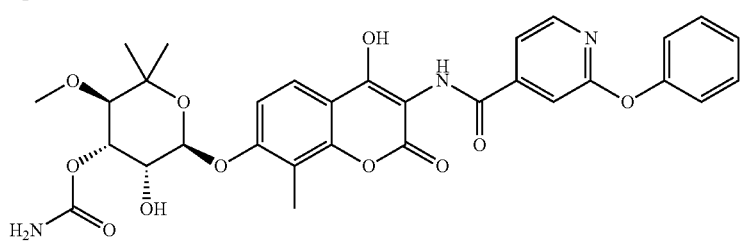
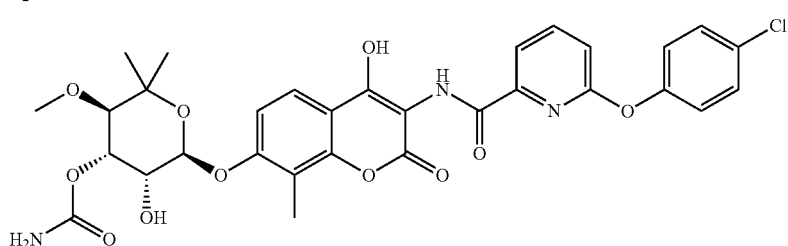
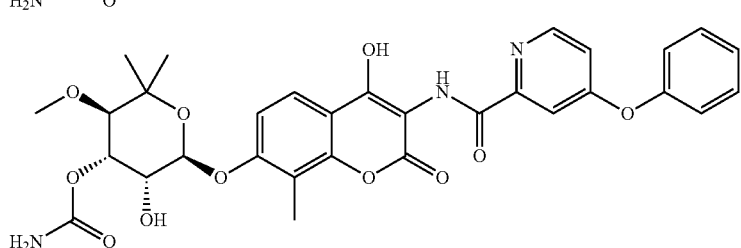
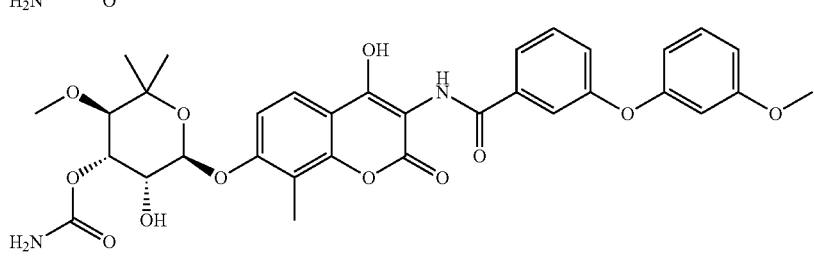
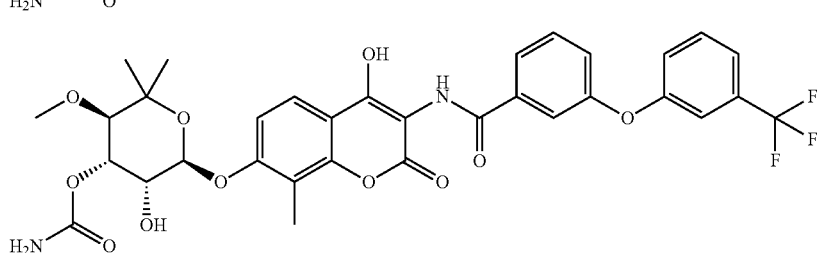
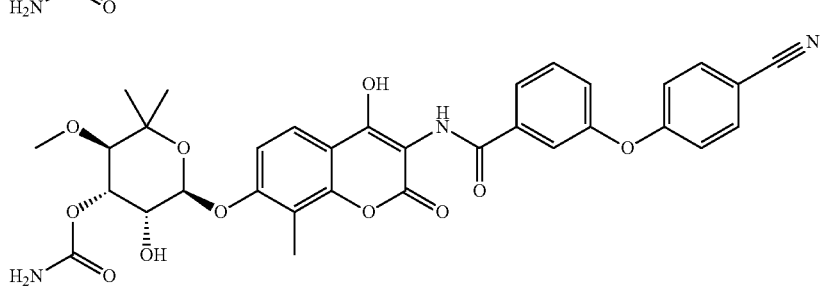

-continued
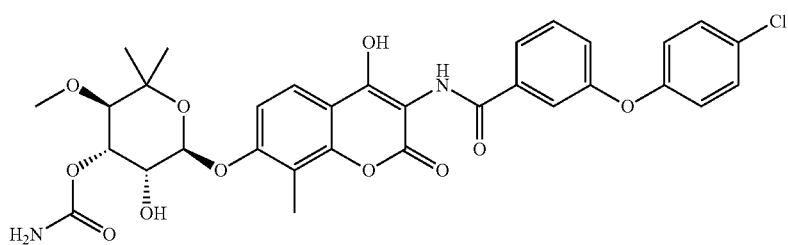
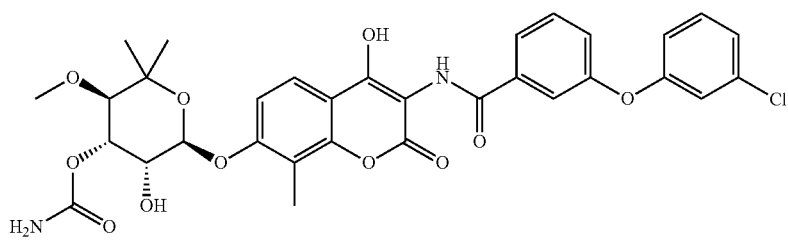
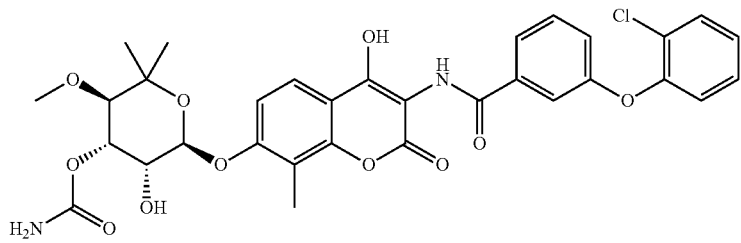
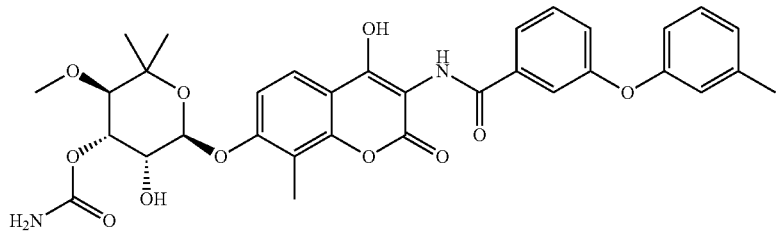
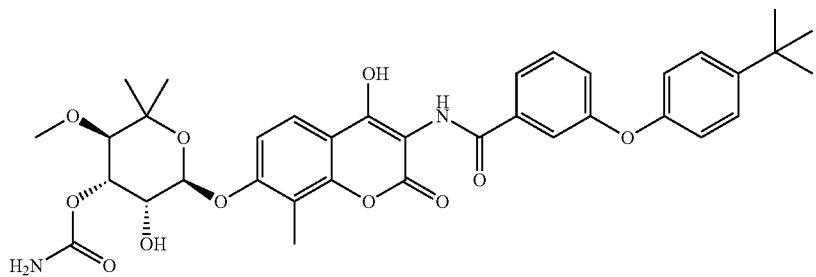
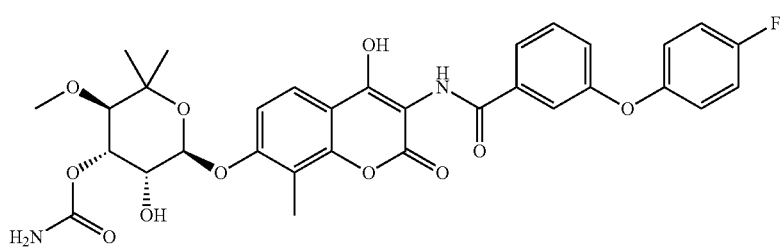

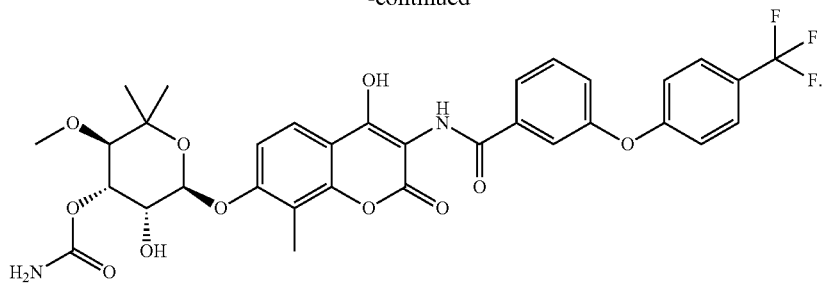
5. The compound of claim 3, selected from the following table:
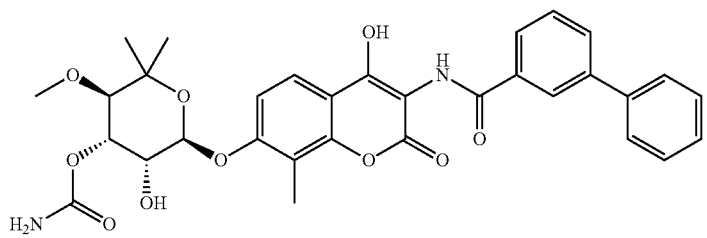
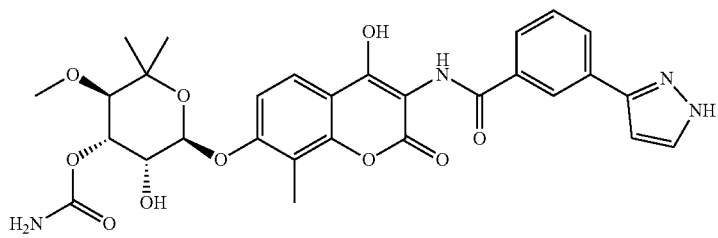
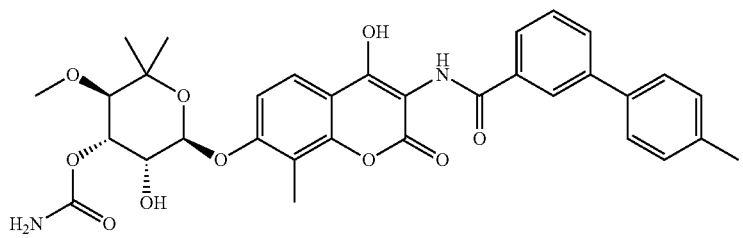
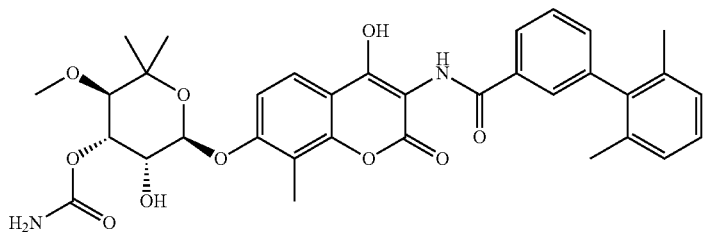
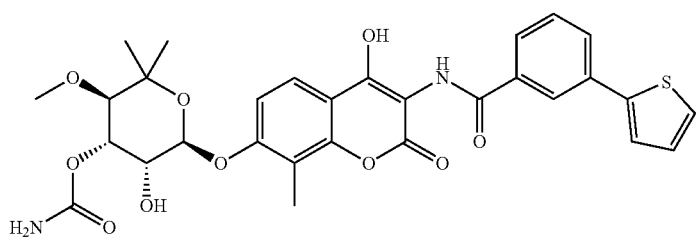

-continued
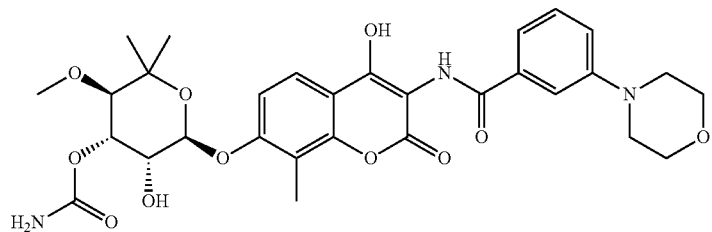
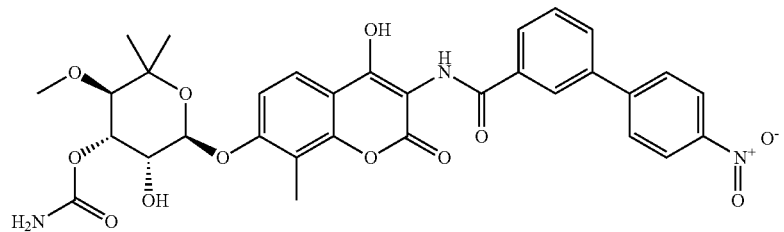
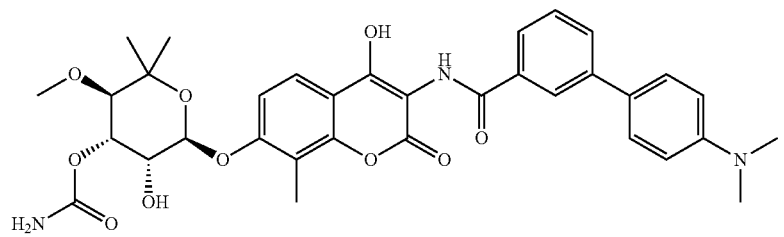
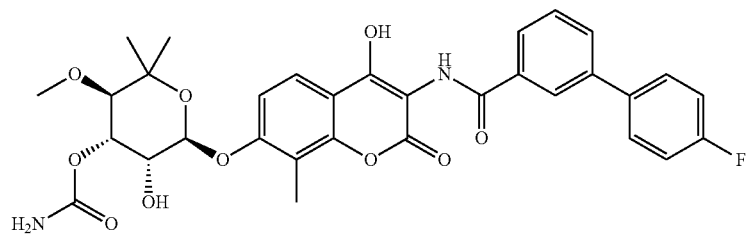
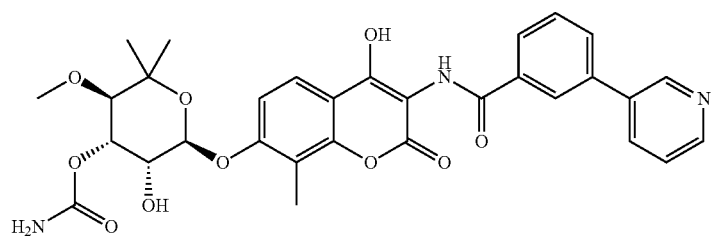
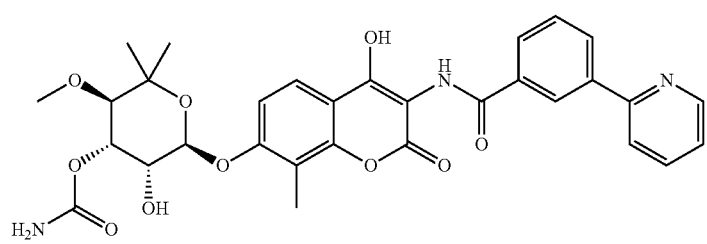
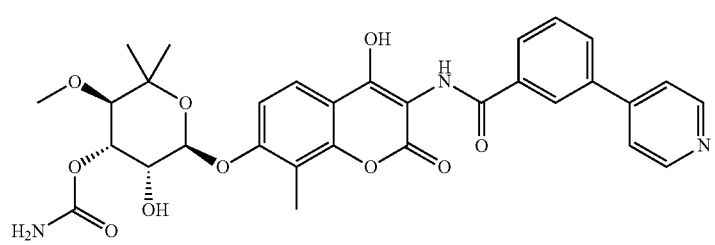

-continued
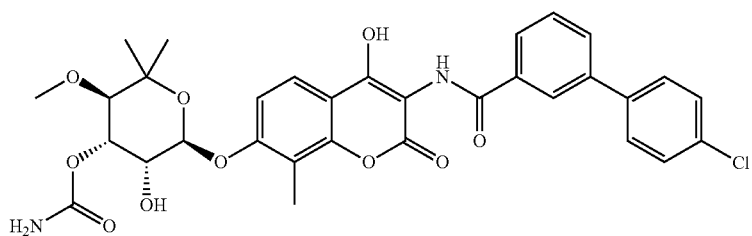
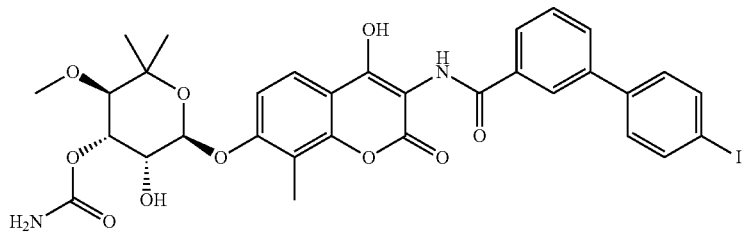
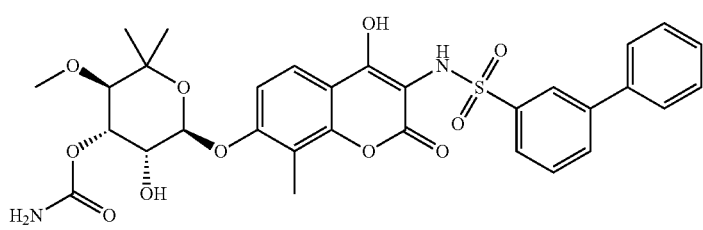
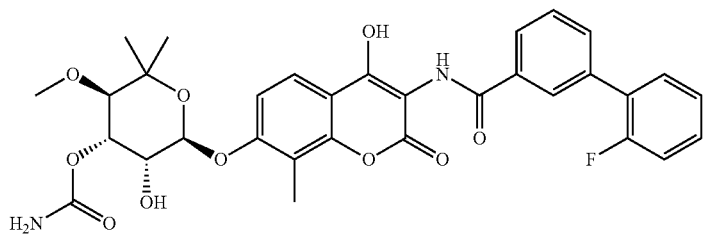
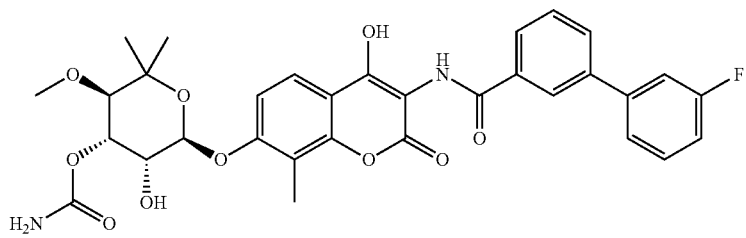
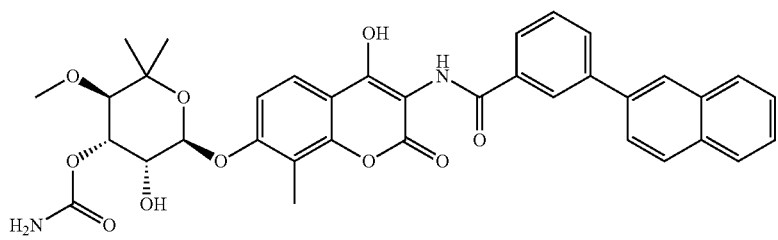
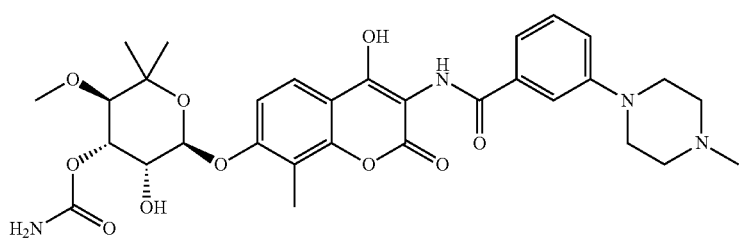

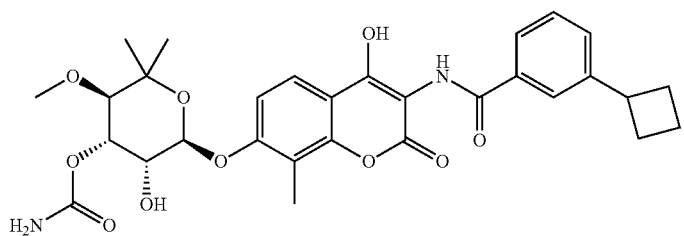
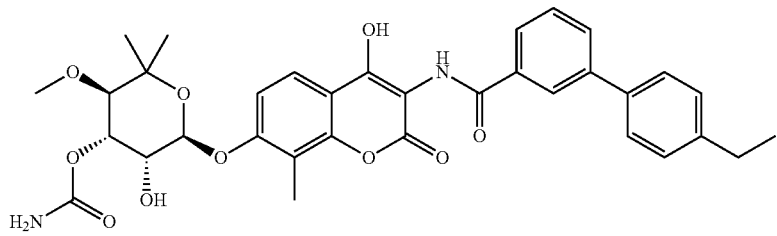
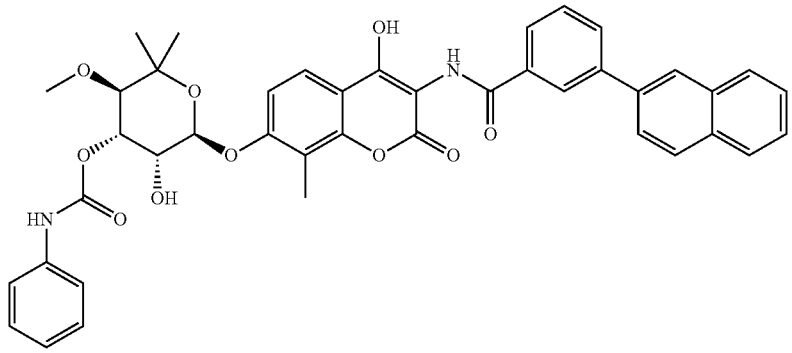
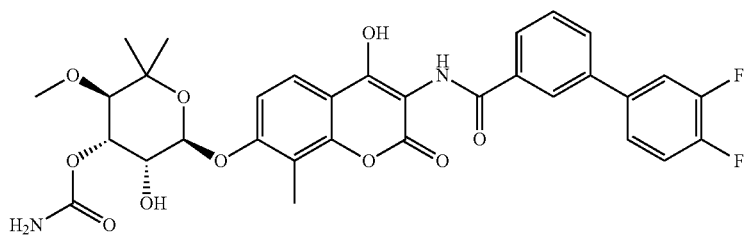
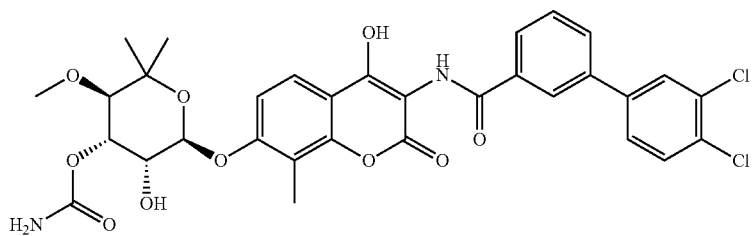
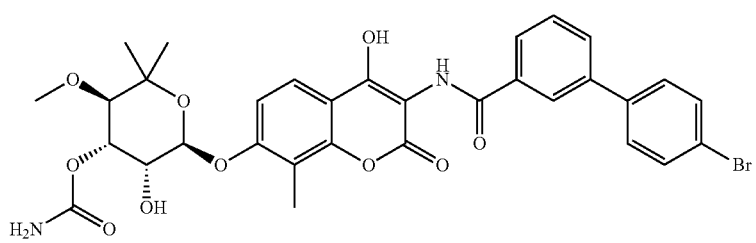

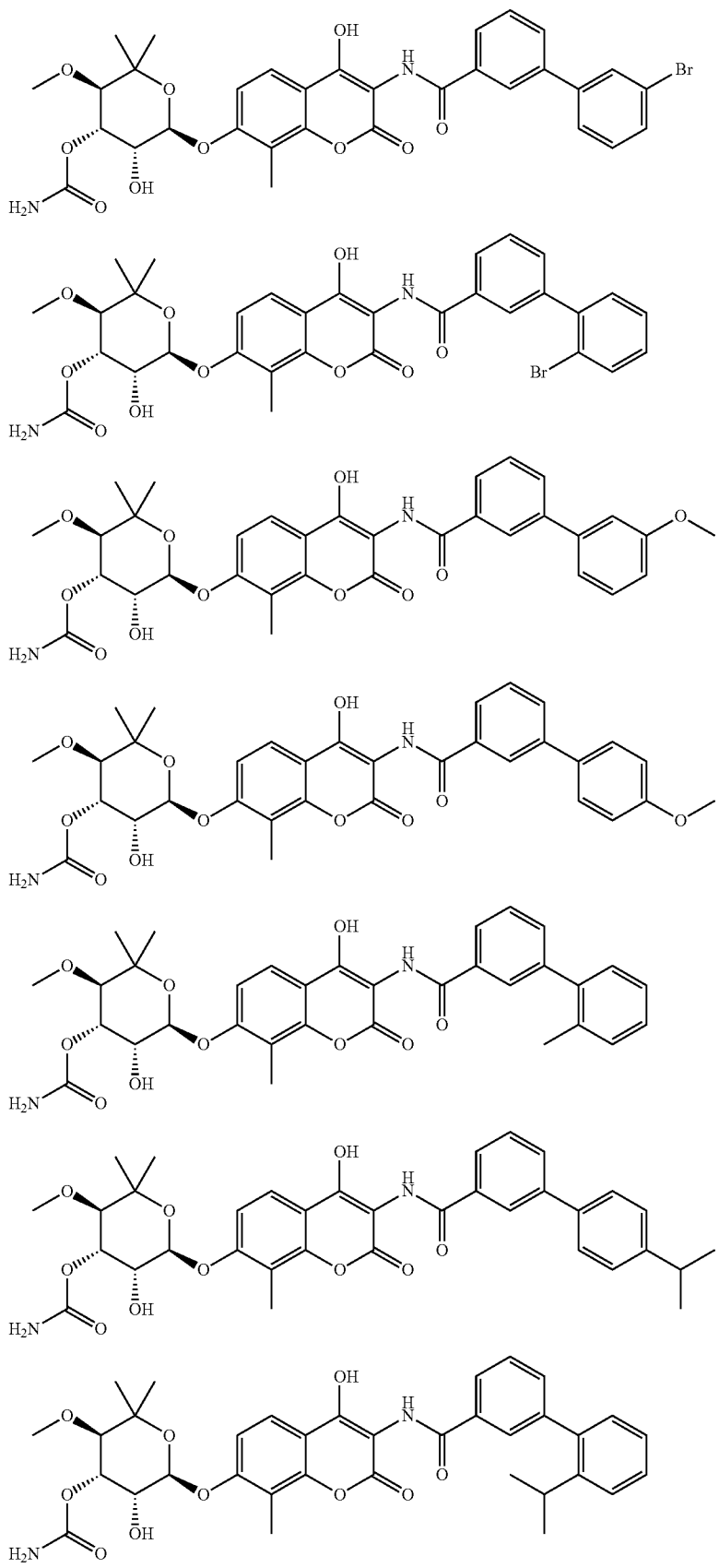

-continued
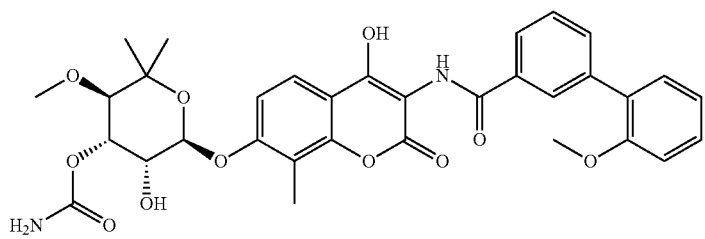
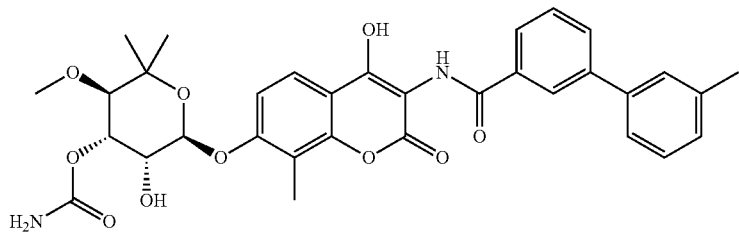
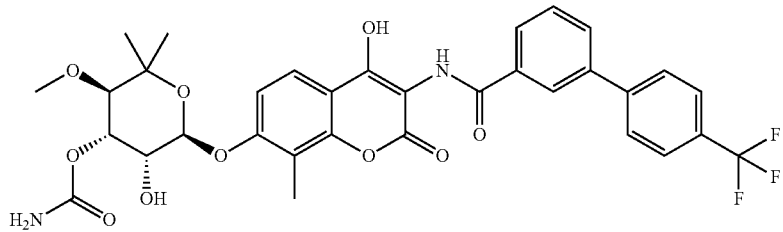
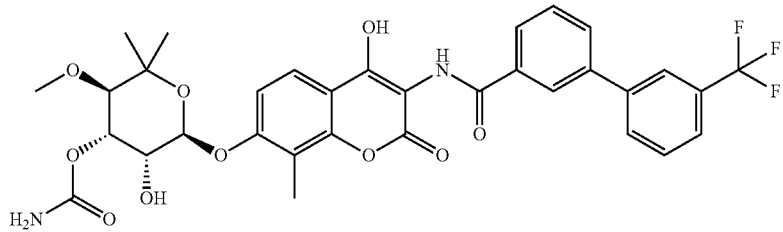
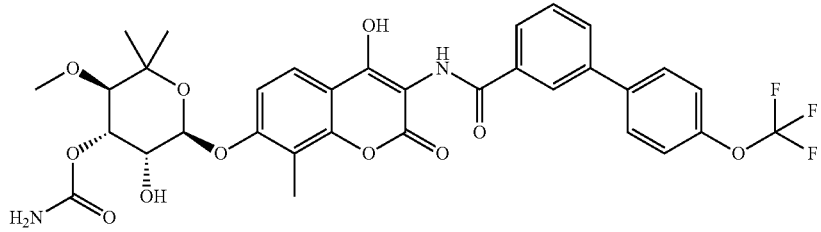
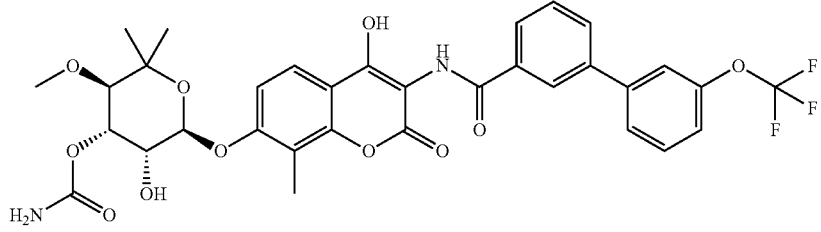
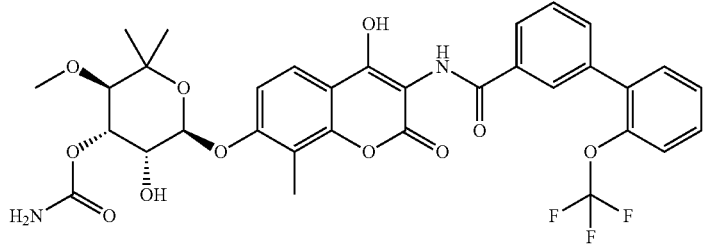

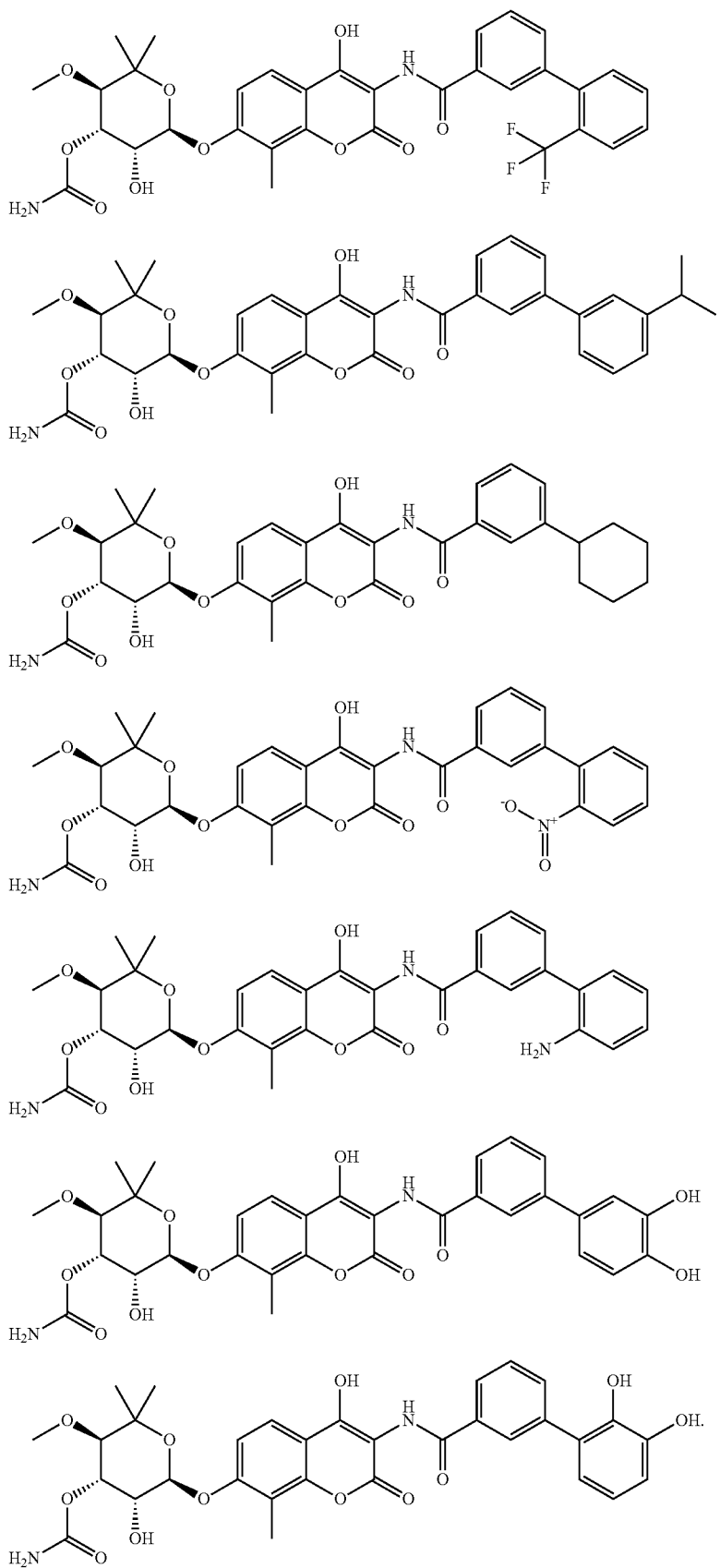

6. A pharmaceutical composition comprising the compound of claim 3 and a pharmaceutically acceptable excipient.

7. A compound of formula (XY):

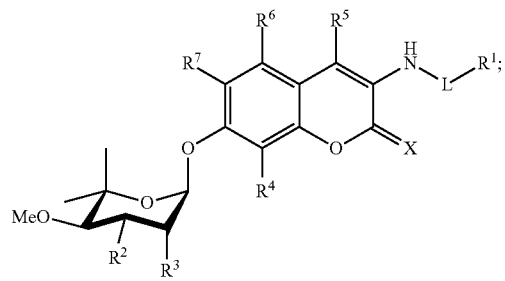

(XY)

or a pharmaceutically acceptable salt thereof,
wherein
X is O or S;
L is —CO— or —SO$_2$—;
each of R$^2$ and R$^3$ is independently hydroxyl, —O—CO—NH—R$^{10}$, or —O—CO—R$^{11}$;
each of R$^4$, R$^6$, and R$^7$ is independently hydrogen, halogen, optionally substituted C$_{1-6}$ alkyl, optionally substituted C$_{1-6}$ alkoxy, or optionally substituted C$_{6-10}$ aryl;
R$^5$ is halogen, hydroxyl, or optionally substituted C$_{1-6}$ alkoxy;
R$^{10}$, when present, is hydrogen, optionally substituted C$_{1-6}$ alkyl, optionally substituted C$_{3-10}$ cycloalkyl, or optionally substituted C$_{6-10}$ aryl; and
R$^{11}$, when present, is optionally substituted C$_{1-9}$ heteroaryl or optionally substituted C$_{6-10}$ aryl; and
R$^1$ is selected from the group consisting of

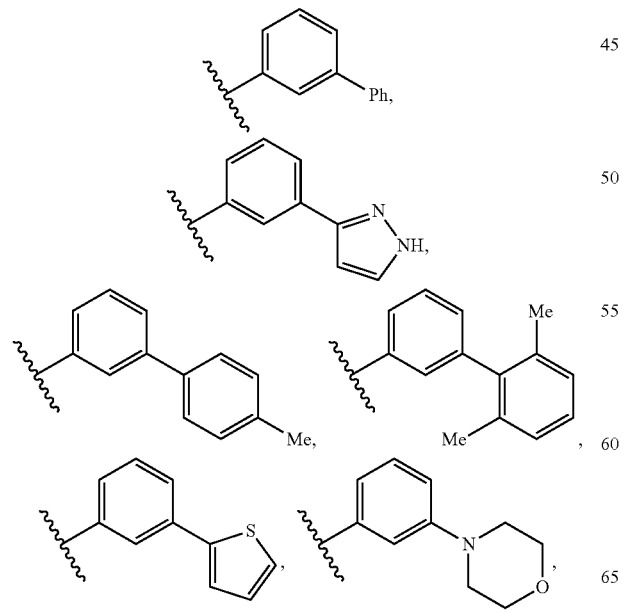

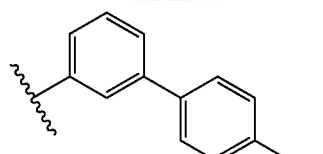

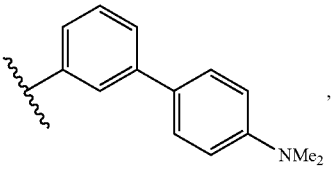

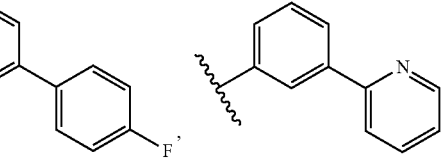

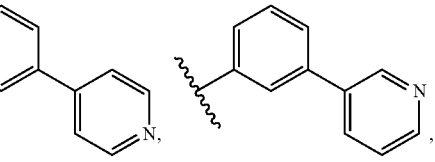

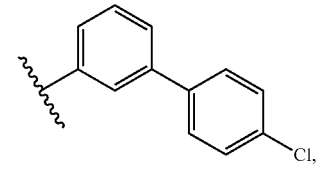

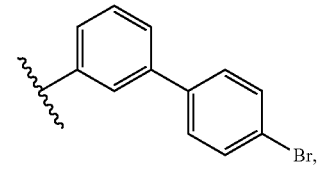

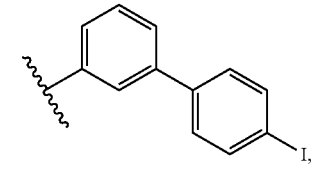

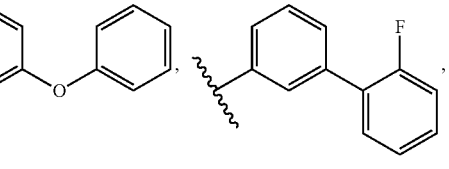

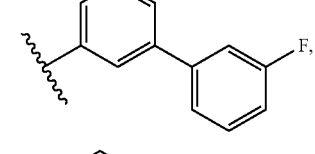

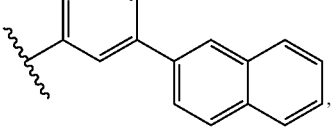

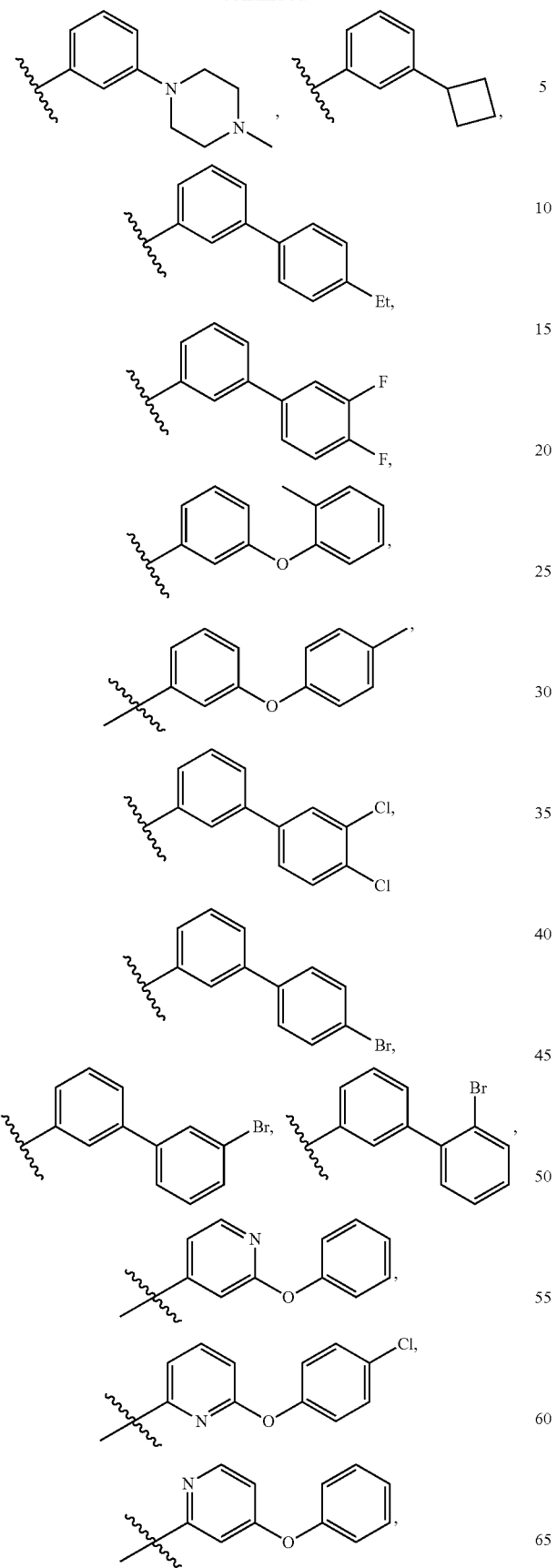
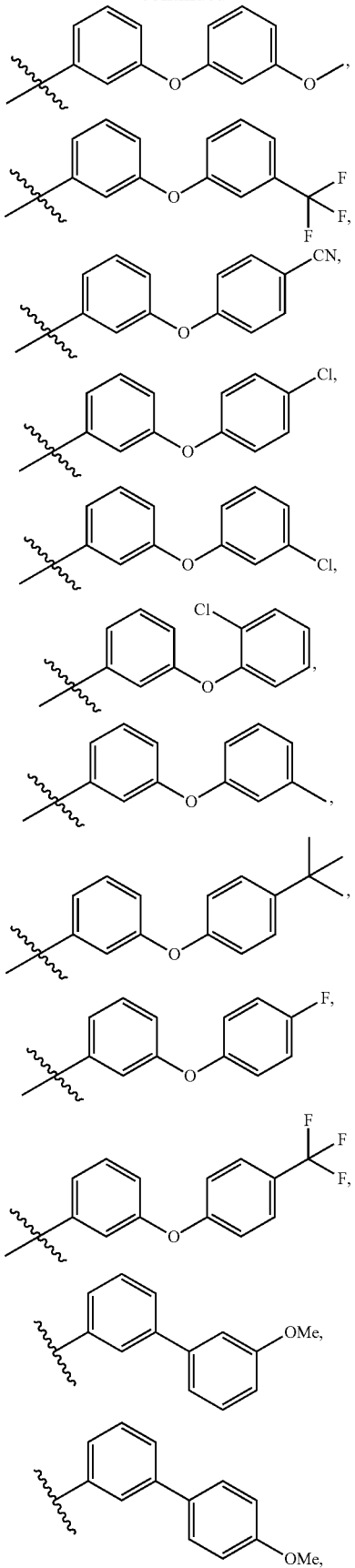

297
-continued
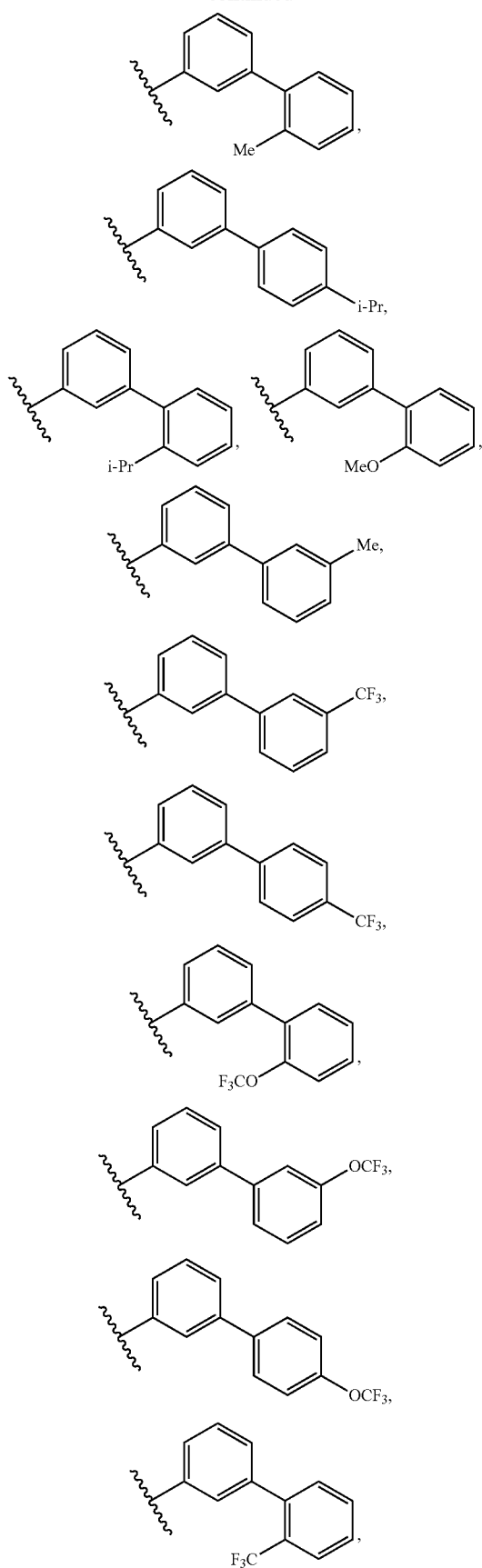
298
-continued
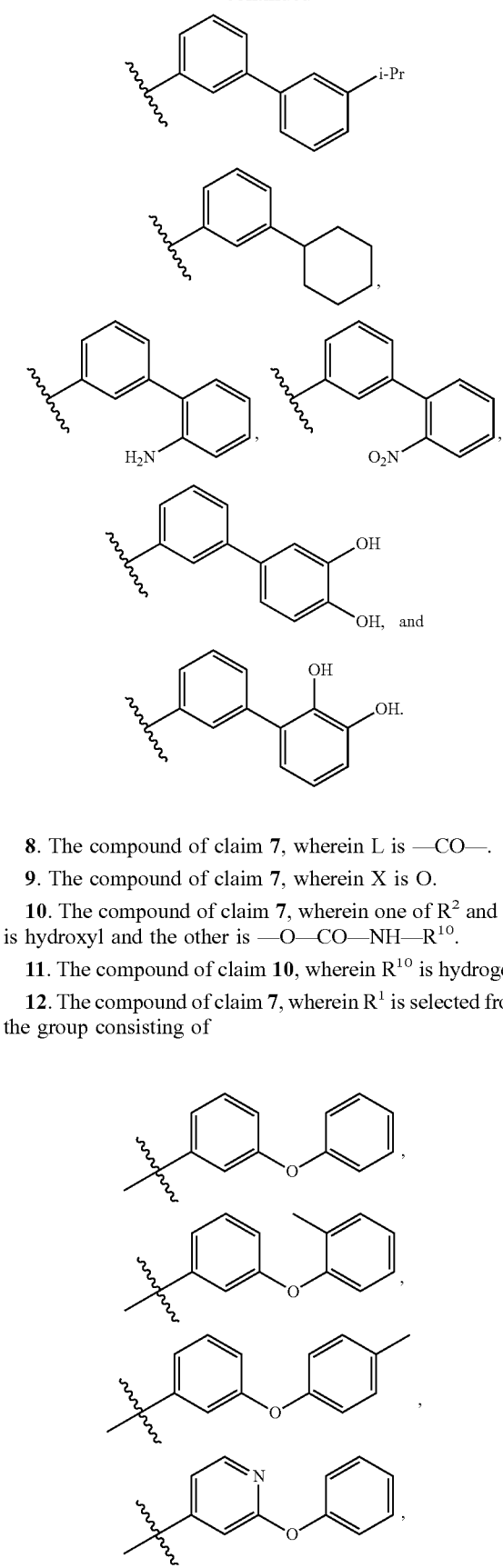
8. The compound of claim 7, wherein L is —CO—.
9. The compound of claim 7, wherein X is O.
10. The compound of claim 7, wherein one of $R^2$ and $R^3$ is hydroxyl and the other is —O—CO—NH—$R^{10}$.
11. The compound of claim 10, wherein $R^{10}$ is hydrogen.
12. The compound of claim 7, wherein $R^1$ is selected from the group consisting of

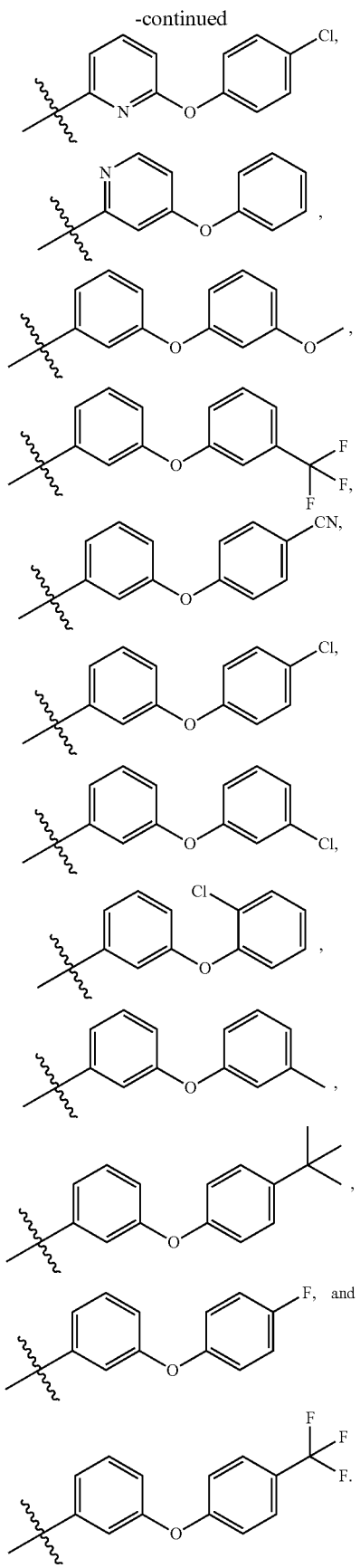
13. The compound of claim 7, wherein R¹ is selected from the group consisting of
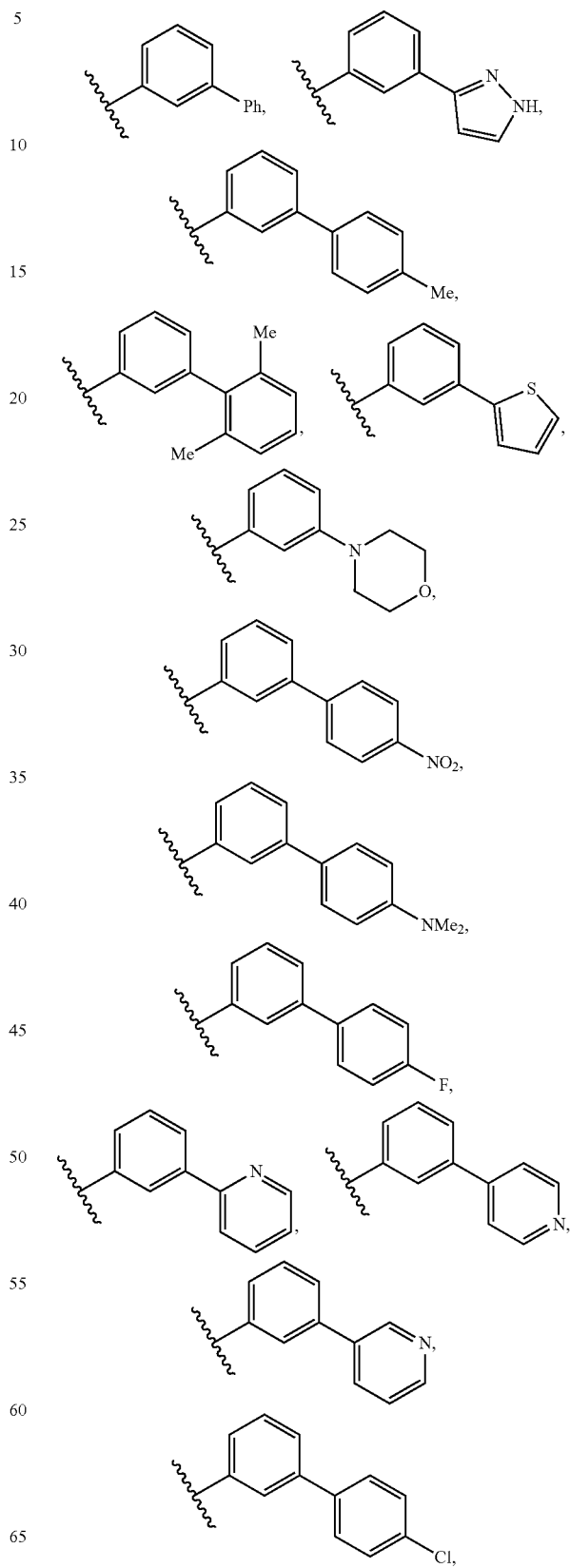

-continued
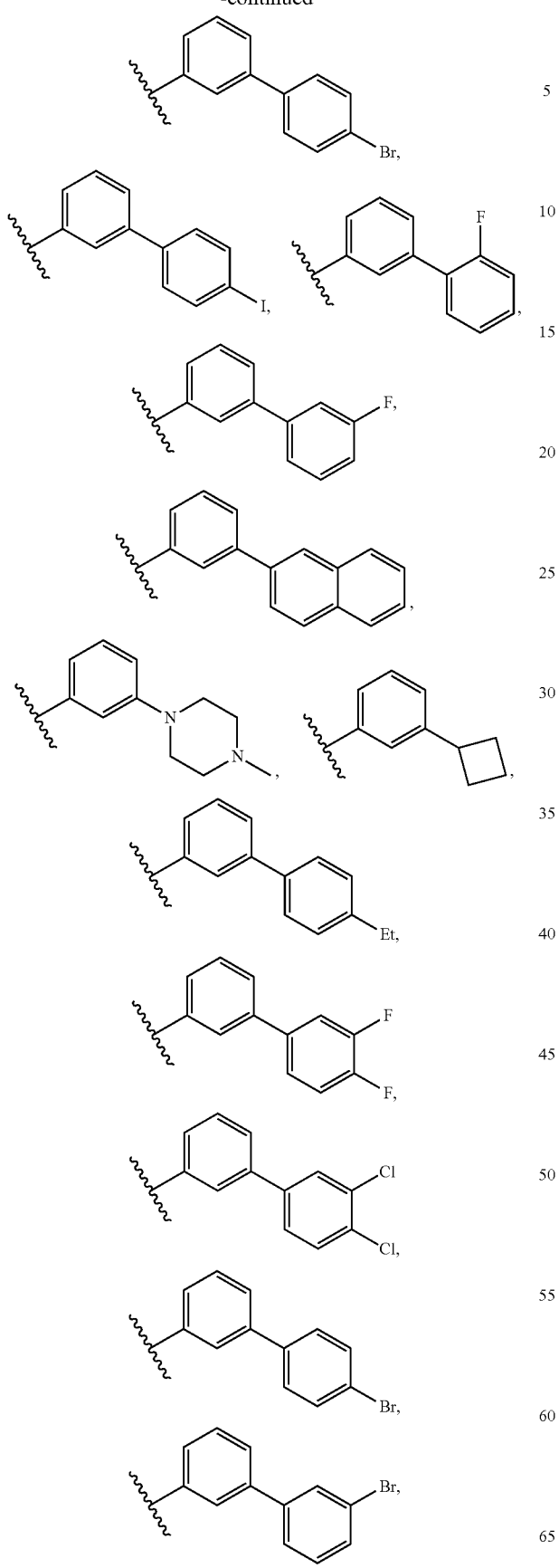
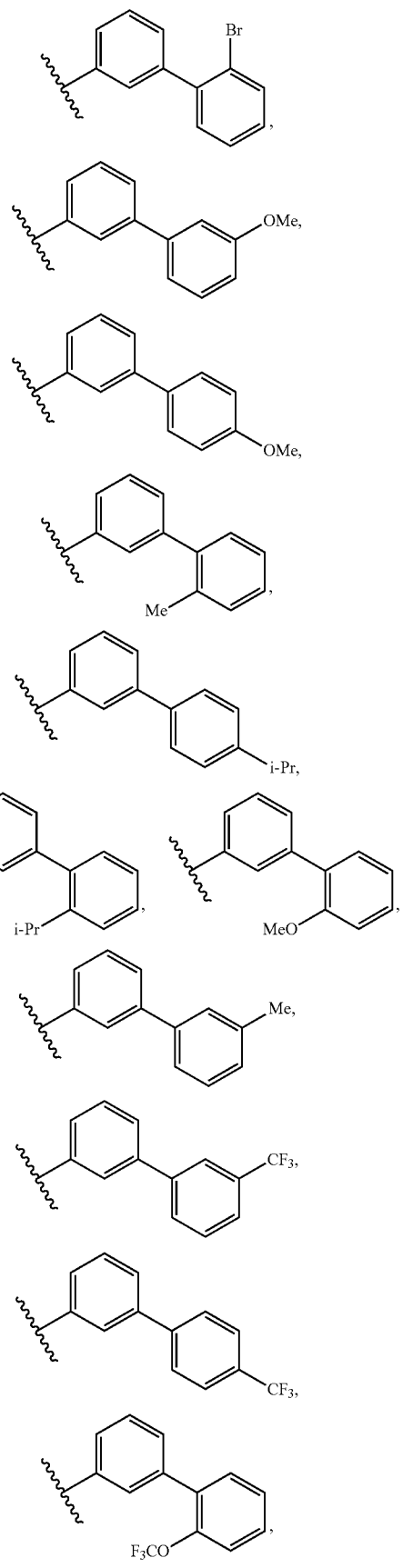

303
-continued
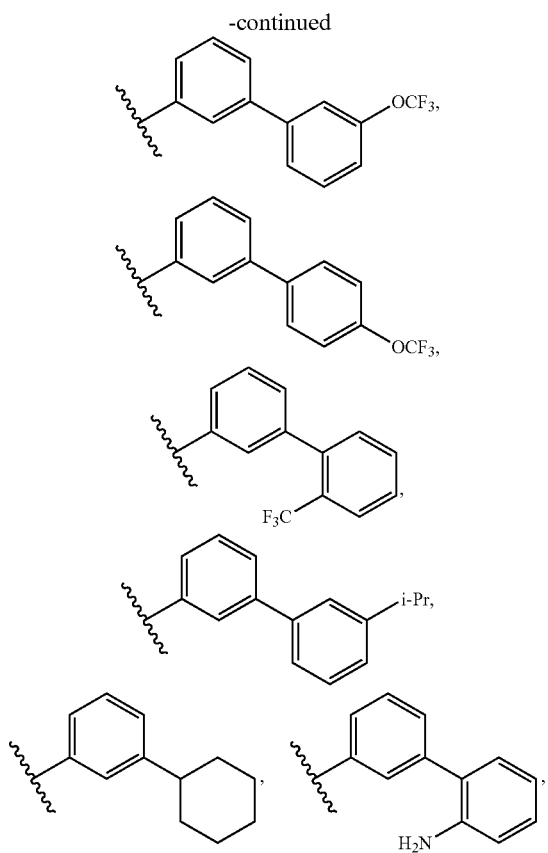
304
-continued
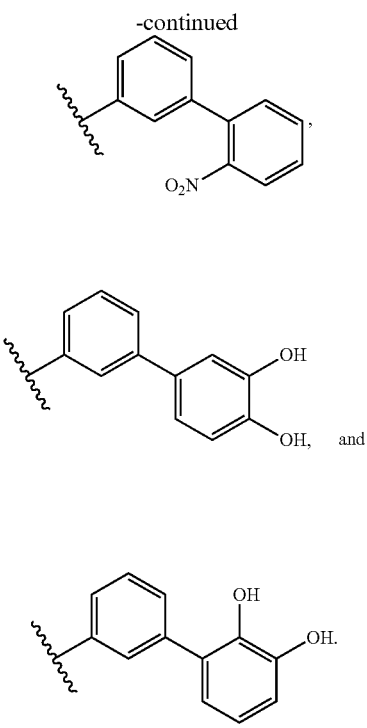
14. A pharmaceutical composition comprising the compound of claim 7 and a pharmaceutically acceptable excipient.
* * * * *